United States Patent
Gatti McArthur et al.

(10) Patent No.: US 7,446,113 B2
(45) Date of Patent: Nov. 4, 2008

(54) ACETYLENYL-PYRAZOLO-PYRIMIDINE DERIVATIVES

(75) Inventors: Silvia Gatti McArthur, Basel (CH);
Erwin Goetschi, Reinach (CH); Wylie Solang Palmer, Mountain View, CA (US); Juergen Wichmann, Steinen (DE); Thomas Johannes Woltering, Grenzach-Wyhlen (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 11/726,807

(22) Filed: Mar. 23, 2007

(65) Prior Publication Data
US 2007/0167460 A1    Jul. 19, 2007

Related U.S. Application Data

(62) Division of application No. 11/375,834, filed on Mar. 15, 2006, now Pat. No. 7,238,808.

(30) Foreign Application Priority Data
Mar. 23, 2005   (EP)   .................. 05102332

(51) Int. Cl.
*A61K 31/4439* (2006.01)
*C07D 471/04* (2006.01)
*C07D 491/04* (2006.01)
*C07D 498/04* (2006.01)
*C07D 513/04* (2006.01)
*C07D 515/04* (2006.01)
*A61K 31/5355* (2006.01)
*A61K 31/5025* (2006.01)
*A61K 31/4985* (2006.01)
*A61K 31/519* (2006.01)
*C07D 413/06* (2006.01)
*C07D 487/04* (2006.01)
*A61P 35/00* (2006.01)

(52) U.S. Cl. ............... 514/300; 514/233.2; 514/248; 514/259.1; 514/259.3; 544/117; 544/236; 544/281; 546/121

(58) Field of Classification Search .............. 514/300; 546/121
See application file for complete search history.

(56) References Cited

U.S. PATENT DOCUMENTS

| | | | |
|---|---|---|---|
| 3,725,428 | A | 4/1973 | Janiak |
| 4,028,374 | A | 6/1977 | Pelosi, Jr. et al. |
| 5,099,021 | A | 3/1992 | Worther et al. |
| 6,878,720 | B2 | 4/2005 | Altmann et al. |
| 6,958,341 | B2 * | 10/2005 | Wilde et al. ............... 514/259.3 |
| 2003/0139426 | A1 | 7/2003 | Wilde et al. |
| 2007/0049606 | A1 * | 3/2007 | Banville et al. ........... 514/259.1 |
| 2007/0072879 | A1 * | 3/2007 | McArthur et al. ........ 514/259.3 |
| 2007/0191395 | A1 * | 8/2007 | Kawakami et al. ....... 514/259.31 |
| 2007/0244111 | A1 * | 10/2007 | Gebauer et al. ........... 514/233.2 |

FOREIGN PATENT DOCUMENTS

| | | |
|---|---|---|
| DE | 1 953 149 | 5/1970 |
| EP | 0 199 400 A | 10/1986 |
| EP | 295 656 | 12/1988 |
| EP | 0343893 | 11/1989 |
| EP | 0404440 A | 12/1990 |
| EP | 427 963 | 5/1991 |
| EP | 0604657 | 7/1994 |
| EP | 0 891 978 A2 | 1/1999 |
| EP | 0 891 978 B1 | 1/1999 |
| FR | 2 753 970 A | 4/1998 |
| GB | 1 345 552 A | 1/1974 |
| GB | 1 538 822 A | 1/1979 |
| WO | WO 99/37630 | 1/1990 |
| WO | WO 97/29109 A1 | 8/1997 |
| WO | WO 99/24035 | 5/1999 |
| WO | WO 00/18767 | 4/2000 |
| WO | WO 00/27819 A | 5/2000 |
| WO | WO 01/19360 A2 | 9/2000 |
| WO | WO 01/97786 | 12/2001 |
| WO | WO 02/083652 | 10/2002 |
| WO | WO 02/092086 | 11/2002 |
| WO | WO 03/048132 A2 | 6/2003 |
| WO | WO 03/049741 | 6/2003 |
| WO | WO 03/053946 | 7/2003 |
| WO | WO 2004/092135 | 10/2004 |

(Continued)

OTHER PUBLICATIONS

D'Onofrio, et al., J. Neurochem. (Mar. 2003) vol. 84(6) pp. 1288-1295.

(Continued)

*Primary Examiner*—Mark L Berch
*Assistant Examiner*—Cecilia M Jaisle
(74) *Attorney, Agent, or Firm*—George W. Johnston; Patricia S. Rocha-Tramaloni; Kimberly J. Prior

(57) ABSTRACT

The present invention relates to compounds of formula (I):

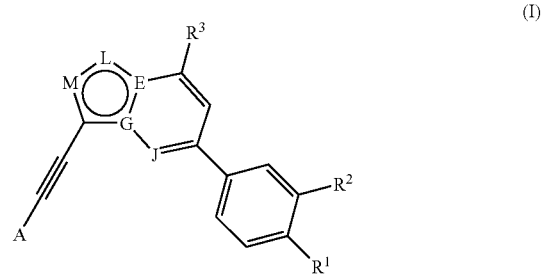

wherein $R^1$ to $R^3$, A, M, L, E, G, and J are as defined in the description and claims. The invention also relates to a process for the manufacture of such compounds, pharmaceutical compositions containing them, and methods for treating CNS disorders.

13 Claims, No Drawings

FOREIGN PATENT DOCUMENTS

| | | |
|---|---|---|
| WO | WO 2004/111040 | 12/2004 |
| WO | WO 2005/040171 | 5/2005 |
| WO | WO 2005/123738 | 12/2005 |

OTHER PUBLICATIONS

Database Chemcats Online, Chemical Abstract Service, Columbus, Ohio, US, XP002316354.
Fraley et al., Bioorg. Med. Chem. Lett., 12, pp. 3537-3541 (2002).
Poulsen, et al., Bioorganic & Medicinal Chemistry, vol. 6 (1998) pp. 619-641.
Müller, et al., Bioorganic & Medicinal Chemistry, vol. 6, (1998) pp. 707-719.
Kim, et al., J. Med. Chem., (1998), vol. 41, pp. 2835-2845.
Li, et al., J. Med. Chem., (1998), vol. 41, pp. 3186-3201.
Baraldi, et al., J. Med. Chem., (1998), vol. 41, pp. 2126-2133.
Li, et al., J. Med. Chem., (1999), vol. 42, pp. 706-721.
Baraldi, et al., J. Med. Chem., (1996), vol. 39, pp. 1164-1171.
Colotta, et al., Arch. Pharm. Pharm. Med. Chem., vol. 332, pp. 39-41 (1999).
Auchampach, et al., Am. J. Physiol. vol. 276, H1113-1116 (1999).
Haas, et al., Naunyn-Schmiedeberg's, Arch. Pharmacol. vol. 362, pp. 375-381 (2000).
Patent Abstracts of Japan, vol. 1999, No. 10, JP 11 130761a.
Pandeya, S. N. et al., Indian Drugs (1985), 23(3), 146-51.
Daidone, G. et al., Il Farmaco vol. 44, No. 5 (1989), pp. 465-473.
The Merck Index 12th Ed. (1996) p. 506.
Abstract corresponding to FR 2 753 970 (B14).

* cited by examiner

ACETYLENYL-PYRAZOLO-PYRIMIDINE DERIVATIVES

PRIORITY TO RELATED APPLICATIONS

This application is a division of U.S. application Ser. No. 11/375,834, filed Mar. 15, 2006, now pending; which claims the benefit of European Application No. 05102332.3, filed Mar. 23, 2005. The entire contents of the above-identified applications are hereby incorporated by reference.

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are chronic and acute pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia, depressions and glioma since mGluR2 antagonists have been found to reduce cell proliferation in human glioma cells (J. Neurochem. Mar. 2003, 84(6): 1288-95).

SUMMARY OF THE INVENTION

The present invention provides compounds of formula (I), a process for the manufacture thereof, pharmaceutical compositions containing them, and methods for treating CNS disorders with them.

In particular, the present invention provides compounds of formula (I)

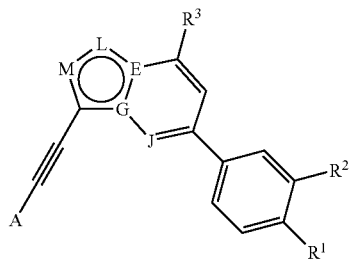

wherein
either E and J are N, G is C and one of L or M is N and the other is CH;
or L and G are N, E is C, and J and M are CH;
or J, G and L are N, E is C and M is CH;
or E and L are N, J and M are CH and G is C;
$R^1$ is H, halo, $CF_3$, $CHF_2$, or $C_{1-6}$-alkyl;
$R^2$ is H, halo, $C_{1-6}$-alkyl, $C_{1-6}$-alkoxy, $CF_3$ or $CHF_2$;
$R^3$ is H, —C($CH_3$)$_2$OH, linear $C_{1-4}$-alkyl or $C_{3-4}$-cycloalkyl each of which is optionally substituted by one or more substituents selected from the group consisting of 1 to 6 F and 1 to 2 OH;
A is selected from the group consisting of aryl and a 5 or 6-membered heteroaryl each of which is optionally substituted by one to four $R^a$;
$R^a$ is halo, hydroxy, cyano, $CF_3$, $NR^eR^f$, $C_{1-6}$-alkyl optionally substituted by amino or hydroxy, $C_{1-6}$-alkoxy, $C_{3-4}$-cycloalkyl, CO—$NR^bR^c$, $SO_2$—$NR^bR^c$; or $SO_2$—$R^d$; $R^b$ and $R^c$ are the same or different and are selected from the group consisting of:
H;
straight or branched $C_{1-6}$-alkyl optionally substituted by one or more substituents selected from the group consisting of:
F, cyano, hydroxy, $C_{1-6}$-alkoxy, —NH—C(O)—O—$C_{1-6}$-alkyl, amino, ($C_{1-6}$-alkyl)amino, di($C_{1-6}$-alkyl)amino, $C_{3-6}$-cycloalkyl, heterocycloalkyl having 5 or 6 ring atoms, aryl and 5 or 6-membered heteroaryl;
$C_{3-6}$-cycloalkyl;
aryl; and
heteroaryl;
or $R^b$ and $R^c$, together with the nitrogen atom to which they are attached, form a heterocyclic ring of 4 to 6 ring members optionally substituted by hydroxy or $C_{1-6}$-alkyl;
$R^d$ is OH or $C_{1-6}$-alkyl;
$R^e$ and $R^f$ are H, $C_{1-6}$-alkyl optionally substituted by hydroxy, —C(O)—$C_{1-6}$-alkyl or S(O)$_2$—$C_{1-6}$-alkyl;

and pharmaceutically acceptable salts thereof.

Compounds of general formula I are metabotropic glutamate receptor antagonists. Compounds of formula I are distinguished by valuable therapeutic properties.

The compounds of formula (I) can also be used in form of their prodrugs. Examples are esters, N-oxides, phosphate esters, glycoamide esters, glyceride conjugates and the like. The prodrugs can add to the value of the present compounds advantages in absorption, pharmacokinetics in distribution and transport to the brain.

DETAILED DESCRIPTION OF THE INVENTION

Unless otherwise stated, the following terms used in the present description have the definitions given herein. The definitions apply irrespective of whether the terms in question appear alone or in combination. It must be noted that, as used in the specification and the appended claims, the singular forms "a", "an," and "the" include plural forms unless the context clearly dictates otherwise.

The term "alkyl" or "lower alkyl" denotes straight-chain or branched saturated hydrocarbon residues with 1 to 7 carbon residues, for example, 1 to 6 carbon atoms ($C_{1-6}$alkyl), preferably with 1 to 4 carbon atoms ($C_{1-4}$alkyl), such as methyl, ethyl, n-propyl, i-propyl, i-butyl, t-butyl, and the like.

The term "alkoxy" or "lower alkoxy" denotes a lower alkyl residue in the sense of the foregoing definition bound via an oxygen atom. Examples of "lower alkoxy" residues include methoxy, ethoxy, isopropoxy and the like. Alkoxy groups of the invention can be substituted by one or more halogen atom. Examples of lower alkoxy substituted by one or more halogen include 2,2,2-trifluoroethoxy groups.

The term "$C_1$-$C_7$-alkylamino" denotes an —$NHR^7$ group, wherein $R^7$ is a $C_1$-$C_7$alkyl group as defined herein above.

The term "di($C_1$-$C_7$)alkylamino" denotes a —$NR^7R^8$ group, wherein $R^7$ and $R^8$ are independently selected from $C_1$-$C_7$ alkyl groups as defined herein above. Examples of di($C_1$-$C_7$)alkylamino groups include, but are not limited to, di(methyl)amino, di(ethyl)amino, methylethylamino, as well as those groups specifically illustrated by the examples herein below.

The term "aryl" represents an aromatic carbocyclic group consisting of one individual ring, or one or more fused rings in which at least one ring is aromatic in nature. Preferred aryl groups are phenyl and naphthyl.

The term "heteroaryl" or "5 or 6-membered heteroaryl" refers to an aromatic having 5 to 6 ring atoms and containing one or more heteroatoms selected from nitrogen, oxygen and sulphur.

Preferred are those heteroaryl groups having at least one nitrogen. Examples of such heteroaryl groups include pyridinyl, pyrazinyl, pyrimidinyl or pyridazinyl, and in particular, pyridin-2-yl, pyridin-3-yl, pyridine-4-yl, pyrimidin-5-yl, thiazol-2-yl and thiophen-2-yl.

The term "halogen" or "halo" embraces fluorine, chlorine, bromine and iodine.

The term "cycloalkyl" means a cyclic alkyl group containing 3 to 12, preferably 3 to 8 and still more preferably 3 to 6 carbon atoms, such as cyclopropyl, cyclobutyl, cyclopentyl or cyclohexyl. Cycloalkyl containing 3 to 4 carbon atoms are the most preferred.

The term "heterocycloalkyl having 5 or 6 ring atoms" or a "5 or 6-membered heterocycloalkyl group" denotes a heterocyclic ring having 5 or 6 ring members comprising at least one carbon atom as a ring member and 1, 2 or 3 heteroatom(s) ring members selected from N, O or S, the remaining ring members being carbon atoms. Examples of 5 or 6-membered heterocycloalkyl rings include, but are not limited to, 1H-tetrazole; 2H-tetrazole; 1,2,3- and 1,24-triazole; imidazole; pyrrole; 1,2,3-, 1,3,4- or 1,2,5-thiadiazine; 1,4-oxazine; 1,2- or 1,4-thiazine; 4-morpholinyl; 1-pyrrolidinyl; 1-piperazinyl, preferably 4-morpholinyl; 1-pyrrolidinyl and 1-piperazinyl.

Substituents for such 5 or 6-membered heterocyclic ring include, but are not limited to, halo, amino, nitro, cyano, hydroxy, $C_{-1-6}$-alkyl optionally substituted by hydroxy, $C_{1-6}$-alkoxy, $C_{1-6}$-alkenyl, $C_{3-8}$-cycloalkyl, or $CF_3$, preferably $C_{1-6}$-alkyl or $CF_3$.

"Thiophenyl" is synonymous to "thienyl" and indicates a substituent that is a five-membered hetaryl ring containing one ring sulfur atom as derived from thiophene.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable addition salt" refers to any salt derived from an inorganic or organic acid or base.

"Therapeutically effective amount" means an amount that is effective to prevent, alleviate or ameliorate symptoms of disease or prolong the survival of the subject being treated.

The present invention provides compounds of formula (I)

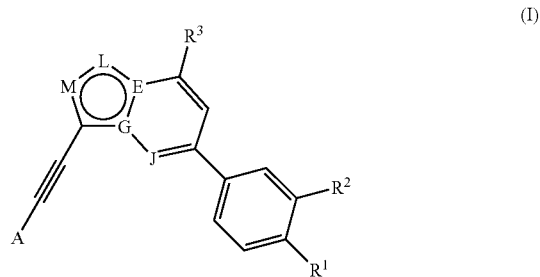

(I)

wherein
either E and J are N, G is C and one of L or M is N and the other is CH;
or L and G are N, E is C, and J and M are CH;
or J, G and L are N, E is C and M is CH;
or E and L are N, J and M are CH and G is C;
$R^1$ is H, halo, $CF_3$, $CHF_2$, or $C_{1-6}$-alkyl;
$R^2$ is H, halo, $C_{1-6}$-alkyl, $C_{1-6}$-alkoxy, $CF_3$ or $CHF_2$;
$R^3$ is H, —$C(CH_3)_2OH$, linear $C_{1-4}$-alkyl or $C_{3-4}$-cycloalkyl each of which is optionally substituted by one or more substituents selected from the group consisting of 1 to 6 F and 1 to 2 OH;
A is selected from the group consisting of aryl and a 5 or 6-membered heteroaryl each of which is optionally substituted by one to four $R^a$;
$R^a$ is halo, hydroxy, cyano, $CF_3$, $NR^eR^f$, $C_{1-6}$-alkyl optionally substituted by amino or hydroxy, $C_{1-6}$-alkoxy, $C_{3-4}$-cycloalkyl, CO—$NR^bR^c$, $SO_2$—$NR^bR^c$; or $SO_2$—$R^d$;
$R^b$ and $R^c$ are the same or different and are selected from the group consisting of:
  H;
  straight or branched $C_{1-6}$-alkyl optionally substituted by one or more substituents selected from the group consisting of:
    F, cyano, hydroxy, $C_{1-6}$-alkoxy, —NH—C(O)—O—$C_{1-6}$-alkyl, amino, ($C_{1-6}$-alkyl)amino, di($C_{1-6}$-alkyl)amino, $C_{3-6}$-cycloalkyl, heterocycloalkyl having 5 or 6 ring atoms, aryl and 5 or 6-membered heteroaryl;
  $C_{3-6}$-cycloalkyl;
  aryl; and
  heteroaryl;
or $R^b$ and $R^c$, together with the nitrogen atom to which they are attached, form a heterocyclic ring of 4 to 6 ring members optionally substituted by hydroxy or $C_{1-6}$-alkyl;
$R^d$ is OH or $C_{1-6}$-alkyl;
$R^e$ and $R^f$ are H, $C_{1-6}$-alkyl optionally substituted by hydroxy, —C(O)—$C_{1-6}$-alkyl or $S(O)_2$—$C_{1-6}$-alkyl;

and pharmaceutically acceptable salts thereof.

Also encompassed by the compounds of the invention are those compounds of formula (I):

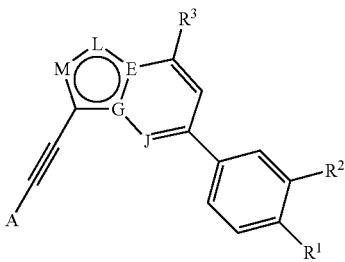

(I)

wherein
either E and J are N, G is C and one of L or M is N and the other is CH;
or L and G are N, E is C, and J and M are CH;
$R^1$ is H; halo; $CF_3$; $CHF_2$; or $C_{1-6}$-alkyl;
$R^2$ is H; halo; $C_{1-6}$-alkyl; $C_{1-6}$-alkoxy; $CF_3$; or $CHF_2$;
$R^3$ is H; —$C(CH_3)_2OH$; linear $C_{1-4}$-alkyl or $C_{3-4}$-cycloalkyl each of which is optionally substituted by one or more substituents selected from the group consisting of 1 to 6 F and 1 to 2 OH;
A is selected from the group consisting of aryl and 5 or 6-membered heteroaryl each of which is optionally substituted by one to four $R^a$;
$R^a$ is F; hydroxy; amino; $C_{1-6}$-alkyl optionally substituted by hydroxy; $C_{1-6}$-alkoxy; $C_{3-4}$-cycloalkyl; —CO—$R^b$; $SO_2$—$R^c$; or $SO_2$—$NR^dR^e$;
$R^b$ is amino;
$R^c$ is OH or $C_{1-6}$-alkyl;
$R^d$ and $R^e$ are the same or different and are selected from the group consisting of:
H;
straight or branched $C_{1-6}$-alkyl optionally substituted by one or more substituents selected from the group consisting of
F, cyano, hydroxy, di($C_{1-6}$-alkyl)amino, $C_{3-6}$-cycloalkyl, heterocycloalkyl having 5 or 6 ring atoms, aryl and 5 or 6-membered heteroaryl;
$C_{3-6}$-cycloalkyl;
aryl; and
heteroaryl;
or $R^d$ and $R^e$, together with the nitrogen atom to which they are attached, form a heterocyclic ring of 4 to 6 ring members optionally substituted by hydroxy and $C_{1-6}$-alkyl;

and pharmaceutically acceptable salts thereof.

Also encompassed by the compounds of formula (I) according to the invention are those compounds of formula (Ia):

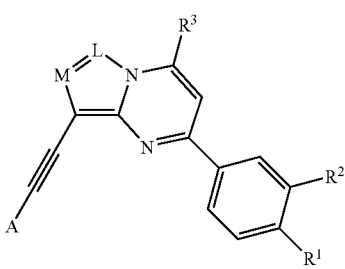

(Ia)

wherein,
one of L or M is N and the other is CH;
and $R^1$, $R^2$, $R^3$ and A are as defined hereinabove.

Also encompassed by the compounds of formula (Ia) according to the invention are those compounds of formula (Ia1):

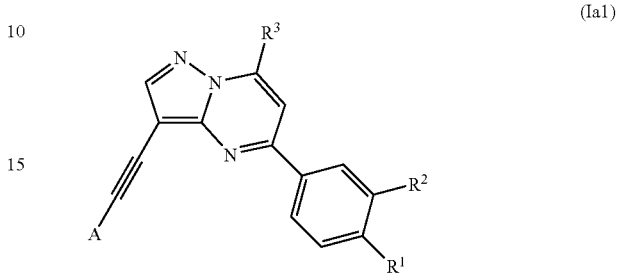

(Ia1)

wherein $R^1$, $R^2$, $R^3$ and A are as defined hereinabove.

In certain embodiments of the invention, the compounds of formula (Ia1) are compounds wherein A is selected from the group consisting of phenyl, pyridin-2-yl, pyridin-3-yl, pyridine-4-yl, pyrimidin-4-yl, pyrimidin-5-yl, pyridazin-2-yl, pyridazin-3-yl, thiazol-2-yl, thiazol-5-yl, and thiophen-2-yl each of which is optionally substituted by one to four $R^a$.

In certain embodiments of the invention, the compounds of formula (Ia1) are compounds wherein A is phenyl optionally substituted by one to four $R^a$, for example the following compounds:

3-[7-Trifluoromethyl-5-(4-trifluoromethyl-phenyl)-pyrazolo[1,5-a]pyrimidin-3-ylethynyl]-benzenesulfonamide;

N-(2-Hydroxy-1,1-dimethyl-ethyl)-3-[7-trifluoromethyl-5-(4-trifluoromethyl-phenyl)-pyrazolo[1,5-a]pyrimidin-3-ylethynyl]-benzenesulfonamide;

N-(2-Hydroxy-1,1-dimethyl-ethyl)-2-methoxy-5-[7-trifluoromethyl-5-(4-trifluoromethyl-phenyl)-pyrazolo[1,5-a]pyrimidin-3-ylethynyl]-benzenesulfonamide;

2,4-Difluoro-5-[7-trifluoromethyl-5-(4-trifluoromethyl-phenyl)-pyrazolo[1,5-a]pyrimidin-3-ylethynyl]-benzenesulfonamide;

N-tert-Butyl-3-[7-trifluoromethyl-5-(4-trifluoromethyl-phenyl)-pyrazolo[1,5-a]pyrimidin-3-ylethynyl]-benzenesulfonamide;

5-[7-Difluoromethyl-5-(4-trifluoromethyl-phenyl)-pyrazolo[1,5-a]pyrimidin-3-ylethynyl]-2,4-difluoro-benzenesulfonamide;

3-[7-Difluoromethyl-5-(4-trifluoromethyl-phenyl)-pyrazolo[1,5-a]pyrimidin-3-ylethynyl]-N-(2-hydroxy-1,1-dimethyl-ethyl)-benzenesulfonamide;

3-[7-Difluoromethyl-5-(4-trifluoromethyl-phenyl)-pyrazolo[1,5-a]pyrimidin-3-ylethynyl]-N-(2-hydroxy-1-hydroxymethyl-1-methyl-ethyl)-benzenesulfonamide;

N-(2-Hydroxy-ethyl)-2-methyl-5-[7-trifluoromethyl-5-(4-trifluoromethyl-phenyl)-pyrazolo[1,5-a]pyrimidin-3-ylethynyl]-benzenesulfonamide;

2-Methyl-5-[7-trifluoromethyl-5-(4-trifluoromethyl-phenyl)-pyrazolo[1,5-a]pyrimidin-3-ylethynyl]-benzenesulfonamide;

4-[7-Trifluoromethyl-5-(4-trifluoromethyl-phenyl)-pyrazolo[1,5-a]pyrimidin-3-ylethynyl]-benzenesulfonamide;

3-(3-Methanesulfonyl-phenylethynyl)-7-trifluoromethyl-5-(4-trifluoromethyl-phenyl)-pyrazolo[1,5-a]pyrimidine;

3-[5-(3-Ethoxy-4-trifluoromethyl-phenyl)-7-trifluoromethyl-pyrazolo[1,5-a]pyrimidin-3-ylethynyl]-N-(2-hydroxy-1,1-dimethyl-ethyl)-benzenesulfonamide;
3-[7-Difluoromethyl-5-(4-trifluoromethyl-phenyl)-pyrazolo[1,5-a]pyrimidin-3-ylethynyl]-benzenesulfonamide;
5-[7-Difluoromethyl-5-(4-trifluoromethyl-phenyl)-pyrazolo[1,5-a]pyrimidin-3-ylethynyl]-N-(2-hydroxy-1,1-dimethyl-ethyl)-2-methoxy-benzenesulfonamide;
3-Fluoro-4-[7-trifluoromethyl-5-(4-trifluoromethyl-phenyl)-pyrazolo[1,5-a]pyrimidin-3-ylethynyl]-benzenesulfonamide;
N-(2-Morpholin-4-yl-ethyl)-3-[7-trifluoromethyl-5-(4-trifluoromethyl-phenyl)-pyrazolo[1,5-a]pyrimidin-3-ylethynyl]-benzenesulfonamide;
N-(2-Cyano-ethyl)-3-[7-trifluoromethyl-5-(4-trifluoromethyl-phenyl)-pyrazolo[1,5-a]pyrimidin-3-ylethynyl]-benzenesulfonamide;
4-[7-Difluoromethyl-5-(4-trifluoromethyl-phenyl)-pyrazolo[1,5-a]pyrimidin-3-ylethynyl]-3-fluoro-benzenesulfonamide;
4-[7-Difluoromethyl-5-(4-trifluoromethyl-phenyl)-pyrazolo[1,5-a]pyrimidin-3-ylethynyl]-benzenesulfonamide;
2-Fluoro-5-[7-trifluoromethyl-5-(4-trifluoromethyl-phenyl)-pyrazolo[1,5-a]pyrimidin-3-ylethynyl]-benzenesulfonamide;
1-{4-[7-Trifluoromethyl-5-(4-trifluoromethyl-phenyl)-pyrazolo[1,5-a]pyrimidin-3-ylethynyl]-phenyl}-ethanol;
5-[7-Difluoromethyl-5-(4-trifluoromethyl-phenyl)-pyrazolo[1,5-a]pyrimidin-3-ylethynyl]-2-fluoro-benzenesulfonamide;
5-[7-Difluoromethyl-5-(4-trifluoromethyl-phenyl)-pyrazolo[1,5-a]pyrimidin-3-ylethynyl]-2-methyl-benzenesulfonamide;
5-[7-Difluoromethyl-5-(4-trifluoromethyl-phenyl)-pyrazolo[1,5-a]pyrimidin-3-ylethynyl]-N-(2-hydroxy-ethyl)-2-methyl-benzenesulfonamide;
3-Phenylethynyl-7-trifluoromethyl-5-(4-trifluoromethyl-phenyl)-pyrazolo[1,5-a]pyrimidine;
4-[5-(4-Chloro-phenyl)-7-cyclopropyl-pyrazolo[1,5-a]pyrimidin-3-ylethynyl]-benzenesulfonamide;
3-[5-(4-Chloro-phenyl)-7-cyclopropyl-pyrazolo[1,5-a]pyrimidin-3-ylethynyl]-N-(2-hydroxy-1,1-dimethyl-ethyl)-benzenesulfonamide;
5-[5-(4-Chloro-phenyl)-7-cyclopropyl-pyrazolo[1,5-a]pyrimidin-3-ylethynyl]-N-(2-hydroxy-1,1-dimethyl-ethyl)-2-methoxy-benzenesulfonamide;
3-[5-(4-Chloro-phenyl)-7-cyclopropyl-pyrazolo[1,5-a]pyrimidin-3-ylethynyl]-benzenesulfonamide;
5-[5-(4-Chloro-phenyl)-pyrazolo[1,5-a]pyrimidin-3-ylethynyl]-N-(2-hydroxy-1,1-dimethyl-ethyl)-2-methoxy-benzenesulfonamide;
4-[7-Cyclopropyl-5-(4-trifluoromethyl-phenyl)-pyrazolo[1,5-a]pyrimidin-3-ylethynyl]-benzenesulfonamide;
5-[7-Cyclopropyl-5-(4-trifluoromethyl-phenyl)-pyrazolo[1,5-a]pyrimidin-3-ylethynyl]-2,4-difluoro-benzenesulfonamide;
5-[7-Cyclopropyl-5-(4-trifluoromethyl-phenyl)-pyrazolo[1,5-a]pyrimidin-3-ylethynyl]-N-(2-hydroxy-1,1-dimethyl-ethyl)-2-methoxy-benzenesulfonamide;
3-[7-Cyclopropyl-5-(4-trifluoromethyl-phenyl)-pyrazolo[1,5-a]pyrimidin-3-ylethynyl]-benzenesulfonamide;
5-[7-Cyclopropyl-5-(3,4-dichloro-phenyl)-pyrazolo[1,5-a]pyrimidin-3-ylethynyl]-2,4-difluoro-benzenesulfonamide;
3-[7-Cyclopropyl-5-(3,4-dichloro-phenyl)-pyrazolo[1,5-a]pyrimidin-3-ylethynyl]-benzenesulfonamide;
4-[7-Cyclopropyl-5-(3,4-dichloro-phenyl)-pyrazolo[1,5-a]pyrimidin-3-ylethynyl]-benzenesulfonamide;
5-[5-(3,4-Dichloro-phenyl)-7-trifluoromethyl-pyrazolo[1,5-a]pyrimidin-3-ylethynyl]-2,4-difluoro-benzenesulfonamide;
3-[5-(3,4-Dichloro-phenyl)-7-trifluoromethyl-pyrazolo[1,5-a]pyrimidin-3-ylethynyl]-benzenesulfonamide;
4-[5-(3,4-Dichloro-phenyl)-7-trifluoromethyl-pyrazolo[1,5-a]pyrimidin-3-ylethynyl]-benzenesulfonamide;
3-[5-(4-Chloro-phenyl)-7-trifluoromethyl-pyrazolo[1,5-a]pyrimidin-3-ylethynyl]-N-(2-hydroxy-1,1-dimethyl-ethyl)-benzenesulfonamide;
5-[5-(4-Chloro-phenyl)-7-trifluoromethyl-pyrazolo[1,5-a]pyrimidin-3-ylethynyl]-2,4-difluoro-benzenesulfonamide;
3-[5-(4-Chloro-phenyl)-7-trifluoromethyl-pyrazolo[1,5-a]pyrimidin-3-ylethynyl]-benzenesulfonamide;
3-[5-(4-Chloro-phenyl)-7-trifluoromethyl-pyrazolo[1,5-a]pyrimidin-3-ylethynyl]-benzenesulfonamide;
3-[5-(4-Chloro-3-methyl-phenyl)-7-trifluoromethyl-pyrazolo[1,5-a]pyrimidin-3-ylethynyl]-N-(2-hydroxy-1,1-dimethyl-ethyl)-benzenesulfonamide;
N-(2-Hydroxy-1,1-dimethyl-ethyl)-3-[7-trifluoromethyl-5-(3-trifluoromethyl-phenyl)-pyrazolo[1,5-a]pyrimidin-3-ylethynyl]-benzenesulfonamide;
4-[5-(4-Chloro-3-methyl-phenyl)-7-trifluoromethyl-pyrazolo[1,5-a]pyrimidin-3-ylethynyl]-benzenesulfonamide;
5-[5-(4-Chloro-3-methyl-phenyl)-7-trifluoromethyl-pyrazolo[1,5-a]pyrimidin-3-ylethynyl]-2,4-difluoro-benzenesulfonamide;
3-[5-(4-Chloro-3-methyl-phenyl)-7-trifluoromethyl-pyrazolo[1,5-a]pyrimidin-3-ylethynyl]-benzenesulfonamide;
4-[7-Trifluoromethyl-5-(3-trifluoromethyl-phenyl)-pyrazolo[1,5-a]pyrimidin-3-ylethynyl]-benzenesulfonamide;
2,4-Difluoro-5-[7-trifluoromethyl-5-(3-trifluoromethyl-phenyl)-pyrazolo[1,5-a]pyrimidin-3-ylethynyl]-benzenesulfonamide;
3-[7-Trifluoromethyl-5-(3-trifluoromethyl-phenyl)-pyrazolo[1,5-a]pyrimidin-3-ylethynyl]-benzenesulfonamide;
N,N-Dimethyl-4-[7-trifluoromethyl-5-(4-trifluoromethyl-phenyl)-pyrazolo[1,5-a]pyrimidin-3-ylethynyl]-benzenesulfonamide;
3-[4-(Morpholine-4-sulfonyl)-phenylethynyl]-7-trifluoromethyl-5-(4-trifluoromethyl-phenyl)-pyrazolo[1,5-a]pyrimidine;
N-Methyl-4-[7-trifluoromethyl-5-(4-trifluoromethyl-phenyl)-pyrazolo[1,5-a]pyrimidin-3-ylethynyl]-benzenesulfonamide;
N-(2-Methoxy-ethyl)-4-[7-trifluoromethyl-5-(4-trifluoromethyl-phenyl)-pyrazolo[1,5-a]pyrimidin-3-ylethynyl]-benzenesulfonamide;
N-(2-Hydroxy-ethyl)-4-[7-trifluoromethyl-5-(4-trifluoromethyl-phenyl)-pyrazolo[1,5-a]pyrimidin-3-ylethynyl]-benzenesulfonamide;
N-(2-Dimethylamino-ethyl)-4-[7-trifluoromethyl-5-(4-trifluoromethyl-phenyl)-pyrazolo[1,5-a]pyrimidin-3-ylethynyl]-benzenesulfonamide;
3-[3-(morpholine-4-sulfonyl)-phenylethynyl]-7-trifluoromethyl-5-(4-trifluoromethyl-phenyl)-pyrazolo[1,5-a]pyrimidine;
N-Methyl-3-[7-trifluoromethyl-5-(4-trifluoromethyl-phenyl)-pyrazolo[1,5-a]pyrimidin-3-ylethynyl]-benzenesulfonamide;
N-(2-Methoxy-ethyl)-3-[7-trifluoromethyl-5-(4-trifluoromethyl-phenyl)-pyrazolo[1,5-a]pyrimidin-3-ylethynyl]-benzenesulfonamide;

N-(2-Hydroxy-ethyl)-3-[7-trifluoromethyl-5-(4-trifluoromethyl-phenyl)-pyrazolo[1,5-a]pyrimidin-3-ylethynyl]-benzenesulfonamide;
N-(2-Dimethylamino-ethyl)-3-[7-trifluoromethyl-5-(4-trifluoromethyl-phenyl)-pyrazolo[1,5-a]pyrimidin-3-ylethynyl]-benzenesulfonamide;
5-[7-Difluoromethyl-5-(4-trifluoromethyl-phenyl)-pyrazolo[1,5-a]pyrimidin-3-ylethynyl]-N-(2-dimethylamino-ethyl)-2,4-difluoro-benzenesulfonamide;
5-[7-Difluoromethyl-5-(4-trifluoromethyl-phenyl)-pyrazolo[1,5-a]pyrimidin-3-ylethynyl]-2,4-difluoro-N-(2-hydroxy-ethyl)-benzenesulfonamide;
4-[7-Difluoromethyl-5-(4-trifluoromethyl-phenyl)-pyrazolo[1,5-a]pyrimidin-3-ylethynyl]-N,N-dimethyl-benzenesulfonamide;
7-Difluoromethyl-3-[4-(morpholine-4-sulfonyl)-phenylethynyl]-5-(4-trifluoromethyl-phenyl)-pyrazolo[1,5-a]pyrimidine;
4-[7-difluoromethyl-5-(4-trifluoromethyl-phenyl)-pyrazolo[1,5-a]pyrimidin-3-ylethynyl]-N-methyl-benzenesulfonamide;
4-[7-Difluoromethyl-5-(4-trifluoromethyl-phenyl)-pyrazolo[1,5-a]pyrimidin-3-ylethynyl]-N-(2-methoxy-ethyl)-benzenesulfonamide;
4-[7-Difluoromethyl-5-(4-trifluoromethyl-phenyl)-pyrazolo[1,5-a]pyrimidin-3-ylethynyl]-N-(2-hydroxy-ethyl)-benzenesulfonamide;
7-Difluoromethyl-3-[3-(morpholine-4-sulfonyl)-phenylethynyl]-5-(4-trifluoromethyl-phenyl)-pyrazolo[1,5-a]pyrimidine;
3-[7-Difluoromethyl-5-(4-trifluoromethyl-phenyl)-pyrazolo[1,5-a]pyrimidin-3-ylethynyl]-N-methyl-benzenesulfonamide;
3-[7-Difluoromethyl-5-(4-trifluoromethyl-phenyl)-pyrazolo[1,5-a]pyrimidin-3-ylethynyl]-N-(2-methoxy-ethyl)-benzenesulfonamide;
3-[7-Difluoromethyl-5-(4-trifluoromethyl-phenyl)-pyrazolo[1,5-a]pyrimidin-3-ylethynyl]-N-(2-hydroxy-ethyl)-benzenesulfonamide;
3-[7-Difluoromethyl-5-(4-trifluoromethyl-phenyl)-pyrazolo[1,5-a]pyrimidin-3-ylethynyl]-N-(2-dimethylamino-ethyl)-benzenesulfonamide;
4-[7-Methyl-5-(4-trifluoromethyl-phenyl)-pyrazolo[1,5-a]pyrimidin-3-ylethynyl]-benzenesulfonamide;
3-[7-Methyl-5-(4-trifluoromethyl-phenyl)-pyrazolo[1,5-a]pyrimidin-3-ylethynyl]-benzenesulfonamide;
4-[5-(4-Chloro-phenyl)-7-(1-hydroxy-1-methyl-ethyl)-pyrazolo[1,5-a]pyrimidin-3-ylethynyl]-benzenesulfonamide;
4-[5-(4-Chloro-phenyl)-7-hydroxymethyl-pyrazolo[1,5-a]pyrimidin-3-ylethynyl]-benzenesulfonamide;
3-[5-(4-Methyl-piperazine-1-sulfonyl)-thiophen-2-ylethynyl]-7-trifluoromethyl-5-(4-trifluoromethyl-phenyl)-pyrazolo[1,5-a]pyrimidine;
5-[7-Difluoromethyl-5-(3-trifluoromethyl-phenyl)-pyrazolo[1,5-a]pyrimidin-3-ylethynyl]-2,4-difluoro-benzenesulfonamide;
3-[7-Difluoromethyl-5-(3-trifluoromethyl-phenyl)-pyrazolo[1,5-a]pyrimidin-3-ylethynyl]-benzenesulfonamide;
3-[5-(4-Chloro-3-methyl-phenyl)-7-difluoromethyl-pyrazolo[1,5-a]pyrimidin-3-ylethynyl]-benzenesulfonamide;
5-[5-(4-Chloro-3-methyl-phenyl)-7-difluoromethyl-pyrazolo[1,5-a]pyrimidin-3-ylethynyl]-thiophene-2-sulfonic acid amide;
4-[5-(4-Chloro-3-methyl-phenyl)-7-difluoromethyl-pyrazolo[1,5-a]pyrimidin-3-ylethynyl]-benzenesulfonamide;
5-[5-(4-Chloro-3-methyl-phenyl)-7-difluoromethyl-pyrazolo[1,5-a]pyrimidin-3-ylethynyl]-2,4-difluoro-benzenesulfonamide;
4-[7-Difluoromethyl-5-(3-trifluoromethyl-phenyl)-pyrazolo[1,5-a]pyrimidin-3-ylethynyl]-benzenesulfonamide;
{4-[7-Trifluoromethyl-5-(4-trifluoromethyl-phenyl)-pyrazolo[1,5-a]pyrimidin-3-ylethynyl]-phenyl}-methanol;
(2-{5-[7-Difluoromethyl-5-(4-trifluoromethyl-phenyl)-pyrazolo[1,5-a]pyrimidin-3-ylethynyl]-2,4-difluoro-benzenesulfonylamino}-ethyl)-carbamic acid tert-butyl ester;
1-{4-[7-Trifluoromethyl-5-(4-trifluoromethyl-phenyl)-pyrazolo[1,5-a]pyrimidin-3-ylethynyl]-phenyl}-ethylamine;
4-[7-Difluoromethyl-5-(3-ethoxy-phenyl)-pyrazolo[1,5-a]pyrimidin-3-ylethynyl]-benzenesulfonamide;
4-[7-Trifluoromethyl-5-(4-trifluoromethyl-phenyl)-pyrazolo[1,5-a]pyrimidin-3-ylethynyl]-benzamide;
3-[7-Difluoromethyl-5-(3-ethoxy-phenyl)-pyrazolo[1,5-a]pyrimidin-3-ylethynyl]-benzenesulfonamide;
2-{4-[7-Trifluoromethyl-5-(4-trifluoromethyl-phenyl)-pyrazolo[1,5-a]pyrimidin-3-ylethynyl]-phenyl}-propan-2-ol;
{3-[7-Trifluoromethyl-5-(4-trifluoromethyl-phenyl)-pyrazolo[1,5-a]pyrimidin-3-ylethynyl]-phenyl}-methanol;
N-{4-[7-Trifluoromethyl-5-(4-trifluoromethyl-phenyl)-pyrazolo[1,5-a]pyrimidin-3-ylethynyl]-phenyl}-acetamide;
4-[5-(4-Chloro-phenyl)-7-methyl-pyrazolo[1,5-a]pyrimidin-3-ylethynyl]-benzenesulfonamide;
2-[5-(4-Chloro-phenyl)-3-(4-hydroxymethyl-phenylethynyl)-pyrazolo[1,5-a]pyrimidin-7-yl]-propan-2-ol;
2-{4-[5-(4-Chloro-phenyl)-7-hydroxymethyl-pyrazolo[1,5-a]pyrimidin-3-ylethynyl]-phenyl}-propan-2-ol;
2-{4-[5-(4-Chloro-phenyl)-7-cyclopropyl-pyrazolo[1,5-a]pyrimidin-3-ylethynyl]-phenyl}-propan-2-ol;
2-{4-[5-(4-Chloro-phenyl)-7-methyl-pyrazolo[1,5-a]pyrimidin-3-ylethynyl]-phenyl}-propan-2-ol; and
4-[5-(4-Chloro-phenyl)-7-cyclopropyl-pyrazolo[1,5-a]pyrimidin-3-ylethynyl]-N-methyl-benzamide.

In certain embodiments of the invention, the compounds of formula (Ia1) are compounds wherein A is pyridin-2-yl optionally substituted by one to four $R^a$, for example 3-Pyridin-2-ylethynyl-7-trifluoromethyl-5-(4-trifluoromethyl-phenyl)-pyrazolo[1,5-a]pyrimidine.

In certain embodiments of the invention, the compounds of formula (Ia1) are compounds wherein A is pyridin-3-yl optionally substituted by one to four $R^a$, for example the following compounds:
3-Pyridin-3-ylethynyl-7-trifluoromethyl-5-(4-trifluoromethyl-phenyl)-pyrazolo[1,5-a]pyrimidine;
5-[7-Trifluoromethyl-5-(4-trifluoromethyl-phenyl)-pyrazolo[1,5-a]pyrimidin-3-ylethynyl]-pyridine-3-sulfonic acid amide;
3-(2-Cyclopropyl-pyridin-3-ylethynyl)-7-trifluoromethyl-5-(4-trifluoromethyl-phenyl)-pyrazolo[1,5-a]pyrimidine;
3-(6-Methyl-pyridin-3-ylethynyl)-7-trifluoromethyl-5-(4-trifluoromethyl-phenyl)-pyrazolo[1,5-a]pyrimidine;
3-(2-Cyclopropyl-pyridin-5-ylethynyl)-7-trifluoromethyl-5-(4-trifluoromethyl-phenyl)-pyrazolo[1,5-a]pyrimidine;
5-[7-Trifluoromethyl-5-(4-trifluoromethyl-phenyl)-pyrazolo[1,5-a]pyrimidin-3-ylethynyl]-pyridine-3-sulfonic acid (2-hydroxy-1,1-dimethyl-ethyl)-amide;
3-(2-Methyl-pyridin-3-ylethynyl)-7-trifluoromethyl-5-(4-trifluoromethyl-phenyl)-pyrazolo[1,5-a]pyrimidine;
5-[7-Trifluoromethyl-5-(4-trifluoromethyl-phenyl)-pyrazolo[1,5-a]pyrimidin-3-ylethynyl]-pyridine-3-sulfonic acid bis-(2-hydroxy-ethyl)-amide;

5-[7-Trifluoromethyl-5-(4-trifluoromethyl-phenyl)-pyrazolo[1,5-a]pyrimidin-3-ylethynyl]-pyridine-3-sulfonic acid (2-hydroxy-1-hydroxymethyl-1-methyl-ethyl)-amide;

5-[7-Trifluoromethyl-5-(4-trifluoromethyl-phenyl)-pyrazolo[1,5-a]pyrimidin-3-ylethynyl]-nicotinamide;

5-[7-Trifluoromethyl-5-(4-trifluoromethyl-phenyl)-pyrazolo[1,5-a]pyrimidin-3-ylethynyl]-pyridine-3-sulfonic acid tert-butylamide;

6-Methoxy-5-[7-trifluoromethyl-5-(4-trifluoromethyl-phenyl)-pyrazolo[1,5-a]pyrimidin-3-ylethynyl]-pyridine-3-sulfonic acid (2-hydroxy-1,1-dimethyl-ethyl)-amide;

5-(4-Chloro-phenyl)-3-pyridin-3-ylethynyl-7-trifluoromethyl-pyrazolo[1,5-a]pyrimidine;

5-[7-Trifluoromethyl-5-(4-trifluoromethyl-phenyl)-pyrazolo[1,5-a]pyrimidin-3-ylethynyl]-pyridine-3-sulfonic acid (2-hydroxy-1,1-bis-hydroxymethyl-ethyl)-amide;

6-Methoxy-5-[7-trifluoromethyl-5-(4-trifluoromethyl-phenyl)-pyrazolo[1,5-a]pyrimidin-3-ylethynyl]-pyridine-3-sulfonic acid (2-hydroxy-1-hydroxymethyl-1-methyl-ethyl)-amide;

5-[7-Difluoromethyl-5-(4-trifluoromethyl-phenyl)-pyrazolo[1,5-a]pyrimidin-3-ylethynyl]-pyridine-3-sulfonic acid (2-hydroxy-1-hydroxymethyl-1-methyl-ethyl)-amide;

5-[7-Difluoromethyl-5-(4-trifluoromethyl-phenyl)-pyrazolo[1,5-a]pyrimidin-3-ylethynyl]-pyridine-3-sulfonic acid (2-hydroxy-1,1-dimethyl-ethyl)-amide;

5-[7-Trifluoromethyl-5-(4-trifluoromethyl-phenyl)-pyrazolo[1,5-a]pyrimidin-3-ylethynyl]-pyridine-3-sulfonic acid (2-hydroxy-1-methyl-ethyl)-amide;

5-[7-Difluoromethyl-5-(4-trifluoromethyl-phenyl)-pyrazolo[1,5-a]pyrimidin-3-ylethynyl]-pyridine-3-sulfonic acid amide;

5-[7-Trifluoromethyl-5-(4-trifluoromethyl-phenyl)-pyrazolo[1,5-a]pyrimidin-3-ylethynyl]-pyridine-3-sulfonic acid;

3-(5-Methanesulfonyl-pyridin-3-ylethynyl)-7-trifluoromethyl-5-(4-trifluoromethyl-phenyl)-pyrazolo[1,5-a]pyrimidine;

5-[7-Trifluoromethyl-5-(4-trifluoromethyl-phenyl)-pyrazolo[1,5-a]pyrimidin-3-ylethynyl]-pyridin-2-ylamine;

3-(6-Methoxy-pyridin-3-ylethynyl)-7-trifluoromethyl-5-(4-trifluoromethyl-phenyl)-pyrazolo[1,5-a]pyrimidine;

3-(5-Methoxy-pyridin-3-ylethynyl)-7-trifluoromethyl-5-(4-trifluoromethyl-phenyl)-pyrazolo[1,5-a]pyrimidine;

5-[7-Trifluoromethyl-5-(4-trifluoromethyl-phenyl)-pyrazolo[1,5-a]pyrimidin-3-ylethynyl]-pyridin-3-ol;

5-[5-(4-Cloro-phenyl)-7-cyclopropyl-pyrazolo[1,5-a]pyrimidin-3-ylethynyl]-pyridine-3-sulfonic acid amide;

5-[5-(4-Cloro-phenyl)-7-cyclopropyl-pyrazolo[1,5-a]pyrimidin-3-ylethynyl]-pyridine-3-sulfonic acid (2-hydroxy-1,1-dimethyl-ethyl)-amide;

5-[5-(4-Chloro-phenyl)-7-cyclopropyl-pyrazolo[1,5-a]pyrimidin-3-ylethynyl]-pyridine-3-sulfonic acid (2-hydroxy-1-hydroxymethyl-1-methyl-ethyl)-amide;

5-[5-(4-Chloro-phenyl)-pyrazolo[1,5-a]pyrimidin-3-ylethynyl]-pyridine-3-sulfonic acid amide;

5-[5-(4-Chloro-phenyl)-pyrazolo[1,5-a]pyrimidin-3-ylethynyl]-pyridine-3-sulfonic acid (2-hydroxy-1,1-dimethyl-ethyl)-amide;

5-[7-Cyclopropyl-5-(4-trifluoromethyl-phenyl)-pyrazolo[1,5-a]pyrimidin-3-ylethynyl]-pyridine-3-sulfonic acid (2-hydroxy-1,1-dimethyl-ethyl)-amide;

5-[7-Cyclopropyl-5-(4-trifluoromethyl-phenyl)-pyrazolo[1,5-a]pyrimidin-3-ylethynyl]-pyridine-3-sulfonic acid (2-hydroxy-1-hydroxymethyl-1-methyl-ethyl)-amide;

5-[5-(3,4-Dichloro-phenyl)-7-trifluoromethyl-pyrazolo[1,5-a]pyrimidin-3-ylethynyl]-pyridine-3-sulfonic acid (2-hydroxy-1-hydroxymethyl-1-methyl-ethyl)-amide;

3-Pyridin-3-ylethynyl-7-trifluoromethyl-5-(3-trifluoromethyl-phenyl)-pyrazolo[1,5-a]pyrimidine;

3-Methyl-5-[7-trifluoromethyl-5-(4-trifluoromethyl-phenyl)-pyrazolo[1,5-a]pyrimidin-3-ylethynyl]-pyridin-2-ylamine;

5-[7-Difluoromethyl-5-(4-trifluoromethyl-phenyl)-pyrazolo[1,5-a]pyrimidin-3-ylethynyl]-3-methyl-pyridin-2-ylamine;

5-[7-Difluoromethyl-5-(4-trifluoromethyl-phenyl)-pyrazolo[1,5-a]pyrimidin-3-ylethynyl]-6-methyl-pyridin-2-ylamine;

3-(6-Fluoro-pyridin-3-ylethynyl)-7-trifluoromethyl-5-(4-trifluoromethyl-phenyl)-pyrazolo[1,5-a]pyrimidine;

5-[7-Difluoromethyl-5-(4-trifluoromethyl-phenyl)-pyrazolo[1,5-a]pyrimidin-3-ylethynyl]-pyridin-2-ylamine;

5-[5-(3-Ethoxy-4-trifluoromethyl-phenyl)-7-trifluoromethyl-pyrazolo[1,5-a]pyrimidin-3-ylethynyl]-pyridin-2-ylamine;

5-[7-Trifluoromethyl-5-(4-trifluoromethyl-phenyl)-pyrazolo[1,5-a]pyrimidin-3-ylethynyl]-pyridin-3-ylamine;

Methyl-{5-[7-trifluoromethyl-5-(4-trifluoromethyl-phenyl)-pyrazolo[1,5-a]pyrimidin-3-ylethynyl]-pyridin-2-yl}-amine;

2-{5-[7-Trifluoromethyl-5-(4-trifluoromethyl-phenyl)-pyrazolo[1,5-a]pyrimidin-3-ylethynyl]-pyridin-2-ylamino}-ethanol;

5-[7-Difluoromethyl-5-(4-trifluoromethyl-phenyl)-pyrazolo[1,5-a]pyrimidin-3-ylethynyl]-pyridine-2-carboxylic acid amide;

5-[7-Difluoromethyl-5-(3-ethoxy-phenyl)-pyrazolo[1,5-a]pyrimidin-3-ylethynyl]-pyridin-2-ylamine;

N-(Methylsulfonyl)-N-{5-[7-trifluoromethyl-5-(4-trifluoromethyl-phenyl)-pyrazolo[1,5-a]pyrimidin-3-ylethynyl]-pyridin-2-yl}-methanesulfonamide;

N-{5-[7-Trifluoromethyl-5-(4-trifluoromethyl-phenyl)-pyrazolo[1,5-a]pyrimidin-3-ylethynyl]-pyridin-2-yl}-methanesulfonamide;

2-Amino-5-[7-difluoromethyl-5-(4-trifluoromethyl-phenyl)-pyrazolo[1,5-a]pyrimidin-3-ylethynyl]-nicotinonitrile;

2-Amino-5-[7-trifluoromethyl-5-(4-trifluoromethyl-phenyl)-pyrazolo[1,5-a]pyrimidin-3-ylethynyl]-nicotinonitrile;

3-Trifluoromethyl-5-[7-trifluoromethyl-5-(4-trifluoromethyl-phenyl)-pyrazolo[1,5-a]pyrimidin-3-ylethynyl]-pyridin-2-ylamine;

5-[5-(4-Chloro-phenyl)-7-trifluoromethyl-pyrazolo[1,5-a]pyrimidin-3-ylethynyl]-3-trifluoromethyl-pyridin-2-ylamine;

N-{5-[7-Trifluoromethyl-5-(4-trifluoromethyl-phenyl)-pyrazolo[1,5-a]pyrimidin-3-ylethynyl]-pyridin-2-yl}-acetamide;

5-[7-Difluoromethyl-5-(3-trifluoromethyl-phenyl)-pyrazolo[1,5-a]pyrimidin-3-ylethynyl]-pyridin-2-ylamine;

5-[7-Trifluoromethyl-5-(3-trifluoromethyl-phenyl)-pyrazolo[1,5-a]pyrimidin-3-ylethynyl]-pyridin-2-ylamine;

5-[7-Trifluoromethyl-5-(4-trifluoromethyl-phenyl)-pyrazolo[1,5-a]pyrimidin-3-ylethynyl]-pyridine-2-carbonitrile;

5-[5-(3-Methyl-4-trifluoromethyl-phenyl)-7-trifluoromethyl-pyrazolo[1,5-a]pyrimidin-3-ylethynyl]-pyridin-2-ylamine;

5-[7-Cyclopropyl-5-(4-trifluoromethyl-phenyl)-pyrazolo[1,5-a]pyrimidin-3-ylethynyl]-pyridin-2-ylamine;

5-[5-(4-Chloro-phenyl)-7-cyclopropyl-pyrazolo[1,5-a]pyrimidin-3-ylethynyl]-pyridin-2-ylamine;
5-[5-(4-Chloro-phenyl)-7-methyl-pyrazolo[1,5-a]pyrimidin-3-ylethynyl]-pyridin-2-ylamine;
[3-(6-Amino-pyridin-3-ylethynyl)-5-(4-chloro-phenyl)-pyrazolo[1,5-a]pyrimidin-7-yl]-methanol;
5-[5-(4-Chloro-phenyl)-7-ethyl-pyrazolo[1,5-a]pyrimidin-3-ylethynyl]-pyridin-2-ylamine;
5-[5-(4-Trifluoromethyl-phenyl)-pyrazolo[1,5-a]pyrimidin-3-ylethynyl]-pyridin-2-ylamine; and
5-[5-(4-Chloro-phenyl)-7-trifluoromethyl-pyrazolo[1,5-a]pyrimidin-3-ylethynyl]-pyridin-2-ylamine.

In certain embodiments of the invention, the compounds of formula (Ia1) are compounds wherein A is pyridin-4-yl optionally substituted by one to four $R^a$, for example 3-(2-Methyl-pyridin-4-ylethynyl)-7-trifluoromethyl-5-(4-trifluoromethyl-phenyl)-pyrazolo[1,5-a]pyrimidine and 3-Pyridin-4-ylethynyl-7-trifluoromethyl-5-(4-trifluoromethyl-phenyl)-pyrazolo[1,5-a]pyrimidine.

In certain embodiments of the invention, the compounds of formula (Ia1) are compounds wherein A is thiazol-2-yl or thiazol-5-yl each of which is optionally substituted by one to four $R^a$, for example the following compounds:
2-[7-Trifluoromethyl-5-(4-trifluoromethyl-phenyl)-pyrazolo[1,5-a]pyrimidin-3-ylethynyl]-thiazole-5-sulfonic acid;
2-[7-Trifluoromethyl-5-(4-trifluoromethyl-phenyl)-pyrazolo[1,5-a]pyrimidin-3-ylethynyl]-thiazole-5-sulfonic acid (2-hydroxy-1,1-dimethyl-ethyl)-amide;
2-[7-Trifluoromethyl-5-(4-trifluoromethyl-phenyl)-pyrazolo[1,5-a]pyrimidin-3-ylethynyl]-thiazole-5-sulfonic acid amide;
2-[5-(3-Ethoxy-4-trifluoromethyl-phenyl)-7-trifluoromethyl-pyrazolo[1,5-a]pyrimidin-3-ylethynyl]-thiazole-5-sulfonic acid (2-hydroxy-1,1-dimethyl-ethyl)-amide;
4-Methyl-2-[7-trifluoromethyl-5-(4-trifluoromethyl-phenyl)-pyrazolo[1,5-a]pyrimidin-3-ylethynyl]-thiazole-5-sulfonic acid (2-hydroxy-1,1-dimethyl-ethyl)-amide;
2-[5-(4-Chloro-phenyl)-7-cyclopropyl-pyrazolo[1,5-a]pyrimidin-3-ylethynyl]-thiazole-5-sulfonic acid (2-hydroxy-1,1-dimethyl-ethyl)-amide;
2-[7-Cyclopropyl-5-(4-trifluoromethyl-phenyl)-pyrazolo[1,5-a]pyrimidin-3-ylethynyl]-thiazole-5-sulfonic acid (2-hydroxy-1,1-dimethyl-ethyl)-amide;
2-[5-(3,4-Dichloro-phenyl)-7-trifluoromethyl-pyrazolo[1,5-a]pyrimidin-3-ylethynyl]-thiazole-5-sulfonic acid (2-hydroxy-1,1-dimethyl-ethyl)-amide;
2-[5-(4-Chloro-3-methyl-phenyl)-7-trifluoromethyl-pyrazolo[1,5-a]pyrimidin-3-ylethynyl]-thiazole-5-sulfonic acid amide;
2-[7-Trifluoromethyl-5-(3-trifluoromethyl-phenyl)-pyrazolo[1,5-a]pyrimidin-3-ylethynyl]-thiazole-5-sulfonic acid amide;
2-[7-Trifluoromethyl-5-(3-trifluoromethyl-phenyl)-pyrazolo[1,5-a]pyrimidin-3-ylethynyl]-thiazole-5-sulfonic acid (2-hydroxy-1,1-dimethyl-ethyl)-amide; and
N-{5-[7-Trifluoromethyl-5-(4-trifluoromethyl-phenyl)-pyrazolo[1,5-a]pyrimidin-3-ylethynyl]-thiazol-2-yl}-acetamide.

In certain embodiments of the invention, the compounds of formula (Ia1) are those compounds wherein A is thiophen-2-yl optionally substituted by one to four $R^a$, for example the following compounds:
5-[5-(4-Chloro-phenyl)-7-cyclopropyl-pyrazolo[1,5-a]pyrimidin-3-ylethynyl]-thiophene-2-sulfonic acid amide;
5-[7-Cyclopropyl-5-(4-trifluoromethyl-phenyl)-pyrazolo[1,5-a]pyrimidin-3-ylethynyl]-thiophene-2-sulfonic acid amide;
5-[7-Cyclopropyl-5-(3,4-dichloro-phenyl)-pyrazolo[1,5-a]pyrimidin-3-ylethynyl]-thiophene-2-sulfonic acid amide;
5-[5-(3,4-Dichloro-phenyl)-7-trifluoromethyl-pyrazolo[1,5-a]pyrimidin-3-ylethynyl]-thiophene-2-sulfonic acid amide;
5-[5-(4-Chloro-phenyl)-7-trifluoromethyl-pyrazolo[1,5-a]pyrimidin-3-ylethynyl]-thiophene-2-sulfonic acid amide;
5-[7-Trifluoromethyl-5-(4-trifluoromethyl-phenyl)-pyrazolo[1,5-a]pyrimidin-3-ylethynyl]-thiophene-2-sulfonic acid amide;
5-[7-Trifluoromethyl-5-(4-trifluoromethyl-phenyl)-pyrazolo[1,5-a]pyrimidin-3-ylethynyl]-thiophene-2-sulfonic acid tert-butylamide;
5-[5-(4-Chloro-3-methyl-phenyl)-7-trifluoromethyl-pyrazolo[1,5-a]pyrimidin-3-ylethynyl]-thiophene-2-sulfonic acid amide;
5-[5-(4-Chloro-3-methyl-phenyl)-7-trifluoromethyl-pyrazolo[1,5-a]pyrimidin-3-ylethynyl]-thiophene-2-sulfonic acid tert-butylamide;
5-[7-Trifluoromethyl-5-(3-trifluoromethyl-phenyl)-pyrazolo[1,5-a]pyrimidin-3-ylethynyl]-thiophene-2-sulfonic acid tert-butylamide;
5-[7-Trifluoromethyl-5-(3-trifluoromethyl-phenyl)-pyrazolo[1,5-a]pyrimidin-3-ylethynyl]-thiophene-2-sulfonic acid amide;
5-[7-Trifluoromethyl-5-(4-trifluoromethyl-phenyl)-pyrazolo[1,5-a]pyrimidin-3-ylethynyl]-thiophene-2-sulfonic acid (2-hydroxy-1,1-dimethyl-ethyl)-amide;
5-[7-Methyl-5-(4-trifluoromethyl-phenyl)-pyrazolo[1,5-a]pyrimidin-3-ylethynyl]-thiophene-2-sulfonic acid amide;
5-[5-(4-Chloro-phenyl)-7-(1-hydroxy-1-methyl-ethyl)-pyrazolo[1,5-a]pyrimidin-3-ylethynyl]-thiophene-2-sulfonic acid amide;
5-[5-(4-Chloro-phenyl)-7-hydroxymethyl-pyrazolo[1,5-a]pyrimidin-3-ylethynyl]-thiophene-2-sulfonic acid amide;
5-[7-Trifluoromethyl-5-(4-trifluoromethyl-phenyl)-pyrazolo[1,5-a]pyrimidin-3-ylethynyl]-thiophene-2-sulfonic acid (2-morpholin-4-yl-ethyl)-amide;
5-[7-Trifluoromethyl-5-(4-trifluoromethyl-phenyl)-pyrazolo[1,5-a]pyrimidin-3-ylethynyl]-thiophene-2-sulfonic acid (2-dimethylamino-ethyl)-amide;
5-[7-Difluoromethyl-5-(3-trifluoromethyl-phenyl)-pyrazolo[1,5-a]pyrimidin-3-ylethynyl]-thiophene-2-sulfonic acid amide;
5-[7-Difluoromethyl-5-(3-trifluoromethyl-phenyl)-pyrazolo[1,5-a]pyrimidin-3-ylethynyl]-thiophene-2-sulfonic acid tert-butylamide;
5-[7-Trifluoromethyl-5-(4-trifluoromethyl-phenyl)-pyrazolo[1,5-a]pyrimidin-3-ylethynyl]-thiophene-2-sulfonic acid bis-(2-hydroxy-ethyl)-amide;
5-[7-Trifluoromethyl-5-(4-trifluoromethyl-phenyl)-pyrazolo[1,5-a]pyrimidin-3-ylethynyl]-thiophene-2-sulfonic acid (2-hydroxy-1-hydroxymethyl-ethyl)-amide;
5-[7-Difluoromethyl-5-(4-trifluoromethyl-phenyl)-pyrazolo[1,5-a]pyrimidin-3-ylethynyl]-thiophene-2-sulfonic acid amide;
5-[7-Difluoromethyl-5-(4-trifluoromethyl-phenyl)-pyrazolo[1,5-a]pyrimidin-3-ylethynyl]-thiophene-2-sulfonic acid tert-butylamide;
5-[7-Difluoromethyl-5-(4-trifluoromethyl-phenyl)-pyrazolo[1,5-a]pyrimidin-3-ylethynyl]-thiophene-2-sulfonic acid (2-hydroxy-1,1-dimethyl-ethyl)-amide;

5-[7-Difluoromethyl-5-(3-trifluoromethyl-phenyl)-pyrazolo[1,5-a]pyrimidin-3-ylethynyl]-thiophene-2-sulfonic acid (2-hydroxy-1,1-dimethyl-ethyl)-amide;
5-[5-(4-Chloro-3-methyl-phenyl)-7-difluoromethyl-pyrazolo[1,5-a]pyrimidin-3-ylethynyl]-thiophene-2-sulfonic acid tert-butylamide;
5-[5-(4-Chloro-3-methyl-phenyl)-7-difluoromethyl-pyrazolo[1,5-a]pyrimidin-3-ylethynyl]-thiophene-2-sulfonic acid amide;
5-[5-(4-Chloro-3-methyl-phenyl)-7-difluoromethyl-pyrazolo[1,5-a]pyrimidin-3-ylethynyl]-thiophene-2-sulfonic acid (2-hydroxy-1,1-dimethyl-ethyl)-amide;
5-[7-Difluoromethyl-5-(3-ethoxy-phenyl)-pyrazolo[1,5-a]pyrimidin-3-ylethynyl]-thiophene-2-sulfonic acid amide;
7-Difluoromethyl-3-[5-(4-methyl-piperazine-1-sulfonyl)-thiophen-2-ylethynyl]-5-(3-trifluoromethyl-phenyl)-pyrazolo[1,5-a]pyrimidine;
3-[5-(4-Methyl-piperazine-1-sulfonyl)-thiophen-2-ylethynyl]-7-trifluoromethyl-5-(3-trifluoromethyl-phenyl)-pyrazolo[1,5-a]pyrimidine;
5-[7-Difluoromethyl-5-(3-trifluoromethyl-phenyl)-pyrazolo[1,5-a]pyrimidin-3-ylethynyl]-thiophene-2-sulfonic acid (2-dimethylamino-ethyl)-amide;
5-[7-Trifluoromethyl-5-(3-trifluoromethyl-phenyl)-pyrazolo[1,5-a]pyrimidin-3-ylethynyl]-thiophene-2-sulfonic acid (2-dimethylamino-ethyl)-amide;
7-Difluoromethyl-3-[5-(4-methyl-piperazine-1-sulfonyl)-thiophen-2-ylethynyl]-5-(4-trifluoromethyl-phenyl)-pyrazolo[1,5-a]pyrimidine;
5-[7-Difluoromethyl-5-(4-trifluoromethyl-phenyl)-pyrazolo[1,5-a]pyrimidin-3-ylethynyl]-thiophene-2-sulfonic acid (2-dimethylamino-ethyl)-amide;
5-(4-Chloro-3-methyl-phenyl)-7-difluoromethyl-3-[5-(4-methyl-piperazine-1-sulfonyl)-thiophen-2-ylethynyl]-pyrazolo[1,5-a]pyrimidine;
5-[5-(4-Chloro-3-methyl-phenyl)-7-difluoromethyl-pyrazolo[1,5-a]pyrimidin-3-ylethynyl]-thiophene-2-sulfonic acid (2-dimethylamino-ethyl)-amide;
5-[5-(4-Chloro-3-methyl-phenyl)-7-trifluoromethyl-pyrazolo[1,5-a]pyrimidin-3-ylethynyl]-thiophene-2-sulfonic acid (2-dimethylamino-ethyl)-amide;
5-(4-Chloro-3-methyl-phenyl)-3-[5-(4-methyl-piperazine-1-sulfonyl)-thiophen-2-ylethynyl]-7-trifluoromethyl-pyrazolo[1,5-a]pyrimidine;
3-[5-(Piperazine-1-sulfonyl)-thiophen-2-ylethynyl]-7-trifluoromethyl-5-(4-trifluoromethyl-phenyl)-pyrazolo[1,5-a]pyrimidine;
3-[5-(Piperazine-1-sulfonyl)-thiophen-2-ylethynyl]-7-trifluoromethyl-5-(3-trifluoromethyl-phenyl)-pyrazolo[1,5-a]pyrimidine;
5-[7-Trifluoromethyl-5-(3-trifluoromethyl-phenyl)-pyrazolo[1,5-a]pyrimidin-3-ylethynyl]-thiophene-2-sulfonic acid (2-amino-ethyl)-amide;
5-[7-Trifluoromethyl-5-(4-trifluoromethyl-phenyl)-pyrazolo[1,5-a]pyrimidin-3-ylethynyl]-thiophene-2-sulfonic acid (2-amino-ethyl)-amide;
5-[7-Difluoromethyl-5-(3-trifluoromethyl-phenyl)-pyrazolo[1,5-a]pyrimidin-3-ylethynyl]-thiophene-2-sulfonic acid bis-(2-hydroxy-ethyl)-amide;
5-[7-Difluoromethyl-5-(3-trifluoromethyl-phenyl)-pyrazolo[1,5-a]pyrimidin-3-ylethynyl]-thiophene-2-sulfonic acid (2-hydroxy-1-hydroxymethyl-ethyl)-amide;
5-[7-Trifluoromethyl-5-(3-trifluoromethyl-phenyl)-pyrazolo[1,5-a]pyrimidin-3-ylethynyl]-thiophene-2-sulfonic acid bis-(2-hydroxy-ethyl)-amide;
5-[7-Difluoromethyl-5-(4-trifluoromethyl-phenyl)-pyrazolo[1,5-a]pyrimidin-3-ylethynyl]-thiophene-2-sulfonic acid bis-(2-hydroxy-ethyl)-amide;
5-[7-Difluoromethyl-5-(4-trifluoromethyl-phenyl)-pyrazolo[1,5-a]pyrimidin-3-ylethynyl]-thiophene-2-sulfonic acid (2-hydroxy-1-hydroxymethyl-ethyl)-amide;
5-[7-Trifluoromethyl-5-(3-trifluoromethyl-phenyl)-pyrazolo[1,5-a]pyrimidin-3-ylethynyl]-thiophene-2-sulfonic acid (2-hydroxy-1-hydroxymethyl-ethyl)-amide;
5-[7-Trifluoromethyl-5-(4-trifluoromethyl-phenyl)-pyrazolo[1,5-a]pyrimidin-3-ylethynyl]-thiophene-2-sulfonic acid (pyridin-4-ylmethyl)-amide;
5-[7-Trifluoromethyl-5-(4-trifluoromethyl-phenyl)-pyrazolo[1,5-a]pyrimidin-3-ylethynyl]-thiophene-2-sulfonic acid (pyridin-3-ylmethyl)-amide;
5-[4-Difluoromethyl-2-(4-trifluoromethyl-phenyl)-imidazo[1,5-a]pyrimidin-8-ylethynyl]-2,4-difluoro-benzenesulfonamide;
5-[7-Difluoromethyl-5-(4-trifluoromethyl-phenyl)-pyrazolo[1,5-a]pyrimidin-3-ylethynyl]-thiophene-2-sulfonic acid (pyridin-3-ylmethyl)-amide;
5-[7-Trifluoromethyl-5-(4-trifluoromethyl-phenyl)-pyrazolo[1,5-a]pyrimidin-3-ylethynyl]-thiophene-2-sulfonic acid pyridin-3-ylamide;
5-[7-Trifluoromethyl-5-(4-trifluoromethyl-phenyl)-pyrazolo[1,5-a]pyrimidin-3-ylethynyl]-thiophene-2-sulfonic acid pyridin-4-ylamide;
5-[7-Difluoromethyl-5-(4-trifluoromethyl-phenyl)-pyrazolo[1,5-a]pyrimidin-3-ylethynyl]-thiophene-2-sulfonic acid pyridin-3-ylamide;
5-[7-Difluoromethyl-5-(4-trifluoromethyl-phenyl)-pyrazolo[1,5-a]pyrimidin-3-ylethynyl]-thiophene-2-sulfonic acid pyridin-4-ylamide;
5-[7-Trifluoromethyl-5-(4-trifluoromethyl-phenyl)-pyrazolo[1,5-a]pyrimidin-3-ylethynyl]-thiophene-2-sulfonic acid (2,6-dimethyl-pyridin-4-ylmethyl)-amide;
5-[5-(4-Chloro-phenyl)-7-methyl-pyrazolo[1,5-a]pyrimidin-3-ylethynyl]-thiophene-2-sulfonic acid amide;
5-[5-(4-Chloro-phenyl)-pyrazolo[1,5-a]pyrimidin-3-ylethynyl]-thiophene-2-sulfonic acid amide;
5-[7-tert.-Butyl-5-(4-chloro-phenyl)-pyrazolo[1,5-a]pyrimidin-3-ylethynyl]-thiophene-2-sulfonic acid amide;
5-[7-Methyl-5-(4-trifluoromethyl-phenyl)-pyrazolo[1,5-a]pyrimidin-3-ylethynyl]-thiophene-2-sulfonic acid (2-hydroxy-1-hydroxymethyl-ethyl)-amide;
5-[7-Methyl-5-(4-trifluoromethyl-phenyl)-pyrazolo[1,5-a]pyrimidin-3-ylethynyl]-thiophene-2-sulfonic acid (2-hydroxy-ethyl)-amide;
5-[5-(4-Trifluoromethyl-phenyl)-pyrazolo[1,5-a]pyrimidin-3-ylethynyl]-thiophene-2-sulfonic acid amide; and
5-[5-(4-Chloro-phenyl)-7-cyclopropyl-pyrazolo[1,5-a]pyrimidin-3-ylethynyl]-thiophene-2-sulfonic acid (2-pyridin-4-yl-ethyl)-amide.

In certain embodiments of the invention, the compounds of formula (Ia1) are those compounds wherein A is pyrimidin-4-yl or pyrimidin-5-yl each of which is optionally substituted by one to four $R^a$, for example:

3-Pyrimidin-5-ylethynyl-7-trifluoromethyl-5-(4-trifluoromethyl-phenyl)-pyrazolo[1,5-a]pyrimidine;
3-(2-Chloro-pyrimidin-5-ylethynyl)-7-trifluoromethyl-5-(4-trifluoromethyl-phenyl)-pyrazolo[1,5-a]pyrimidine;
3-(2-Chloro-pyrimidin-4-ylethynyl)-7-trifluoromethyl-5-(4-trifluoromethyl-phenyl)-pyrazolo[1,5-a]pyrimidine;
5-[7-Trifluoromethyl-5-(4-trifluoromethyl-phenyl)-pyrazolo[1,5-a]pyrimidin-3-ylethynyl]-pyrimidin-2-ylamine;
5-[7-Difluoromethyl-5-(4-trifluoromethyl-phenyl)-pyrazolo[1,5-a]pyrimidin-3-ylethynyl]-pyrimidin-2-ylamine;

N-Acetyl-N-{5-[7-trifluoromethyl-5-(4-trifluoromethyl-phenyl)-pyrazolo[1,5-a]pyrimidin-3-ylethynyl]-pyrimidin-2-yl}-acetamide;

N-{5-[7-Trifluoromethyl-5-(4-trifluoromethyl-phenyl)-pyrazolo[1,5-a]pyrimidin-3-ylethynyl]-pyrimidin-2-yl}-acetamide;

5-[5-(3-Methyl-4-trifluoromethyl-phenyl)-7-trifluoromethyl-pyrazolo[1,5-a]pyrimidin-3-ylethynyl]-pyrimidin-2-ylamine;

5-[5-(4-Chloro-phenyl)-7-cyclopropyl-pyrazolo[1,5-a]pyrimidin-3-ylethynyl]-pyrimidin-2-ylamine;

5-[7-Cyclopropyl-5-(4-trifluoromethyl-phenyl)-pyrazolo[1,5-a]pyrimidin-3-ylethynyl]-pyrimidin-2-ylamine;

5-[7-Methyl-5-(4-trifluoromethyl-phenyl)-pyrazolo[1,5-a]pyrimidin-3-ylethynyl]-pyrimidin-2-ylamine;

5-[5-(4-Chloro-phenyl)-7-methyl-pyrazolo[1,5-a]pyrimidin-3-ylethynyl]-pyrimidin-2-ylamine; and 5-[5-(4-Chloro-phenyl)-7-trifluoromethyl-pyrazolo[1,5-a]pyrimidin-3-ylethynyl]-pyrimidin-2-ylamine.

In certain embodiments of the invention, the compounds of formula (Ia 1) are those compounds wherein A is pyridazin-3-yl optionally substituted by one to four $R^a$, for example:

6-[7-Trifluoromethyl-5-(4-trifluoromethyl-phenyl)-pyrazolo[1,5-a]pyrimidin-3-ylethynyl]-pyridazin-3-ylamine; and 6-[5-(4-Chloro-phenyl)-7-trifluoromethyl-pyrazolo[1,5-a]pyrimidin-3-ylethynyl]-pyridazin-3-ylamine.

In certain embodiments of the invention, the compounds of formula (Ia1) are those compounds wherein A is pyrazin-2-yl optionally substituted by one to four $R^a$, for example:

5-[7-Trifluoromethyl-5-(4-trifluoromethyl-phenyl)-pyrazolo[1,5-a]pyrimidin-3-ylethynyl]-pyrazin-2-ylamine; and 5-[7-Difluoromethyl-5-(4-trifluoromethyl-phenyl)-pyrazolo[1,5-a]pyrimidin-3-ylethynyl]-pyrazin-2-ylamine.

Also encompassed by the compounds of formula (I) according to the invention are those compounds of formula (Ia2):

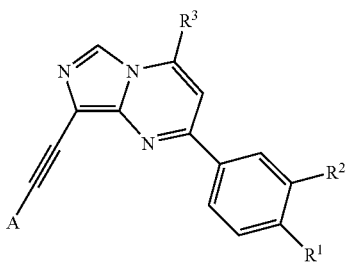

(Ia2)

wherein $R^1$, $R^2$, $R^3$ and A are as defined hereinabove.

In certain embodiments of the invention, the compounds of formula (Ia2) are those compounds wherein A is phenyl optionally substituted by one to four $R^a$, for example:

2,4-Difluoro-5-[4-trifluoromethyl-2-(4-trifluoromethyl-phenyl)-imidazo[1,5-a]pyrimidin-8-ylethynyl]-benzenesulfonamide;

4-[4-Trifluoromethyl-2-(4-trifluoromethyl-phenyl)-imidazo[1,5-a]pyrimidin-8-ylethynyl]-benzenesulfonamide;

5-[4-Difluoromethyl-2-(4-trifluoromethyl-phenyl)-imidazo[1,5-a]pyrimidin-8-ylethynyl]-thiophene-2-sulfonic acid amide; and 5-[7-Difluoromethyl-5-(4-trifluoromethyl-phenyl)-pyrazolo[1,5-a]pyrimidin-3-ylethynyl]-thiophene-2-sulfonic acid (pyridin-4-ylmethyl)-amide.

In certain embodiments of the invention, the compounds of formula (Ia2) are compounds wherein A is thiophen-2-yl optionally substituted by one to four $R^a$, for example:

5-[4-Trifluoromethyl-2-(4-trifluoromethyl-phenyl)-imidazo[1,5-a]pyrimidin-8-ylethynyl]-thiophene-2-sulfonic acid amide;

5-[4-Trifluoromethyl-2-(4-trifluoromethyl-phenyl)-imidazo[1,5-a]pyrimidin-8-ylethynyl]-thiophene-2-sulfonic acid (2-dimethylamino-ethyl)-amide; and 4-[4-Difluoromethyl-2-(4-trifluoromethyl-phenyl)-imidazo[1,5-a]pyrimidin-8-ylethynyl]-benzenesulfonamide.

In certain embodiments of the invention, the compounds of formula (Ia2) are compounds wherein A is pyridin-3-yl optionally substituted by one to four $R^a$, for example:

8-Pyridin-3-ylethynyl-4-trifluoromethyl-2-(4-trifluoromethyl-phenyl)-imidazo[1,5-a]pyrimidine; and 5-[4-Trifluoromethyl-2-(4-trifluoromethyl-phenyl)-imidazo[1,5-a]pyrimidin-8-ylethynyl]-pyridin-2-ylamine.

In certain embodiments of the invention, the compounds of formula (Ia2) are compounds wherein A is pyrimidin-5-yl optionally substituted by one to four $R^a$, for example:

5-[4-Trifluoromethyl-2-(4-trifluoromethyl-phenyl)-imidazo[1,5-a]pyrimidin-8-ylethynyl]-pyrimidin-2-ylamine.

Also encompassed by the compounds of formula (I) according to the invention are those compounds of formula (Ib):

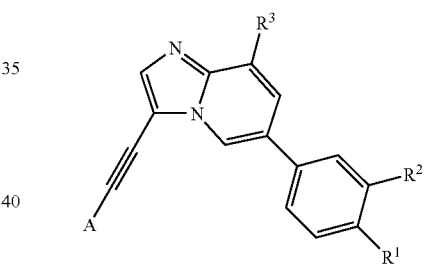

(Ib)

wherein $R^1$, $R^2$, $R^3$ and A are as defined hereinabove.

In certain embodiments of the invention, the compounds of formula (Ib) are those compounds wherein A is phenyl optionally substituted by one to four $R^a$, for example:

4-[8-Trifluoromethyl-6-(4-trifluoromethyl-phenyl)-imidazo[1,2-a]pyridin-3-ylethynyl]-benzenesulfonamide;

2,4-Difluoro-5-[8-trifluoromethyl-6-(4-trifluoromethyl-phenyl)-imidazo[1,2-a]pyridin-3-ylethynyl]-benzenesulfonamide;

3-[8-Trifluoromethyl-6-(4-trifluoromethyl-phenyl)-imidazo[1,2-a]pyridin-3-ylethynyl]-benzenesulfonamide;

1-{4-[8-Trifluoromethyl-6-(4-trifluoromethyl-phenyl)-imidazo[1,2-a]pyridin-3-ylethynyl]-phenyl}-ethanol; and 4-[8-Trifluoromethyl-6-(4-trifluoromethyl-phenyl)-imidazo[1,2-a]pyridin-3-ylethynyl]-benzamide.

In certain embodiments of the invention, the compounds of formula (Ib) are those compounds wherein A is pyridine-3-yl optionally substituted by one to four $R^a$, for example:

3-Pyridin-3-ylethynyl-8-trifluoromethyl-6-(4-trifluoromethyl-phenyl)-imidazo[1,2-a]pyridine;

5-[8-Trifluoromethyl-6-(4-trifluoromethyl-phenyl)-imidazo[1,2-a]pyridin-3-ylethynyl]-pyridin-2-ylamine;

5-[8-Methyl-6-(4-trifluoromethyl-phenyl)-imidazo[1,2-a]pyridin-3-ylethynyl]-pyridin-2-ylamine;

5-[6-(4-Chloro-phenyl)-8-methyl-imidazo[1,2-a]pyridin-3-ylethynyl]-pyridin-2-ylamine;

3-(6-Amino-pyridin-3-ylethynyl)-6-(4-trifluoromethyl-phenyl)-imidazo[1,2-a]pyridine-8-carbonitrile;

5-[8-Methyl-6-(4-trifluoromethyl-phenyl)-imidazo[1,2-a]pyridin-3-ylethynyl]-pyridine-3-sulfonic acid (2-hydroxy-1,1-dimethyl-ethyl)-amide;

5-[8-Methyl-6-(4-trifluoromethyl-phenyl)-imidazo[1,2-a]pyridin-3-ylethynyl]-pyridine-3-sulfonic acid amide;

5-[6-(4-Chloro-phenyl)-8-methyl-imidazo[1,2-a]pyridin-3-ylethynyl]-pyridine-3-sulfonic acid (2-hydroxy-1,1-dimethyl-ethyl)-amide;

5-[6-(4-Chloro-phenyl)-8-methyl-imidazo[1,2-a]pyridin-3-ylethynyl]-pyridine-3-sulfonic acid amide;

5-[6-(4-Chloro-phenyl)-8-cyclopropyl-imidazo[1,2-a]pyridin-3-ylethynyl]-pyridin-2-ylamine;

5-[6-(4-Trifluoromethyl-phenyl)-imidazo[1,2-a]pyridin-3-ylethynyl]-pyridin-2-ylamine;

5-[8-Fluoro-6-(4-trifluoromethyl-phenyl)-imidazo[1,2-a]pyridin-3-ylethynyl]-pyridin-2-ylamine; and 5-[6-(4-Chloro-phenyl)-8-fluoro-imidazo[1,2-a]pyridin-3-ylethynyl]-pyridin-2-ylamine.

In certain embodiments of the invention, the compounds of formula (Ib) are those compounds wherein A is thiophen-2-yl optionally substituted by one to four $R^a$, for example:

5-[8-Trifluoromethyl-6-(4-trifluoromethyl-phenyl)-imidazo[1,2-a]pyridin-3-ylethynyl]-thiophene-2-sulfonic acid amide;

5-[6-(4-Chloro-phenyl)-8-methyl-imidazo[1,2-a]pyridin-3-ylethynyl]-thiophene-2-sulfonic acid amide;

5-[8-Methyl-6-(4-trifluoromethyl-phenyl)-imidazo[1,2-a]pyridin-3-ylethynyl]-thiophene-2-sulfonic acid amide;

5-[8-Cyano-6-(4-trifluoromethyl-phenyl)-imidazo[1,2-a]pyridin-3-ylethynyl]-thiophene-2-sulfonic acid amide;

5-[6-(4-Trifluoromethyl-phenyl)-imidazo[1,2-a]pyridin-3-ylethynyl]-thiophene-2-sulfonic acid amide; and 5-[8-Cyclopropyl-6-(4-trifluoromethyl-phenyl)-imidazo[1,2-a]pyridin-3-ylethynyl]-thiophene-2-sulfonic acid amide.

In certain embodiments of the invention, the compounds of formula (Ib) are those compounds wherein A is thiazol-2-yl optionally substituted by one to four $R^a$, for example:

2-[8-Trifluoromethyl-6-(4-trifluoromethyl-phenyl)-imidazo[1,2-a]pyridin-3-ylethynyl]-thiazole-5-sulfonic acid (2-hydroxy-1,1-dimethyl-ethyl)-amide.

In certain embodiments of the invention, the compounds of formula (Ib) are those compounds wherein A is pyrimidin-5-yl optionally substituted by one to four $R^a$, for example:

5-[8-Methyl-6-(4-trifluoromethyl-phenyl)-imidazo[1,2-a]pyridin-3-ylethynyl]-pyrimidin-2-ylamine;

5-[6-(4-Chloro-phenyl)-8-methyl-imidazo[1,2-a]pyridin-3-ylethynyl]-pyrimidin-2-ylamine;

3-(2-Amino-pyrimidin-5-ylethynyl)-6-(4-trifluoromethyl-phenyl)-imidazo[1,2-a]pyridine-8-carbonitrile;

5-[6-(4-Trifluoromethyl-phenyl)-imidazo[1,2-a]pyridin-3-ylethynyl]-pyrimidin-2-ylamine;

5-[8-Fluoro-6-(4-trifluoromethyl-phenyl)-imidazo[1,2-a]pyridin-3-ylethynyl]-pyrimidin-2-ylamine; and 5-[6-(4-Chloro-phenyl)-8-fluoro-imidazo[1,2-a]pyridin-3-ylethynyl]-pyrimidin-2-ylamine.

Also encompassed by the compounds of formula (I) according to the invention are these compounds of formula (Ic):

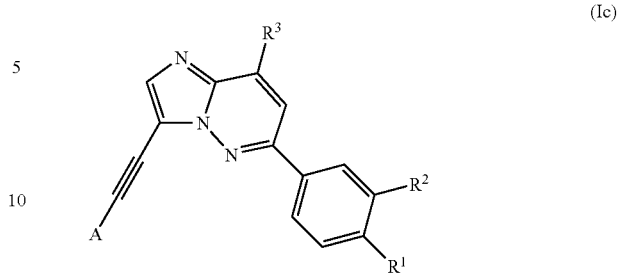

wherein $R^1$, $R^2$, $R^3$ and A are as defined hereinabove.

In certain embodiments of the invention, the compounds of formula (Ic) are those compounds wherein A is pyridin-3-yl optionally substituted by one to four $R^a$, for example:

5-[8-Trifluoromethyl-6-(4-trifluoromethyl-phenyl)-imidazo[1,2-b]pyridazin-3-ylethynyl]-pyridin-2-ylamine.

In certain embodiments of the invention, the compounds of formula (Ic) are those compounds wherein A is thiophen-2-yl optionally substituted by one to four $R^a$, for example:

5-[8-Trifluoromethyl-6-(4-trifluoromethyl-phenyl)-imidazo[1,2-b]pyridazin-3-ylethynyl]-thiophene-2-sulfonic acid amide.

In certain embodiments of the invention, the compounds of formula (Ic) are those compounds wherein A is pyrimidin-5-yl optionally substituted by one to four $R^a$, for example:

5-[8-Trifluoromethyl-6-(4-trifluoromethyl-phenyl)-imidazo[1,2-b]pyridazin-3-ylethynyl]-pyrimidin-2-ylamine.

Also encompassed by the compounds of formula (I) according to the invention are the compounds of formula (Id):

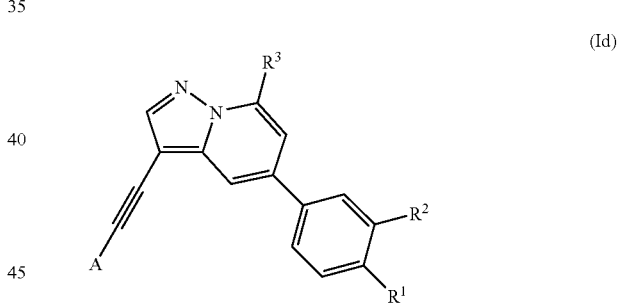

wherein $R^1$, $R^2$, $R^3$ and A are as defined hereinabove.

In certain embodiments of the invention, the compounds of formula (Id) are those compounds wherein A is pyridin-3-yl optionally substituted by one to four $R^a$, for example:

5-[7-Cyclopropyl-5-(4-trifluoromethyl-phenyl)-pyrazolo[1,5-a]pyridin-3-ylethynyl]-pyridin-2-ylamine; and 5-[7-Trifluoromethyl-5-(4-trifluoromethyl-phenyl)-pyrazolo[1,5-a]pyridin-3-ylethynyl]-pyridin-2-ylamine.

The pharmaceutically acceptable addition salts of the compounds of the invention can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid, citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formulae I, Ia, Ia1, Ib and Ic.

The invention also encompasses a process for the preparation of the compounds of formula (Ia1) according to the invention, said process comprising reacting a compound of formula (VIIIb):

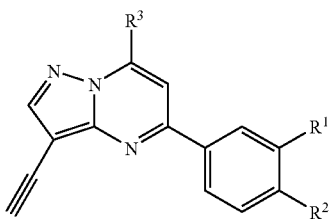
(VIIIb)

with a compound of formula (XV)

(XV)

wherein,
R$^1$, R$^2$, R$^3$ and A are as defined hereinabove and Z is either bromide, iodide or trifluoromethylsulfonate;

to obtain the compound of formula (Ia1), and if desired converting the compound of formula (Ia1) into its pharmaceutically acceptable addition salt.

The invention further encompasses an alternative process for the preparation of compounds of formula (Ia1), said process comprising reacting a compound of formula (VI):

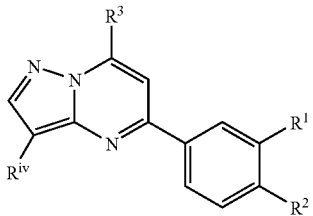
(VI)

with a compound of formula (XVI)

(XVI)

wherein,
R$^1$, R$^2$, R$^3$ and A are as defined hereinabove,
R$^{iv}$ is I or Br;

to obtain the compound of formula (Ia1), and if desired converting the compound of formula (Ia1) into its pharmaceutically acceptable addition salt.

The invention further encompasses a process for the preparation of compounds of formula (Ia2) according to the invention, said process comprising reacting a compound of formula (XXXIV)

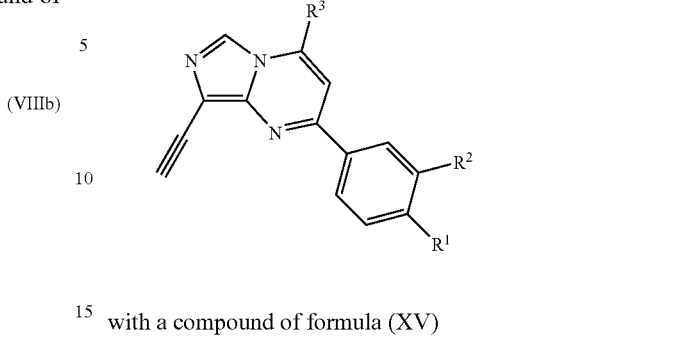
(XXXIV)

with a compound of formula (XV)

(XV)

wherein,
R$^1$, R$^2$, R$^3$ and A are as defined hereinabove and Z is either bromide, iodide or trifluoromethylsulfonate;

to obtain the compound of formula (Ia2), and if desired converting the compound of formula (Ia2) into its pharmaceutically acceptable addition salt.

The invention still further encompasses a process for the preparation of compounds of formula (Ib) according to the invention, said process comprising reacting a compound of formula (XXVI)

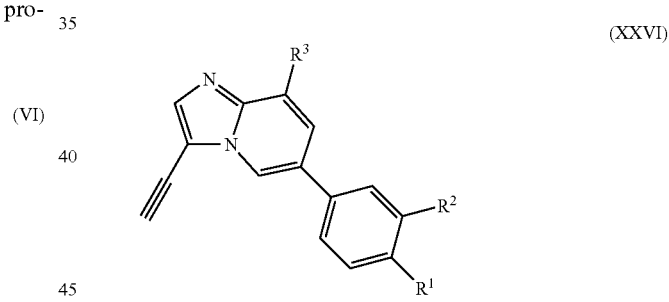
(XXVI)

with a compound of formula (XV)

(XV)

wherein,
R$^1$, R$^2$, R$^3$ and A are as defined hereinabove and Z is either bromide, iodide or trifluoromethylsulfonate;

to obtain the compound of formula (Ib), and if desired converting the compound of formula (Ib) into its pharmaceutically acceptable addition salt.

The compounds of formula VIIIb are those compounds of formula VIII wherein R$^{iii}$ is H. The syntheses of the intermediate compounds of formula VIIIb above, wherein R$^3$ is CF$_3$ or CHF$_2$ and R$^1$, R$^2$ are as defined hereinabove may be carried out in accordance with the following general procedure Ia which procedure is outlined below in scheme 1a. The intermediate compounds of formula VIIIb above wherein $R^1$, $R^2$, $R^3$ are as defined hereinabove, but $R^3$ is different from $CF_3$ or $CHF_2$, can be prepared according to step 3.1a of the general procedure Ia from an intermediate compound VIc wherein $R^2$, $R^3$ are as defined hereinabove, but $R^3$ is different from $CF_3$ or $CHF_2$. The compounds of formula VIc are those compounds of formula VI wherein $R^{ii}$ is I. The syntheses of such intermediate compounds VIc may be carried out in accordance with the following general procedure Ib which procedure is outlined below in scheme 1b.

As for the reaction of the compound of formula (VIIIb) with the compound of formula (XV), it may be for example carried out in accordance with the following general procedure II which procedure is outlined below in scheme 2. In the schemes 1a, 1b, and 2, $R^1$, $R^2$, $R^3$, A, are as defined hereinabove. Procedures Ia,b and II are applicable for the preparation of all the compounds according to formula 1a1.

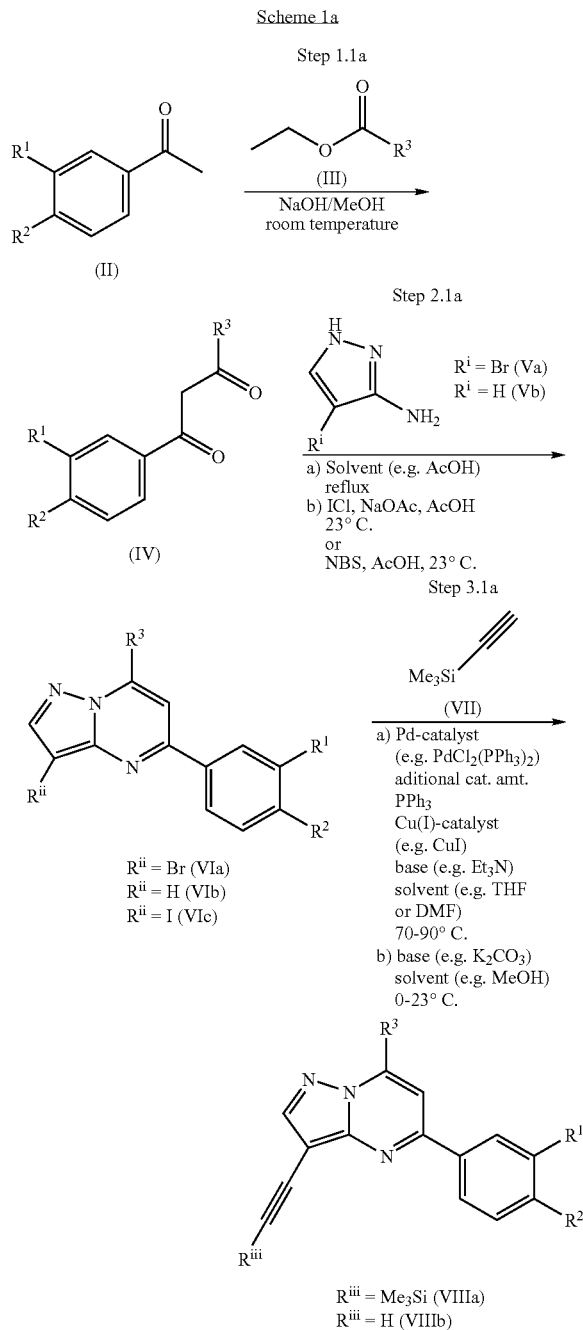

General Procedure Ia

Step 1.1a:

To a stirred solution of compound of formula (III) in an organic solvent (e.g. tert-butyl-methyl-ether) is added at room temperature a solution of sodium methoxide in methanol followed by a solution of compound of formula (II) in an organic solvent (e.g. tert-butyl-methyl-ether). The reaction mixture is stirred at room temperature for about 19 h, cooled, acidified and extracted (e.g. with diethyl ether). The combined organic layers are washed and dried (e.g. $MgSO_4$) and evaporated to give crude the compound of formula (IV) which can be used without further purification.

Step 2a.1a:

A stirred mixture of commercially available 3-amino-4-bromo-pyrazole (compound of formula (Va)) or commercially available 3-amino-pyrazole (compound of formula (Vb)) and compound of formula (IV) in an organic acid (e.g. acetic acid) is heated under reflux conditions for about 3 h. The reaction mixture is cooled to 23° C. and slowly diluted with water. The precipitate is collected by filtration to give the compounds of formula (VIa) or (VIb).

Step 2b.1a:

To a stirred mixture of compounds of formula (VIb) in an organic solvent (e.g. acetic acid, acetonitrile or chloroform) is either added sodium acetate and iodine monochloride or N-bromosuccinimide, and the mixture is stirred at 23° C. until tlc or HPLC analysis indicate complete conversion. The reaction mixture is slowly diluted with water, and the precipitate is collected by filtration or extracted into an organic solvent (e.g. ethyl acetate) to give the compounds of formula (VIc) or (VIa). Step 3a.1a:

To a stirred solution of compound of formula (VI) in a solvent (e.g. THF or DMF) is added at room temperature commercially available trimethylsilylacetylene (compound of formula (VII)), a palladium-catalyst (e.g. $PdCl_2(PPh_3)_2$), additional catalytic amount of triphenylphosphine, and an amine base (e.g. triethylamine), and the mixture is purged with argon gas. Then, a copper(I)-catalyst (e.g. CuI) is added, and the mixture is stirred at 70 to 90° C. until thin layer chromatography or HPLC analysis reveals complete conversion. The reaction mixture is cooled to room temperature, either diluted with ethyl acetate, filtered through celite and evaporated to dryness to yield the crude product, or directly coated on silica gel. The crude product is purified (e.g. by flash chromatography on silica gel) to yield the product (compound of formula (VIIIa)), which can be further purified (e.g. by crystallization from ethanol/ether/heptane).

Step 3b.1a:

To a stirred solution of compound of formula (VIIIa) in a protic organic solvent (e.g. methanol) is added at 0° C. a catalytic amount of a carbonate base (e.g. potassium carbonate). The reaction mixture is stirred at 0° C. for about 6 h, acidified and extracted (e.g. with tert-butylmethylether). The combined organic layers are washed and dried (e.g. $Na_2SO_4$) and evaporated to give crude product, which is purified (e.g. by flash chromatography on silica gel) to yield the product (compound of formula (VIIIb)), which can be further purified (e.g. by crystallization from ethanol/ether/heptane).

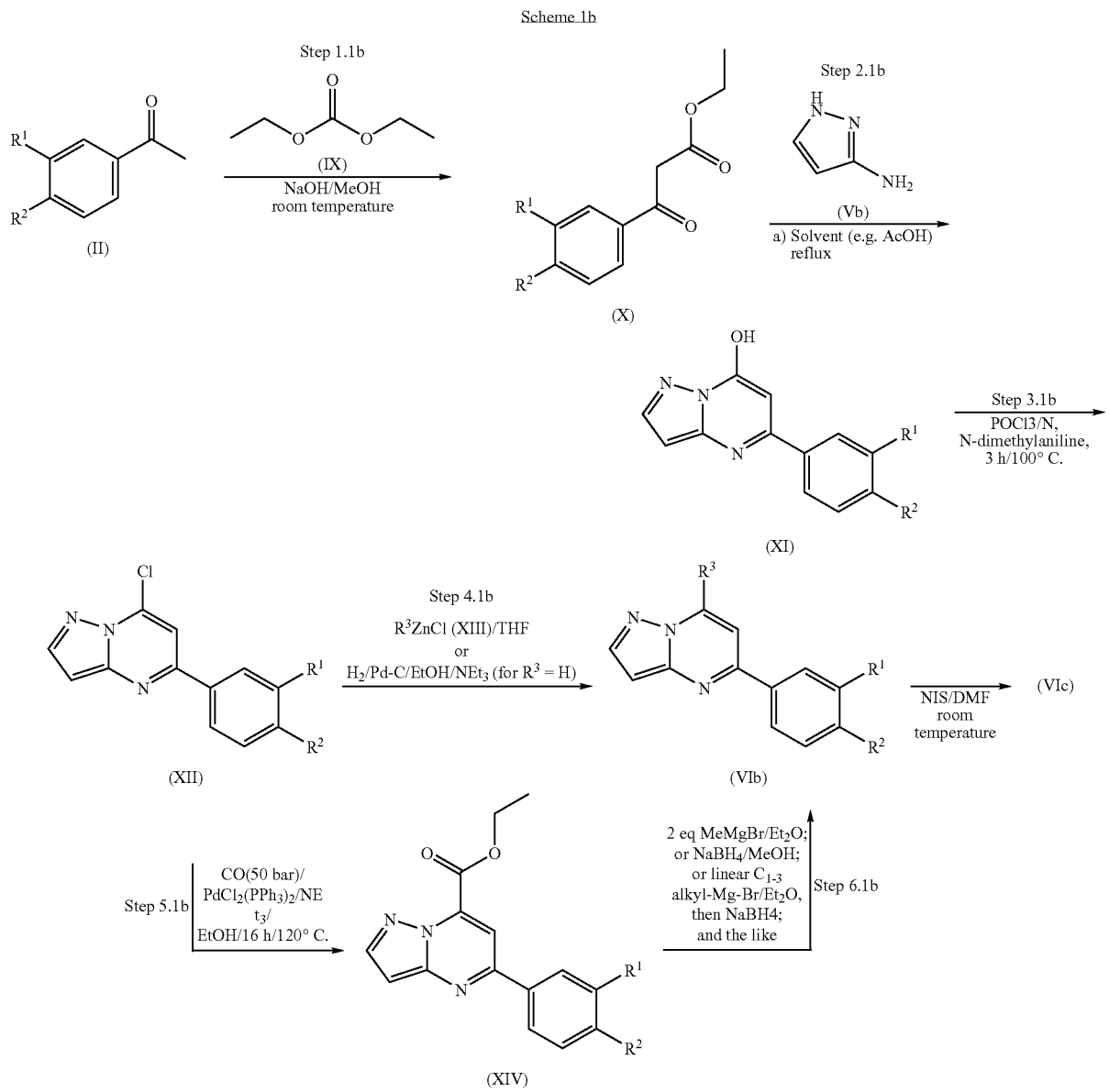

Scheme 1b

General Procedure Ib

Step 1.1b:

To a suspension of sodium hydride in toluene are added subsequently diethyl carbonate (IX) and a compound of formula (II). The solution is slowly warmed up to 100° C., during which process hydrogen gas is produced. The mixture is stirred at reflux temperature for 6 to 15 h. After cooling the mixture to 10° C., acetic acid is added, followed by ice-water and conc. HCl. The mixture is extracted (e.g. with ethyl acetate). The organic layers are successively washed with aqueous $NaHCO_3$ solution, water and brine, dried (e.g. with $NaSO_4$), and evaporated. The remaining crude product of formula (X) can be used directly in the next step or, preferably, is purified, e.g. by distillation.

Step 2.1b:

A mixture of a compound of formula (X) and 3-aminopyrazole is heated (Vb), either neat with stirring at about 150° C. for 2 to 6 h, or in a solvent (such as e.g. ethanol or acetic acid) for 1 to 20 h. The product of formula (XI) can be isolated by triturating the cooled reaction mixture with a solvent (e.g. ethanol or ethyl acetate) or by simply cooling the reaction mixture and collecting the crystallized product, or by precipitating the product with water.

Step 3.1b:

A compound of formula (XI) is heated to 80 to 100° C. for 1 to 15 h while stirring with $POCl_3$, preferably in the presence of a basic catalyst (e.g. dimethyl aniline). The mixture is cooled and evaporated in vacuo. The residue is partitioned between water and an organic solvent (e.g. dichloromethane or ethyl acetate), the organic layers are washed with water and brine, dried (e.g. with $NaSO_4$), and evaporated. The remaining crude product of formula (XII) can be used directly in the next step or, preferably, is purified, e.g. by crystallization.

Step 4.1b:

For the preparation of a compound (VIb), wherein $R^3$ represents linear $C_{1-4}$-alkyl or $C_{3-4}$-cycloalkyl, a solution of a compound of formula (XII), $R^3ZnCl$ (XIIIa) or $Zn(R^3)_2$ (XIIIb), and a Pd(0) catalyst (e.g. Pd(PPh$_3$)$_4$ in THF is heated to 40 to 70° C. for 0.5 to 6 h. To the cooled reaction mixture is added saturated aqueous ammonium chloride. The mixture is extracted with ethyl acetate, and the organic layers are washed with water and brine, dried (e.g. with NaSO$_4$), and evaporated. The crude product can be used directly in the next step or, firstly, can be purified by chromatography and/or crystallization. In this transformation, optional hydroxyl substituents in the residue $R^3$ have to be protected by a suitable protecting group, e.g. a trimethylsilyl or an acetyl group.

For the preparation of a compound (VIb), wherein $R^3$ represents hydrogen, a solution of a compound of formula (XII) in a solvent (e.g. in ethanol) is stirred in an atmosphere of hydrogen in the presence of palladium on charcoal and of a base (e.g. triethylamine) at 20° C. for 0.1-2 h. The mixture is filtered, and the solvent is evaporated to afford a compound of formula (VIb) wherein $R^3$ is hydrogen.

Step 5.1b:

A compound of formula (XIV) is prepared by heating a solution of a compound of formula (XII) under standard reaction conditions used for carbonylation reactions of reactive chloro compounds, e.g. in ethanol in the presence of triethylamine and of a palladium catalyst, such as PdCl$_2$(PPh$_3$)$_4$), under an atmosphere of carbon monoxide under a pressure of 50 bar for 16 h at 120° C. The resulting ethyl ester of formula (XIV) can be purified by chromatography and/or crystallization.

Step 6.1b:

For the preparation of a compound (VIb), wherein $R^3$ represents a 2-hydroxy-prop-2-yl group, a compound of formula (XIV) is treated with about 2 equivalent of methylmagnesium bromide in diethyl ether at 0-20° C. for 1-3 h. The mixture is poured into diluted aqueous acid (e.g. 10% H$_2$SO$_4$), and the product is extracted with ethyl acetate. The organic layer is washed with water and brine, dried (e.g. with NaSO$_4$), and evaporated to afford a compound (VIb), wherein $R^3$ is a 2-hydroxy-prop-2-yl group.

For the preparation of a compound (VIb), wherein $R^3$ represents a hydroxymethyl group, a solution of a compound of formula (XIV) in methanol and an optional cosolvent (e.g. THF) is treated portionwise with about 10 equivalents of NaBH$_4$ at 0 to 10° C. over 0.5 to 2 h. The mixture is poured into diluted aqueous acid (e.g. 3 N HCl), and the product is extracted with ethyl acetate. The organic layer is washed with water and brine, dried (e.g. with NaSO$_4$), and evaporated to afford a compound (VIb), wherein $R^3$ is a hydroxylmethyl group.

For the preparation of a compound (VIb), wherein $R^3$ represents a 1-hydroxy-linear $C_{1-4}$-alkyl group, a solution of a compound of formula (XIV) in THF is at first treated at −70 to −20° C. with a solution of linear $C_{1-4}$-alkylmagnesium bromide or linear $C_{1-4}$-alkylmagnesium chloride followed by reduction, either in situ or after isolation, of the resulting ketone intermediate using a suitable reducing agent (e.g. NaBH$_4$) to afford a compound of formula (VIb) wherein $R^3$ represents a 1-hydroxy-linear $C_{1-4}$-alkyl group.

Step 7.1b:

A compound of formula (VIc) can be obtained by treatment of a compound of formula (VIb) with a suitable iodination reagent (e.g. NIS) in an inert solvent (e.g. N,N-dimethylformamide) at 0-70° C.

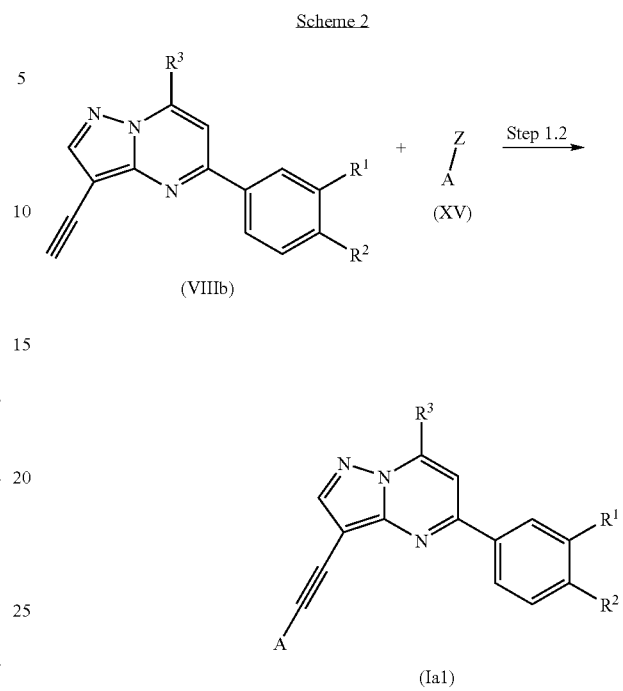

General Procedure II

Step 1.2:

To a stirred solution of the compounds of formula (VIIb) and of formula (XV) (Z is either bromide, iodide or trifluoromethylsulfonate, and A is as defined hereinabove) in a solvent (e.g. THF or DMF) is added at room temperature an amine base (e.g. triethylamine), and the mixture is purged with argon gas for about 10-20 min. Then a palladium-catalyst (e.g. PdCl$_2$(PPh$_3$)$_2$), additional catalytic amount of triphenylphosphine and a copper(I)-catalyst (e.g. CuI) are added, and the mixture is stirred at 70 to 90° C. until thin layer chromatography or HPLC analysis reveal complete conversion of the minor component. The reaction mixture is cooled to room temperature, then either diluted with ethyl acetate, filtered through celite, and evaporated to dryness to yield the crude product, or directly coated on silica gel. The crude product was purified (e.g. by flash chromatography on silica gel) to yield the product (compound of formula (I)), which can be further purified (e.g. by crystallization from ethanol/ ether/heptane).

Compounds of the formula (Ia1) can be also be prepared alternatively as depicted in scheme 3 with steps 1.3 and 2.3.

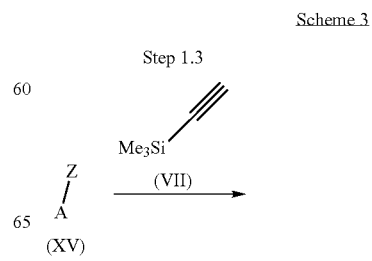

-continued

Step 2.3

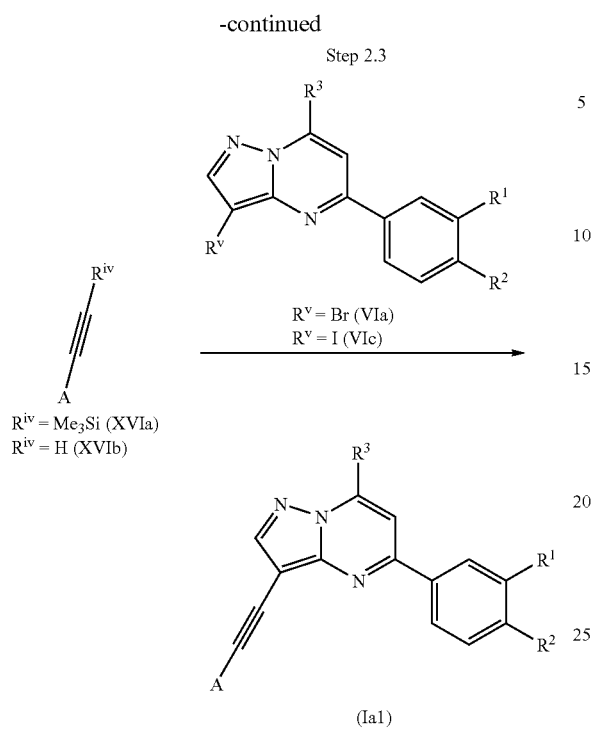

(Ia1)

-continued

Step 4.4

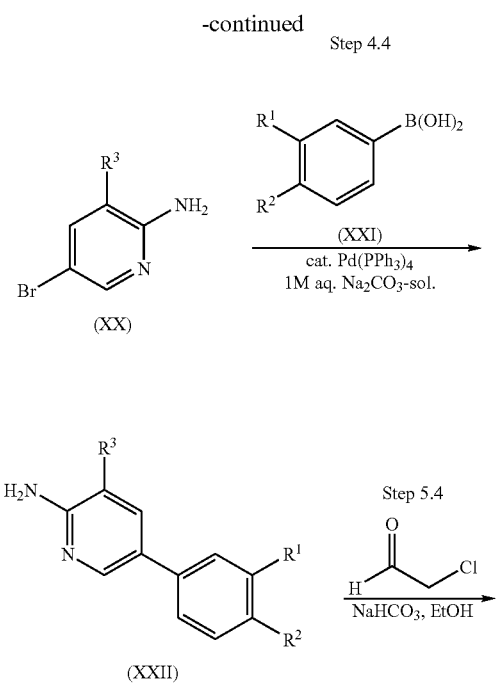

The procedures for the steps 1.3 and 2.3 can be used as described above under general procedures Ia and II, i.e. compounds of the general formula (XV) wherein A is as defined hereinabove and Z is either bromide, iodide or trifluoromethylsulfonate can be transformed according to the procedures given for step 3a.1a and 3b.1a into compounds of general formula (XVI) (e.g. (XVIa) and (XVIb) respectively). The compounds of general formula (XVIb) can be coupled with compounds of general formula (VI) (e.g (VIa) or (VIc)) wherein $R^1$, $R^2$ and $R^3$ are as defined in formula (I) above according to the procedure given for step 2.3 to obtain the compounds of the general formula (Ia1).

The synthesis of the compounds of formula (Ib) according to the invention can be carried out in accordance with the following general procedure III which procedure is outlined below in scheme 4, wherein $R^1$, $R^2$, $R^3$ and A are as defined hereinabove.

Scheme 4

Step 1.4

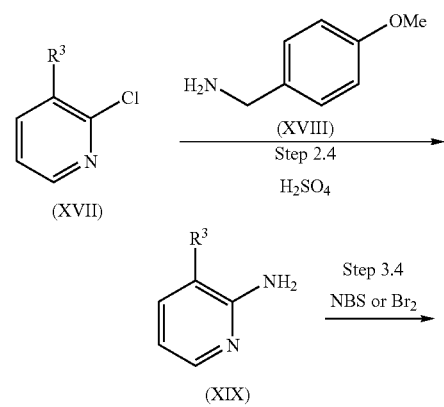

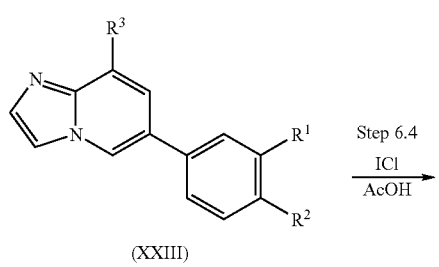

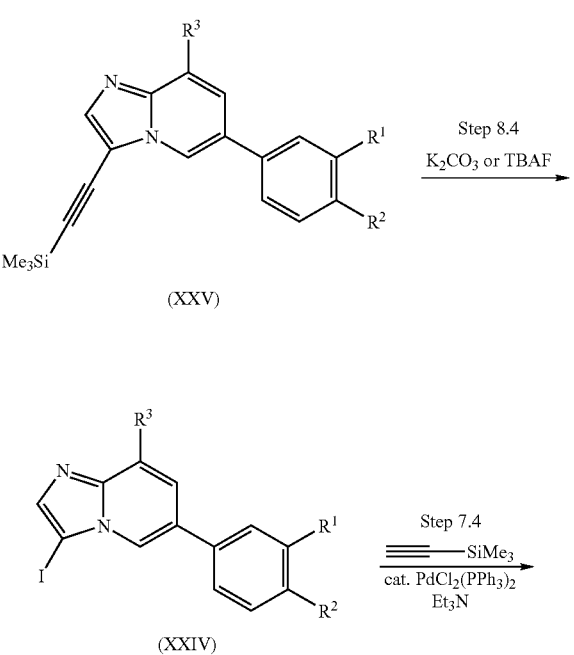

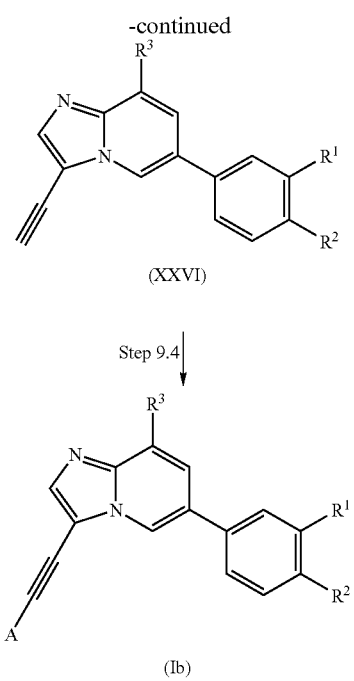

General Procedure III

Step 1.4

Commercially available compounds of formulae (XVII) and (XVIII) are mixed in a suitable solvent (e.g. n-butanol), treated with an amine (e.g. DIPEA), and heated until reaction is complete. The reaction mixture is then concentrated, and the product is extracted with an aqueous acid (25% HCl). The product is neutralized with NaOH, extracted with a suitable organic solvent (e.g. Ether, TBME, DCM), and purified by distillation to give the benzylamine adduct.

Step 2.4

The product resulting from the reaction of compounds (XVII) and (XVIII) is then acidified (e.g. with concentrated acid such as $H_2SO_4$), and the compound of formula (XIX) is recovered after isolation and purification using conventional methods.

Step 3.4

To a solution of the compound of formula (XIX) in a solvent (e.g. acetonitrile, EtOH) is added a brominating agent (e.g. NBS or bromine). The compound of formula (XX) is then isolated and purified using conventional methods.

Step 4.4

The compound of formula (XXII) is obtained by reaction of the compound of formula (XX) with a compound of formula (XXI) using a palladium catalyst (e.g. $Pd(PPh_3)_4$) in a suitable solvent (e.g. DME) and base (e.g. 1M aq. $Na_2CO_3$ solution). The compound of formula (XXII) is then isolated and purified using conventional methods.

Step 5.4

The compound of formula (XXIII) is obtained by reaction of the compound of formula (XXII) with a chloroacetaldehyde solution in water, a base (e.g. $NaHCO_3$) and in a suitable solvent (e.g. ethanol). The compound of formula (XXIII) is then isolated and purified using conventional methods.

Step 6.4

The compound of formula (XXIV) is obtained by reaction of the compound of formula (XXIII) with a solution of iodine monochloride in acetic acid in the presence of sodium acetate. The compound of formula (XXIV) is then isolated and purified using conventional methods.

Step 7.4

The compound of formula (XXV) is obtained by reaction of the compound of formula (XXIV) with trimethylsilylacetylene, a catalyst (e.g. $PdCl_2(PPh_3)_2$, $Pd(PPh_3)_4$), a base (e.g. triethylamine, diisopropylamine) in a suitable solvent (e.g. THF, DMF, DME). The compound of formula (XXV) is then isolated and purified using conventional methods.

Step 8.4

The trimethylsilyl moiety of the compound of formula (XXV) is then removed (e.g. by adding $K_2CO_3$ in MeOH or by using TBAF in THF). The compound of formula (XXVI) is isolated and purified using conventional methods.

Step 9.4

Step 9.4 can be performed as described in general procedure II herein above.

The synthesis of the compounds of formula (Ia2) according to the invention may be carried out in accordance with the following general procedure IV which procedure is outlined below in scheme 5, wherein $R^1$, $R^2$, $R^3$ and A are as defined hereinabove.

Scheme 5

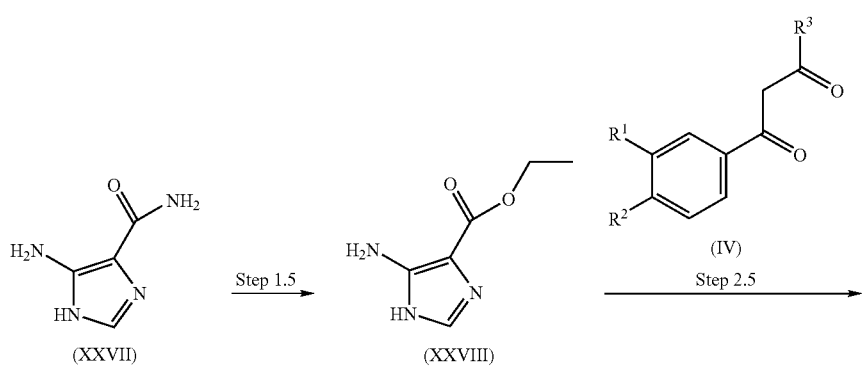

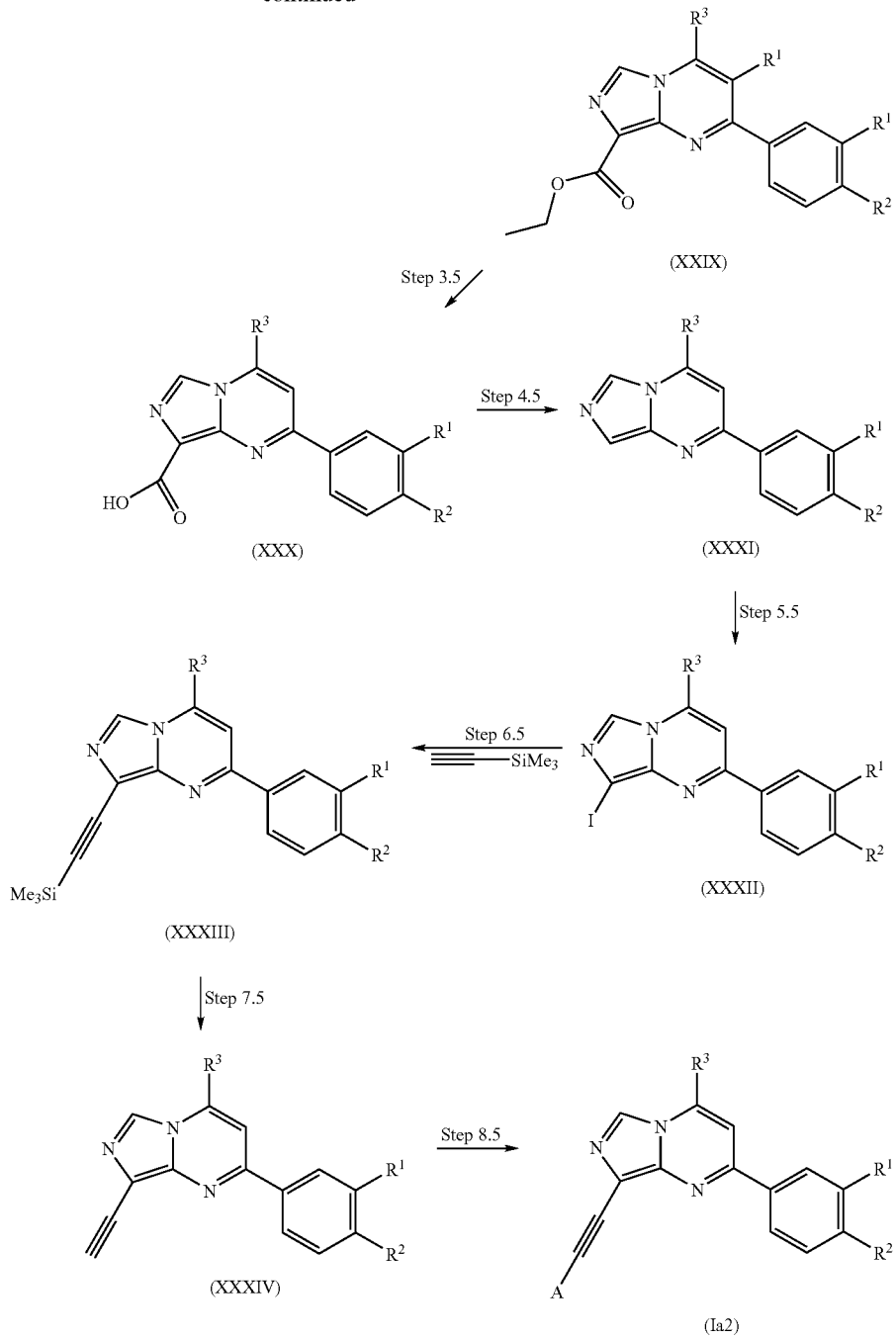

General Procedure IV

Step 1.5

A stirred solution of a commercially available compound of formula (XXVII) (e.g. in methanesulfonic acid) and ethanol is stirred. While stirring a sodium hydroxide solution is added. The compound of formula (XXVIII) is recovered using conventional methods.

Step 2.5

A compound of formula (IV) and the compound of formula (XXVIII) are reacted. The compound of formula (XXIX) is recovered using conventional methods.

Step 3.5

The ester of formula (XXIX) is then converted into its corresponding carboxylic acid of formula (XXX) (e.g. using a potassium hydroxide solution, water and acetic acid). The compound of formula (XXX) is then recovered using conventional methods.

Step 4.5

The compound of formula (XXXI) is obtained by heating the compound of formula (XXX). The compound of formula (XXXI) is then recovered using conventional methods.

Step 5.5

The compound of formula (XXXII) is obtained by reaction of the compound of formula (XXXI) with a solution of iodine monochloride in acetic acid in the presence of sodium acetate. The compound of formula (XXXII) is then isolated and purified using conventional methods.

Steps 6.5 to 8.5

Steps 6.5 to 8.5 can be performed as described in steps 7.4 to 9.4 according to general procedure III for the compounds of formula (Ia2).

The compounds of formula (I) and their pharmaceutically acceptable salts are metabotropic glutamate receptor antagonists and can be used for the treatment or prevention of acute and/or chronic neurological disorders, such as psychosis, schizophrenia, Alzheimer's disease, cognitive disorders and memory deficits. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia, depression and glioma.

The present invention also provides pharmaceutical compositions containing compounds of formula (I) or pharmaceutically acceptable salts thereof and a pharmaceutically acceptable carrier. Such pharmaceutical compositions can be administered orally, e.g. in the form of tablets, coated tablets, dragées, hard and soft gelatin capsules, solutions, emulsions or suspensions. However, the administration can also be effected rectally, e.g. in the form of suppositories, or parenterally, e.g. in the form of injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such method comprises bringing one or more compounds of formula (I) or pharmaceutically acceptable salts thereof and, if desired, one or more other therapeutically valuable substances into a galenical dosage form together with one or more therapeutically inert carriers.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The compounds of the present invention are group II mGlu receptor antagonists. The compounds show activities, as measured in the assay described below, of 0.150 µM or less, typically 0.030 µM or less, and ideally of 0.010 µM or less. In the table below are described some specific Ki values of some representative compounds.

| | Ex. No. | | | | | | |
|---|---|---|---|---|---|---|---|
| | 1 | 86 | 91 | 157 | 178 | 179 | 180 |
| $K_i$ mGlu2 (µM) | 0.002 | 0.003 | 0.004 | 0.008 | 0.008 | 0.001 | 0.009 |

[$^3$H]-LY354740 Binding on mGlu2 Transfected CHO Cell Membranes.

Transfection and Cell Culture cDNA encoding the rat mGlu2 receptor protein in pBluescript II was subcloned into the eukaryotic expression vector pcDNA I-amp from Invitrogen Ltd (Paisley, UK). This vector construct (pcD1mGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (2 mM final concentration) and 10% dialyzed fetal calf serum from Gibco-Invitrogen (Carlsbad, Calif., USA). Selection was made in the presence of G-418 (1000 ug/mL final) and MCPG??. Clones were identified by reverse transcription of 5 µg total RNA, followed by PCR using mGlu2 receptor specific primers 5'-atcactgcttgggtttctg-gcactg-3' and 5'-agcatcactgtgggtggcataggagc-3' in 60 mM Tris HCl (pH 10), 15 mM (NH4)$_2$SO$_4$, 2 mM MgCl$_2$, 25 units/mLTaq Polymerase with 30 cycles annealing at 60° C. for 1 min., extention at 72° C. for 30 s, and 1 min. 95° C. denaturation.

Membrane Preparation

Cells, cultured as above, were harvested and washed three times with cold PBS and frozen at −80° C. The pellet was resuspended in cold 20 mM HEPES-NaOH buffer containing 10 mM EDTA (pH 7.4) and homogenized with a polytron (Kinematica, AG, Littau, Switzerland) for 10 s at 10 000 rpm. After centrifugation for 30 min. at 4° C., the pellet was washed once with the same buffer, and once with cold 20 mM HEPES-NaOH buffer containing 0.1 mM EDTA, (pH 7.4). Protein content was measured using the micro BCA method from Pierce-Perbio (Rockford, Ill., USA) using bovine serum albumin as standard.

[$^3$H]-LY354740 Binding

After thawing, the membranes were resuspended in cold 50 mM Tris-HCl buffer containing 2 mM MgCl$_2$ (pH 7) (binding buffer). The final concentration of the membranes in the assays was 25 µg protein/ml. Inhibition experiments were performed with membranes incubated with 10 nM [$^3$H]-LY354740 at room temperature, for 1 hour, in presence of various concentrations of the compound to be tested. Following the incubations, membranes were filtered onto Whatmann GF/B glass fiber filters and washed 5 times with cold binding buffer. Non specific binding was measured in the presence of 10 µM DCG IV. After transfer of the filters into plastic vials containing 10 mL of Ultima-gold scintillation fluid from Perkin-Elmer (Boston, Mass., USA), the radioactivity was measured by liquid scintillation in a Tri-Carb 2500 TR counter (Packard, Zürich, Switzerland).

Data Analysis.

The inhibition curves were fitted with a four parameter logistic equation giving IC$_{50}$ values, and Hill coefficients.

EXAMPLES

Synthesis of Starting Material

Some of the starting materials used in the general procedures I and II are commercially available. However some of said starting materials have been prepared according to the procedures as outlined hereafter and, unless otherwise specified, the intermediate compounds described therein are novel compounds. Other starting materials useful in the general procedures I and II can be prepared taking into account the following examples of preparation and using known methods:

Synthesis of Acetophenones Derivatives (Starting Material of Formula II)

Example A.1

3-Methyl-4-trifluoromethyl-acetophenone

The 1-(3-methyl-4-trifluoromethyl-phenyl)-ethanone was prepared by the following sequence:

Step 1: 5-Methyl-2-nitro-4-trifluoromethyl-phenylamine

Under argon atmosphere, a suspension of potassium tert-butanolate (71.6 g, 625 mmol) in DMSO (150 mL) was placed in a 1.5 L flask, fitted with a mechanical stirrer. Then diethyl malonate (97.9 mL, 625 mmol) was added drop wise at 20-30° C. under ice bath cooling. To the thick white suspension was the added solid commercially available 5-chloro-2-nitro-4-trifluoromethyl-phenylamine [CAS-No. 35375-74-7] (60.14 g, 250 mmol) in one portion, the mixture was diluted with DMSO (100 mL) and the red solution warmed up to 60° C. and stirred for 20 h at 60° C. The mixture was cooled to 23° C. and a solution of potassium hydroxide (85%, 65.24 g, 1 mol) in water (100 mL) was added drop wise. The mixture was then heated to 100° C. and stirred for further 4 h. The mixture was cooled to 23° C., diluted with water (ca. 1000 mL), acidified with 37% HCl 3 to pH 3, and extracted three times with tert-butyl methyl ether (TBME) The organic layers were washed with brine, dried over MgSO$_4$ and evaporated to give a brown solid, which was triturated with hot heptane, filtered off and washed with heptane to give the title compound as a brown solid (50.0 g, 91%), which was used without further purification. MS (ISN) 218.9 [M–H].

Step 2: 1-Bromo-5-methyl-2-nitro-4-trifluoromethyl-benzene

To a rapidly stirred mixture of tert-butyl nitrite (45.33 mL, 382 mmol) and copper(II) bromide (76.1 g, 341 mmol) in acetonitrile (450 mL) at 65° C. was added cautiously solid 5-methyl-2-nitro-4-trifluoromethyl-phenylamine from step 1 (50.0 g, 227 mmol). After the addition was complete, stirring was continued for further 1 h at 65° C. The mixture was cooled to 23° C. and poured into 1 N HCl (1 L), extracted twice with TBME, the organic layer was washed with brine, dried over MgSO$_4$. Removal of the solvent in vacuum left a brown oil, which was purified by silica gel column chromatography with heptane/ethyl acetate 9:1 to give the title compound as a yellow liquid (49.8 g, 77%). MS (EI) 283.0 [M] and 285.0 [M$^+$2].

Step 3: 5-Methyl-2-nitro-4-trifluoromethyl-benzonitrile

A mixture of 1-bromo-5-methyl-2-nitro-4-trifluoromethyl-benzene from step 2 (49.80 g, 175 mmol) and copper(I) cyanide (16.5 g, 184 mmol) in 1-methyl-2-pyrrolidone (NMP) (180 mL) was heated up to 150° C. and stirred for 30 min under nitrogen atmosphere. The mixture was cooled to 23° C. and poured into 1 N HCl, extracted with TBME, washed with brine and dried over Na$_2$SO$_4$. Removal of the solvent in vacuum left a brown oil, which was purified by silica gel column chromatography with heptane/ethyl acetate 4:1→2:1 to give the title compound as a light yellow solid (35.48 g, 88%). MS (EI) 230.1 [M].

Step 4: 2-Amino-5-methyl-4-trifluoromethyl-benzonitrile

Iron powder (37.42 g, 670 mmol) was added in small portions to a stirred suspension of finely grinded 5-methyl-2-nitro-4-trifluoromethyl-benzonitrile from step 3 (34.58 g, 150 mmol) in methanol (75 mL) and 37% HCl (93 mL). The internal temperature was kept between 40 and 60° C. by external water bath cooling. The resulting brown solution was stirred for 1 h at 50° C., giving a green suspension. The mixture was poured into ice cold water (600 mL), the precipitated solid was filtered off and washed with water to give a green solid, which was dissolved in boiling ethanol (700 mL), activated carbon (ca. 10 g) was added, and the mixture was refluxed for 1 h. The hot solution was filtered, and the solvent was evaporated in vacuum to leave the title compound as a brown-yellow solid (23.55 g, 78%), which was used without further purification. MS (EI) 200.1 [M].

Step 5: 3-Methyl-4-trifluoromethyl-benzonitrile

To a solution of 2-amino-5-methyl-4-trifluoromethyl-benzonitrile from step 4 (23.34 g, 117 mmol) in dry THF (350 mL) was added isoamyl nitrite (34.3 mL, 257 mmol), and the mixture was refluxed for 20 h. Additional isoamyl nitrite (16.6 mL, 129 mmol) was added and the mixture was refluxed for further 20 h. The mixture was cooled to 23° C. and diluted with TBME, the organic layer was washed with 1 N HCl, sat. NaHCO$_3$-sol. and brine, dried over Na$_2$SO$_4$.

Removal of the solvent in vacuum left a brown oil (25.82 g), which was purified by bulb to bulb distillation to give a yellow liquid (20.11 g), which was finally purified by distillation to give the title compound as a yellow liquid (17.10 g, 79%; bp 38-42° C. at 0.8 mbar). MS (EI) 185.1 [M].

Step 6: 3-Methyl-4-trifluoromethyl-benzoic acid

A mixture of 3-methyl-4-trifluoromethyl-benzonitrile from step 5 (16.25 g, 88 mmol) and 3 N NaOH (88 mL, 264 mmol) in dioxane (90 mL) was refluxed for 18 h. The mixture was cooled to 23° C., diluted with TBME, acidified with 1 N HCl to pH 1 and extracted twice with TBME. The combined organic layers were washed with brine, dried over MgSO$_4$. Removal of the solvent in vacuum left the title compound as an off white solid (14.46 g, 81%), which was used without further purification. MS (ISN) 203.1 [M–H].

Step 7: N-Methoxy-3,N-dimethyl-4-trifluoromethyl-benzamide

To a suspension of 3-methyl-4-trifluoromethyl-benzoic acid from step 6 (14.1 g, 69.1 mmol), N,O-dimethylhydroxylamine hydrochloride (10.78 g, 111 mmol), N-methylmorpholine (12.14 mL, 111 mmol) and 4-DMAP (844 mg, 691 mmol) in DCM (230 mL) at 0° C. were added 1-(3-dimethylaminopropyl)-3-ethylcarbodiimide hydrochloride (EDC) (15.98 g, 82.9 mmol) and DMF (85 mL). The mixture was warmed up to 23° C. and was stirred for 18 h under nitrogen atmosphere. The mixture was diluted with TBME, washed with water and twice brine, dried over $Na_2SO_4$. Removal of the solvent in vacuum left the title compound as a brown oil (16.92 g, 99%), which was used without further purification. MS (ISP) 248.0 [$M^+H$].

Step 8: 1-(3-Methyl-4-trifluoromethyl-phenyl)-ethanone

To a solution of N-methoxy-3,N-dimethyl-4-trifluoromethyl-benzamide from step 7 (16.90 g, 68.36 mmol) in THF (280 mL) at −5° C. was added a 3 M methylmagnesium bromide solution in diethyl ether (45.6 mL, 136.7 mmol). The mixture was stirred at 0° C. for 1 h, then was warmed up to 23° C. and stirring was continued at 23° C. for further 1.5 h under nitrogen atmosphere. Then 1 N HCl (100 mL) was added drop wise to the mixture and stirring was continued for 30 min. The mixture was diluted with EtOAc and the aqueous layer was separated, the organic layer was washed with brine and dried over $MgSO_4$. Removal of the solvent in vacuum left the title compound as a light brown liquid (12.87 g, 93.1%), which was used without further purification. MS (EI) 202.1 [M].

Example A.2

3-Ethoxy-4-trifluoromethyl-acetophenone

The 1-(3-ethoxy-4-trifluoromethyl-phenyl)-ethanone was prepared by the following sequence:

Step 1: 5-Ethoxy-2-nitro-4-trifluoromethyl-phenylamine

To EtOH (500 mL) was added potassium metal (ca. 21 g, ca. 537 mmol), and the vigorous reaction had to be cooled with an ice bath. Stirring was continued until all potassium metal was dissolved. Solid commercially available 5-chloro-2-nitro-4-trifluoromethyl-phenylamine [CAS-No. 35375-74-7] (57.74 g, 240 mmol) was added in one portion, and the resulting dark red mixture was stirred at 55-60° C. for 4 days. The warm reaction mixture was slowly poured into $H_2O$ (ca. 2000 mL), adjusted pH with conc. HCl to pH 2, the yellow precipitate was filtered off, washed with $H_2O$ and dried in air at 60° C. to give a yellow solid (57.81 g, 96%), which was used without further purification. MS (ISN) 249 [M⁻H].

Step 2: 1-Bromo-5-ethoxy-2-nitro-4-trifluoromethyl-benzene

Solid 5-ethoxy-2-nitro-4-trifluoromethyl-phenylamine from step 1 (57.81 g, 231 mmol) was added slowly over 15 min to a rapidly stirred mixture of tert-butyl nitrite (45.8 mL, 347 mmol) and anhydrous copper(II) bromide (77.4 g, 347 mmol) in acetonitrile (462 mL), which was heated to 65° C. in an oil bath. Stirring at 65° C. was continued for 30 min, the reaction mixture was cooled to 23° C., poured into 1 N HCl, saturated with solid NaCl, extracted with TBME, dried over $MgSO_4$. Removal of the solvent in vacuum left a dark brown oil (74.5 g). Silica gel column chromatography with heptane/EtOAc 4:1 gave the title compound as a yellow solid (63.03 g, 87%). MS (EI) 313.0 [M] and 315.0 [$M^+2$].

Step 3: 5-Ethoxy-2-nitro-4-trifluoromethyl-benzonitrile

A mixture of 1-bromo-5-ethoxy-2-nitro-4-trifluoromethyl-benzene from step 2 (61.81 g, 197 mmol) and CuCN (18.51 g, 207 mmol) in NMP (197 mL) was heated to 150° C. for 30 min. Cooled to 23° C., poured into 1 N HCl, extracted with TBME, washed with brine, dried over $Na_2SO_4$. Removal of the solvent in vacuum left a brown oil. Silica gel column chromatography with heptane/EtOAc 4:1 gave the title compound as a yellow solid (46.73 g, 91%). MS (EI) 260.1 [M].

Step 4: 2-Amino-5-ethoxy-4-trifluoromethyl-benzonitrile

Iron powder (40.96 g, 733 mmol) was added in small portions over 5 min to a stirred suspension of finely grinded 5-ethoxy-2-nitro-4-trifluoromethyl-benzonitrile from step 3 (42.79 g, 164.5 mmol) in MeOH (85 mL) and conc. HCl (102 mL) with water bath cooling keeping the internal temperature at 40-50° C. The resulting mixture was stirred for further 1 h at ca. 50° C. and then poured into ice cold $H_2O$ (700 mL). The precipitate was filtered, washed with water, dried, and dissolved in boiling EtOH (800 mL), activated carbon (ca. 10 g) was added, the mixture was refluxed for 45 min, the hot solution was filtered and evaporated to dryness to leave a yellow solid (31.81 g, 84%), which was used without further purification. MS (EI) 230.1 [M].

Step 5: 3-Ethoxy-4-trifluoromethyl-benzonitrile

To a solution of 2-amino-5-ethoxy-4-trifluoromethyl-benzonitrile from step 4 (31.62 g, 137.4 mmol) in dry THF (410 mL) was added isoamyl nitrite (40.4 mL, 302 mmol), and the mixture was refluxed for 16 h. The solvent was removed in vacuum to give an orange oil, which was dissolved in sat. $NaHCO_3$-sol., extracted three times with diethyl ether. The combined organic layers were washed with 1 N HCl and brine, dried over $Na_2SO_4$. Removal of the solvent in vacuum left an orange oil, which was purified by double Kugelrohr distillation (up to 160° C. bath temperature at 1.5 mbar) to give the title compound as a light yellow solid (25.06 g, 85%). MS (EI) 185.1 [M].

Step 6: 3-Ethoxy-4-trifluoromethyl-benzoic acid

A mixture 3-ethoxy-4-trifluoromethyl-benzonitrile from step 5 (11.5 g, 62.1 mmol) and 3 N NaOH (62.1 mL, 186.4 mmol) in dioxane (62 mL) was refluxed for 20 h. The mixture was cooled to 23° C., diluted with TBME, acidified with 1 N HCl to pH 1 and extracted twice with TBME. The combined organic layers were washed with brine, dried over $MgSO_4$. Removal of the solvent in vacuum left the title compound as an off white solid (13.81 g, 95%), which was used without further purification. MS (ISN) 233.1 [M−H].

Step 7: 3-Ethoxy-N-methoxy-N-methyl-4-trifluoromethyl-benzamide

To a mixture of 3-ethoxy-4-trifluoromethyl-benzoic acid from step 6 (13.76 g, 59 mmol), N,O-dimethylhydroxylamine hydrochloride (9.17 g, 94 mmol), N-methylmorpholine (9.51 mL, 94 mmol) and 4-DMAP (718 mg, 6 mmol) in DCM (185 mL) and DMF (38 mL) at 0° C. was added 1-(3-dimethylaminopropyl)-3-ethylcarbodiimide hydrochloride (EDC) (13.52 g, 70 mmol), and the mixture was stirred at 23° C. for 18 h. Poured onto ice cold 1 N HCl, extracted with TBME, washed with sat. $NaHCO_3$-sol. and brine, dried over $Na_2SO_4$. Removal of the solvent in vacuum left the title compound as a light brown oil (16.15 g, 100%, which was used without further purification. MS (ISP) 278.4 [M+H].

Step 8: 1-(3-Ethoxy-4-trifluoromethyl-phenyl)-ethanone

To a solution of 3-ethoxy-N-methoxy-N-methyl-4-trifluoromethyl-benzamide from step 7 (15.96 g, 58 mmol) in THF (182 mL) at −5° C. was added methylmagnesium bromide (3

M in Et$_2$O, 38.37 mL, 115 mmol). The mixture was stirred at 0° C. for 15 min, then warmed up to 23° C., stirring was continued for further 3 h at 23° C. Cooled to 0° C., 1 N HCl (274 mL) was added dropwise, stirring was continued at 23° C. for 15 min, the mixture was diluted with TBME, the phases were separated, the organic layer was washed with water and brine, dried over MgSO$_4$. Removal of the solvent in vacuum left a yellow solid (13.10 g, 98%), which was used without further purification. MS (EI) 232.2 [M].

Example A.3

3-(2,2,2-Trifluoro-ethoxy)-4-trifluoromethyl-acetophenone

The 1-[3-(2,2,2-trifluoro-ethoxy)-4-trifluoromethyl-phenyl]-ethanone was prepared by the following sequence:

Step 1: 2-Nitro-5-(2,2,2-trifluoro-ethoxy)-4-trifluoromethyl-phenylamine

Commercially available 5-chloro-2-nitro-4-trifluoromethyl-phenylamine [CAS-No. 35375-74-7] (72.2 g, 300 mmol) was dissolved in DMSO (600 mL) and 2,2,2-trifluoroethanol (270 mL) were added at 23° C., the slightly exothermic reaction was cooled with a ice bath. KOH (85%, 99.0 g, 1500 mmol) were added slowly and the dark red reaction mixture was stirred at 23° C. for 4 days. Transferred into a 3 L flask and 1500 mL H$_2$O were added under ice bath cooling, acidified with 3 N HCl and stirred at 23° C. for 3 h, filtered off the yellow precipitate, washed with H$_2$O and dried in air at 60° C. to give the title compound as a yellow solid (89.47 g, 98%). MS (ISN) 303.1 [M⁻H].

Step 2: 1-Bromo-2-nitro-5-(2,2,2-trifluoro-ethoxy)-4-trifluoromethyl-benzene

Solid 2-nitro-5-(2,2,2-trifluoro-ethoxy)-4-trifluoromethyl-phenylamine from step 1 (24.28 g, 80 mmol) was added slowly over 15 min to a rapidly stirred mixture of tert-butyl nitrite (14.23 mL, 120 mmol) and anhydrous copper(II) bromide (26.75 g, 120 mmol) in acetonitrile (160 mL), which was heated to 65° C. in an oil bath. Stirring at 65° C. was continued for 2 h, the reaction mixture was cooled to 23° C., poured into 1 N HCl, saturated with solid NaCl, extracted with TBME, dried over MgSO$_4$. Removal of the solvent in vacuum left a dark brown oil (35.57 g). Silica gel column chromatography with heptane/EtOAc 4:1 gave the title compound as an orange solid (30.54 g, 104%), which was used without further purification. MS (EI) 367 [M] and 369 [M$^+$2].

Step 3: 2-Nitro-5-(2,2,2-trifluoro-ethoxy)-4-trifluoromethyl-benzonitrile

A mixture of 1-bromo-2-nitro-5-(2,2,2-trifluoro-ethoxy)-4-trifluoromethyl-benzene from step 2 (30.54 g, 83.0 mmol) and CuCN (7.80 g, 87.1 mmol) in NMP (83 mL) was heated to 150° C. for 30 min. Cooled to 23° C., poured into 1 N HCl, extracted with EtOAc, washed with brine, dried over Na$_2$SO$_4$. Removal of the solvent in vacuum left a dark brown oil (33.9 g). Silica gel column chromatography with heptane/EtOAc 9:1→4:1 gave the title compound as a yellow solid (22.05 g, 85%). MS (EI) 314 [M].

Step 4: 2-Amino-5-(2,2,2-trifluoro-ethoxy)-4-trifluoromethyl-benzonitrile

Iron powder (15.80 g, 283.0 mmol) was added in small portions over 5 min to a stirred suspension of finely grinded 2-nitro-5-(2,2,2-trifluoro-ethoxy)-4-trifluoromethyl-benzonitrile from step 3 (19.93 g, 63.4 mmol) in MeOH (32 mL) and conc. HCl (40 mL) with water bath cooling keeping the internal temperature at 25-35° C. The resulting mixture was stirred for further 1 h at ca. 30° C. and then poured into ice cold H$_2$O (400 mL). The precipitate was filtered, washed with water, dried, and dissolved in boiling EtOH (400 mL), activated carbon (ca. 10 g) was added, the mixture was refluxed for 45 min, the hot solution was filtered and evaporated to dryness to leave a dark green solid (15.96 g, 84%), which was further purified by silica gel column chromatography with heptane/EtOAc 4:1 to give the title compound as a yellow solid (14.56 g, 81%). MS (ISN) 283 [M−H].

Step 5: 3-(2,2,2-Trifluoro-ethoxy)-4-trifluoromethyl-benzonitrile

To a solution of 2-amino-5-(2,2,2-trifluoro-ethoxy)-4-trifluoromethyl-benzonitrile from step 4 (14.47 g, 50.9 mmol) in dry THF (153 mL) was added isoamyl nitrite (15.0 mL, 112.0 mmol), and the mixture was refluxed for 20 h. The solvent was removed in vacuum to give an orange oil, which was dissolved in TBME, washed with 1 N HCl, sat. NaHCO$_3$-sol. and brine, dried over Na$_2$SO$_4$. Removal of the solvent in vacuum left a brown solid (15.05 g), which was purified by Kugelrohr distillation (up to 155° C. bath temperature at 1.2 mbar) to give the title compound as a light yellow solid (10.83 g, 79%). MS (EI) 269 [M].

Step 6: 3-(2,2,2-Trifluoro-ethoxy)-4-trifluoromethyl-benzoic acid

A mixture of 3-(2,2,2-trifluoro-ethoxy)-4-trifluoromethyl-benzonitrile from step 5 (8.75 g, 33 mmol) and 3 M NaOH (3.9 g, 98 mmol in 33 mL H2O) in dioxane (33 mL) was refluxed for 7.5 h. Poured onto ice, acidified with conc. HCl to pH 1, saturated with solid NaCl, extracted with TBME, dried over MgSO$_4$. Removal of the solvent in vacuum left the title compound as an off-white solid (9.22 g, 98%), which was used without further purification. MS (ISN) 286.9 [M−H].

Step 7: N-Methoxy-N-methyl-3-(2,2,2-trifluoro-ethoxy)-4-trifluoromethyl-benzamide To a mixture of 3-(2,2,2-trifluoro-ethoxy)-4-trifluoromethyl-benzoic acid from step 6 (9.22 g, 32 mmol), N,O-dimethylhydroxylamine hydrochloride (5.00 g, 51 mmol), N-methylmorpholine (5.62 mL, 51 mmol) and 4-DMAP (391 mg, 3.2 mmol) in DCM (100 mL) and DMF (20 mL) at 0° C. was added 1-(3-dimethylaminopropyl)-3-ethylcarbodiimide hydrochloride (EDC) (7.36 g, 38 mmol). The mixture was stirred at 23° C. for 18 h., poured onto ice cold 1 N HCl, extracted with TBME, washed with sat. NaHCO$_3$-sol. and brine, and dried over Na$_2$SO$_4$. Removal of the solvent in vacuum left the title compound as a brown oil (10.555 g, 100%), which was used without further purification. MS (EI) 331.0 [M].

Step 8: 1-[3-(2,2,2-Trifluoro-ethoxy)-4-trifluoromethyl-phenyl]-ethanone

To a solution of N-methoxy-N-methyl-3-(2,2,2-trifluoro-ethoxy)-4-trifluoromethyl-benzamide from step 7 (10.467 g, 32 mmol) in THF (100 mL) at −5° C. was added methylmagnesium bromide (3 M in Et$_2$O, 21.1 mL, 64 mmol). The mixture was stirred at 0° C. for 15 min, then warmed up to 23° C., stirring was continued for further 1.5 h at 23° C. Cooled to 0° C., 1 N HCl (150 mL) was added drop wise, stirring was continued at 23° C. for 15 min, the mixture was diluted with TBME, the phases were separated, the organic layer was washed with water and brine, dried over MgSO4. Removal of the solvent in vacuum left a yellow solid (9.021 g, 100%), which was used without further purification. MS (EI) 286.1 [M].

Synthesis of Bromo, Iodo or Trifluoromethylsulfonate Derivatives

Starting Material of Formula XV

Example B.1

5-Bromo-pyridine-3-sulfonic acid amide

Step 1: Pyridine-3-sulfonyl chloride

A mixture of pyridine-3-sulfonic acid (10.3 g, 64.8 mmol), phosphorus pentachloride (20.82 g, 100 mmol) and phosphorus oxychloride (10 mL, 109 mmol) was heated to reflux for 3 h (according to *J. Org. Chem.* 1989, 54(2), 389.). Evaporated to dryness to give a yellow solid, dissolved in ice water and methyl-tert-butyl ether, added cautiously sat. $NaHCO_3$-sol. until neutralized, saturated with solid NaCl, separated phases, dried organic layer over $Na_2SO_4$. Removal of the solvent in vacuum to give the title compound as an orange liquid (10.85 g, 94%). MS (ISP) 178.1 $[(M+H)^+]$ and 180.0 $[(M+2H)^+]$.

Step 2: 5-Bromo-pyridine-3-sulfonic acid amide

A mixture of pyridine-3-sulfonyl chloride (20 g, 112.6 mmol) and bromine (6.94 g, 135 mmol) were heated in a sealed tube at 130° C. for 8.5 h (according to *J. Med. Chem.* 1980, 23, 1380.). Cooled to 23° C., added portion wise to cold conc. $NH_4OH$-sol. (60 mL), diluted with DCM (80 mL) and stirred at 23° C. for 30 min. Adjusted pH with conc. HCl to pH 8 (external cooling necessary), saturated with solid NaCl, extracted with EtOAc (3×200 mL), dried over $Na_2SO_4$. Removal of the solvent in vacuum left a brown solid, which was purified by silica gel column chromatography with heptane/EtOAc 1:1 to give the title compound as a yellow solid (1.34 g, 28%). MS (ISP) 237.0 $[(M+H)^+]$, 239.0 $[(M+2H)^+]$. mp 178-179° C.

Example B.2

5-Bromo-pyridine-3-sulfonic acid (2-hydroxy-1,1-dimethyl-ethyl)-amide

Step 1: 5-Bromo-pyridine-3-sulfonic acid

A mixture of pyridine-3-sulfonyl chloride (Example B.1 step 1) (20 g, 112.6 mmol) and bromine (6.94 g, 135 mmol) were heated in a sealed tube at 130° C. for 8 h (according to *J. Med. Chem.* 1980, 23, 1380.). Cooled to 23° C., the slimy solid was successively transferred with $H_2O$ (200 mL) to a larger flask, heated at 100° C. for 1.5 h. Decanted the hot solution from some undissolved brown slimy solid, concentrated in vacuum to a small volume, diluted with acetone (ca. 170 mL), cooled in an ice bath, the precipitate was filtered off, washed with little acetone and dried in air at 60° C. to give the title compound as a light yellow solid (15.37 g, 57%). MS (ISN) 235.8 $[(M-H)^-]$ and 237.7 $[(M+2-H)^-]$; mp>300° C.

Step 2: 5-Bromo-pyridine-3-sulfonyl chloride

A mixture of 5-bromo-pyridine-3-sulfonic acid (Example B.2 step 1) (7.14 g, 30 mmol), phosphorus pentachloride (9.68 g, 47 mmol) and phosphorus oxychloride (20 mL) was heated to reflux for 4 h (according to *J. Org. Chem.* 1989, 54(2), 389.). The reaction mixture was concentrated to dryness to give a yellow semisolid, dissolved in ice water and tert-butyl-methyl-ether, and cautiously added sat. $NaHCO_3$-sol. until neutralized, saturated with solid NaCl, separated phases, dried organic layer over $Na_2SO_4$. Removal of the solvent in vacuum gave the title compound as a yellow solid (7.57 g, 98%). MS (EI) 254.9 $[(M)^+]$, 256.9 $[(M+2)^+]$ and 258.9 $[(M+4)^+]$; mp 64° C.

Step 3: 5-Bromo-pyridine-3-sulfonic acid (2-hydroxy-1,1-dimethyl-ethyl)-amide

General Procedure III—Sulfonamide-Formation:

To a solution of 5-bromo-pyridine-3-sulfonyl chloride (Example B.2 step 2) (1.28 g, 5 mmol) in THF (20 mL, dioxane, or other suitable solvent) at 0° C. was added an excess of the amine, 2-amino-2-methyl-1-propanol (5 mL, 55 mmol), and the mixture was stirred at 23° C. for 14 h. Alternatively, $Et_3N$ can be added in excess with only one equivalent of the amine. The reaction is worked up by neutralization with an acid (5% citric acid, 1N HCl, or dilute AcOH), and extracted with a suitable organic solvent (ether, EtOAc, or $CH_2Cl_2$), washed with sat. $NaHCO_3$-sol. and brine, dried over $Na_2SO_4$, filtered and concentrated to give a dark brown oil, which was purified by column chromatography with heptane/EtOAc (or $CH_2Cl_2$/MeOH/$Et_3N$) gave the title compound as a light brown solid (640 mg, 41%). Typically, no chromatography is necessary and the sulfonamide purified by recrystallization. MS (ISP)=309.2 $[(M+H)^+]$, 311.1 $[(M+2H)^+]$. mp 112° C.

Example B.3

5-Bromo-pyridine-3-sulfonic acid tert-butylamide

Prepared by general procedure III from 5-bromo-pyridine-3-sulfonyl chloride (Example B.2 step 2) (500 mg, 2 mmol) and tert-butylamine (1.03 mL, 10 mmol) to give the title compound as a white solid (620 mg, 108%). MS (ISP) 293.0 $[(M+H)^+]$, 295.2 $[(M+2H)^+]$. mp 110° C.

Example B.4

5-Bromo-pyridine-3-sulfonic acid (2-hydroxy-1-hydroxymethyl-1-methyl-ethyl)-amide Prepared by general procedure III from 5-bromo-pyridine-3-sulfonyl chloride (Example B.2 step 2) (500 mg, 2 mmol) and 2-amino-2-methyl-1,3-propanediol (1.03 g, 10 mmol) to give the title compound as a light brown oil (170 mg, 26%). MS (ISP) 325.1 $[(M+H)^+]$, 327.2 $[(M+2H)^+]$.

Example B.5

5-Bromo-pyridine-3-sulfonic acid bis-(2-hydroxy-ethyl)-amide

Prepared by general procedure III from 5-bromo-pyridine-3-sulfonyl chloride (Example B.2 step 2) (500 mg, 2 mmol) and diethanolamine (1.03 g, 10 mmol) to give the title compound as an off-white solid (270 mg, 42%). MS (ISP) 325.1 $[(M+H)^+]$, 327.1 $[(M+2H)^+]$.

Example B.6

3-Bromo-N-(2-hydroxy-1,1-dimethyl-ethyl)-benzenesulfonamide

Prepared by general procedure III from 2-amino-2-methyl-1-propanol (8.91 g, 100 mmol) and commercially available 3-bromobenzenesulfonyl chloride (2.88 mL, 20 mmol) to give the title compound as a white solid (5.47 g, 89%). MS (ISN) 306.1 $[(M-H)^-]$, 308.2 $[(M+2-H)^-]$. mp 138° C.

Example B.7

5-Bromo-N-(2-hydroxy-1,1-dimethyl-ethyl)-2-methoxy-benzenesulfonamide

Prepared by general procedure III from 2-amino-2-methyl-1-propanol (2.23 g, 25 mmol) and commercially available 5-bromo-2methoxybenzenesulfonyl chloride (1.43 g, 5 mmol) to give the title compound as an off-white solid (1.68 g, 99%). MS (ISN) 336.2 [(M−H)−], 338.1 [(M+2−H)−]. mp 168° C.

Example B.8

3-Bromo-N-tert-butyl-benzenesulfonamide

Prepared by general procedure III from tert-butylamine (3.16 mL, 30 mmol) and commercially available 3-bromobenzenesulfonyl chloride (1.44 mL, 10 mmol) to give the title compound as a light yellow solid (3.11 g, 106%). MS (ISN) 290.1 [(M−H)−], 292.2 [(M+2−H)−].

Example B.9

3-Bromo-N-(2-hydroxy-1-hydroxymethyl-1-methyl-ethyl)-benzenesulfonamide

Prepared by general procedure III from 2-amino-2-methyl-1,3-propanediol (2.71 g, 25 mmol) and commercially available 3-bromobenzenesulfonyl chloride (0.72 mL, 5 mmol) to give the title compound as a white solid (0.91 g, 12%). MS (ISN) 322.1 [(M−H)−], 324.1 [(M+2−H)−].

Example B.10

Trifluoro-methanesulfonic acid 2-cyclopropyl-pyridin-3-yl ester

The title compound was prepared by the following sequence:

Step 1) Trifluoro-methanesulfonic acid 2-bromo-pyridin-3-yl ester

To a solution of 2-bromo-3-hydroxypyridine [CAS 6602-32-0, commercially available] (25.0 g, 144 mmol) in anhydrous pyridine (145 mL) at −10° C. (ice/NaCl) was drop wise added Tf$_2$O (24.2 mL, 147 mmol) keeping the temperature below −5° C. (30 min). The cooling bath was removed and mixture was allowed to reach 23° C., stirred at 23° C. for 75 min, poured into sat. NaHCO$_3$-sol., extracted with DCM, washed with brine, dried over Na$_2$SO$_4$. Removal of the solvent in vacuum left a brown oil, which was purified by vacuum distillation: bp 65° C. (0.82 mbar) (42 g colorless oil, with some solid); triturated with hexane, filtered the undesired solid off, washed with hexane, collected the mother liquor, evaporated the solvent to give the title compound as a colorless liquid (41.52 g, 94%). MS (TOF ESP) 306 [(M+H)+], 307.85 [(M+2+H)+].

Step 2) Trifluoro-methanesulfonic acid 2-bromo-pyridin-3-yl ester

To a solution trifluoro-methanesulfonic acid 2-bromo-pyridin-3-yl ester (Example B.10 step 1) (5 g, 21 mmol) and Pd(PPh$_3$)$_4$ (199 mg, 1 mol %) in THF (25 mL) was added cycloropylzinc chloride (0.4M in THF, 43 mL, 22 mmol), and the mixture was stirred under argon atmosphere at 70° C. for 3 h. Cooled to 23° C., poured into sat. NaHCO$_3$-solution, extracted with ether, washed with brine, dried over Na$_2$SO$_4$. Removal of the solvent in vacuum left a brown oil, which was purified by silica gel chromatography with heptane/EtOAc (9: 1) to give the title compound as a colorless liquid (3.2 g, 57%). MS (ISP) 268.2 [(M+H)+].

Example B.11

5-Bromo-2-cyclopropyl-pyridine

To a solution 2,5-dibromopyridine [CAS 624-28-2, commercially available] (5 g, 21 mmol) and Pd(PPh$_3$)$_4$ (244 mg, 1 mol %) in THF (25 mL) was added cycloropylzinc chloride (0.4M in THF, 53 mL, 26 mmol), and the mixture was stirred under argon atmosphere at 70° C. for 3 h. Cooled to 23° C., poured into sat. NaHCO$_3$-solution, extracted with ether, washed with brine, dried over Na$_2$SO$_4$. Removal of the solvent in vacuum left a brown oil, which was purified by silica gel chromatography with heptane-EtOAc (9:1) to give the title compound as a colorless liquid (4.3 g, 103%). MS (EI) 197 [(M)+] and 199 [(M+2)+].

Example B.12

5-Bromo-6-methoxy-pyridine-3-sulfonic acid (2-hydroxy-1,1-dimethyl-ethyl)-amide The title compound was prepared by the following sequence:

Step 1) 5-Bromo-6-chloro-pyridine-3-sulfonic acid (2-hydroxy-1,1-dimethyl-ethyl)-amide Prepared by general procedure III from 3-bromo-2-chloropyridine-5-sulphonylchloride (580 mg, 2 mmol) and 2-amino-2-N-methyl-i-propanol (178 mg, 2 mmol) to give 5-bromo-6-chloro-pyridine-3-sulfonic acid (2-hydroxy-1,1-dimethyl-ethyl)-amide as a light yellow solid (620 mg, 90%). MS (ISP) 343.0[(M+H)+]).

Step 2) To a solution of 3-bromo-2-chloropyridine-5-sulphonylchloride (600 mg, 2 mmol) in MeOH (5 mL), was added a solution of sodium methoxide (c=5.4 mol/l in MeOH, 10 mmol). The reaction mixture was stirred at RT for 48 h, then poured onto 1N HCl and extracted with two portions of EtOAc, dried over Na$_2$SO$_4$, filtered and concentrated to give the title compound as a white solid (480 mg, 81%). MS (ISP) 339.0 [(M+H)+].

Example B.13

2-Chloro-thiazole-5-sulfonic acid amide

Step 1) 2-Chloro-thiazole-5-sulfonyl chloride

A mixture of 2-Bromo-thiazole-5-sulfonic acid (57.3 g, 235 mmol, prepared from 2-Bromo-thiazole-5-sulfonic acid according to *Helv. Chim. Acta.*, 1945, 28, 985), phosphorous pentachloride (77.8 g, 373 mmol) and POCl3 (36.3 mL, 397 mmol) was refluxed for 3 h (development of bromine during the reaction). Evaporated to dryness, poured onto ice, added EtOAc, neutralized with sat. NaHCO3-sol., saturated with solid NaCl, extracted with EtOAc, dried the organic layer over Na2SO4. Removal of the solvent in vacuum gave 2-Chloro-thiazole-5-sulfonyl chloride as a yellow liquid (49.4 g, 96%). MS (ISP) 217.1 [(M+H)+].

Step 2) 2-Chloro-thiazole-5-sulfonic acid amide

Prepared by general procedure III from 2-Chloro-thiazole-5-sulfonyl chloride (1.1 g, 5 mmol) and NH$_4$OH (0.42 mL, 6 mmol) with Et₃N (0.77 mL, 6 mmol to give the title compound as a light-brown solid (610 mg, 61%). MS (ISN) 197 [(M–H)⁻].

Example B.14

2-Chloro-thiazole-5-sulfonic acid (2-hydroxy-1,1-dimethyl-ethyl)-amide

Prepared by general procedure III from 2-chloro-thiazole-5-sulfonyl chloride (2.0 g, 9 mmol, example B.13, step 1) and 2-amino-2-methyl-1-propanol (0.95 g, 9 mmol) to give the title compound (1.65 g, 33%) as an off-white solid. MS (EI) 269.2[(M)$^{+] and}$ 271.2[(M+2)⁺].

Example B.15

5-Bromo-6-methoxy-pyridine-3-sulfonic acid (2-hydroxy-1-hydroxymethyl-1-methyl-ethyl)-amide Step 1) 5-Bromo-6-chloro-pyridine-3-sulfonic acid (2-hydroxy-1-hydroxymethyl-1-methyl-ethyl)-amide Prepared by general procedure III from 3-bromo-2-chloropyridine-5-sulphonylchloride (580 mg, 2 mmol) and 2-amino-2-methyl-1,3-propanediol (231 mg, 2 mmol) to give 5-Bromo-6-chloro-pyridine-3-sulfonic acid (2-hydroxy-1-hydroxymethyl-1-methyl-ethyl)-amide (600 mg, 83%) as a yellow solid. MS (ISN) 357[(M–H)⁻], 359.0[(M+2–H)⁻], 361.0[(M+4–H)⁻].

Step 2) 5-Bromo-6-methoxy-pyridine-3-sulfonic acid (2-hydroxy-1-hydroxymethyl-1-methyl-ethyl)-amid To a solution of 5-Bromo-6-chloro-pyridine-3-sulfonic acid (2-hydroxy-1-hydroxymethyl-1-methyl-ethyl)-amide (550 mg, 2 mmol) in MeOH (5 mL) was added a solution of sodium methoxide (c=5.4 mol/L in MeOH, 10 mmol) at rt for 48 h. The reaction mixture was poured into a 1N solution of HCl and was extracted with 2 portions of EtOAc, dried over Na₂SO₄, filtered, concentrated, and purified by column chromatography (heptane/EtOAc, 1:1) to give the title compound (0.28 g, 51%) as a white solid. MS (ISN) 353.1 [(M–H)⁻], 355.1 [(M+2–H)⁻].

Example B.16

5-Bromo-pyridine-3-sulfonic acid (2-hydroxy-1-methyl-ethyl)-amide

Prepared by general procedure III from 5-bromo-pyridine-3-sulfonyl chloride (1.2 g, 5 mmol) and (D, L)-2-amino-1-propanol (387 mg, 5 mmol) with Et3N (0.72 mL, 5 mmol) to give the title compound (1.00 g, 72%) as an off-white solid. MS (ISP) 294.9[(M+H)⁺], 97.1[(M+2+H)⁺].

Example B.17

5-Bromo-N-(2-hydroxy-ethyl)-2-methyl-benzenesulfonamide

Prepared by general procedure III from 5-Bromo-2-methyl-benzenesulfonyl chloride (1.6 g, 6 mmol, synthesized according to *J. Am. Chem. Soc.,* 1940, 62, 511-514) and ethanolamine (1.0 mL, 17 mmol) to give the title compound (1.02 g, 58%) as a pale-yellow solid. MS (ISP) 294.1[(M+H)⁺], 296.2[(M+2+H)⁺].

Example B.18

5-Bromo-2-methyl-benzenesulfonamide

Prepared by general procedure III from 5-Bromo-2-methyl-benzenesulfonyl chloride (1.89 g, 7 mmol) and ammonium hydroxide (20 mL) to give the title compound (0.96 g, 55%) as a white solid. MS (ISN) 248.0[(M–H)⁻], 250.0[(M+2–H)⁻].

Example B.19

3-Bromo-5-methanesulfonyl-pyridine

Step 1) 3-Bromo-5-methanesulfanyl-pyridine

A solution of 3,5-dibromopyridine (10.0 g, 41 mmol) in DMF was treated with sodium methanethiolate (3.54 g, 46 mmol) at ambient temperature under Argon for 18 h. The reaction mixture was partitioned between water and EtOAc, washed organic layer with sat. NaCl soln., dried over MgSO4, filtered and concentrated to give 3-Bromo-5-methanesulfanyl-pyridine (8.80 g, 95% yield, 91% pure) as a colorless liquid. MS (ISP) 204.0 [(M+H)⁺], 206.0[(M+-2+H)⁺].

Step 2) 3-Bromo-5-methanesulfonyl-pyridine

To a solution of 3-bromo-5-methanesulfanyl-pyridine (8.80 g, 43 mmol) in CH₂Cl₂ was treated slowly portionwise with 3-chloroperbenzoic acid (21.26 g, 86 mmol) at rt (exothermic reaction). The reaction mixture was stirred for 30 minutes at rt under Argon, then diluted with an additional portion of CH₂Cl₂ and washed with 1N NaOH solution. The aqueous layer was extracted with 3 portions of CH₂Cl₂ and the combined layers were dried over MgSO4, filtered and concentrated to give the title compound (4.75 g, 47%) as a white solid. MS (ISP) 236.1[(M+H)⁺], 237.9[(M+2+H)⁺].

Example B.20

3-Bromo-N-(2-morpholin-4-yl-ethyl)-benzenesulfonamide

Prepared by general procedure III from 3-Bromobenzenesulfonyl chloride (5.0 g, 20 mmol) and 4-(2-Aminoethyl)-morpholine (2.80 mL, 22 mmol) to give the title compound (6.34 g, 93%) as a white solid. MS (ISN) 347.1[(M–H)⁻], 349.3[(M+2–H)⁻].

Example B.21

3-Bromo-N-(2-cyano-ethyl)-benzenesulfonamide

Prepared by general procedure III from 3-Bromobenzenesulfonyl chloride (10.0 g, 38 mmol) and 3-aminopropanonitrile (2.96 g, 42 mmol) to give the title compound (6.14 g, 55%) of an off-white solid. MS (ISP) 308.1 [(M+NH₄)⁺].

Example B.22

2-Chloro-4-methyl-thiazole-5-sulfonic acid (2-hydroxy-1,1-dimethyl-ethyl)-amide

Step 1) Thiocyanato-propan-2-one was prepared according to *Tet. Let.,* 2003, 44, 4393. To a solution of chloroacetone (19.5 g, 200 mmol) in EtOH (200 mL) was added solid sodium thiocyanate (19.5 g, 240 mmol). The reaction mixture was stirred at 23° C. for 2.5 days. The precipitate was filtered off, washed with EtOH, and the filtrate was evaporated to remove all EtOH. The remaining brown liquid was diluted with TBME (ca. 250 mL), the precipitate was filtered off, evaporated to dryness, taken up in TBME again, filtered some more precipitate off and evaporated to dryness to give thiocyanato-propan-2-one (22.16 g, 96%) as a brown liquid. MS (EI) 115[(M+H)$^+$].

Step 2) 2-Chloro-4-methyl-thiazole was prepared according to patent EP 1 216 997 A2 To a solution of thiocyanato-propan-2-one (22.8 g, 198 mmol) in $CH_2Cl_2$ (600 mL) at 10° C. was bubbled HCl-gas for 20 min. The icebath was removed, and the reaction mixture was allowed to warm to rt, stirred overnight at rt. The reaction mixture was neutralized by careful addition of $NaHCO_3$-solution, extracted twice with $CH_2Cl_2$, dried over $Na_2SO_4$, filtered, and concentrated to give 2-chloro-4-methyl-thiazole (33 g, 73% pure, 91% yield) as a brown liquid.

Step 3) 2-Chloro-4-methyl-thiazole-5-sulfonyl chloride prepared according to patent DE 100 44 328 A1.

2-Chloro-4-methyl-thiazole (33 g, 180 mmol) was added dropwise to a solution of thionyl chloride (32.7 mL, 451 mmol) and chlorosulfonic acid (60.2 mL, 902 mmol). The reaction mixture was stirred for 48 h at 120° C., cooled then poured onto ice-water and extracted 3 times with $CH_2Cl_2$, dried over $Na_2SO_4$, filtered, and concentrated to give a crude liquid. The product was isolated by simple distillation (17 mbar at 85-95° C.) to give 2-Chloro-4-methyl-thiazole-5-sulfonyl chloride (17.85 g, 43%) as a light-yellow liquid. MS (ISP) 233.0[(M+H)$^+$].

Step 4) 2-Chloro-4-methyl-thiazole-5-sulfonic acid (2-hydroxy-1,1-dimethyl-ethyl)-amide Prepared by general procedure III from 2-Chloro-4-methyl-thiazole-5-sulfonyl chloride (1.0 g, 4 mmol,) and 2-amino-2-N-methyl-1-propanol (384 mg, 4 mmol) to give the title compound (0.37 g, 30%) as an off-white solid. MS (ISP) 285 [(M+H)$^+$], 287[(M+2+H)$^+$].

Example B.23

2-Chloro-4-methyl-thiazole-5-sulfonic acid amide

Prepared by general procedure III from 2-Chloro-4-methyl-thiazole-5-sulfonyl chloride (1.0 g, 4 mmol,) and ammonium hydroxide (0.32 mL, 4 mmol) to give 2-Chloro-4-methyl-thiazole-5-sulfonic acid amide (0.75 g, 81%) as a white solid. MS (ISP) 213.0 [(M+H)$^{+1,}$ 215.1[(M+2+H)$^+$].

Example B.24

5-Chloro-thiophene-2-sulfonic acid (2-hydroxy-1,1-dimethyl-ethyl)-amide

Prepared by general procedure III from commercially available 5-chloro-thiophene-2-sulfonyl chloride (1.0 g, 4.61 mmol) and 2-amino-2-methyl-1-propanol (1.23 g, 13.8 mmol) to give the title compound (0.96 g, 77%) as a white solid. MS (ISN) 268.1 [(M−H)$^−$], mp 112° C.

Example B.25

4-Bromo-N,N-dimethyl-benzenesulfonamide

Prepared by general procedure III from 4-bromobenzenesulfonyl chloride (9.59 g, 38 mmol) and excess aq. dimethylamine to give the title compound (7.61 g, 77%) as a white crystalline solid. MS (ISP) 266.1[(M+H)$^+$].

Example B.26

4-(4-Bromo-benzenesulfonyl)-morpholine

Prepared by general procedure III from 4-bromobenzenesulfonyl chloride (5.0 g, 20 mmol) and morpholine (1.88 g, 22 mmol) to give the title compound (5.90 g, 98%) as a white crystalline solid. MS (ISP) 306.1[(M+H)$^+$].

Example B.27

4-Bromo-N-methyl-benzenesulfonamide

Prepared by general procedure III from 4-bromobenzenesulfonyl chloride (5.0 g, 20 mmol) and a 2M solution of methylamine in EtOH (10.8 mL, 22 mmol) to give the title compound (3.1 g, 63%) as an off-white crystalline solid. MS (ISP) 267.1[(M+H)$^+$].

Example B.28

4-Bromo-N-(2-methoxy-ethyl)-benzenesulfonamide

Prepared by general procedure III from 4-bromobenzenesulfonyl chloride (5.0 g, 20 mmol) and 2-methoxyethyl amine (1.62 g, 22 mmol) to give the title compound (5.5 g, 95%) as an off-white crystalline solid. MS (ISP) 294.1[(M+H)$^+$].

Example B.29

4-Bromo-N-(2-hydroxy-ethyl)-benzenesulfonamide

Prepared by general procedure III from 4-bromobenzenesulfonyl chloride (5.0 g, 20 mmol) and ethanolamine (1.32 g, 22 mmol) to give the title compound (5.4 g, 98%) as an off-white solid. MS (ISP) 280.0[(M+H)$^+$].

Example B.30

4-Bromo-N-(2-dimethylamino-ethyl)-benzenesulfonamide

Prepared by general procedure III from 4-bromobenzenesulfonyl chloride (5.0 g, 20 mmol) and dimethyl-ethylenediamine (1.89 g, 22 mmol) to give the title compound (5.9 g, 98%) as an off-white solid. MS (ISP) 307.2[(M+H)$^+$].

Example B.31

4-(3-Bromo-benzenesulfonyl)-morpholine

Prepared by general procedure III from 3-bromobenzenesulfonyl chloride (5.0 g, 20 mmol) and morpholine (1.89 g, 22 mmol) to give the title compound (5.9 g, 98%) as a white solid. MS (ISP) 306.1[(M+H)$^+$].

Example B.32

3-Bromo-N-methyl-benzenesulfonamide

Prepared by general procedure III from 3-bromobenzenesulfonyl chloride (5.0 g, 20 mmol) and 2M solution of methylamine in EtOH (10.8 mL, 22 mmol) to give the title compound (4.3 g, 88%) as a white solid. MS (ISP) 250.0[(M+H)$^+$].

Example B.33

3-Bromo-N-(2-methoxy-ethyl)-benzenesulfonamide

Prepared by general procedure III from 3-bromobenzenesulfonyl chloride (5.0 g, 20 mmol) and 2-methoxyethyl amine (1.62 g, 22 mmol) to give the title compound (5.7 g, 99%) as light-yellow liquid. MS (ISP) 294.0[(M+H)$^+$].

Example B.34

3-Bromo-N-(2-hydroxy-ethyl)-benzenesulfonamide

Prepared by general procedure III from 3-bromobenzenesulfonyl chloride (5.0 g, 20 mmol) and ethanolamine (1.32 g, 22 mmol) to give the title compound (5.45 g, 99%) as a white solid. MS (ISP) 280.0[(M+H)$^+$].

Example B.35

3-Bromo-N-(2-dimethylamino-ethyl)-benzenesulfonamide

Prepared by general procedure III from 3-bromobenzenesulfonyl chloride (5.0 g, 20 mmol) and dimethyl-ethylenediamine (1.90 g, 22 mmol) to give the title compound (6.0 g, 99%) as a white solid. MS (ISP) 307.2[(M+H)$^+$].

Example B.36

5-Bromo-N-(2-dimethylamino-ethyl)-2,4-difluorobenzenesulfonamide

Prepared by general procedure III from 5-bromo-2,4-difluorobenzene sulfonyl chloride (1.0 g, 3.4 mmol) and N,N-Dimethylethylenediamine (333 mg, 3.77 mmol) to give the title compound (1.18 g, 100%) as an off-white solid. MS (ISP) 344.9[(M+H)$^+$].

Example B.37

5-Bromo-2,4-difluoro-N-(2-hydroxy-ethyl)-benzenesulfonamide

Prepared by general procedure III from 5-bromo-2,4-difluorobenzene sulfonyl chloride (1.0 g, 3.4 mmol) and ethanolamine (231 mg, 3.77 mmol) to give the title compound (1.06 g, 100%) as an off-white solid. MS (ISP) 315.8[(M+H)$^+$].

Example B.38

5-Chloro-thiophene-2-sulfonic acid (2-morpholin-4-yl-ethyl)-amide

To a stirred solution of 4-(2-aminoethyl)-morpholine (1.80 g, 13.8 mmol) in THF (20 mL) was added at 0° C. (ice water bath) commercially available 5-chloro-thiophene-2-sulfonyl chloride (1.0 g, 4.61 mmol) and triethylamine (0.71 mL, 5.07 mmol). The reaction mixture was stirred at room temperature for 16 h and evaporated. The crude product was further purified by flash chromatography (ethyl acetate/heptane) to yield the title compound (1.34 g, 93%) as a colorless oil. MS (ISN) 309.0 [(M−H)$^−$].

Example B.39

5-Chloro-thiophene-2-sulfonic acid (2-dimethylamino-ethyl)-amide

To a stirred solution of 2-dimethylamino-ethylamine (1.61 g, 13.8 mmol) in THF (20 mL) was added at 0° C. (ice water bath) commercially available 5-chloro-thiophene-2-sulfonyl chloride (1.0 g, 4.61 mmol) and triethylamine (0.71 mL, 5.07 mmol). The reaction mixture was stirred at room temperature for 16 h and evaporated. The crude product was further purified by flash chromatography (ethyl acetate/MeOH) to yield the title compound (1.23 g, 99%) as a light yellow oil. MS (ISP) 269.0 [(M+H)$^+$].

Example B.40

5-Chloro-thiophene-2-sulfonic acid bis-(2-hydroxy-ethyl)-amide

To a stirred solution of diethanolamine (1.45 g, 13.8 mmol) in THF (20 mL) was added at 0° C. (ice water bath) commercially available 5-chloro-thiophene-2-sulfonyl chloride (1.0 g, 4.61 mmol) and triethylamine (0.71 mL, 5.07 mmol). The reaction mixture was stirred at room temperature for 16 h and evaporated. The crude product was further purified by flash chromatography (ethyl acetate/heptane) to yield the title compound (1.15 g, 88%) as a white solid. MS (ISN) 284.3 [(M−H)$^−$], mp 69° C.

Example B.41

1-(5-Chloro-thiophene-2-sulfonyl)-4-methyl-piperazine hydrochloride

To a stirred solution of commercially available 5-chloro-thiophene-2-sulfonyl chloride (1.0 g, 4.61 mmol) in pyridine (10 mL) was added at room temperature commercially available 1-methylpiperazine (0.46 g, 4.61 mmol). The reaction mixture was stirred at room temperature for 1 h and evaporated. The crude product was further purified by flash chromatography (ethyl acetate/methanol) to yield the title compound (0.92 g, 63%) as an off-white solid. MS (ISP) 280.9 [(M+H)$^+$], mp 242° C.

Example B.42

5-Chloro-thiophene-2-sulfonic acid (2-hydroxy-1-hydroxymethyl-ethyl)-amide

To a stirred solution of 2-amino-1,3-propanediol (1.26 g, 13.8 mmol) in THF (20 mL) was added at 0° C. (ice water bath) commercially available 5-chloro-thiophene-2-sulfonyl chloride (1.0 g, 4.61 mmol) and triethylamine (0.71 mL, 5.07 mmol). The reaction mixture was stirred at room temperature for 16 h and evaporated. The crude product was further purified by flash chromatography (ethyl acetate/heptane) to yield the title compound (0.96 g, 77%) as an off-white solid. MS (ISP) 272.2 [(M+H)$^+$], mp 101° C.

Example B.43

[2-(5-Bromo-2,4-difluoro-benzenesulfonylamino)-ethyl]-carbamic Acid Tert-butyl Ester To a stirred solution of commercially available tert-butyl N-2(aminoethyl)carbamate (605 mg, 3.77 mmol) with Et$_3$N (0.53 mL, 3.77 mmol) in THF (40 mL) at 0° C. was portionwise added commercially available 5-bromo-2,4-difluorobenzene sulfonyl chloride (1.0 g, 3.4 mmol). The ice bath was removed and the reaction was allowed to reach 23° C. The reaction mixture was extracted twice with EtOAc and water, the organic layers were washed with brine and dried over MgSO4, filtered and evaporated to obtain the product as an off-white solid (1.43 g, 100%). MS (ISP) 314.9 [(M+H-Boc)$^+$].

Example B.44

5-Bromo-pyridin-3-ylamine

To a solution of NaOH (22.9 g, 572 mmol) in water (245 mL) at 0-5° C. (ice salt bath) was added bromine (9.44 mL, 184 mmol) maintaining the temperature at 0-5° C., to produce a sodium hypobromite solution. To this NaOBr-sol. was added commercially available 3-bromonicotinamide (30.15 g, 150 mmol) all at once with vigorous stirring. After being stirred for 15 min, the solution is clear and mixture was heated to 70-75° C. for 45 min. Cooled to 23° C., saturated with solid NaCl, extracted with TBME/THF (3×300 mL), dried over Na$_2$SO$_4$. Removal of the solvent in vacuum gave a dark brown oil which was purified by silica gel column chromatography with heptane/EtOAc 1:1→2:3 to give the title compound as a brown solid (16.036 g, 62%). MS (ISP) 173.1 [(M+H)$^+$], 175.2 [(M+2+H)$^+$].

Example B.45

(5-Bromo-pyridin-2-yl)-methyl-amine

A solution of 5-bromo-2-fluoropyridine (2.5 g, 14 mmol) in THF (50 mL) was stirred with a solution of methylamine in THF (c=2 mol/L) (35 mL, 70 mmol) at 23° C. for 16 h. Water was added and the mixture was extracted with ether, the organic layer was dried over Na$_2$SO$_4$. Removal of the solvent in vacuum left a residue which was purified by silica gel column chromatography with heptane/ether, followed by trituration with heptane to give the title compound as a white solid (630 mg, 24%). MS (ISP) 187.1 [(M+H)$^+$], 189.2 [(M+2+H)$^+$].

Example B.46

2-(5-Bromo-pyridin-2-ylamino)-ethanol

Prepared from 5-bromo-2-fluoropyridine (2.5 g, 14 mmol) and ethanolamine (4.34 g, 70 mmol) as described in example B.45. Obtained as a colorless oil (400 mg, 13%). MS (ISP) 217.2 [(M+H)$^+$], 219.1 [(M+2+H)$^+$].

Example B.47

-Bromo-pyridine-2-carboxylic Acid Amide

To a cooled solution (0° C.) of commercially available 5-bromopyridine-2-carboxylic acid (1 g, 5 mmol) in THF (20 mL) and DMF (1 mL) was dropwise added thionylchloride (0.54 mL, 7 mmol), removed the icebath and stirred at 23° C. for 1 h. Cooled to 0° C., dropwise added of an excess of 25% aqueous ammoniumhydroxid solution (3.7 mL, 50 mmol) and stirred at 0° C. for 30 min. Filtered the precipitated solid off and dissolved in AcOEt, washed the AcOEt-layer once with brine, dried over Na$_2$SO$_4$. Removal of the solvent in vacuum left a white solid, which was triturated with heptane and dried in HV to give the title compound as a white solid (500 mg, 50%). MS (ISP) 201.1 [(M+H)$^+$], 203.1 [(M+2+H)$^+$].

Example B.48

5-Iodo-3-trifluoromethyl-pyridin-2-ylamine

A mixture of 5-bromo-3-trifluoromethyl-pyridin-2-ylamine (example C.18 step 3) (723 mg, 3 mmol), sodium iodide (900 mg, 6 mmol), copper (I) iodide (29 mg, 5 mol %) and N,N'-dimethylethylendiamine (26 mg, 10 mol %) in n-butanol (6 mL) was stirred at reflux under argon atmosphere for 18 h. The reaction mixture was cooled to 23° C., extracted with ethyl acetate and water, the organic layers were dried over MgSO$_4$, filtered and evaporated to leave the title compound as a brown solid (880 mg, 102%), which was used without further purification. MS (ISN) 287.0 [(M−H)$^−$].

Example B.49

5-Bromo-thiophene-2-sulfonic acid (2-dimethylamino-ethyl)-amide

To a stirred solution of commercially available 5-bromo-thiophene-2-sulfonyl chloride (3.0 g, 11.5 mmol) in THF (22 ml) was added at room temperature triethylamine (1.76 ml, 12.6 mmol), the mixture was cooled (ice-water) and a solution of commercially available N,N-dimethyl-ethylenediamine (3.76 ml, 34.4 mmol) in THF (22 ml) was added drop wise. The reaction mixture was stirred at room temperature for 16 h and evaporated. The crude product was further purified by column chromatography (dichloromethane/methanol/NH$_4$OH 16:1:0.1) to yield the title compound (3.49 g, 97%) as a light yellow oil. MS (ISN) 310.9 [(M−H)$^−$].

Example B.50

1-(5-Bromo-thiophene-2-sulfonyl)-4-methyl-piperazine

To a stirred solution of commercially available 5-bromo-thiophene-2-sulfonyl chloride (3.0 g, 11.5 mmol) in THF (22 ml) was added at room temperature triethylamine (1.76 ml, 12.6 mmol), the mixture was cooled (ice-water), and a solution of commercially available 1-methylpiperazine (3.82 ml, 34.4 mmol) in THF (22 ml) was added drop wise. The reaction mixture was stirred at room temperature for 16 h and evaporated. The crude product was further purified by flash chromatography (dichloromethane/methanol) and subsequent crystallization from dichloromethane/hexane to yield the title compound (3.12 g, 84%) as a white solid. MS (ISP) 324.8 [(M+H)$^+$], mp 122° C.

Example B.51

[2-(5-Bromo-thiophene-2-sulfonylamino)-ethyl]-carbamic Acid Tert-butyl Ester

To a stirred solution of commercially available 5-bromo-thiophene-2-sulfonyl chloride (1.0 g, 3.82 mmol) in THF (8 ml) was added at room temperature triethylamine (0.59 ml, 4.21 mmol), the mixture was cooled (ice-water) and a solution of commercially available N-BOC-ethylenediamine (1.82 ml, 11.5 mmol) in THF (8 ml) was added drop wise. The reaction mixture was stirred at room temperature for 16 h and evaporated. The crude product was further purified by flash chromatography (ethyl acetate/heptane) and subsequent crystallization from dichloromethane/hexane to yield the title compound (1.41 g, 96%) as a white solid. MS (ISN) 383.0 [(M−H)⁻], mp 106° C.

Example B.52

4-(5-Bromo-thiophene-2-sulfonyl)-piperazine-1-carboxylic Acid Tert-butyl Ester

To a stirred solution of commercially available 5-bromo-thiophene-2-sulfonyl chloride (1.0 g, 3.82 mmol) in THF (8 ml) was added at room temperature triethylamine (0.59 ml, 4.21 mmol), the mixture was cooled (ice-water) and a solution of commercially available 1-BOC-piperazine (2.14 g, 11.5 mmol) in THF (8 ml) was added drop wise. The reaction mixture was stirred at room temperature for 16 h and evaporated. The crude product was further purified by flash chromatography (ethyl acetate/heptane) and subsequent crystallization from dichloromethane/hexane to yield the title compound (1.35 g, 86%) as a white solid. MS (ISP) 413.2 [(M+H)⁺], mp 127° C.

Example B.53

5-Bromo-thiophene-2-sulfonic acid bis-(2-hydroxy-ethyl)-amide

To a stirred solution of diethanolamine (1.45 g, 13.8 mmol) in THF (20 ml) was added at 0° C. (ice water bath) commercially available 5-bromo-thiophene-2-sulfonyl chloride (1.0 g, 3.82 mmol) and triethylamine (0.71 ml, 5.07 mmol). The reaction mixture was stirred at room temperature for 16 h and evaporated. The crude product was further purified by flash chromatography (ethyl acetate/heptane) to yield the title compound (0.98 g, 77%) as a white solid. MS (ISP) 330.0 [(M+H)⁺], mp 70° C.

Example B.54

5-Bromo-thiophene-2-sulfonic acid (2-hydroxy-1-hydroxymethyl-ethyl)-amide

To a stirred solution of 2-amino-1,3-propanediol (1.26 g, 13.8 mmol) in THF (20 ml) was added at 0° C. (ice water bath) commercially available 5-bromo-thiophene-2-sulfonyl chloride (1.0 g, 3.82 mmol) and triethylamine (0.71 ml, 5.07 mmol). The reaction mixture was stirred at room temperature for 16 h and evaporated. The crude product was further purified by flash chromatography (ethyl acetate/heptane) to yield the title compound (0.87 g, 72%) as a white solid. MS (ISN) 313.9 [(M−H)⁻], mp 80° C.

Example B.55

5-Bromo-thiophene-2-sulfonic acid (pyridin-4-ylmethyl)-amide

To a stirred solution of 4-aminomethyl-pyridine (1.24 g, 11.5 mmol) in THF (8 ml) was added at 0° C. (ice water bath) commercially available 5-bromo-thiophene-2-sulfonyl chloride (1.0 g, 3.82 mmol) dissolved in THF (8 ml) and triethylamine (0.59 ml, 4.21 mmol). The reaction mixture was stirred at room temperature for 16 h and evaporated. The crude product was further purified by flash chromatography (dichloromethane/methanol) and crystallization from dichloromethane/hexane to yield the title compound (1.21 g, 95%) as a white solid. MS (ISN) 330.8 [(M−H)⁻], mp 159° C.

Example B.56

5-Bromo-thiophene-2-sulfonic acid (pyridin-3-ylmethyl)-amide

To a stirred solution of 3-aminomethyl-pyridine (1.24 g, 11.5 mmol) in THF (8 ml) was added at 0° C. (ice water bath) commercially available 5-bromo-thiophene-2-sulfonyl chloride (1.0 g, 3.82 mmol) dissolved in THF (8 ml) and triethylamine (0.59 ml, 4.21 mmol). The reaction mixture was stirred at room temperature for 16 h and evaporated. The crude product was further purified by flash chromatography (dichloromethane/methanol) and crystallization from dichloromethane/hexane to yield the title compound (1.23 g, 97%) as a white solid. MS (ISN) 331.0 [(M−H)⁻], mp 125° C.

Example B.57

5-Bromo-thiophene-2-sulfonic acid pyridin-4-ylamide

A mixture of 5-bromo-thiophene-2sulphonyl chloride (1.31 g, 5.0 mmol), 4-dimethylamino-pyridine (0.61 g, 5.0 mmol) and 4-amino-pyridine (0.71 g, 7.5 mmol) in pyridine (20 ml) was stirred at 50° C. for 16 h. THE reaction mixture was evaporated and diluted with dichloromethane/MeOH/NH₄OH 80:10:1. The formed precipitate was collected by filtration to yield the title compound (1.53 g, 96%) as an off-white solid, which was used without further purification. MS (ISN) 317.0 [(M−H)⁻], mp 310° C.

Example B.58

5-Bromo-thiophene-2-sulfonic acid (2,6-dimethyl-pyridin-4-ylmethyl)-amide

To a stirred solution of commercially available 4-aminomethyl-2,6-dimethyl-pyridine [CAS-No. 324571-98-4] (0.24 g, 1.76 mmol) in THF (8 ml) was added at 0° C. (ice water bath) commercially available 5-bromo-thiophene-2-sulfonyl chloride (0.46 g, 1.76 mmol) dissolved in THF (8 ml) and triethylamine (0.27 ml, 1.94 mmol). The reaction mixture was stirred at room temperature for 16 h and evaporated. The crude product was further purified by flash chromatography (ethyl acetate/heptane) and crystallization from dichloromethane/hexane to yield the title compound (0.33 g, 52%) as a light red solid. MS (ISN) 359.0 [(M−H)⁻], mp 138° C.

Example B.59

5-Bromo-thiophene-2-sulfonic acid (2-hydroxy-ethyl)-amide

A mixture of 5-bromo-thiophene-2-sulfonyl chloride (1.5 g, 4. mmol) and ethanolamine (0.72 mL, 12 mmol) in dichloromethane (8 mL)/sat. NaHCO₃ solution (8 mL) was stirred at 20° C. for 28 h. The mixture was partitioned between AcOEt (50 mL) and H₂O (150 mL). The organic layer was dried (Na₂SO₄) and evaporated to give the title compound (1.07 g, 93%) as a pale-yellow oil. MS (ISP) 284.0 [(M−H)⁻].

Example B.60

5-Bromo-thiophene-2-sulfonic acid (2-pyridin-4-yl-ethyl)-amide

By applying in analogous manner the procedures described in example B.59, but ethanolamine is replaced by 4-(2-aminoethyl)pyridine. Pale-yellow solid. MS (ISP) 349.3 [(M+H)$^+$]; mp 133-134° C.

Synthesis of Intermediates Compounds of Formulae VIII, XXVI and XXXIV

Some of the intermediates compounds, e.g. the 4,4,4-trifluoro-1-(aryl)-butane-1,3-dione derivatives which can be used according to the general procedure I are commercially available. However some of said intermediates have been prepared from acetophenones according to the procedures as outlined hereafter and unless otherwise specified, these compounds are novel.

Example C.1

3-Ethynyl-7-trifluoromethyl-5-(4-trifluoromethyl-phenyl)-pyrazolo[1,5-a]pyrimidine Method 1:

Step 1) 4,4,4-Trifluoro-1-(4-trifluoromethyl-phenyl)-butane-1,3-dione

To a stirred solution of ethyl trifluoroacetate (69.8 mL, 585 mmol) in tert-butyl-methyl-ether (304 mL) was added at room temperature a 5.4 M solution of sodium methanolate in methanol (116.1 mL, 627 mmol) followed by a solution of commercially available 4-trifluoromethyl-acetophenone (100.0 g, 531 mmol) in tert-butyl-methyl-ether (76 mL). The reaction mixture was stirred at room temperature for 2 h, poured into ice/water (500 mL), acidified with 1 N HCl until pH 1 was achieved, and extracted with tert-butyl-methyl-ether (2×200 mL). The combined organic layers were washed with brine (2×50 mL), dried (Na$_2$SO$_4$) and evaporated to give crude 4,4,4-trifluoro-1-(4-trifluoromethyl-phenyl)-butane-1,3-dione (153.05 g, 101%) as a yellow liquid, which was used without further purification.

Step 2a) 3-Bromo-7-trifluoromethyl-5-(4-trifluoromethyl-phenyl)-pyrazolo[1,5-a]pyrimidine A stirred mixture of commercially available 3-amino-4-bromo-pyrazole (14.00 g, 86.4 mmol) and 4,4,4-trifluoro-1-(4-trifluoromethyl-phenyl)-butane-1,3-dione (Example C.1 step 1) (24.56 g, 86.4 mmol) in acetic acid (170 mL) was heated under reflux conditions for 2.5 h. The reaction mixture was cooled to room temperature, diluted with water (340 mL), the precipitate was filtered off, washed with water and dried in air at 60° C. to give the 3-bromo-7-trifluoromethyl-5-(4-trifluoromethyl-phenyl)-pyrazolo[1,5-a]pyrimidine (31.77 g, 90%) as a yellow solid. MS (EI) 410.0 [(M)$^+$], 412.0 [(M+2)$^+$]; mp 136° C.

Step 3a) 7-Trifluoromethyl-5-(4-trifluoromethyl-phenyl)-3-trimethylsilanylethynyl-pyrazolo[1,5-a]-pyrimidine A mixture of 3-bromo-7-trifluoromethyl-5-(4-trifluoromethyl-phenyl)-pyrazolo[1,5-a]pyrimidine (Example C.1 step 2a) (12.30 g, 30 mmol), trimethylsilylacetylene (8.3 mL, 60 mmol) and Et$_3$N (6.3 mL, 45 mmol) in THF (30 mL) was stirred for 10 min at 23° C. while being purged with Argon, then PdCl$_2$(PPh$_3$)$_2$ (105 mg, 0.5 mol %), PPh$_3$ (20 mg, 0.25 mol %) and CuI (17 mg, 0.3 mol %) were added. Stirring was continued at 75° C. for 38 h. After 22 h, trimethylsilylacetylene (2.1 mL) and Et$_3$N (2.1 mL) was added. Cooled to 23° C., diluted with ethyl acetate (100 mL), filtered through celite, washed with ethyl acetate. Removal of the solvent in vacuum left the 7-trifluoromethyl-5-(4-trifluoromethyl-phenyl)-3-trimethylsilanylethynyl-pyrazolo[1,5-a]-pyrimidine (13.65 g, 106%) as an orange solid, which can directly be used in the subsequent step. An analytical sample was obtained by silica gel column chromatography with heptane/EtOAc. MS (ISP) 427.0 [(M)$^+$]; mp 136° C.

Step 3b) 3-Ethynyl-7-trifluoromethyl-5-(4-trifluoromethyl-phenyl)-pyrazolo[115-a]pyrimidine To a solution of 7-trifluoromethyl-5-(4-trifluoromethyl-phenyl)-3-trimethylsilanylethynyl-pyrazolo[1,5-a]-pyrimidine (Example C.1 step 3a) (13.65 g, ca. 26 mmol) in THF (40 mL) and MeOH (100 mL) at 0° C. was added K$_2$CO$_3$ (362 mg, 10 mol %), and the mixture was stirred at 0° C. for 6 h. Diluted with TBME and ice water, separated phases, washed organic layer with brine, dried over Na$_2$SO$_4$. Removal of the solvent in vacuum left a dark brown solid, which was purified by silica gel column chromatography with heptane/EtOAc 9:1 followed by trituration with heptane to give the 3-ethynyl-7-trifluoromethyl-5-(4-trifluoromethyl-phenyl)-pyrazolo[-1,5-a]pyrimidine (7.90 g, 89%) as a yellow solid. MS (ISP) 356.0 [(M+H)$^+$]; mp 138° C.

Method 2:

Step 1) 7-Trifluoromethyl-5-(4-trifluoromethyl-phenyl)-pyrazolo[1,5-a]pyrimidine A mixture of 4,4,4-trifluoro-1-(4-trifluoromethyl-phenyl)-butane-1,3-dione (Example C.1, method 1, step 1) (2.84 g, 10 mmol) and 3-aminopyrazole (0.83 g, 10 mmol) in acetic acid (20 mL) were refluxed for 4 h. The reaction mixture was cooled to rt and poured into ice water (200 mL), extracted with EtOAc, dried over MgSO$_4$, filtered and concentrated, and triturated with toluene, and dried to give 7-trifluoromethyl-5-(4-trifluoromethyl-phenyl)-pyrazolo[1,5-a]pyrimidine (3.28 g, 99%) as a yellow solid. MS (ISP) 332.1 [(M+H)$^+$]; mp 110-111° C.

Step 2) 3-Iodo-7-trifluoromethyl-5-(4-trifluoromethyl-phenyl)-pyrazolo[1,5-a]pyrimidine To a stirred solution of 7-trifluoromethyl-5-(4-trifluoromethyl-phenyl)-pyrazolo[1,5-a]pyrimidine (21.60 g, 65 mmol) in acetic acid (130 mL) containing anhydrous NaOAc (6.045 g, 74 mmol), was slowly added iodine monochloride (19.65 mL, 3.75M in HOAc). The reaction mixture was stirred at rt overnight. The suspension was diluted with water, the yellow crystalline filtrated, washed with water and dried in vacuum overnight to give 3-iodo-7-trifluoromethyl-5-(4-trifluoromethyl-phenyl)-pyrazolo[1,5-a]pyrimidine (31.1 g, 100%) as yellow crystalline solid. MS (ISP) 458.2 [(M+H)$^+$].

Step 3a) 7-Trifluoromethyl-5-(4-trifluoromethyl-phenyl)-3-trimethylsilanylethynyl-pyrazolo[1,5-a]-pyrimidine Prepared from 3-iodo-7-trifluoromethyl-5-(4-trifluoromethyl-phenyl)-pyrazolo[1,5-a]pyrimidine (87.5 g, 191 mmol) and trimethylsilylacetylene (54 mL, 390 mmol) as described in Example C.1, method 1, step 3a, to give the 7-trifluoromethyl-5-(4-trifluoromethyl-phenyl)-3-trimethylsilanylethynyl-pyrazolo[1,5-a]pyrimidine (82.71 g, 100%) as a yellow-orange solid.

Example C.2

7-Difluoromethyl-3-ethynyl-5-(4-trifluoromethyl-phenyl)-pyrazolo[1,5-a]pyrimidine

Step 1) 4,4-Difluoro-1-(4-trifluoromethyl-phenyl)-butane-1,3-dione

Prepared from commercially available ethyl difluoroacetate (14.49 g, 117 mmol) and commercially available 4-(trifluoromethyl)acetophenone (15.36 g, 80 mmol) as described in example C.1 step 1 to give 4,4-difluoro-1-(4-trifluoromethyl-phenyl)-butane-1,3-dione (21.60 g, 101%) as a light brown oil. MS (ISN) 265.0 [(M−H)$^-$].

Step 2a) 3-Bromo-7-difluoromethyl-5-(4-trifluoromethyl-phenyl)-pyrazolo[1,5-a]pyrimidine Prepared from 4,4-difluoro-1-(4-trifluoromethyl-phenyl)-butane-1,3-dione (example C.2 step 1) (21.40 g, 80 mmol) and commercially available 3-amino-4-bromopyrazole (13.29 g, 80 mmol) as described in example C.1, step 2a to give 3-bromo-7-difluoromethyl-5-(4-trifluoromethyl-phenyl)-pyrazolo[1,5-a]pyrimidine (29.14 g, 92%) as a yellow solid. MS (ISP) 392.0 [(M+H)$^+$], 394.0 [(M+2+H)$^+$].

Step 3a) 7-Difluoromethyl-5-(4-trifluoromethyl-phenyl)-3-trimethylsilanylethynyl-pyrazolo[1,5-a]-pyrimidine Prepared from 3-bromo-7-difluoromethyl-5-(4-trifluoromethyl-phenyl)-pyrazolo[1,5-a]pyrimidine (18.6 g, 45 mmol) and commercially available trimethylsilylacetylene (11.1 mL, 80 mmol) as described in example C.1, step 3a to give 7-difluoromethyl-5-(4-trifluoromethyl-phenyl)-3-trimethylsilanylethynyl-pyrazolo[1,5-a]pyrimidine (16.3 g, 99%) as an orange-solid. MS (ISP) 410.1[(M+H)$^+$].

Step 3b) 7-Difluoromethyl-3-ethynyl-5-(4-trifluoromethyl-phenyl)-pyrazolo[1,5-a]pyrimidine Prepared from 7-Difluoromethyl-5-(4-trifluoromethyl-phenyl)-3-trimethylsilanylethynyl-pyrazolo[1,5-a]-pyrimidine (18.6 g, 45 mmol) as described in example C.1, step 3b to give the title compound (13.37 g, 87%) as a yellow solid. MS (ISN) 336.3[(M−H)$^-$].

Example C.3

5-(3-Ethoxy-4-trifluoromethyl-phenyl)-3-ethynyl-7-trifluoromethyl-pyrazolo[1,5-a]pyrimidine

Step 1) 1-(3-Ethoxy-4-trifluoromethyl-phenyl)-4,4,4-trifluoro-butane-1,3-dione

Prepared from commercially available ethyl trifluoroacetate (7.15 g, 50 mmol) and 3-ethoxy-4-trifluoromethyl-acetophenone (example A.2) (8.00 g, 34 mmol) as described in example C.1 step 1 to give the 1-(3-ethoxy-4-trifluoromethyl-phenyl)-4,4,4-trifluoro-butane-1,3-dione (11.07 g, 98%) as a light brown solid. MS (ISN) 327.2 [(M−H)$^-$].

Step 2a) 3-Bromo-5-(3-ethoxy-4-trifluoromethyl-phenyl)-7-trifluoromethyl-pyrazolo[1.5-a]-pyrimidine Prepared from 1-(3-ethoxy-4-trifluoromethyl-phenyl)-4,4,4-trifluoro-butane-1,3-dione (example C.3 step 1) (8.00 g, 24 mmol) and commercially available 3-amino-4-bromopyrazole (4.03 g, 24 mmol) as described in example C.1 step 2a to give the 3-bromo-5-(3-ethoxy-4-trifluoromethyl-phenyl)-7-trifluoromethyl-pyrazolo[1,5-a]pyrimidine (10.12 g, 91%) as a yellow solid. MS (ISP) 454.0 [(M+H)$^+$] and 456.0 [(M+2+H)$^+$].

Step 3a) 5-(3-Ethoxy-4-trifluoromethyl-phenyl)-3-ethynyl-7-trifluoromethyl-pyrazolo[1,5-a]pyrimidine A mixture of 3-bromo-5-(3-ethoxy-4-trifluoromethyl-phenyl)-7-trifluoromethyl-pyrazolo[1,5-a]pyrimidine (7.43 g, 16 mmol; HPLC 4.700 min), trimethylsilylacetylene (2.72 mL, 20 mmol) and diisopropylamine (2.77 mL, 20 mmol) in dioxane (50 mL) was stirred for 10 min at 23° C. while being purged with Argon, then palladium (II) acetate (110 mg, 3 mol %), PPh$_3$ (257 mg, 6 mol %) and CuI (62 mg, 2 mol %) were added. Stirring was continued at rt overnight. All reagents were added again using the same amounts, argon was bubbled for 20 minutes through the solution and the reaction mixture was again stirred at 75° C. overnight. An additional 200 mg of PPh$_3$, 400 mg of PdCl$_2$(PPh$_3$)$_2$, 200 mg of CuI, 6 mL of Et$_3$N and 10 mL of trimethylsilylacetylene were added and stirred for 5 days at 75° C. The cooled reaction mixture was diluted with 200 mL of EtOAc, filtered through Celite, and concentrated to give the trimethylsilyl-adduct as a crude brown solid. This material (12.0 g, 34 mmol, purity: 64.5%) was dissolved in THF (30 mL) and treated with MeOH (75 mL) at 0° C. and added K$_2$CO$_3$ (227 mg, 10 mol %) and the mixture was stirred at 0° C. for 6 hours. The reaction mixture was diluted with TBME and ice water, separated, the organic layer washed with brine, dried over MgSO$_4$, filtered and evaporated to give a light brown solid. The crude product was purified by flash chromatography with n-heptane/EtOAc (100: 0 to 50: 50) to give 6.27 g (yield: 96%) of 5-(3-ethoxy-4-trifluoromethyl-phenyl)-3-ethynyl-7-trifluoromethyl-pyrazolo[1,5-a]pyrimidine as a light brown solid. MS (ISP) 400.2[(M+H)$^+$].

Example C.4

5-(4-Chloro-phenyl)-3-ethynyl-7-trifluoromethyl-pyrazolo[1,5-a]pyrimidine

Step 2a and 2b) 5-(4-Chloro-phenyl)-3-iodo-7-trifluoromethyl-pyrazolo[1,5-a]pyrimidine A mixture of commercially available 1-(4-chlorophenyl)-4,4,4-trifluoro-1,3-butanedione (8.65 g, 34.52 mmol) and commercially available 3-aminopyrazole (2.87 g, 34.52 mmol) in acetic acid (70 mL) was refluxed for 3 h (intermediate 5-(4-chloro-phenyl)-7-trifluoromethyl-pyrazolo[1,5-a]pyrimidine). Cooled to 23° C., added sodium acetate (3.54 g, 43.2 mmol) and a solution of iodine monochloride (2.11 mL, 41.4 mmol) in acetic acid (12 mL) was added dropwise, whereupon the reaction mixture solidified 2 min after complete addition. Added acetic acid (50 mL) and the mixture was stirred at 23° C. for additional 1 h. Diluted slowly with water (up to 400 mL), stirred at 23° C. for 30 min, the precipitate was filtered off, washed with water and dried in air at 50° C. to give a yellow solid, which was dissolved in EtOAc, washed with sat. NaHCO$_3$-sol. and sat. Na$_2$SO$_3$-sol. and brine, dried over Na$_2$SO$_4$. Removal of the solvent in vacuum gave 5-(4-chloro-phenyl)-3-iodo-7-trifluoromethyl-pyrazolo[1,5-a]pyrimidine as a yellow solid (14.30 g, 98%). MS (EI) 422.9 [(M)$^+$] and 425.0 [(M+2)$^+$]; mp 155° C.

Step 3a) 5-(4-Chloro-phenyl)-7-trifluoromethyl-3-trimethylsilanylethynyl-pyrazolo[1,5-a]pyrimidine A mixture of 5-(4-chloro-phenyl)-3-iodo-7-trifluoromethyl-pyrazolo[1,5-a]pyrimidine (example C.4 step 2a and 2b) (13.96 g, 32.96 mmol), trimethylsilylacetylene (5.5 mL, 39.72 mmol) and Et$_3$N (9.2 mL, 67.9 mmol) in dry DMF (33 mL) was stirred for 10 min at 23° C. while being purged with Argon, then PdCl$_2$(PPh$_3$)$_2$ (116 mg, 0.5 mol %), PPh$_3$ (43 mg, 0.5 mol %) and CuI (19 mg, 0.3 mol %) were added. Stirring was continued at 90° C. for 4 h. The react mixture was then cooled to 23° C., diluted with EtOAc, washed water (twice) and brine, dried over $Na_2SO_4$. Removal of the solvent left an orange solid (13.30 g, 102%). MS (ISP) 394.1 [(M+H)$^+$-] and 396.1 [(M+2+H)$^+$]; mp 198° C.

Step 3b) 5-(4-Chloro-phenyl)-3-ethynyl-7-trifluoromethyl-pyrazolo[1,5-a]pyrimidine To a solution of 5-(4-Chloro-phenyl)-7-trifluoromethyl-3-trimethylsilanylethynyl-pyrazolo[1,5-a]pyrimidine (13.3 g, 34 mmol) in THF (60 mL) and MeOH (150 mL) at 0° C. was added $K_2CO_3$ (467 mg, 10 mol %) and the mixture was stirred at 0° C. for 6 h, diluted with TBME and ice water, separated, washed with brine, dried over $Na_2SO_4$, concentrated and purified by column chromatography (heptane/EtOAc 100:0-90:10), triturated in heptane, filtered and dried to give the title compound (5.0 g, 45%) as an orange crystalline solid. MS (ISP) 322.2 [(M+H)$^+$] and 324.2 [(M+2+H)$^+$]; mp 102-103° C.

Example C.5

5-(4-Chloro-phenyl)-7-cyclopropyl-3-ethynyl-pyrazolo[1,5-a]pyrimidine

Step 1) 5-(4-Chloro-phenyl)-pyrazolo[5-a]pyrimidine-7-ol

A mixture of ethyl 3-(4-chloro-phenyl)-3-oxo-propionate (5.8 g, 26.0 mmol) and 2H-pyrazol-3-ylamine (2.1 g, 26.0 mmol) was stirred at 150° C. for 2 h. EtOAc (22 mL) was successively added to the cooled mixture and stirring was continued at 0° C. for 0.5 h. The crystals were isolated by filtration to give 5-(4-chloro-phenyl)-pyrazolo[1,5-a]pyrimidine-7-ol (4.80 g, 75%) as a white solid. MS (ISP) 246.1 [(M+H)$^+$]; mp 306-308° C.

Step 2) 7-Chloro-5-(4-chloro-phenyl)-pyrazolo[1,5-a]pyrimidine

A mixture of 5-(4-chloro-phenyl)-pyrazolo[1,5-a]pyrimidine-7-ol (4.8 g, 19.5 mmol), phosphorous oxychloride (7.2 mL, 78 mmol), and N,N-dimethylaniline (0.87 mL, 7.0 mmol) was stirred at 100° C. for 2 h. The mixture was evaporated in vacuo and the residue was partitioned between water and dichloromethane. The organic phase was washed with water, dried ($Na_2SO_4$), and evaporated in vacuo. The remaining solid was crystallized from EtOAc to give 7-chloro-5-(4-chloro-phenyl)-pyrazolo[1,5-a]pyrimidine (3.50 g, 66%) as a yellow solid; mp 151-153° C.

Step 3) 5-(4-Chloro-phenyl)-7-cyclopropyl-pyrazolo[1,5-a]pyrimidine

To a solution of 7-chloro-5-(4-chloro-phenyl)-pyrazolo[1,5-a]pyrimidine (2.1 g, 8.0 mmol) and tetrakis(triphenylphosphine)palladium (0.92 g, 0.8 mmol) in THF (14 mL) was added at 20° C. 0.25 M cyclopropylzinc chloride/THF suspension (ca. 128 mL, 32 mmol; freshly prepared by stirring a mixture of 64 mL of 0.5 M cyclopropylmagnesium bromide/THF and 64 mL of 0.5 M zinc chloride/THF for 1 h at 0° C., followed by 1 h at 20° C.) and the mixture was refluxed in an atmosphere of argon for 1.5 h. After the slow addition at 0° C. of saturated aqueous $NH_4Cl$ solution (20 mL), the mixture was partitioned between EtOAc and 10% sodium chloride solution. The organic layer was dried ($Na_2SO_4$) and evaporated in vacuo. The residue was chromatographed on silica gel using EtOAc/hexane (1:5 v/v) as eluent to give 5-(4-chloro-phenyl)-7-cyclopropyl-pyrazolo-[1,5-a]pyrimidine (1.50 g, 69%) as an off-white solid. MS (ISP) 270.4 [(M+H)$^+$]; mp 137-138° C.

Step 4) 5-(4-Chloro-phenyl)-7-cyclopropyl-3-iodo-pyrazolo[1,5-a]pyrimidine

A mixture of 5-(4-chloro-phenyl)-7-cyclopropyl-pyrazolo[1,5-a]pyrimidine (1.08 g, 4.0 mmol) and N-iodo-succinimide (0.90 g, 4.0 mmol) in N,N-dimethylformamide (8 mL) was stirred at 20° C. for 40 min. The heterogeneous mixture was partitioned between EtOAc and water. The organic layer was dried ($Na_2SO_4$) and evaporated in vacuo. The residue was triturated with diethyl ether to give 5-(4-chloro-phenyl)-7-cyclopropyl-3-iodo-pyrazolo[1,5-a]pyrimidine (1.45 g, 92%) as a yellow solid. MS (ISP) 395.8 [(M+H)$^+$]; mp 189-190° C.

Step 5) 5-(4-Chloro-phenyl)-7-cyclopropyl-3-ethynyl-pyrazolo[1,5-a]pyrimidine

A mixture of 5-(4-chloro-phenyl)-7-cyclopropyl-3-iodo-pyrazolo[1,5-a]pyrimidine (example C.5, step 4) (1.58 g, 4.0 mmol), trimethylsilylacetylene (0.78 mL, 6.0 mmol), and $Et_3N$ (12.0 mL, 45 mmol) in N,N-dimethylformamide (12 mL) was stirred for 10 min at 20° C. while being purged with Argon. Then, $PdCl_2(PPh_3)_2$ (56 mg, 2 mol %), $PPh_3$ (42 mg, 4 mol %) and CuI (15 mg, 4 mol %) were added and stirring was continued at 75° C. for 15 h in an atmosphere of argon. The mixture was cooled to 20° C. and partitioned between EtOAc and water. The organic layer was dried ($Na_2SO_4$) and evaporated in vacuo. The residue (2.2 g) was dissolved in a mixture of THF (8 mL) and MeOH (20 mL), potassium carbonate (0.11 g, 0.8 mmol) was added, and the solution was stirred for 2 h at 0° C. followed by 1 h at 20° C. The mixture was partitioned between EtOAc and 10% sodium chloride solution. The organic layer was dried ($Na_2SO_4$) and evaporated in vacuo. The residue was chromatographed on silica gel using EtOAc/cyclohexane (1:5 v/v) as eluent and crystallization from EtOAc/cyclohexane gave 5-(4-chloro-phenyl)-7-cyclopropyl-3-ethynyl-pyrazolo[1,5-a]pyrimidine (0.47 g, 40%) as a yellow solid; mp 181-182° C.

Example C.6

5-(4-Chloro-phenyl)-3-ethynyl-pyrazolo[1,5-a]pyrimidine

Step 1) 5-(4-Chloro-phenyl)-pyrazolo[1,5-a]pyrimidine

A mixture of 7-chloro-5-(4-chloro-phenyl)-pyrazolo[1,5-a]pyrimidine (example C.5, step 2) (1.06 g, 4.0 mmol), triethylamine (0.84 mL), and 5% Pd-C (0.1 g) in EtOH (40 mL) was stirred in an atmosphere of hydrogen for 1.5 h. The catalyst was filtered off, the solution was evaporated in vacuo and the residue was crystallized from EtOAc/cyclohexane to give 5-(4-chloro-phenyl)-pyrazolo[1,5-a]pyrimidine (0.62 g, 67%) as a pale-yellow solid. MS (ISP) 230.4 [(M+H)$^+$]; mp 178-180° C.

Step 2) 5-(4-Chloro-phenyl)-3-ethynyl-pyrazolo[1,5-a]pyrimidine 5-(4-Chloro-phenyl)-pyrazolo[1,5-a]pyrimidine was subjected in analogous manner to the procedures described in example C.5 steps 3-5, to give 5-(4-chloro-phenyl)-3-ethynyl-pyrazolo[1,5-a]pyrimidine as a yellow solid. MS (ISP) 254.4 [(M+H)$^+$]; mp 128-129° C.

Example C.7

7-Cyclopropyl-3-ethynyl-5-(4-trifluoromethyl-phenyl)-pyrazolo[1,5-a]pyrimidine

Steps 1-2) 7-Chloro-5-(4-trifluoromethyl-phenyl)-pyrazolo[1,5-a]pyrimidine

By applying in analogous manner the procedures described in example C.5 step 1-2, but in step 1, ethyl 3-(4-chloro-phenyl)-3-oxo-propionate is replaced by ethyl 3-(4-trifluoromethyl-phenyl)-3-oxo-propionate. Yellow solid. NMR (DMSO-$d_6$) ☐ 7.01 (d, J=2 Hz, 1 H); 7.93 (d, J=8 Hz, 2 H); 8.20 (s, 1H); 8.41 (d, J=2 Hz, 1H); 8.47 (d, J=8 Hz, 2H) ppm.

Steps 3-4) 7-Cyclopropyl-3-iodo-5-(4-trifluoromethyl-phenyl)-pyrazolo[1,5-a]pyrimidine By subjecting 7-chloro-5-(4-trifluoromethyl-phenyl)-pyrazolo[1,5-a]pyrimidine in analogous manner to the procedures described in example C.5 steps 3-4. Yellow solid. MS (ISP) 430.4 [(M+H)$^+$]; mp. 181-183° C.

Step 5) 7-Cyclopropyl-3-ethynyl-5-(4-trifluoromethyl-phenyl)-pyrazolo[1,5-a]pyrimidine By subjecting 7-cyclopropyl-3-iodo-5-(4-trifluoromethyl-phenyl)-pyrazolo[1,5-a]pyrimidine in analogous manner to the procedure described in example C.5 step 5. Yellow solid. MS (ISP) 328.3 [(M+H)$^+$]; mp 164-167° C.

Example C.8

7-Cyclopropyl-5-(3,4-dichloro-phenyl)-3-ethynyl-pyrazolo[1,5-a]pyrimidine

By applying in analogous manner the procedures described in example C.5 steps 1-5, but replacing in step 1 ethyl 3-(4-chloro-phenyl)-3-oxo-propionate by ethyl 3-(3,4-dichloro-phenyl)-3-oxo-propionate. The title compound was obtained as a yellow solid. MS (ISP) 328.1 [(M+H)$^+$]; mp 194-196° C.

Example C.9

5-(3,4-Dichloro-phenyl)-3-ethynyl-7-trifluoromethyl-pyrazolo[1,5-a]pyrimidine

Step 1) 5-(3,4-Dichloro-phenyl)-7-trifluoromethyl-pyrazolo[1,5-a]pyrimidine

A mixture of 2H-pyrazol-3-ylamine (4.0 g, 48 mmol) and 1-(3,4-dichloro-phenyl)-4,4,4-trifluoro-butane-1,3-dione (11.4 g, 40 mmol) in acetic acid (80 mL) was heated at reflux for 4 h. The solution was poured into ice-cold 10% aqueous ammonia and the mixture was stirred at 0° C. for 0.5 h. The solid was isolated by filtration, triturated with EtOH (40 mL), and dried to give 5-(3,4-dichloro-phenyl)-7-trifluoromethyl-pyrazolo[1,5-a]pyrimidine as a pale-yellow solid. MS (ISP) 332.1[(M+H)$^+$]; mp 130-131° C.

Step 2) 5-(3,4-Dichloro-phenyl)-3-ethynyl-7-trifluoromethyl-pyrazolo[1,5-a]pyrimidine By subjecting 5-(3,4-dichloro-phenyl)-7-trifluoromethyl-pyrazolo[1,5-a]pyrimidine in analogous manner to the procedures described in example C.5 steps 4-5. The title compound 5-(3,4-dichloro-phenyl)-3-ethynyl-7-trifluoromethyl-pyrazolo[1,5 a]pyrimi-dine was obtained as a pale-yellow solid. MS (ISP) 355.9 [(M+H)$^+$]; mp 157-158° C.

Example C.10

3-Ethynyl-7-trifluoromethyl-5-(3-trifluoromethyl-phenyl)-pyrazolo[1,5-a]pyrimidine

Step 1) 4,4,4-Trifluoro-1-(3-trifluoromethyl-phenyl)-butane-1,3-dione

To a stirred solution of ethyl trifluoroacetate (6.98 mL, 58.5 mmol) in tert-butyl-methyl-ether (30 mL) was added at room temperature a 5.4 M solution of sodium methanolate in methanol (11.6 mL, 62.7 mmol) followed by a solution of commercially available 3-trifluoromethyl-acetophenone (10.0 g, 53.1 mmol) in tert-butyl-methyl-ether (8 mL). The reaction mixture was stirred at room temperature for 2 h, poured into ice/water (70 mL), acidified with 1 N HCl until pH 1 was achieved, and extracted with tert-butyl-methyl-ether (2×70 mL). The combined organic layers were washed with brine (2×30 mL), dried ($Na_2SO_4$) and evaporated to give crude 4,4,4-trifluoro-1-(3-trifluoromethyl-phenyl)-butane-1,3-dione (14.9 g, 100%) as a yellow liquid, which was used without further purification.

Step 2) 5-(3-Trifluoromethyl-phenyl)-7-trifluoromethyl-pyrazolo[1,5-a]pyrimidine A mixture of 4,4,4-trifluoro-1-(3-trifluoromethyl-phenyl)-butane-1,3-dione (10.3 g, 36.1 mmol) and commercially available 3-aminopyrazole (3.0 g, 36.1 mmol) in acetic acid (100 mL) was refluxed for 4 h and evaporated. The crude product was further purified by crystallization (ethyl acetate/hexane) to yield 5-(3-trifluoromethyl-phenyl)-7-trifluoromethyl-pyrazolo[1,5-a]pyrimidine (11.4 g, 95%) as a light yellow solid. MS (ISP) 323.3[(M+H)$^+$]; mp 96° C.

Step 3) 3-Iodo-7-trifluoromethyl-5-(3-trifluoromethyl-phenyl)-pyrazolo[1,5-a]pyrimidine To a stirred solution of 5-(3-trifluoromethyl-phenyl)-7-trifluoromethyl-pyrazolo[1,5-a]pyrimidine (5.0 g, 15.1 mmol) in acetic acid (25 mL) was added at room temperature sodium acetate (1.40 g, 17.1 mmol) and drop wise a solution of iodine monochloride (2.77 g, 17.1 mmol) in acetic acid (10 mLl). The reaction mixture was stirred at room temperature for 16 h, diluted slowly with water (up to 100 mL), stirred at room temperature for 30 min, the precipitate was filtered off, washed with water and dried to give 3-iodo-7-trifluoromethyl-5-(3-trifluoromethyl-phenyl)-pyrazolo[1,5-a]pyrimidine (6.49 g, 94%) as a yellow solid. MS (EI) 457.0[(M)$^+$]; mp 142° C.

Step 4) 3-ethynyl-7-trifluoromethyl-5-(3-trifluoromethyl-phenyl)-pyrazolo[1.5-a]pyrimidine A mixture of 3-iodo-7-trifluoromethyl-5-(3-trifluoromethyl-phenyl)-pyrazolo[1,5-a]pyrimidine (6.49 g, 14.2 mmol), trimethylsilylacetylene (3.54 mL, 25.6 mmol) and triethylamine (3.94 mL, 28.4 mmol) in N,N-dimethylformamide (15 mL) was stirred for 10 min at room temperature while being purged with Argon, then $PdCl_2(PPh_3)_2$ (100 mg, 1 mol %), $PPh_3$ (37 mg, 1 mol %) and CuI (8 mg, 0.3 mol %) were added. Stirring was continued at 90° C. for 4.5 h. The reaction mixture was cooled to room temperature, diluted with ethyl acetate (150 mL), washed with water (2×50 mL) and brine (70 mL), dried ($MgSO_4$) and evaporated to give 7-trifluoromethyl-5-(3-trifluoromethyl-phenyl)-3-trimethylsilanylethynyl-pyrazolo[1,5-a]pyrimidine (6.2 g, 102%) as a light brown solid, which was dissolved in THF (30 mL) and MeOH (70 mL), while stirring at 0° C. potassium carbonate (200 mg, 1.45 mmol) was added and the mixture was stirred at 0° C. for 5 h. The mixture was diluted with ice water (200 mL) and extracted with TBME (3×200 mL). The combined organic layers were washed with brine (300 mL), dried (MgSO₄) and evaporated. The crude product was further purified by silica gel column chromatography (heptane/EtOAc 9:1) followed by trituration with heptane to give 3-ethynyl-7-trifluoromethyl-5-(3-trifluoromethyl-phenyl)-pyrazolo[1,5-a]pyrimidine (3.23 g, 63%) as an orange solid. MS (EI) 355.0[(M)+]; mp 154° C.

Example C.11

5-(4-Chloro-3-methyl-phenyl)-3-ethynyl-7-trifluoromethyl-pyrazolo[1,5-a]pyrimidine Step 1) 1-(4-chloro-3-methyl-phenyl)-4,4,4-trifluoro-butane-1,3-dione To a stirred solution of ethyl trifluoroacetate (3.88 mL, 32.6 mmol) in tert-butyl-methyl-ether (40 mL) was added at room temperature a 5.4 M solution of sodium methanolate in methanol (6.5 mL, 35 mmol) followed by a solution of commercially available 4-chloro-3-methyl-acetophenone (5.0 g, 29.6 mmol; mixture with 75% correct starting material) in tert-butyl-methyl-ether (10 mL). The reaction mixture was stirred at room temperature for 16 h, poured into ice/water (70 mL), acidified with 1 N HCl until pH 1 was achieved, and extracted with diethyl-ether (2×100 mL). The combined organic layers were washed with brine (2×60 mL), dried (MgSO₄) and evaporated. The crude product was purified by column chromatography on silica gel (ethyl acetate/heptane 1:1) to give 7.91 g of a mixture which was further purified by crystallization from hexane to yield 1-(4-chloro-3-methyl-phenyl)-4,4,4-trifluoro-butane-1,3-dione (3.96 g, 50%) as a light red solid.

Step 2) 5-(4-chloro-3-methyl-phenyl)-7-trifluoromethyl-pyrazolo[1,5-a]pyrimidine A mixture of 1-(4-chloro-3-methyl-phenyl)-4,4,4-trifluoro-butane-1,3-dione (3.95 g, 14.9 mmol) and commercially available 3-aminopyrazole (1.24 g, 14.9 mmol) in acetic acid (40 mL) was refluxed for 5.5 h and evaporated. The crude product was further purified by crystallization (ethyl acetate/hexane) to yield 5-(4-chloro-3-methyl-phenyl)-7-trifluoromethyl-pyrazolo[1,5-a]pyrimidine (4.57 g, 98%) as a yellow solid. MS (EI) 311.2 [(M)⁺]; mp 114° C.

Step 3) 5-(4-chloro-3-methyl-phenyl)-3-iodo-7-trifluoromethyl-pyrazolo[1,5-a]pyrimidine To a stirred solution of 5-(4-chloro-3-methyl-phenyl)-7-trifluoromethyl-pyrazolo[1,5-a]pyrimidine (4.57 g, 15.2 mmol) in acetic acid (25 mL) was added at room temperature sodium acetate (1.36 g, 16.6 mmol) and drop wise a solution of iodine monochloride (2.69 g, 16.6 mmol) in acetic acid (10 mL). The reaction mixture was stirred at room temperature for 19 h, diluted slowly with water (up to 100 mL), stirred at room temperature for 30 min, the precipitate was filtered off, washed with water and dried to give 5-(4-chloro-3-methyl-phenyl)-3-iodo-7-trifluoromethyl-pyrazolo-[1,5-a]pyrimidine (5.96 g, 93%) as a yellow solid. MS (EI) 436.9 [(M)⁺]; mp 151° C.

Step 4) 5-(4-chloro-3-methyl-phenyl)-3-ethynyl-7-trifluoromethyl-pyrazolo[1,5-a]pyrimidine A mixture of 5-(4-chloro-3-methyl-phenyl)-3-iodo-7-trifluoromethyl-pyrazolo[1,5-a]pyrimidine (5.85 g, 12.4 mmol), trimethylsilylacetylene (3.33 mL, 24.1 mmol) and triethylamine (3.71 mL, 26.7 mmol) in N,N-dimethylformamide (20 mL) was stirred for 10 min at room temperature while being purged with Argon, then PdCl₂(PPh₃)₂ (94 mg, 1 mol %), PPh₃ (35 mg, 1 mol %) and CuI (8 mg, 0.3 mol %) were added. Stirring was continued at 90° C. for 4 h. The reaction mixture was cooled to room temperature, diluted with ethyl acetate (150 mL), washed with water (2×50 mL) and brine (70 mL), dried (MgSO₄) and evaporated to give 5-(4-chloro-3-methyl-phenyl)-7-trifluoromethyl-3-trimethylsilanylethynyl-pyrazolo[1,5-a]pyrimidine (5.79 g, 106%) as an orange solid, which was dissolved in THF (70 mL) and MeOH (70 mL), while stirring at 0° C. potassium carbonate (196 mg, 1.42 mmol) was added and the mixture was stirred at 0° C. for 5 h. The mixture was diluted with ice water (250 mL) and extracted with TBME (3×250 mL). The combined organic layers were washed with brine (300 mL), dried (MgSO4) and evaporated. The crude product was further purified by column chromatography on silica gel (heptane/EtOAc 9:1) followed by trituration with heptane to give 5-(4-chloro-3-methyl-phenyl)-3-ethynyl-7-trifluoromethyl-pyrazolo[1,5-a]pyrimidine (3.22 g, 68%) as an orange solid. MS (EI) 335.0[(M+H)⁺]; mp 166° C.

Example C.12

3-Ethynyl-7-methyl-5-(4-trifluoromethyl-phenyl)-pyrazolo[1,5-a]pyrimidine

Step 1) 7-Methyl-5-(4-trifluoromethyl-phenyl)-pyrazolo[1,5-a]pyrimidinel

To a solution of 7-chloro-5-(4-trifluoromethyl-phenyl)-pyrazolo[1,5-a]pyrimidine (1.49 g, 5.0 mmol) and tetrakis (triphenylphosphin)palladium (1.73 g, 1.5 mmol) in THF (50 mL) was added at 20° C. 2 M dimethylzinc/toluene solution (6.25 mL, 12.5 mmol) and the mixture was refluxed in an atmosphere of argon for 2 h. After the slow addition at 0° C. of sat. aqueous NH₄Cl solution (12 mL), the mixture was partitioned between AcOEt and 10% sodium chloride solution. The organic layer was evaporated in vacuo and the residue was chromatographed on silica gel using AcOEt/hexane (1:3 v/v) as eluent to give the title compound (1.17 g, 84%). Pale yellow solid. MS (ISN) 276.1 [(M–H)⁻]; mp 89-90° C.

Step 2) 3-Iodo-7-methyl-5-(4-trifluoromethyl-phenyl)-pyrazolo[1,5-a]pyrimidine

By subjecting 7-methyl-5-(4-trifluoromethyl-phenyl)-pyrazolo[1,5-a]pyrimidine in analogous manner to the procedure described in example C.5 step 4, the title compound was obtained. Yellow solid. MS (ISP) 404.1 [(M+H)⁺]; mp. 132-134° C.

Step 3) 3-Ethynyl-7-methyl-5-(4-trifluoromethyl-phenyl)-pyrazolo[1.5-a]pyrimidine By subjecting 3-iodo-7-methyl-5-(4-trifluoromethyl-phenyl)-pyrazolo[1,5-a]pyrimidine in analogous manner to the procedures described in example C.5 step 5, the title compound was obtained.Yellow solid. MS (ISP) 302.1 [(M+H)⁺]; mp 166-168° C.

Example C.13

2-[5-(4-Chloro-phenyl)-3-ethynyl-pyrazolo[1,5-a]pyrimidine-7-yl]-propan-2-ol

Step 1) 5-(4-Chloro-phenyl)-pyrazolo[1,5-a]pyrimidine-7-carboxylic acid ethyl ester A solution of 7-chloro-5-(4-chloro-phenyl)-pyrazolo[1,5-a]pyrimidine (2.0 g, 7.56 mmol), PdCl₂(PPh₃)₄ (1.06 g, 1.5 mmol), and triethylamine (1.59 mL, 11.36 mmol) in EtOH (240 mL) was purged with argon and thereafter heated under an atmosphere of carbon monoxide under a pressure of 50 bar for 16 h at 120° C. The reaction mixture was cooled and evaporated in vacuo and the crude product was chromatographed at $SiO_2$ using $AcOEt/CH_2Cl_2$/cyclohexane (1:1:3 v/v/v) as eluent to give 5-(4-chloro-phenyl)-pyrazolo[1,5-a] pyrimidine-7-carboxylic acid ethyl ester (1.62 g, 71%). Yellow solid. MS (ISP) 302.3 [(M+H)$^+$]; mp 160-161° C.

Step 2) 2-[5-(4-Chloro-phenyl)-pyrazolo[1,5-a]pyrimidine-7-yl]-propan-2-ol

To a suspension of 5-(4-chloro-phenyl)-pyrazolo[1,5-a] pyrimidine-7-carboxylic acid ethyl ester (150 mg, 0.5 mmol) in diethyl ether (3 mL) was added at 0° C. 3 M methylmagnesium bromide/diethyl ether (0.37 mL, 1.1 mmol). The mixture was stirred at 20° C. for 2 h and then poured into 10% aqueous sulfuric acid. The mixture was extracted with AcOEt and the organic layer was washed with $H_2O$, dried ($Na_2SO_4$) and evaporated in vacuo. The residue was triturated with cyclohexane to give 2-[5-(4-chloro-phenyl)-pyrazolo[1,5-a] pyrimidine-7-yl]-propan-2-ol (91 g, 63%). Off-white solid. MS (ISP) 288.1 [(M+H)$^+$]; mp 113-115° C.

Step 3) 2-[ 5-(4-Chloro-phenyl)-3-ethynyl-pyrazolo[1,5-a] pyrimidine-7-yl]-propan-2-ol By subjecting 2-[5-(4-chloro-phenyl)-pyrazolo[1,5-a]pyrimidine-7-yl]-propan-2-ol in analogous manner to the procedures described in example C.5 steps 4-5, the title compound was obtained.Yellow solid. MS (ISP) 312.0 [(M+H)$^+$]; mp 152-153° C.

Example C.14

[5-(4-Chloro-phenyl)-3-ethynyl-pyrazolo[1,5-a]pyrimidine-7-yl]-methanol

Step 1) [5-(4-Chloro-phenyl)-pyrazolo[1,5-a]pyrimidine-7-yl]-methanol

To a suspension of 5-(4-chloro-phenyl)-pyrazolo[1,5-a] pyrimidine-7-carboxylic acid ethyl ester (60 mg, 0.2 mmol) in MeOH/tetrahydrofuran (1:1 v/v, 1 mL) was added at 0° C. over 5 min sodium borohydride (75 mg, 2.0 mmol). The mixture was stirred at 0° C. for 1 h and then poured into ice-cold 3 N HCl (3 mL). The mixture was extracted with AcOEt and the organic layer was washed with $H_2O$, dried ($Na_2SO_4$), and evaporated in vacuo. The residue was chromatographed on silica gel using AcOEt/cyclohexane (1:2 v/v) as eluent to give [5-(4-chloro-phenyl)-pyrazolo[1,5-a]pyrimidine-7-yl]-methanol (45 mg, 87%). Pale yellow solid. MS (ISN) 258.1 [(M–H)$^-$]; mp 185-186° C.

Step 2) [5-(4-Chloro-phenyl)-3-iodo-pyrazolo[1,5-a]pyrimidine-7-yl]-methanol

By subjecting [5-(4-chloro-phenyl)-pyrazolo[1,5-a]pyrimidine-7-yl]-methanol in analogous manner to the procedure described in example C.5 step 4. Yellow solid. MS (ISN) 384.0 [(M–H)$^-$]; mp 186-188° C.

Step 3) [5-(4-Chloro-phenyl)-3-ethynyl-pyrazolo[1,5-a]pyrimidine-7-yl]-methanol

By subjecting [5-(4-chloro-phenyl)-3-iodo-pyrazolo[1,5-a]pyrimidine-7-yl]-methanol in analogous manner to the procedure described in example C.5 steps 5, the title compound was obtained.Yellow solid. MS (ISP) 284.1 [(M+H)$^+$].

Example C.15

7-Difluoromethyl-3-ethynyl-5-(3-trifluoromethyl-phenyl)-pyrazolo[1,5-a]pyrimidine 1) To a stirred solution of ethyl difluoroacetate (3.63 g, 29.3 mmol) in tert-butyl-methyl-ether (40 mL) was added at room temperature a 5.4 M solution of sodium methanolate in methanol (5.81 mL, 31.3 mmol) followed by a solution of commercially available 3-trifluoromethyl-acetophenone (5.0 g, 26.6 mmol) in tert-butyl-methyl-ether (10 mL). The reaction mixture was stirred at room temperature for 16 h, poured into ice/water (70 mL), acidified with 1 N HCl until pH 1 was achieved, and extracted with ethyl acetate (2×100 mL). The combined organic layers were washed with brine (2×60 mL), dried (MgSO$_4$) and evaporated to give crude 4,4-difluoro-1-(3-trifluoromethyl-phenyl)-butane-1,3-dione (6.75 g, 95%) as a light red oil, which was used without further purification.

2) A mixture of 4,4-difluoro-1-(3-trifluoromethyl-phenyl)-butane-1,3-dione (6.75 g, 25.4 mmol) and commercially available 3-aminopyrazole (2.11 g, 25.4 mmol) in acetic acid (70 mL) was refluxed for 7 h and evaporated. The crude product was further purified by crystallization (ethyl acetate/hexane) to yield 5-(3-trifluoromethyl-phenyl)-7-difluoromethyl-pyrazolo[1,5-a]pyrimidine (6.52 g, 82%) as a light yellow solid. MS (EI) 313.1 [(M)$^+$]; mp 127° C.

3) To a stirred solution of 5-(3-trifluoromethyl-phenyl)-7-difluoromethyl-pyrazolo[1,5-a]pyrimidine (6.35 g, 20.3 mmol) in acetic acid (30 mL) was added at room temperature sodium acetate (1.88 g, 22.9 mmol) and drop wise a solution of iodine monochloride (3.72 g, 22.9 mmol) in acetic acid (10 mL). The reaction mixture was stirred at room temperature for 16 h, diluted slowly with water (300 mL), stirred at room temperature for 30 min, the precipitate was filtered off, washed with water and dried to give 3-iodo-7-difluoromethyl-5-(3-trifluoromethyl-phenyl)-pyrazolo[1,5-a]pyrimidine (8.47 g, 95%) as a yellow solid. MS (EI) 439.0 [(M)$^+$]; mp 130° C.

4) A mixture of 3-iodo-7-difluoromethyl-5-(3-trifluoromethyl-phenyl)-pyrazolo[1,5-a]pyrimidine (8.23 g, 18.7 mmol), trimethylsilylacetylene (4.67 mL, 33.7 mmol) and triethylamine (5.22 mL, 37.5 mmol) in N,N-dimethylformamide (20 mL) was stirred for 10 min at room temperature while being purged with Argon, then PdCl$_2$(PPh$_3$)$_2$ (132 mg, 1 mol %), PPh$_3$ (49 mg, 1 mol %) and CuI (11 mg, 0.3 mol %) were added. Stirring was continued at 90° C. for 4.5 h. The reaction mixture was cooled to room temperature, diluted with water (100 mL) and extracted with ethyl acetate (2×100 mL). The combined organic layers were washed with water (2×50 mL) and brine (70 mL), dried (MgSO$_4$) and evaporated to give 7-difluoromethyl-5-(3-trifluoromethyl-phenyl)-3-trimethylsilanylethynyl-pyrazolo[1,5-a]pyrimidine (8.68 g) as a light brown solid, which was dissolved in THF (42 mL) and MeOH (98 mL), while stirring at 0° C. potassium carbonate (293 mg, 2 mmol) was added and the mixture was stirred at 0° C. for 5 h. The mixture was diluted with ice water (150 mL) and extracted with TBME (3×200 mL). The combined organic layers were washed with brine (100 mL), dried (MgSO4) and evaporated. The crude product was further purified by silica gel column chromatography (heptane/EtOAc 4:1) followed by trituration with heptane to give 7-difluoromethyl-3-ethynyl-5-(3-trifluoromethyl-phenyl)-pyrazolo[1,5-a]pyrimidine (4.34 g, 61%) as an orange solid. MS (EI) 337.1 [(M)$^+$]; mp 149° C.

Example C.16

5-(4-Chloro-3-methyl-phenyl)-7-difluoromethyl-3-ethynyl-pyrazolo[1,5-a]pyrimidine 1) To a stirred solution of ethyl difluoroacetate (5.67 g, 45.7 mmol) in tert-butyl-methyl-ether (40 mL) was added at room temperature a 5.4 M solution of sodium methanolate in methanol (9.07 mL, 49 mmol) followed by a solution of commercially available 4-chloro-3-methyl-acetophenone (7.0 g, 41.5 mmol; mixture with 75% correct starting material) in tert-butyl-methyl-ether (10 mL). The reaction mixture was stirred at room temperature for 16 h, poured into ice/water (70 mL), acidified with 1 N HCl until pH 1 was achieved, and extracted with diethyl-ether (2×100 mL). The combined organic layers were washed with brine (2×60 mL), dried (MgSO$_4$) and evaporated. The crude product was purified by column chromatography on silica gel (ethyl acetate/heptane 1:3) to give 1-(4-chloro-3-methyl-phenyl)-4,4-difluoro-butane-1,3-dione (7.18 g, 70%) as a light red oil.

2) A mixture of 1-(4-chloro-3-methyl-phenyl)-4,4-difluoro-butane-1,3-dione (7.18 g, 29.1 mmol) and commercially available 3-aminopyrazole (2.42 g, 29.1 mmol) in acetic acid (70 mL) was refluxed for 4.5 h and evaporated. The crude product was further purified by crystallization (ethyl acetate/hexane) to yield 5-(4-chloro-3-methyl-phenyl)-7-difluoromethyl-pyrazolo[1,5-a]pyrimidine (5.33 g, 62%) as an off-white solid. MS (EI) 293.2 [(M)$^+$]; mp 107° C.

3) To a stirred solution of 5-(4-chloro-3-methyl-phenyl)-7-difluoromethyl-pyrazolo[1,5-a]pyrimidine (5.1 g, 17.4 mmol) in acetic acid (25 mL) was added at room temperature sodium acetate (1.61 g, 19.6 mmol) and drop wise a solution of iodine monochloride (3.19 g, 19.6 mmol) in acetic acid (10 mL). The reaction mixture was stirred at room temperature for 19 h, diluted slowly with water (300 mL), stirred at room temperature for 30 min, the precipitate was filtered off, washed with water and dried to give 5-(4-chloro-3-methyl-phenyl)-3-iodo-7-difluoromethyl-pyrazolo[1,5-a]pyrimidine (7.03 g, 96%) as a yellow solid. MS (EI) 419.9 [(M)t]; mp 144° C.

4) A mixture of 5-(4-chloro-3-methyl-phenyl)-3-iodo-7-difluoromethyl-pyrazolo[1,5-a]pyrimidine (7.01 g, 16.7 mmol), trimethylsilylacetylene (4.16 mL, 30.0 mmol) and triethylamine (4.66 mL, 33.4 mmol) in N,N-dimethylformamide (18 mL) was stirred for 10 min at room temperature while being purged with Argon, then PdCl$_2$(PPh$_3$)$_2$ (117 mg, 1 mol %), PPh$_3$ (44 mg, 1 mol %) and CuI (10 mg, 0.3 mol %) were added. Stirring was continued at 90° C. for 4.5 h. The reaction mixture was cooled to room temperature, diluted with water (100 mL) and extracted with ethyl acetate (2×100 mL). The combined organic layers were washed with water (2×50 mL) and brine (70 mL), dried (MgSO$_4$), evaporated and further purified by column chromatography on silica gel (dischloromethane/heptane 7:3) to give 5-(4-chloro-3-methyl-phenyl)-7-difluoromethyl-3-trimethylsilanylethynyl-pyrazolo[1,5-a]pyrimidine (4.73 g, 73%) as an orange solid, which was dissolved in THF (74 mL) and MeOH (56 mL), while stirring at 0° C. potassium carbonate (168 mg, 1.22 mmol) was added and the mixture was stirred at 0° C. for 5 h. The mixture was diluted with ice water (250 mL) and extracted with TBME (3×250 mL). The combined organic layers were washed with brine (200 mL), dried (MgSO4) and evaporated. The crude product was further purified by flash chromatography on silica gel (heptane/EtOAc) followed by crystallization from methyl acetate/hexane to give 5-(4-chloro-3-methyl-phenyl)-3-ethynyl-7-difluoromethyl-pyrazolo[1,5-a]pyrimidine (3.8 g, 72%) as a light brown solid. MS (EI) 317.2 [(M)$^+$]; mp 143° C.

Example C.17

8-Ethynyl-4-trifluoromethyl-2-(4-trifluoromethyl-phenyl)-imidazo[1.5-a]pyrimidine 1) A stirred solution of commercially available 5-amino-1H-imidazole-4-carboxamide (25 g, 198 mmol) in methanesulfonic acid (107 mL) and ethanol (400 mL) was stirred at reflux conditions for 12d, evaporated and water (300 mL) was added. While stirring and cooling (ice/water) sodium hydroxide solution (32%) was added until pH=6 was reached. The water layer was saturated with sodium chloride and extracted with ethyl acetate (3×200 mL). The combined organic layers were dried (MgSO$_4$), evaporated and the crude product purified crystallization (ethyl acetate/ethanol) to yield 5-amino-1H-imidazole-4-carboxylic acid ethyl ester (13.7 g, 45%) as a light brown solid. MS (EI) 155.1 [(M)$^+$]; mp 178° C.

2) A mixture of 4,4,4-trifluoro-1-(4-trifluoromethyl-phenyl)-butane-1,3-dione (10.0 g, 35.2 mmol) and 5-amino-1H-imidazole-4-carboxylic acid ethyl ester (5.0 g, 32.2 mmol) in acetic acid (120 mL) was refluxed for 24 h and evaporated. The crude product was further purified by column chromatography on silica gel (ethyl acetate/heptane) and crystallization (diethyl acetate/hexane) to yield 4-trifluoromethyl-2-(4-trifluoromethyl-phenyl)-imidazo[1,5-a]pyrimidine-8-carboxylic acid ethyl ester (5.65 g, 43%) as a yellow solid. MS (EI) 403.1 [(M)$^+$]; mp 243° C.

3) A mixture of 4-trifluoromethyl-2-(4-trifluoromethyl-phenyl)-imidazo[1,5-a]pyrimidine-8-carboxylic acid ethyl ester (5.6 g, 13.9 mmol), 2M potassium hydroxide solution (111 mL) and water (55 mL) was stirred at room temperature for 5 h, cooled (ice-water), and acetic acid (30 mL) was added. The mixture was evaporated, acetic acid (150 mL) was added and the stirred solution was heated under reflux conditions for 20 min. The reaction mixture was evaporated, water (150 mL) was added followed by extraction with ethyl acetate (2×300 mL). The combined organic layers were washed with brine (2×150 mL), dried (MgSO$_4$) and evaporated. The crude product was further purified by cholumn chromatography on silica gel (ethyl acetate/heptane 1:1) to yield 4-trifluoromethyl-2-(4-trifluoromethyl-phenyl)-imidazo[1,5-a]pyrimidine-8-carboxylic acid (1.93 g, 37%) as a yellow solid. MS (ISN) 374.3 [(M−H)$^-$]; mp 231° C.

4) 4-Trifluoromethyl-2-(4-trifluoromethyl-phenyl)-imidazo[1,5-a]pyrimidine-8-carboxylic acid (1.9 g, 5.06 mmol) was heated up to the melting point and the crude product purified by column chromatography on silica gel (ethyl acetate/heptane 1:1) to yield 4-trifluoromethyl-2-(4-trifluoromethyl-phenyl)-imidazo[1,5-a]pyrimidine (0.75 g, 45%) as a yellow solid. MS (EI) 331.1 [(M)$^+$]; mp 158° C.

5) To a stirred solution of 4-trifluoromethyl-2-(4-trifluoromethyl-phenyl)-imidazo[1,5-a]pyrimidine (1.05 g, 3.17 mmol) in acetic acid (4 mL) was added at room temperature sodium acetate (0.29 g, 3.58 mmol) and drop wise a solution of iodine monochloride (0.53 g, 3.58 mmol) in acetic acid (4 mL). The reaction mixture was stirred at room temperature for 19 h, diluted slowly with water (100 mL), stirred at room temperature for 30 min, the precipitate was filtered off, washed with water and dried to give 8-iodo-4-trifluoromethyl-2-(4-trifluoromethyl-phenyl)-imidazo[1,5-a]pyrimidine (1.45 g, 100%) as an orange solid. MS (EI) 457.0 [(M)$^+$]; mp 141° C.

6) A mixture of 8-iodo-4-trifluoromethyl-2-(4-trifluoromethyl-phenyl)-imidazo[1,5-a]pyrimidine (1.65 g, 3.61 mmol), trimethylsilylacetylene (0.9 mL, 6.5 mmol) and triethylamine (1.51 mL, 10.8 mmol) in N,N-dimethylformamide (10 mL) was stirred for 10 min at room temperature while being purged with Argon, then $PdCl_2(PPh_3)_2$ (0.76 mg, 0.11 mmol), $PPh_3$ (57 mg, 0.22 mmol) and CuI (7 mg, 0.04 mmol) were added. Stirring was continued at 90° C. for 3.5 h. The reaction mixture was cooled to room temperature, diluted with water (50 mL) and extracted with ethyl acetate (2×100 mL). The combined organic layers were washed with water (50 mL) and brine (50 mL), dried ($MgSO_4$), evaporated and further purified by flash chromatography on silica gel (ethyl acetate/heptane) to give 4-trifluoromethyl-2-(4-trifluoromethyl-phenyl)-8-trimethylsilanylethynyl-imidazo[1,5-a]pyrimidine (0.82 g, 53%) as a brown solid, which was dissolved in THF (10 mL) and MeOH (10 mL), while stirring at 0° C. potassium carbonate (26 mg, 0.19 mmol) was added and the mixture was stirred at 0° C. for 5 h. The mixture was diluted with ice water (50 mL) and extracted with TBME (2×100 mL). The combined organic layers were washed with brine (50 mL), dried (MgSO4) and evaporated. The crude product was further purified by flash chromatography on silica gel (heptane/EtOAc) followed by crystallization from diethyl ether/hexane to give 8-ethynyl-4-trifluoromethyl-2-(4-trifluoromethyl-phenyl)-imidazo[1,5-a]pyrimidine (0.54 g, 42%) as a brown solid. MS (EI) 355.1 [(M)$^-$]; mp 163° C.

Example C.18

3-Ethynyl-8-trifluoromethyl-6-(4-trifluoromethyl-phenyl)-imidazo[1,2-a]pyridine

Step 1) (4-Methoxy-benzyl)-(3-trifluoromethyl-pyridin-2-yl)-amine

A mixture of commercially available 2-chloro-3-trifluoromethylpyridine (64.83 g, 357 mmol), 4-methoxybenzylamine (56 mL, 429 mmol) and DIPEA (73.4 mL, 429 mmol) in n-butanol (100 mL) was refluxed (oilbathtemp. 140° C.) for 3.5 days. Concentrated in vacuum, partitioned between 25% HCl and TBME, reextracted the organic layer twice with 25% HCl, the aqueous layer was made alkaline with 32% NaOH, extracted with TBME, washed with brine and dried over $Na_2SO_4$. Removal of the solvent in vacuum left a brown oil (105.21 g,>100%). Vacuum distillation gave the product as a colorless liquid (83.766 g, 83%, bp 139-141° C. at 1.4 mbar). MS (ISP) 283.1 [(M+H)$^+$].

Step 2) 3-Trifluoromethyl-pyridin-2-ylamine

To conc. $H_2SO_4$ (230 mL) at 5° C. was dropwise added (4-methoxy-benzyl)-(3-trifluoromethyl-pyridin-2-yl)-amine (83.76 g, 297 mmol) keeping the internal temperature below 20° C. Stirring was continued at 23° C. for 30 min, poured onto ice, made alkaline with 32% NaOH-sol. (ca. 800 mL) [external ice cooling necessary!!!], saturated with solid NaCl, extracted twice with THF/TBME/DCM, dried over $Na_2SO_4$. Removal of the solvent in vacuum gave the product as a white solid (44.27 g, 92%). MS (ISP) 163.2 [(M+H)$^+$].

Step 3) 5-Bromo-3-trifluoromethyl-pyridin-2-ylamine

To a solution of 3-trifluoromethyl-pyridin-2-ylamine (16.21 g, 100 mmol) in acetonitrile (300 mL) at 5° C. was added NBS (17.8 g, 100 mmol) and the mixture was stirred at 23° C. for 1 h. Poured onto ice and sat. $NaHCO_3$ soln., extracted with EtOAc, washed with brine, dried over $Na_2SO_4$. Removal of the solvent in vacuum left a yellow solid. Silica gel & cotton wool column filtratation with DCM gave the product as a yellow solid (23.71 g, 98%). MS (ISP) 240.1 [(M+H)$^+$].

Step 4) 3-Trifluoromethyl-5-(4-trifluoromethyl-phenyl)-pyridin-2-ylamine

A mixture of 5-bromo-3-trifluoromethyl-pyridin-2-ylamine (11.5 g, 48 mmol) with 4-trifluormethylphenylboronic acid (9.97 g, 52 mmol), $Pd(PPh_3)_4$ (551 mg, 1 mol %) and 1 M aq. $Na_2CO_3$ soln. (111 mL, 111 mmol) in DME (250 mL) at reflux for 1 h. Poured on icewater, extracted with EtOAc, dried over $Na_2SO_4$ and concentrated. Purified by column chromatography (heptane/AcOEt 2:1), then triturated the collected solids with heptane and a few drops of ether, ultrasound sonication for 10 min, filtrated and dried in to give the product as a white crystalline solid (12.77 g, 87%). MS (ISP) 307.2 [(M+H)$^+$].

Step 5) 8-Trifluoromethyl-6-(4-trifluoromethyl-phenyl)-imidazo[1,2-a]pyridine

To a mixture of 3-trifluoromethyl-5-(4-trifluoromethyl-phenyl)-pyridin-2-ylamine (12.77 g, 42 mmol) and $NaHCO_3$ (5.96 g, 71 mmol) in EtOH (300 mL) was added chloracetaldehyde solution 55% in water (22 mL, 188 mmol), then refluxed overnight. The reaction mixture was concentrated and purified by column chromatography ($CH_2Cl_2/Et_2O$ 1:1) to give the product as a white crystalline solid (9.6 g, 69%). MS (ISP) 331.1 [(M+H)$^+$].

Step 6) 3-Iodo-8-trifluoromethyl-6-(4-trifluoromethyl-phenyl)-imidazo[1,2-a]pyridine To a solution of 8-trifluoromethyl-6-(4-trifluoromethyl-phenyl)-imidazo[1,2-a]pyridine (1.36 g, 4.1 mmol) in 5 mL of acetic acid was added sodium acetate (0.51 g, 6.2 mmol) and a solution of iodine monochloride (2 M, 2.5 mL, 5.0 mmol)- slightly exothermic. The reaction mixture was stirred for 30 min at 23° C., precipitate formed, then partitioned between 60 mL of water and 60 mL of EtOAc. The organic layer was washed with sat. $NaHCO_3$, water, aq. sodium thiosulfate, water, then dried over $Na_2SO_4$, filtered and concentrated to give 1.36 g (72%) of an off-white solid. MS (ISP) 457.3 [(M+H)$^+$].

Step 7) 8-Trifluoromethyl-6-(4-trifluoromethyl-phenyl)-3-trimethylsilanylethynyl-imidazo[1,2-a]pyridine A mixture of 3-iodo-8-trifluoromethyl-6-(4-trifluoromethyl-phenyl)-imidazo[1,2-a]pyridine (8.36 g, 18 mmol), trimethylsilylacetylene (5.1 mL, 37 mmol), $Et_3N$ (7.66 mL, 55 mmol), $PdCl_2(PPh_3)_2$ (64 mg, 0.5 mol %) and $PPh_3$ (48 mg, 1 mol %) in THF (40 mL) was stirred for 10 min at 23° C. while being purged with Argon. Then CuI (10 mg, 0.3 mol %) was added.

Stirring was continued for 16 h at 75° C. The reaction mixture was purified by column chromatography (heptane/AcOEt 10:1) to give the product as a yellow liquid (10.5 g, 100%). MS (ISP) 427.2 [(M+H)$^+$].

Step 8) 3-Ethynyl-8-trifluoromethyl-6-(4-trifluoromethyl-phenyl)-imidazo[1,2-a]pyridine To a solution of 8-trifluoromethyl-6-(4-trifluoromethyl-phenyl)-3-trimethylsilanylethynyl-imidazo[1,2-a]pyridine (10.5 g, 25 mmol) in THF (100 mL) and MeOH (250 mL) at 0° C. was added $K_2CO_3$ (340 mg, 10 mol %) and the mixture was stirred at 0° C. for 6 h. Diluted with TBME and ice water, separated, washed with brine, dried over $Na_2SO_4$, totally evaporated. Purified by column chromatography (heptane/AcOEt) and trituration with heptane and filtration gave the product as an off-white solid (5.8 g, 66%). MS (ISP) 355.0 [(M+H)$^+$].

Example C.19

7-Difluoromethyl-5-(3-ethoxy-phenyl)-3-ethynyl-pyrazolo[1,5-a]pyrimidine

Step 1) 3-Ethoxyacetophenone

Commercially available 3-hydroxyacetophenone (25 g, 184 mmol) was stirred with ethyl iodide (17.8 mL, 220 mmol) and potassium carbonate (126.89 g, 918 mmol) in acetone (500 mL) at 55° C. for 16 h. Cooled to 23° C., filtered the solids off and the solvent was removed in vacuum. The residue was purified by silica gel column chromatography with heptane/ethyl acetate 4:1 to give the title compound as a light yellow liquid (29.5 g, 98%). MS (ISP) 165.2 [(M+H)+].

Step 2) 1-(3-Ethoxy-phenyl)-4,4-difluoro-butane-1,3-dione

Prepared from commercially available ethyl difluoroacetate (16.0 g, 129 mmol) and 3-ethoxyacetophenone (example C.19 step 1) (14.5 g, 88 mmol) as described in example C.1 step 1 to give the title compound (23.90 g, 112%) as a light red oil. MS (ISN) 241.0 [(M−H)−].

Step 3a) 3-Bromo-7-difluoromethyl-5-(3-ethoxy-phenyl)-pyrazolo[1,5-a]pyrimidine

Prepared from 1-(3-ethoxy-phenyl)-4,4-difluoro-butane-1,3-dione (example C.19 step 2) (23.9 g, 99 mmol) and commercially available 3-amino-4-bromopyrazole (15.99 g, 99 mmol) as described in example C.1 step 2a to give the title compound (30.3 g, 83%) as a yellow solid. MS (ISP) 368.0 [(M+H)+], 370.0 [(M+2+H)+].

Step 4a) 7-Difluoromethyl-5-(3-ethoxy-phenyl)-3-trimethylsilanylethynyl-pyrazolo[1,5-a]pyrimidine Prepared from 3-bromo-7-difluoromethyl-5-(3-ethoxy-phenyl)-pyrazolo[1,5-a]pyrimidine (example C.19 step 3a) (20.0 g, 54 mmol) and commercially available trimethylsilylacetylene (15 mL, 109 mmol) as described in example C.1 step 3a to give the title compound (20 g, 95%) as a light brown solid. MS (ISP) 386 [(M+H)+].

Step 4b) 7-Difluoromethyl-5-(3-ethoxy-phenyl)-3-ethynyl-pyrazolo[1,5-a]pyrimidine Prepared from 7-difluoromethyl-5-(3-ethoxy-phenyl)-3-trimethylsilanylethynyl-pyrazolo[1,5-a]pyrimidine (example C.19 step 4a) (20 g, 52 mmol) as described in example C.1 step 3b to give the title compound (9.5 g, 58%) as a yellow solid. MS (ISP) 314.0[(M+H)+].

Example C.20

3-Ethynyl-8-methyl-6-(4-trifluoromethyl-phenyl)-imidazo[1,2-a]pyridine

Step 1) 6-Bromo-8-methyl-imidazo[1,2-a]pyridine

To a solution of commercially available 2-amino-5-bromo-3-picoline (21.48 g, 115 mmol) and bromoacetaldehyde diethyl acetal (90%, 39.6 mL, 230 mmol) in EtOH (110 mL) was added 48% aq. HBr (11 mL) and the mixture was refluxed for 11 h. Cooled to 23° C., diluted with EtOAc, poured into sat. NaHCO3-sol., separated phases, washed with the organic layer with brine, dried over Na2SO4. Removal of the solvent in vacuum (not over 40° C. bath temperature) left an orange liquid, which was directly coated on silica gel for chromatography. Silica gel column filtration with heptane/EtOAc 50:50→0:100 gave the title compound as a light brown solid (17.36 g, 72%).MS (ISP) 211.0 [(M+H)+], 231.1 [(M+2+H)+].

Step 2) 8-Methyl-6-(4-trifluoromethyl-phenyl)-imidazo[1,2-a]pyridine

A mixture of 6-bromo-8-methyl-imidazo[1,2-a]pyridine (example C.20 step 1) (7.0 g, 33 mmol), commercially available 4-(trifluoromethyl)phenylboronic acid (6.929 g, 36 mmol), Pd(PPh3)4 (383 mg, 1 mol %) and 1M Na2CO3-solution (77 mL, 77 mmol) in DME (150 mL) was stirred at reflux for 1 h. Cooled to 23° C., diluted with water, extracted with EtOAc, washed the organic layer with brine, dried over MgSO4. Removal of the solvent in vacuum left a brown solid, which was purified by silica gel column chromatography with EtOAc/MeOH to give the title compound as a white solid (8.29 g, 91%). MS (ISP) 277.1 [(M+H)+].

Step 3) 3-Iodo-8-methyl-6-(4-trifluoromethyl-phenyl)-imidazo[1,2-a]pyridine

To a solution of 8-methyl-6-(4-trifluoromethyl-phenyl)-imidazo[1,2-a]pyridine (example C.20 step 2) (5.0 g, 18 mmol) in 50 mL of acetic acid was added sodium acetate (1.68 g, 20 mmol) and a solution of iodine monochloride (2 M, 10.3 mL, 20.6 mmol)—slightly exothermic. The reaction mixture was stirred at 23° C. for 16 h, then partitioned between 300 mL of water and 300 mL of EtOAc. The organic layer was washed with sat. NaHCO3, water, aq. sodium sulfite, water, then dried over Na2SO4, filtered and concentrated to give the title compound as an off-white solid (6.47 g, 89%). MS (ISP) 403.3 [(M+H)+].

Step 4) 8-Methyl-6-(4-trifluoromethyl-phenyl)-3-trimethylsilanylethynyl-imidazo[1,2-a]pyridine A mixture of 3-iodo-8-methyl-6-(4-trifluoromethyl-phenyl)-imidazo[1,2-a]pyridine (example C.20 step 3) (4.02 g, 10 mmol), trimethylsilylacetylene (2.8 mL, 20 mmol), Et3N (2.1 mL, 15 mmol), PdCl2(PPh3)2 (70 mg, 1 mol %) and PPh3 (26 mg, 1 mol %) in THF (20 mL) was stirred for 10 min at 23° C. while being purged with Argon. Then CuI (19 mg, 1 mol %) was added. Stirring was continued for 16 h at 80° C. The reaction mixture was purified by column chromatography (heptane/AcOEt) to give the title compound as a yellow foam (3.15 g, 85%). MS (ISP) 373.2 [(M+H)+].

Step 5) 3-Ethynyl-8-trifluoromethyl-6-(4-trifluoromethyl-phenyl)-imidazo[1,2-a]pyridine To a solution of 8-methyl-6-(4-trifluoromethyl-phenyl)-3-trimethylsilanylethynyl-imidazo[1,2-a]pyridine (example C.20 step 4) (3.2 g, 9 mmol) in THF (10 mL) and MeOH (25 mL) at 0° C. was added K2CO3 (119 mg, 10 mol %) and the mixture was stirred at 0° C. for 6 h. Diluted with TBME and ice water, separated, washed with brine, dried over Na2SO4, totally evaporated. Purified by column chromatography (heptane/AcOEt) and trituration with diethyl ether and filtration gave the title compound as an off-white solid (2.14 g, 83%). MS (ISP) 301.2 [(M+H)+].

Example C.21

6-(4-Chloro-phenyl)-3-ethynyl-8-methyl-imidazo[1,2-a]pyridine

Step 1) 6-(4-Chloro-phenyl)-8-methyl-imidazo[1,2-a]pyridine

Prepared from 6-bromo-8-methyl-imidazo[1,2-a]pyridine (example C.20 step 1) (7.0 g, 33 mmol) and commercially available 4-chlorophenylboronic acid (6.005 g, 36 mmol) as described in example C.20 step 2. Obtained the title compound as a white solid (6.02 g, 75%). MS (ISP) 243.2 [(M+H)+], 245.1 [(M+2+H)+].

Step 2) 6-(4-Chloro-phenyl)-3-iodo-8-methyl-imidazo[1,2-a]pyridine

Prepared from 6-(4-chloro-phenyl)-8-methyl-imidazo[1,2-a]pyridine (example C.21 step 1) (6.65 g, 27 mmol) and iodine monochloride as described in example C.20 step 3. Obtained the title compound as an off-white solid (8.0 g, 79%). MS (ISP) 369.0 [(M+H)$^+$], 371 [(M+2H) $^+$].

Step 3) 6-(4-Chloro-phenyl)-8-methyl-3-trimethylsilanylethynyl-imidazo[1,2-a]pyridine Prepared from 6-(4-chloro-phenyl)-3-iodo-8-methyl-imidazo[1,2-a]pyridine (example C.21 step 2) (3.686 g, 10 mmol) and trimethylsilylacetylene (2.8 mL, 20 mmol) as described in example C.20 step 4. Obtained the title compound as a yellow foam (2.70 g, 80%). MS (ISP) 339.1 [(M+H)$^+$], 341 [(M+2H)$^+$].

Step 4) 6-(4-Chloro-phenyl)-3-ethynyl-8-methyl-imidazo[1,2-a]pyridine

Prepared form 6-(4-chloro-phenyl)-8-methyl-3-trimethylsilanylethynyl-imidazo[1,2-a]pyridine (example C.21 step 3) (2.7 g, 8 mmol) as described in example C.20 step 5. Obtained the title compound as an off-white solid (1.5 g, 72%). MS (ISP) 267.2 [(M+H)$^+$], 269.1 [(M+2H)$^+$].

Example C.22

3-Iodo-7-trifluoromethyl-5-(4-trifluoromethyl-phenyl)-pyrazolo[1,5-a]pyridine

Step 1) 2,2-Dimethyl-6-(3,3,3-trifluoro-2,2-dihydroxy-propyl)-[1,3]dioxin-4-one

To a solution of hexamethyldisilazane (167 mL, 800 mmol) in THF (200 mL) at 0° C. was cannulated n-BuLi (500 mL, 800 mmol) and the mixture was stirred at 0° C. for 30 min, then cannulated into a solution of freshly distilled 2,2,6-trimethyl-1,3-dioxin-4-one (56.9 g, 400 mmol) in THF (400 mL) at −78° C., keeping the internal temperature below −60° C. Stirring was continued at −78° C. for 1 h, then a solution of ethyl 2,2,2-trifluoroacetate (52.5 mL, 440 mmol) in THF (100 mL) was added quickly (<1 min; internal temperature remained below −70° C.). The cooling bath was removed and stirring was continued at −78 to 0° C. for 2 h. Cooled to −45° C., then HOAc (57.3 mL, 1000 mmol) was added and the mixture was warmed to −10° C. Poured into ice cold 0.5 M HCl (pH 1), extracted with TBME, washed with sat. NaHCO$_3$-sol., icecold 0.5 M HCl and brine, dried over Na$_2$SO$_4$. Removal of the solvent in vacuum (bath temperature below 40° C.) left a yellow oil, added THF (ca. 200 mL), toluene (ca. 50 mL) and H$_2$O (ca. 20 mL) and evaporated to dryness to give the title compound as a light yellow solid (89.27 g, 87%). MS (ISN) 237.0 [(M−H)$^-$].

Step 2) 4-Hydroxy-6-trifluoromethyl-pyran-2-one

A suspension of 2,2-dimethyl-6-(3,3,3-trifluoro-2,2-dihydroxy-propyl)-[1,3]dioxin-4-one (example C.22 step 1) (70 g, 273 mmol) in toluene (500 mL) was placed in a preheated (135° C.) oilbath, needed 10 min to reflux, then was refluxed for 25 min while distilling off about 150 mL of solvent. The hot solution was concentrated in vacuum to about 300 mL, some heptane was added, cooled to 23° C., filtered the precipitate off, washed with little cold toluene and dried in HV to give the title compound a light yellow solid (17.93 g, 36%). MS (ISN) 179.1 [(M−H)$^-$].

Step 3) 4-Bromo-6-trifluoromethyl-pyran-2-one

A mixture of 4-hydroxy-6-trifluoromethyl-pyran-2-one (example C.22 step 2) (10.43 g, 58 mmol), P$_2$O$_5$ (19.57 g, 138 mmol) and tetrabutylammonium bromide (21.66 g, 67 mmol) in toluene (149 mL) was stirred at 100° C. for 1 h. Cooled to 23° C., the phases were separated and the lower phase stirred for a short time with ca. 150 mL hot toluene. The combined organic layers washed with sat. NaHCO$_3$-sol. and brine, dried over Na$_2$SO$_4$, evaporated and dried for a short time at HV (sublimes easily) to give the title compound as a brown solid (8.31 g, 59%), which was purified by silica gel column chromatography with heptane/EtOAc to give the title compound as a yellow solid (5.77 g, 41%). NMR (DMSO-d$_6$) δ7.23 (s, 1 H), 7.50 (s, 1 H) ppm.

Step 4) 6-Trifluoromethyl-4-(4-trifluoromethyl-phenyl)-pyran-2-one

To a solution of commercially available 4-iodobenzotrifluoride (1.36 g, 5.00 mmol) in THF (13 mL) at −78° C. was added isopropylmagnesium chloride (2 M in THF, 2.63 mL, 5.25 mmol) within 2 min keeping the internal temperature below −65° C., stirring was continued at −78 to −20° C. for 60 min. ZnCl$_2$ (1 M in THF, 5.50 mL, 5.50 mmol) was added, the cooling bath was removed, the mixture was allowed to reach 23° C. and stirred at 23° C. for 35 min. Pd(PPh$_3$)$_4$ (58 mg, 1 mol %) and 4-bromo-6-trifluoromethyl-pyran-2-one (example C.22 step 3) (1.22 g, 5.00 mmol) were added at 23° C. and stirring was continued at 23° C. for 30 min [slightly exothermic reaction; internal temperature rose to 45° C.]. Poured into icecold 0.5 M HCl, extracted with EtOAc, washed with sat. NaHCO$_3$-sol. and brine, dried over Na$_2$SO$_4$, evaporated and dried at HV to give an orange solid (1.55 g), which was purified by MPLC to give the title compound as a yellow solid (1.27 g, 82%). MS (EI) [(M)t]; mp 52° C.

Step 5) 1-Amino-6-trifluoromethyl-4-(4-trifluoromethyl-phenyl)-1H-pyridin-2-one

6-Trifluoromethyl-4-(4-trifluoromethyl-phenyl)-pyran-2-one (example C.22 step 4) (3.99 g, 12.95 mmol) was dissolved in n-BuOH (26 mL), N$_2$H$_4$·H$_2$O (3.15 ml, 64.73 mmol) and AcOH (3.71, 64.73 mmol) were added and the reaction mixture was refluxed for 1 h. Evaporated to dryness and the residue was purified by flash chromatography (150 g silica gel) with heptane/EtOAc 7:3 to give the title compound as a white solid (3.20 g, 77%). MS (ISP) 323 [(M+H)$^+$]; mp 125° C.

Step 6) 1-Amino-6-trifluoromethyl-4-(4-trifluoromethyl-phenyl)-1H-pyridine-2-thione A mixture of 1-amino-6-trifluoromethyl-4-(4-trifluoromethyl-phenyl)-1H-pyridin-2-one (example C.22 step 5) (3.19 g, 9.90 mmol) and lawssons's reagent (4.00 g, 0.56 mmol) in toluene (19.8 mL) under N$_2$ was stirred at 80° C. for 2 h. Poured into sat. NaHCO$_3$-sol., extracted with EtOAc, washed the organic layers with brine, dried over Na$_2$SO$_4$ and evaporated to leave a yellow solid, which was purified by flash chromatography (200 g SiO$_2$) with heptane/EtOAc 4:1 to give the title compound as a yellow solid (3.14 g, 94%). MS (ISP) 339 [(M+H)$^+$]; mp 156° C.

Reagent 1) 2-Chloro-3-oxo-propionic acid ethyl ester

A mixture of ethyl formate (40.22 mL, 500 mmol) and ethyl chloroacetate (53.28 mL, 500 mmol) was added to a suspension of KOBut (56.11 g, 500 mmol) in diisopropylether (555 mL) at 0° C. within 1 h, keeping the temperature below 10° C. and the mixture was stirred at 23° C. for 24 h The resulting precipitate was collected by filtration, washed with TBME, dried on rotavap at 40° C. and subsequently in HV to give a light brown solid (82.20 g, 87%). Half of this material was partitioned between diethyl ether and icecold 6 N HCl, the organic layer was washed with brine and dried over Na$_2$SO$_4$. Removal of the solvent in vacuum left a dark brown liquid, which was purified by vacuum distillation to give the title compound a colorless liquid (29.25 g, ca. 40%). bp 70-84° C. (25 mbar).

Step 7) 7-Trifluoromethyl-5-(4-trifluoromethyl-phenyl)-pyrazolo[1,5-a]pyridine-3-carboxylic acid ethyl ester A solution of 1-amino-6-trifluoromethyl-4-(4-trifluoromethyl-phenyl)-1H-pyridine-2-thione (example C.22 step 6) (3.14 g, 9.28 mmol) and 2-chloro-3-oxo-propionic acid ethyl ester (example C.22 reagent 1) (4.19 g, 27.85 mmol) in EtOH (45 mL) was refluxed for 20 h, the added again 2-chloro-3-oxo-propionic acid ethyl ester (example C.22 reagent 1) (2.20 g, 14.61 mmol) and refluxing was continued for another 18 h. Poured into sat. $NaHCO_3$-sol., extracted with EtOAc, washed the organic layer with brine, dried over $Na_2SO_4$ and evaporated to leave a residue, which was purified by flash chromatography (600 g $SiO_2$) with heptane/EtOAc 9:1, followed by trituration with heptane (ca. 50 mL) at −70° C. to give the title compound as a light yellow solid (2.30 g, 62%). MS (ISP) 403 [(M+H)$^+$]; mp 130° C.

Step 8) 7-Trifluoromethyl-5-(4-trifluoromethyl-phenyl)-pyrazolo[1,5-a]pyridine-3-carboxylic acid To a solution of 7-trifluoromethyl-5-(4-trifluoromethyl-phenyl)-pyrazolo[1,5-a]pyridine-3-carboxylic acid ethyl ester (example C.22 step 7) (1.21 g, 3.0 mmol) in THF (15 mL), MeOH (1.8 mL) and $H_2O$ (4.8 mL) was added $LiOH.H_2O$ (0.3.8 g, 9.0 mmol) and the reaction mixture was stirred at 23° C. for 18 h. Poured into ice water, adjusted with 1 N HCl to pH 2-3, filtered the precipitate off, washed with $H_2O$ and dried at HV to give the title compound as an off-white solid (1.08 g, 96%). MS (ISN) 373 [(M−H)$^-$]; mp >250° C.

Step 9) 3-Iodo-7-trifluoromethyl-5-(4-trifluoromethyl-phenyl)-pyrazolo[1,5-a]pyridine A mixture of 7-trifluoromethyl-5-(4-trifluoromethyl-phenyl)-pyrazolo [1,5-a]pyridine-3-carboxylic acid (example C.22 step 8) (650 mg, 1.74 mmol) in acetic acid (20 mL) containing HI (57%, 200 uL) was refluxed for 2 days, but only 30% conversion. Added HBr (48%, 2 mL, 18 mmol) and continued refluxing for 2 h. Cooled to 23° C., added NaOAc (2.5 g, 30 mmol) and ICl (2M in HOAc, 6.1 mL, 12.2 mmol) and the mixture was stirred at 23° C. for 1 h. Added sat. $Na_2SO_3$-sol. to destroy excess ICl, diluted with water, filtered precipitate off, washed with water, dissolved in TBME, washed with sat. $NaHCO_3$-sol. and brine, dried over $Na_2SO_4$. Removal of the solvent in vacuum left the title compound as a light yellow solid (740 mg, 93%; LC-MS shows mixture of bromide and iodide). MS (for iodide) (ISP) 456.2 [(M+H)$^+$].

Example C.23

3-Ethynyl-6-(4-trifluoromethyl-phenyl)-imidazo[1,2-a]pyridine-8-carbonitrile

Step 1) 2-Amino-5-bromo-nicotinonitrile

To a solution of commercially available 2-amino-3-cyanopyridine (15 g, 126 mmol) in ethanol (250 mL) at 0° C. was dropwise added bromine (6.7 mL, 130 mmol) and the mixture was stirred at 0° C. for 2 h, then at 23° C. for 16 h. The solvent was totally evaporated, water (200 mL) was added, then sat. $NaHCO_3$-solution until neutral. Extracted with AcOEt (3×300 mL), the organic layer was dried over $Na_2SO_4$, filtered and totally evaporated. The residue was triturated with ether to give the title compound as a light yellow solid (23.5 g, 94%). MS (ISP) 198.1 [(M+H)$^+$], 200.2 [(M+2+H)$^+$].

Step 2) 6-Bromo-imidazo[1,2-a]pyridine-8-carbonitrile

Prepared from 2-amino-5-bromo-nicotinonitrile (example C.23 step 1) (26 g, 131 mmol) and bromoacetaldehyde diethyl acetal (90%, 45 mL, 263 mmol) as described in example C.20 step 1. Obtained the title compound as a light brown solid (9.3 g, 32%).MS (ISP) 222.1 [(M+H)$^+$], 224 [(M+2+H)$^+$].

Step 3) 6-(4-Trifluoromethyl-phenyl)-imidazo[1,2-a]pyridine-8-carbonitrile

Prepared from 6-bromo-imidazo[1,2-a]pyridine-8-carbonitrile (example C.23 step 2) (1.6 g, 7 mmol) and commercially available 4-trifluoromethylphenylboronic acid (1.505 g, 36 mmol) as described in example C.20 step 2. Obtained the title compound as a white solid (1.2 g, 46%). MS (ISP) 288.0 [(M+H)$^+$].

Step 4) 3-Iodo-6-(4-trifluoromethyl-phenyl)-imidazo[1,2-a]pyridine-8-carbonitrile Prepared from 6-(4-chloro-phenyl)-8-methyl-imidazo[1,2-a]pyridine (example C.23 step 3) (900 mg, 4 mmol) and iodine monochloride as described in example C.20 step 3. Obtained the title compound as a light yellow solid (1.3 g, 99%). MS (ISP) 414.1 [(M+H)$^+$].

Step 5) 6-(4-Trifluoromethyl-phenyl)-3-trimethylsilanylethynyl-imidazo[1,2-a]pyridine-8-carbonitrile Prepared from 3-iodo-6-(4-trifluoromethyl-phenyl)-imidazo[1,2-a]pyridine-8-carbonitrile (example C.23 step 4) (1.3 g, 4 mmol) and trimethylsilylacetylene (0.87 mL, 6 mmol) as described in example C.20 step 4. Obtained the title compound as a light brown solid (1.0 g, 82%). MS (ISP) 384.1 [(M+H)$^+$].

Step 6) 3-Ethynyl-6-(4-trifluoromethyl-phenyl)-imidazo[1,2-a]pyridine-8-carbonitrile Prepared form 6-(4-trifluoromethyl-phenyl)-3-trimethylsilanylethynyl-imidazo[1,2-a]pyridine-8-carbonitrile (example C.23 step 5) (1 g, 3 mmol) as described in example C.20 step 5. Obtained the title compound as a light brown solid (500 mg, 61%). MS (ISP) 312.1 [(M+H)$^+$].

Example C.24

3-Ethynyl-6-(4-trifluoromethyl-phenyl)-imidazo[1,2-a]pyridine

Step 1) 6-(4-Trifluoromethyl-phenyl)-imidazo[1,2-a]pyridine-8-carbonitrile

Prepared from commercially available 6-bromo-imidazo[1,2-a]pyridine (23.2 g, 117 mmol) and commercially available 4-trifluoromethylphenylboronic acid (24.6 g, 129 mmol) as described in example C.20 step 2. Obtained the title compound as a grey solid (18.8 g, 61%). MS (ISP) 263.1 [(M+H)$^+$].

Step 2) 3-Iodo-6-(4-trifluoromethyl-phenyl)-imidazo[1,2-a]pyridine

Prepared from 6-(4-trifluoromethyl-phenyl)-imidazo[1,2-a]pyridine (example C.24 step 1) (2.3 g, 9 mmol) and iodine monochloride as described in example C.20 step 3. Obtained the title compound as a light yellow solid (2.3 g, 67%). MS (ISP) 389.1 [(M+H)$^+$].

Step 3) 6-(4-Trifluoromethyl-phenyl)-3-trimethylsilanylethynyl-imidazo[1,2-a]pyridine Prepared from 3-iodo-6-(4-trifluoromethyl-phenyl)-imidazo[1,2-a]pyridine (example C.24 step 2) (2.3 g, 6 mmol) and trimethylsilylacetylene (1.64 mL, 12 mmol) as described in example C.20 step 4. Obtained the title compound as a yellow solid (1.9 g, 89%). MS (ISP) 359.1 [(M+H)$^+$].

Step 4) 3-Ethynyl-6-(4-trifluoromethyl-phenyl)-imidazo[1,2-a]pyridine
Prepared form 6-(4-trifluoromethyl-phenyl)-3-trimethylsilanylethynyl-imidazo[1,2-a]pyridine (example C.24 step 3) (1.9 g, 5 mmol) as described in example C.20 step 5. Obtained the title compound as a light brown solid (400 mg, 26%). MS (ISP) 287.1 [(M+H)$^+$].

Example C.25

8-Cyclopropyl-3-ethynyl-6-(4-trifluoromethyl-phenyl)-imidazo[1,2-a]pyridine

Step 1) 5-(4-Trifluoromethyl-phenyl)-pyridin-2-ylamine
Prepared from commercially available 2-amino-5-bromopyridine (5.0 g, 29 mmol) and commercially available 4-trifluoromethylphenylboronic acid (6 g, 32 mmol) as described in example C.20 step 2. Obtained the title compound as an off-white solid (56 g, 56%). MS (ISP) 239.2 [(M+H)$^+$].

Step 2) 3-Bromo-5-(4-trifluoromethyl-phenyl)-pyridin-2-ylamine
To a solution of 5-(4-trifluoromethyl-phenyl)-pyridin-2-ylamine (example C.25 step 1) (3.9 g, 16 mmol) in acetonitrile (65 mL) at 0° C. was added NBS (2.914 g, 16 mmol) and the mixture was stirred at 23° C. for 2 h. Poured on ice with sat. NaHCO$_3$-sol., extracted thrice with AcOEt, dried the combined organic layers over Na$_2$SO$_4$, filtered off and evaporated. The residue was purified by silica gel column chromatography with AcOEt followed by trituration with heptane and very little ether to give the title compound as a light brown solid (3.7 g, 71%). MS (ISP) 317 [(M+H)$^+$], 319 [(M+2+H)$^+$].

Step 3) 8-Bromo-6-(4-trifluoromethyl-phenyl)-imidazo[1,2-a]pyridine
To a mixture of 3-bromo-5-(4-trifluoromethyl-phenyl)-pyridin-2-ylamine (example C.25 step 2) (4.96 g, 16 mmol) and sodium bicarbonate (5.256 g, 63 mmol) in EtOH (20 mL) at 50° C. was dropwise added chloroacetaldehyde (50% in water, 3.66 mL, 31 mmol) within 2 h. Cooled to 23° C. and evaporated all volatiles The residue was purified by silica gel column chromatography with dichloromethane/methanol followed by trituration with heptane and very little ether to give the title compound as a white solid (3.4 g, 63%). MS (ISP) 340.9 [(M+H)$^+$], 343.1 [(M+2+H)$^+$].

Step 4) 8-Cyclopropyl-6-(4-trifluoromethyl-phenyl)-imidazo[1,2-a]pyridine
To a Schlenk flask was added 8-bromo-6-(4-trifluoromethyl-phenyl)-imidazo[1,2-a]pyridine (example C.25 step 3) (3.026 g, 8.9 mmol), cyclopropyl boronic acid (103 mg, 13 mmol), tri(cyclohexyl)phosphine (101 mg, 4 mol %), potassium phosphate (6.53 g, 31 mmol), 50 mL of toluene and 2.5 mL of water. The reaction mixture was degassed under Ar for 5 min, then palladium acetate (41 mg, 2 mol %) was added and continued to bubble in Ar, then placed into a 100° C. oil bath for 23 h. The cooled reaction mixture was decanted and filtered through a pad of celite/Si Gel, washed aqueous material with EtOAc and combined organic layers were concentrated to give a green-colored mixture. This residue was purified by silica gel column chromatography with heptane/EtOAc followed by trituration with heptane and very little ether to give the title compound as a green solid (1.79 g, 67%). MS (ISP) 303.1 [(M+H)$^+$].

Step 5) 8-Cyclopropyl-3-iodo-6-(4-trifluoromethyl-phenyl)-imidazo[1,2-a]pyridine
Prepared from 8-cyclopropyl-6-(4-trifluoromethyl-phenyl)-imidazo[1,2-a]pyridine (example C.25 step 4) (2.2 g, 7 mmol) and iodine monochloride as described in example C.20 step 3. Obtained the title compound as a grey solid (3.1 g, 99%). MS (ISP) 429.2 [(M+H)$^+$].

Step 6) 8-Cyclopropyl-6-(4-trifluoromethyl-phenyl)-3-trimethylsilanylethynyl-imidazo[1,2-a]pyridine
Prepared from 8-cyclopropyl-3-iodo-6-(4-trifluoromethyl-phenyl)-imidazo[1,2-a]pyridine (example C.25 step 5) (3.1 g, 7 mmol) and trimethylsilylacetylene (2.00 mL, 14 mmol) as described in example C.20 step 4. Obtained the title compound as an amorphous brown material (2.3 g, 79%). MS (ISP) 399.2 [(M+H)$^+$].

Step 7) 8-Cyclopropyl-3-ethynyl-6-(4-trifluoromethyl-phenyl)-imidazo[ 1,2-a]pyridine
Prepared form 8-cyclopropyl-6-(4-trifluoromethyl-phenyl)-3-trimethylsilanylethynyl-imidazo [1,2-a]pyridine (example C.25 step 6) (2.3 g, 6 mmol) as described in example C.20 step 5. Obtained the title compound as a light brown solid (1.0 g, 53%). MS (ISP) 327.2 [(M+H)$^+$].

Example C.26

3-Iodo-8-trifluoromethyl-6-(4-trifluoromethyl-phenyl)-imidazo[1,2-b]pyridazine

Step 1) 3,3-Bis-ethylsulfanyl-1,1,1,2,2-pentafluoro-propane
To solution of commercially available pentafluoropropionaldehyde hydrate (100 g, 600 mmol) and ethanethiol (90.16 mL, 1200 mmol) in DCM (1200 mL) at −20° C. (dry ice, EtOH) was added dropwise a solution of TiCl$_4$ (198.1 mL, 1800 mmol) in DCM (240 mL) within 30 min keeping the temperature at −20° C. The resulting orange solution was stirred at 23° C. for 2 h. Cooled to 0° C., water (1200 mL) was cautiously added, the organic layer was separated and dried over MgSO$_4$. The solvent was removed by cautious rotary evaporation (470 mbar, 40° C., 100 rpm) to give a turbid colorless liquid (141.15 g, 92%). Vacuum distillation gave the title compound as a colorless liquid (125.89 g, 82%; bp 83-84° C. at 32 mbar). [according to J. Org. Chem. 1993, 58(1), 29-31. ] MS (GC-MS; EI) 254 [(M)$^+$].

Step 2) 1,1-Bis-ethylsulfanyl-2,3,3,3-tetrafluoro-propene
A solution of 3,3-bis-ethylsulfanyl-1,1,1,2,2-pentafluoropropane (example C.26 step 1) (125.8 g, 495 mmol) in DCM (495 mL) and 3M KOH (97.97 g KOH (85%) in 495 mL H$_2$O), with a catalytic amount of n-BuN$_4$Br (4.785 g, 3 mol %), was stirred at 23° C. for 3 h. The organic layer was separated and dried over MgSO$_4$. The solvent was removed by cautious rotary evaporation (470 mbar, 40° C., 100 rpm) to give an orange liquid (ca. 145 g, 125%). Vacuum distillation gave the title compound as a colorless liquid (109.82 g, 95%; bp 86-87° C. at 32 mbar). [according to J. Org. Chem. 1993, 58(1), 29-31.] MS (GC-MS; EI) 234.1 [(M)+].

Step 3) 4,4-Bis-ethylsulfanyl-3-trifluoromethyl-1-(4-trifluoromethyl-phenyl)-but-3-en-1-one
A suspension of KH (35% in mineral oil, 22.92 g, 200 mmol) was added via syringe to a solution of commercially available 4-trifluoromethyl acetophenone (18.82 g, 100 mmol) in THF (120 mL) at 0° C. under nitrogen atmosphere. The mixture was stirred for 15 min, then a solution of 1,1-bis-ethylsulfanyl-2,3,3,3-tetrafluoro-propene (example C.26 step 2) (23.43 g, 100 mmol) in THF (60 mL) was added and the mixture was warmed up to 23° C. and the resulting red solution was stirred for further 18 h. The mixture was poured on ice acidified with 1N HCl and extracted with EtOAc, the organic layer was washed with sat. NaHCO$_3$-solution and brine, dried over MgSO$_4$. Removal of the solvent in vacuum left a red oil, which was purified by silica gel column chromatography with heptane/EtOAc 100/0 to 95/5 to give the title compound as an orange liquid (36.96 g, 92%) [according to Synlett 1995,247. ]. MS (EI) 402.0 [(M)$^+$].

Step 4) 4-Oxo-2-trifluoromethyl-4-(4-trifluoromethyl-phenyl)-thiobutyric acid S-ethyl ester A mixture of 4,4-bis-ethylsulfanyl-3-trifluoromethyl-1-(4-trifluoromethyl-phenyl)-but-3-en-1-one (example C.26 step 3) (36.96 g, 92 mmol) in TFA (54.3 mL) and water (5.8 mL) was refluxed for 18 h under nitrogen atmosphere, the exhaust of the reaction was passed through a NaOCl solution to trap the liberated ethyl mercaptane. The volatiles were evaporated and the mixture was diluted with water and extracted with TBME, the organic layer was washed with sat. NaHCO$_3$-sol. and brine, dried over Na$_2$SO$_4$. Removal of the solvent in vacuum left the title compound as a brown oil (31.2 g, 95%), which was used without further purification [according to J. Fluorine Chem. 2001, 107, 281. ]. MS (EI) 339.0 [(M−F)$^+$].

Step 5) 4-Trifluoromethyl-6-(4-trifluoromethyl-phenyl)-4,5-dihydro-2H-pyridazin-3-one A mixture of 4-oxo-2-trifluoromethyl-4-(4-trifluoromethyl-phenyl)-thiobutyric acid S-ethyl ester (example C.26 step 4) (16.0 g, 45 mmol) and hydrazine monohydrate (2.39 mL, 49 mmol) in EtOH (250 mL) was refluxed for 18 h under nitrogen atmosphere. Cooled to 23° C., the solvents were evaporated to leave the title compound as a brown solid (13.83 g, 100%), which was used without further purification [according to Synthesis 2003, (3), 436.]. MS (ISP) 311.1 [(M+H)$^+$]; mp 135-136° C.

Step 6) 4-Trifluoromethyl-6-(4-trifluoromethyl-phenyl)-2H-pyridazin-3-one

A mixture of 4-trifluoromethyl-6-(4-trifluoromethyl-phenyl)-4,5-dihydro-2H-pyridazin-3-one (example C.26 step 5) (11.33 g, 37 mmol) and CuCl$_2$ (9.82 g, 73 mmol) in acetonitrile (80 mL) was refluxed for 7 h under ambient atmosphere. The mixture was cooled to 23° C., filtered through dicalite, applied onto silica gel and purified by chromatography with heptane/EtOAc 4:1→2:1→1:1 to give the title compound as a light green solid (9.61 g, 85. %) [according to Synthesis 2003, (3), 436.]. MS (ISN) 307.1 [(M−H)$^−$]; mp 179-181° C.

Step 7) 3-Bromo-4-trifluoromethyl-6-(4-trifluoromethyl-phenyl)-pyridazine

A mixture of 4-trifluoromethyl-6-(4-trifluoromethyl-phenyl)-2H-pyridazin-3-one (example C.26 step 6) (9.61 g, 31 mmol), POBr$_3$ (26.8 g, 94 mmol) and DMF (0.72 mL, 9 mmol) was stirred for 3 h at 105° C. under nitrogen atmosphere. The reaction mixture was poured (the mixture was nearly solid) onto water (300 mL) and stirred for 2 h at 23° C., the precipitated solid was filtered off and applied onto silica gel for silica gel column chromatography with heptane/EtOAc 4:1→2:1 to give the title compound as a light brown solid (11.22 g, 97%). MS (ISP) 371 [(M+H)$^+$], 373 [(M+2+H)$^+$]; mp 123-125° C.

Step 8) (4-Methoxy-benzyl)-[4-trifluoromethyl-6-(4-trifluoromethyl-phenyl)-pyridazin-3-yl]-amine A mixture of 3-bromo-4-trifluoromethyl-6-(4-trifluoromethyl-phenyl)-pyridazine (example C.26 step 7) (5.76 g, 16 mmol), DIPEA (3.19 mL, 19 mmol) and 4-methoxybenzylamine (2.4 mL, 19 mmol) in EtOH (25 mL) was refluxed for 18 h under argon atmosphere. Cooled to 23 C, the mixture was poured onto water, the precipitated solid was filtered off, washed with water and dried in air at 60° C. on the heating plate to give the title compound as an off-white solid (6.49 g, 98%). MS (ISP) 428.3 [(M+H)$^+$]; mp 101-103° C.

Step 9) 4-Trifluoromethyl-6-(4-trifluoromethyl-phenyl)-pyridazin-3-ylamine (4-Methoxy-benzyl)-[4-trifluoromethyl-6-(4-trifluoromethyl-phenyl)-pyridazin-3-yl]-amine (example C.26 step 8) (6.48 g, 15 mmol) was added portionwise at 5° C. to conc. H$_2$SO$_4$ (d 1.83, 17.0 mL, 303 mmol).The deep purple solution was stirred for 5 min at 5° C. then the cooling bath was removed and stirring was continued for further 60 min at 23° C. The mixture was poured onto ice, made alkaline with 32% NaOH-sol., saturated with solid NaCl and extracted with THF and TBME, dried the organic layer over MgSO$_4$. Removal of the solvent in vacuum left the title compound as a light yellow solid (4.44 g, 95%), which was used without further purification. MS (ISP) 308.1 [(M+H)$^+$]; mp 186-190° C.

Step 10) 8-Trifluoromethyl-6-(4-trifluoromethyl-phenyl)-imidazo[1,2-b]pyridazine Prepared from 4-trifluoromethyl-6-(4-trifluoromethyl-phenyl)-pyridazin-3-ylamine (example C.26 step 9) (4.44 g, 14.4 mmol) and bromoacetaldehyde diethyl acetal (90%, 4.98 mL, 29 mmol) as described in example C.20 step 1. Obtained the title compound as a yellow solid (4.51 g, 94%) .MS (ISP) 332.0 [(M+H)$^+$].

Step 11) 3-Iodo-8-trifluoromethyl-6-(4-trifluoromethyl-phenyl)-imidazo[1,2-b]pyridazine Prepared from 8-trifluoromethyl-6-(4-trifluoromethyl-phenyl)-imidazo[1,2-b]pyridazine (example C.26 step 10) (4.44 g, 14 mmol) and iodine monochloride as described in example C.20 step 3. Obtained the title compound as a yellow solid (5.803 g, 98%). MS (ISP) 458.2 [(M+H)$^+$].

Example C.27

6-(4-Chloro-phenyl)-8-cyclopropyl-3-iodo-imidazo[1,2-a]pyridine

Steps 1) 5-(4-Chloro-phenyl)-pyridin-2-ylamine

Prepared from commercially available 2-amino-5-bromopyridine (8.65 g, 50 mmol) and commercially available 4-chlorophenylboronic acid (12.08 g, 77 mmol) as described in example C.20 step 2. Obtained the crude 5-(4-chloro-phenyl)-pyridin-2-ylamine as an orange solid (89% pure).

Step 2) 3-Bromo-5-(4-chloro-phenyl)-pyridin-2-ylamine

Prepared from crude 5-(4-chloro-phenyl)-pyridin-2-ylamine (example C.27 step 1) (ca. 50 mmol) in acetonitrile (100 mL) and NBS (9.34 g, 53 mmol) as described in example C.25 step 2. Obtained the crude 3-bromo-5-(4-chloro-phenyl)-pyridin-2-ylamine a dark brown solid (76% pure).

Step 3) 8-Bromo-6-(4-chloro-phenyl)-imidazo[1,2-a]pyridine

Prepared from crude 3-bromo-5-(4-chloro-phenyl)-pyridin-2-ylamine (example C.27 step 2) (ca. 50 mmol) and bromoacetaldehyde diethyl acetal (90%, 17.2 mL, 100 mmol) as described in example C.20 step 1. Obtained the pure 8-bromo-6-(4-chloro-phenyl)-imidazo[1,2-a]pyridine after chromatography as a light brown solid (11.91 g, 77%). MS (ISP) 307.1 [(M+H)$^+$], 309.1 [(M+2+H)$^+$], 311.1 [(M+4+H)$^+$].

Step 4) 6-(4-Chloro-phenyl)-8-cyclopropyl-imidazo[1,2-a]pyridine

Prepared from 8-bromo-6-(4-chloro-phenyl)-imidazo[1,2-a]pyridine (example C.27 step 3) (6.15 g, 20 mmol) and cyclopropylboronic acid (2.23 g, 26 mmol) as described in example C.25 step 4. Obtained the title compound as an orange solid (3.18 g, 59%; 88% pure, contains 12% 8-cyclopropyl-6-(4-cyclopropyl-phenyl)-imidazo[1,2-a]pyridine). MS (ISP) 269.3 [(M+H)$^+$], 271.3 [(M+2+H)$^+$].

Step 5) 6-(4-Chloro-phenyl)-8-cyclopropyl-3-iodo-imidazo[1,2-a]pyridine

Prepared from 6-(4-chloro-phenyl)-8-cyclopropyl-imidazo[1,2-a]pyridine (example C.27 step 4) (3.1 g, 11.5 mmol) and iodine monochloride as described in example C.20 step 3. Obtained the title compound as an off-white solid (1.098 g, 24% pure material, crystallized from EtOAc/heptane; 2.001 g, 42% contains dicylopropyl material). MS (ISP) 394.8 [(M+H)$^+$], 396.9 [(M+2+H)$^+$].

Example C.28

7-Cyclopropyl-3-iodo-5-(4-trifluoromethyl-phenyl)-pyrazolo [1,5-a]pyridine

Step 1) (E)-1-Cyclopropyl-3-(4-trifluoromethyl-phenyl)-propenone

To a solution of commercially available 4-trifluoromethyl-benzaldehyde (6.86 mL, 50 mmol) and commercially available cyclopropylmethylketone (4.68 mL, 50 mmol) in MeOH (10 mL) was added NaOMe-sol. (5.4 M in MeOH, 1.85 mL, 10 mmol) and the mixture was stirred at 23° C. for 2 h [slightly exothermic reaction]. Poured onto ice +1 N HCl (50 mL), saturated with solid NaCl, extracted with TBME, dried over MgSO$_4$. Removal of the solvent in vacuum left the title compound as a light yellow semisolid (12.03 g, 100%). MS (EI) 240.2 [(M)$^+$].

Step 2) 6-Cyclopropyl-4-(4-trifluoromethyl-phenyl)-1H-pyridin-2-one

A mixture of (E)-1-cyclopropyl-3-(4-trifluoromethyl-phenyl)-propenone (example C.28 step 1) (7.21 g, 30 mmol), commercially available 1-ethoxycarbonylmethyl-pyridinium bromide (CAS-no. [17282-40-5]) (8.86 g, 36 mmol) and ammonium acetate (11.56 g, 150 mmol) in EtOH (100 mL) was refluxed for 3 h. Evaporated to dryness, triturated with 1 N HCl and water, filtered the precipitate off, washed with water and dried in air at 60° C. to give the title compound as a red solid (7.29 g, 87%). MS (ISN) 278.2 [(M−H)$^-$].

Step 3) 1-Amino-6-cyclopropyl-4-(4-trifluoromethyl-phenyl)-1H-pyridin-2-one

To a solution of 6-cyclopropyl-4-(4-trifluoromethyl-phenyl)-1H-pyridin-2-one (example C.28 step 2) (4.19 g, 15.0 mmol) in THF (225 mL) and 1M NaOH (90.0 mL, 90.0 mmol) was added dropwise a solution of hydroxylamine-O-sulfonic acid (HOSA) (95%, 5.36 g, 45.0 mmol) in H$_2$O (60 mL) at 0° C. The reaction mixture was stirred at 23° C. for 20 h (76% conversion). Added again at 0° C. 3N NaOH (30 mL, 30.0 mmol) and then hydroxylamine-O-sulfonic acid (HOSA) (95%, 5.36 g, 45.0 mmol) and the reaction mixture was stirred at 23° C. for 3 days (88% conversion). Poured into ice water, extracted with EtOAc, washed the organic layers with brine, dried over Na$_2$SO$_4$. Removal of the solvent in vacuum left a residue (5.17 g) which was purified by silica gel chromatography (400 g SiO$_2$) to give the title compound as a light yellow solid (2.81 g, 64%). MS (ISP) 295.5 [(M+H)$^+$]; mp 132° C.

Step 4) 1-Amino-6-trifluoromethyl-4-(4-trifluoromethyl-phenyl)-1H-pyridine-2-thione Prepared from 1-amino-6-cyclopropyl-4-(4-trifluoromethyl-phenyl)-1H-pyridin-2-one (example C.28 step 3) (2.75 g, 9.34 mmol) and lawssons's reagent (3.78 g, 9.34 mmol) as described in example C.22 step 6. Obtained the title compound as a yellow solid (2.04 g, 70%). MS (ISP) 311 [(M+H)$^+$]; mp 205° C.

Step 5) 7-Cyclopropyl-5-(4-trifluoromethyl-phenyl)-pyrazolo [1,5-a]pyridine-3-carboxylic acid ethyl ester Prepared from 1-amino-6-trifluoromethyl-4-(4-trifluoromethyl-phenyl)-1H-pyridine-2-thione (example C.28 step 4) (2.44 g, 5.4 mmol) and 2-chloro-3-oxo-propionic acid ethyl ester (example C.22 reagent 1) (1.68 g, 16.2 mmol) as described in example C.22 step 7. Obtained the title compound as an off-white solid (1.72 g, 85%). MS (ISP) 375 [(M+H)$^+$]; mp 117° C.

Step 6) 7-Cyclopropyl-5-(4-trifluoromethyl-phenyl)-pyrazolo [1,5-a]pyridine-3-carboxylic acid Prepared from 7-cyclopropyl-5-(4-trifluoromethyl-phenyl)-pyrazolo [1,5-a]pyridine-3-carboxylic acid ethyl ester (example C.28 step 5) (1.95 g, 5.21 mmol) as described in example C.22 step 8. Obtained the title compound as an off-white solid (1.76 g, 98%). MS (ISN) 345 [(M−H)$^-$]; mp 253° C. (dec.).

Step 7) 7-Cyclopropyl-3-iodo-5-(4-trifluoromethyl-phenyl)-pyrazolo[1,5-a]pyridine A mixture of 7-cyclopropyl-5-(4-trifluoromethyl-phenyl)-pyrazolo[1,5-a]pyridine-3-carboxylic acid (example C.28 step 6) (1.03 g, 2.97 mmol) in acetic acid (40 mL) was refluxed for 20 h. Cooled to 23° C., added NaOAc (325 mg, 3.95 mmol) and ICl (2M in HOAc, 1.85 mL, 3.7 mmol) and the mixture was stirred at 23° C. for 2 h. Poured into water, filtered precipitate off, washed with water, dissolved in TBME, washed with sat. NaHCO$_3$-sol.+little sat. Na$_2$SO$_3$-sol. and brine, dried over Na$_2$SO$_4$. Removal of the solvent in vacuum left the title compound as a light red solid (1.257 g, 99%). MS (ISP) 429.2 [(M+H)$^+$].

Example C.29

8-Fluoro-3-iodo-6-(4-trifluoromethyl-phenyl)-imidazo[1,2-a]pyridine

Step 1) (3-Fluoro-pyridin-2-yl)-(4-methoxy-benzyl)-amine

A mixture of commercially available 2-chloro-3-fluoromethylpyridine (10.53 g, 80 mmol), 4-methoxybenzylamine (12.5 mL, 96 mmol), DIPEA (16.5 mL, 96 mmol) and DMAP (150 mg) in n-butanol (20 mL) was refluxed (oilbathtemp. 140° C.) for 12 days. Concentrated in vacuum and directly subjected to chromatography. Silica gel column chromatography gave the title compound as a yellow liquid (6.3 g, 34%). MS (ISP) 233.1 [(M+H)$^+$].

Step 2) 3-Fluoro-pyridin-2-ylamine

To conc. H$_2$SO$_4$ (27 mL, 505 mmol) at 5° C. was added dropwise (3-fluoro-pyridin-2-yl)-(4-methoxy-benzyl)-amine(example C.29 step 1) (6.3 g, 27 mmol) and the mixture was stirred at 5° C. for 5 min, then the cooling bath was removed and stirring was continued at 23° C. for 30 min. Poured onto ice, made alkaline with 32% NaOH-sol., satured with solid NaCl, extracted twice with THF, dried the organic layer over Na$_2$SO$_4$. Removal of the solvent in vacuum gave the title compound as a brown solid (3.0 g, 98%). MS (EI) 112 [(M)$^+$].

Step 3) 5-Bromo-3-fluoro-pyridin-2-ylamine

To a solution of 3-fluoro-pyridin-2-ylamine (example C.29 step 2) (3 g, 26.8 mmol) in acetonitrile (50 mL) at 0° C. was added NBS (4.77 g, 26.8 mmol) and the mixture was stirred at 23° C. for 2 h. Poured on ice with sat. NaHCO$_3$-sol., extracted thrice with AcOEt, dried over Na$_2$SO$_4$. Removal of the solvent in vacuum left a residue, which was purified by silica gel column chromatography with heptane/AcOEt 3:1 to give the title compound as a brown solid (3.1 g, 60%). MS (ISP) 191 [(M+H)$^+$], 193 [(M+2+H)$^+$].

Step 4) 6-Bromo-8-fluoro-imidazo[1,2-a]pyridine

Prepared from 5-bromo-3-fluoro-pyridin-2-ylamine (example C.29 step 3) (3.1 g, 15.7 mmol) and bromoacetaldehyde diethyl acetal (90%, 4.86 mL, 31.3 mmol) as described in example C.20 step 1. Obtained the title compound as a light brown solid (3.0 g, 89%). MS (ISP) 215.1 [(M+H)$^+$], 217.1 [(M+2+H)$^+$].

Step 5) 8-Fluoro-6-(4-trifluoromethyl-phenyl)-imidazo[1,2-a]pyridine

Prepared from 6-bromo-8-fluoro-imidazo[1,2-a]pyridine (example C.29 step 4) (1.5 g, 7 mmol) and commercially available 4-trifluoromethylphenylboronic acid (1.46 g, 7.7 mmol) as described in example C.20 step 2. Obtained the title compound as a light brown solid (1.95 g, 100%). MS (ISP) 281.1 [(M+H)$^+$].

Step 6) 8-Fluoro-3-iodo-6-(4-trifluoromethyl-phenyl)-imidazo[1,2-a]pyridine

Prepared from 8-fluoro-6-(4-trifluoromethyl-phenyl)-imidazo[1,2-a]pyridine (example C.29 step 5) (1.95 g, 7.9 mmol) and iodine monochloride as described in example C.20 step 3. Obtained the title compound as a light brown solid (1.8 g, 78%). MS (ISP) 407.0 [(M+H)$^+$].

Example C.30

6-(4-Chloro-phenyl)-8-fluoro-3-iodo-imidazo[1,2-a]pyridine

Step 1) 6-(4-Chloro-phenyl)-8-fluoro-3-iodo-imidazo[1,2-a]pyridine

Prepared from 6-bromo-8-fluoro-imidazo[1,2-a]pyridine (example C.29 step 4) (1.5 g, 7 mmol) and commercially available 4-chlorophenylboronic acid (1.2 g, 7.7 mmol) as described in example C.20 step 2. Obtained the title compound as a light brown solid (1.72 g, 100%). MS (ISP) 247.1 [(M+H)$^+$], 249 [(M+2+H)$^+$].

Step 2) 6-(4-Chloro-phenyl)-8-fluoro-3-iodo-imidazo[1,2-a]pyridine

Prepared from 6-(4-chloro-phenyl)-8-fluoro-3-iodo-imidazo[1,2-a]pyridine (example C.30 step 1) (1.72 g, 7 mmol) and iodine monochloride as described in example C.20 step 3. Obtained the title compound as an off-white solid (2.14 g, 82%). MS (ISP) 373.0 [(M+H)$^+$], 375 [(M+2+H)$^+$].

Example C.31

4-Difluoromethyl-8-ethynyl-2-(4-trifluoromethyl-phenyl)-imidazo[1,5-a]pyrimidine 1) A mixture of 4,4-difluoro-1-(4-trifluoromethyl-phenyl)-butane-1,3-dione (8.87 g, 33.3 mmol) and 5-amino-1H-imidazole-4-carboxylic acid ethyl ester (5.17 g, 33.3 mmol) in acetic acid (100 ml) was refluxed for 27 h and evaporated. The crude product was further purified by column chromatography on silica gel (ethyl acetate/heptane 7:3) and crystallization (diethyl ether/hexane) to yield 4-difluoromethyl-2-(4-trifluoromethyl-phenyl)-imidazo[1,5-a]pyrimidine-8-carboxylic acid ethyl ester (6.35 g, 49%) as a yellow solid. MS (EI) 385.1 [(M)$^+$]; mp 219° C.

2) A mixture of 4-difluoromethyl-2-(4-trifluoromethyl-phenyl)-imidazo[1,5-a]pyrimidine-8-carboxylic acid ethyl ester (6.0 g, 15.6 mmol), potassium hydroxide 14 g (0.25 mmol) in water (62.5 ml) and methanol (125 ml) was stirred at room temperature for 2 h and at 60° C. for 1 h, cooled (ice-water), and 3N sulfuric acid (90 ml) was added. The formed precipitate (4.32 g) was collected by filtration, acetic acid (65 ml) was added and the stirred solution was heated under reflux conditions for 1 h. The reaction mixture was evaporated, ethyl acetate (30 ml) was added and the mixture was stirred for 30 min at 0° C. The precipitate was collected by filtration and dried to yield 4-difluoromethyl-2-(4-trifluoromethyl-phenyl)-imidazo[1,5-a]pyrimidine-8-carboxylic acid (2.15 g, 39%) as a yellow solid. MS (ISN) 356.0 [(M−H)$^-$]; mp 238° C.

3) 4-Difluoromethyl-2-(4-trifluoromethyl-phenyl)-imidazo[1,5-a]pyrimidine-8-carboxylic acid (2.0 g, 5.60 mmol) was heated up to the melting point and the crude product purified by flash chromatography on silica gel (ethyl acetate/heptane) to yield 4-difluoromethyl-2-(4-trifluoromethyl-phenyl)-imidazo[1,5-a]pyrimidine (1.48 g, 84%) as a yellow solid. MS (EI) 313.2 [(M)$^+$]; mp 173° C.

4) To a stirred solution of 4-difluoromethyl-2-(4-trifluoromethyl-phenyl)-imidazo[1,5-a]pyrimidine (1.56 g, 4.98 mmol) in acetic acid (9 ml) was added at room temperature sodium acetate (0.46 g, 5.63 mmol) and drop wise a solution of iodine monochloride (0.91 g, 5.63 mmol) in acetic acid (4 ml). The reaction mixture was stirred at room temperature for 17 h, diluted slowly with water (150 ml), stirred at room temperature for 30 min, the precipitate was filtered off, washed with water and dried to give 4-difluoromethyl-8-iodo-2-(4-trifluoromethyl-phenyl)-imidazo[1,5-a]pyrimidine (2.45 g, 100%) as a yellow solid. MS (EI) 439.0 [(M)$^+$]; mp 159° C.

5) A mixture of 4-difluoromethyl-8-iodo-2-(4-trifluoromethyl-phenyl)-imidazo[1,5-a]pyrimidine (2.45 g, 5.58 mmol), trimethylsilylacetylene (1.24 ml, 8.94 mmol) and triethylamine (2.08 ml, 14.9 mmol) in N,N-dimethylformamide (10 ml) was stirred for 10 min at room temperature while being purged with Argon, then PdCl$_2$(PPh$_3$)$_2$ (105 mg, 0.15 mmol), PPh$_3$ (78 mg, 0.3 mmol) and CuI (9 mg, 0.05 mmol) were added. Stirring was continued at 90° C. for 5 h. The reaction mixture was cooled to room temperature, diluted with ice-water (50 mL) and extracted with ethyl acetate (3×70 ml). The combined organic layers were washed with water (40 ml) and brine (40 ml), dried (MgSO$_4$) and evaporated to give 4-difluoromethyl-2-(4-trifluoromethyl-phenyl)-8-trimethylsilanylethynyl-imidazo[1,5-a]pyrimidine(1.58 g, 69%) as a brown solid, which was dissolved in THF (15 ml) and MeOH (15 ml), while stirring at 0° C. potassium carbonate (51 mg, 0.37 mmol) was added and the mixture was stirred at 0° C. for 5 h. The mixture was diluted with ice water (50 ml) and extracted with TBME (2×80 ml). The combined organic layers were washed with brine (50 ml), dried (MgSO4) and evaporated. The crude product was further purified by flash chromatography on silica gel (heptane/EtOAc) followed by crystallization from diethyl ether/hexane to give 4-difluoromethyl-8-ethynyl-2-(4-trifluoromethyl-phenyl)-imidazo[1,5-a]pyrimidine (0.61 g, 49%) as a brown solid. MS (EI) 337.1 [(M)$^+$]; mp 135° C.

Example C.32

3-Iodo-5-(3-methyl-4-trifluoromethyl-phenyl)-7-trifluoromethyl-pyrazolo[1,5-a]pyrimidine 1) To a stirred solution of ethyl trifluoroacetate (6.98 ml, 24.7 mmol) in tert-butyl-methyl-ether (30 ml) was added at room temperature a 5.4 M solution of sodium methanolate in methanol (5.48 ml, 29.6 mmol) followed by a solution of 3-methyl-4-trifluoromethyl-acetophenone [CAS-No. 851262-60-7] (5.0 g, 24.7 mmol) in tert-butyl-methyl-ether (5 ml). The reaction mixture was stirred at room temperature for 2 h, poured into ice/water (60 ml), acidified with 1 N HCl until pH 1 was achieved, and extracted with tert-butyl-methyl-ether (2×60 ml). The combined organic layers were washed with brine (2×25 ml), dried ($Na_2SO_4$) and evaporated to give crude 1-(3-methyl-4-trifluoromethyl-phenyl)-4,4,4-trifluoro-butane-1,3-dione (7.36 g, 100%) as a yellow oil, which was used without further purification.

2) A mixture of 1-(3-methyl-4-trifluoromethyl-phenyl)-4,4,4-trifluoro-butane-1,3-dione (2.17 g, 7.28 mmol) and commercially available 3-aminopyrazole (0.73 g, 8.78 mmol) in acetic acid (15 ml) was refluxed for 4 h and evaporated. The crude product was further purified by crystallization (ethyl acetate/heptane) to yield 5-(3-methyl-4-trifluoromethyl-phenyl)-7-trifluoromethyl-pyrazolo[1,5-a]pyrimidine (2.14 g, 85%) as a yellow solid. MS (EI) 345.1 [$(M)^+$]; mp 87° C.

3) To a stirred solution of 5-(3-methyl-4-trifluoromethyl-phenyl)-7-trifluoromethyl-pyrazolo[1,5-a]pyrimidine (2.12 g, 6.14 mmol) in acetic acid (15 ml) was added at room temperature sodium acetate (0.57 g, 6.95 mmol) and drop wise a solution of iodine monochloride (1.13 g, 6.96 mmol) in acetic acid (3.5 ml). The reaction mixture was stirred at room temperature for 16 h, diluted slowly with water (up to 100 ml), stirred at room temperature for 30 min, the precipitate was filtered off, washed with water and dried to give 3-iodo-5-(3-methyl-4-trifluoromethyl-phenyl)-7-trifluoromethyl-pyrazolo[1,5-a]pyrimidine (2.44 g, 84%) as a yellow solid. MS (EI) 471.0 [$(M)^+$]; mp 160° C.

Example C.33

3-Ethynyl-5-(4-trifluoromethyl-phenyl)-pyrazolo[1,5-a]pyrimidine

Steps 1) 3-Iodo-5-(4-trifluoromethyl-phenyl)-pyrazolo[1,5-a]pyrimidine

By subjecting 7-chloro-5-(4-trifluoromethyl-phenyl)-pyrazolo[1,5-a]pyrimidine (example C.7 step 2) in analogous manner to the procedure described in example C.6 step 1, followed by applying to the resulting product in analogous manner the procedure described in example C.5 steps 4. Yellow solid. MS (ISP) 389.9 [$(M+H)^+$]; mp 149-152° C.

Steps 2) 3-Ethynyl-5-(4-trifluoromethyl-phenyl)-pyrazolo[1,5-a]pyrimidine

By subjecting 3-iodo-5-(4-trifluoromethyl-phenyl)-pyrazolo[1,5-a]pyrimidine in analogous manner to the procedure described in example C.5 step 5, the title compound was obtained. Yellow solid. MS (ISP) 288.1 [$(M+H)^+$]; mp 170-172° C.

Synthesis of Intermediate Compounds of Formula XVI

Example D.1

5-Ethynyl-pyridin-2-ylamine

Method 1:

Step 1) 5-Trimethylsilanylethynyl-pyridin-2-ylamine

A mixture of commercially available 2-amino-5-bromopyridine (50.0 g, 289 mmol), trimethylsilylacetylene (112 mL, 809 mmol), $Et_3N$ (120 mL, 867 mmol), $PdCl_2(PPh_3)_2$ (4.06 g, 2 mol %) and $PPh_3$ (1.52 g, 2 mol %) in DMF (290 mL) was purged for 10 min with argon. Then CuI (340 mg, 1 mol %) was added and the reaction mixture was heated up to 90° C., stirring was continued at 90° C. for 4.5 h. Cooled to 23° C., the reaction mixture was concentrated in vacuum to remove all volatiles, poured the residue onto water (300 mL) and extracted with ethyl acetate (3×500 mL). The combined organic layers were washed with water (300 mL) and brine (2×250 mL), dried over $MgSO_4$. Removal of the solvent in vacuum left a dark brown residue which was purified by flash chromatography with n-heptane and acetone to give the title compound as a brown solid (41.65 g, 76%). MS (ISP) 191 [$(M+H)^+$].

Step 2) 5-Ethynyl-pyridin-2-ylamine

To a solution of 5-trimethylsilanylethynyl-pyridin-2-ylamine (example D.1 method 1 step 1) (32.08 g, 169 mmol) in THF (150 mL) and MeOH (350 mL) at 0° C. was added $K_2CO_3$ (2.33 g, 10 mol %) and the mixture was stirred at 0° C. for 5 h. Diluted with ice water (500 mL), extracted with TBME (3×500 mL), washed the combined organic layers with brine, dried over $MgSO_4$. Removal of the solvent in vacuum left a dark brown solid, which was dissolved in hot ethyl acetate and precipitated with n-heptane trituration to give the 5-ethynyl-pyridin-2-ylamine (14.61 g, 73%) as a light brown solid. Evaporation of the mother liquor followed by silica gel column chromatography gave a brown solid which was triturated with ether and n-heptane to give a second crop of the title compound (3.26 g, 16%) as a light brown solid. MS (EI) 118.1 [$(M)^+$]; mp 143° C.

Method 2:

Step 1) 4-(6-Amino-pyridin-3-yl)-2-methyl-but-3-yn-2-ol

A mixture of commercially available 2-amino-5-bromopyridine (25 g, 144 mmol), 2-methyl-3-butyn-2-ol (21.2 mL, 217 mmol), $Et_3N$ (30.2 mL, 217 mmol), $PdCl_2(PPh_3)_2$ (507 mg, 0.5 mol %) and $PPh_3$ (95 mg, 0.25 mol %) in DMF (140 mL) was purged for 10 min with argon. Then CuI (83 mg, 0.3 mol %) was added and the reaction mixture was heated up to 90° C., stirring was continued at 90° C. for 16 h. Cooled to 23° C., the reaction mixture was concentrated in vacuum to remove all volatiles left a dark brown residue which was purified by flash chromatography with n-heptane and ethyl acetate to give the title compound as a brown solid (24 g, 94%, contains residual DMF). MS (ISP) 177.2 [$(M+H)^+$].

Step 2) 5-Ethynyl-pyridin-2-ylamine

A solution of 4-(6-amino-pyridin-3-yl)-2-methyl-but-3-yn-2-ol (example D.1 method 2 step 1) (22.5 g, 128 mmol) in toluene (500 mL) was refluxed in the presence of powdered NaOH (3.83 g, 96 mmol) for 16 h. The solvent was removed under reduced pressure to leave a brown residue which was purified by silica gel column chromatography with dichloromethane and ether, followed by trituration with heptane to give the title compound (5.5 g, 36%) (31.1 g, 100%) as light red solid. MS (EI) 118.1 [(M)+]; mp 143° C.

Example D.2

5-Ethynyl-pyrimidin-2-ylamine

Step 1) 5-Trimethylsilanylethynyl-pyrimidin-2-ylamine
Prepared from commercially available 2-amino-5-iodopyrimidine (60 g, 271 mmol) and trimethylsilylacetylene (49 mL, 354 mmol) as described in example D.1 method 1 step 1. Obtained the title compound as a light brown solid (37.66 g, 73%). MS (ISP) 192 [(M+H)+].

Step 2) 5-Ethynyl-pyrimidin-2-ylamine
Prepared from 5-trimethylsilanylethynyl-pyrimidin-2-ylamine (example D.2 step 1) (3.05 g, 16 mmol) as described in example D.1 method 1 step 2. Obtained the title compound as a light brown solid (1.68 g, 89%). MS (EI) 118.1 [(M)+].

Example D.3

5-Ethynyl-thiophene-2-sulfonic acid amide

Prepared from 5-bromo-thiophene-2-sulfonic acid amide (1.94 g, 8 mmol) and trimethylsilylacetylene (2.2 mL, 12 mmol) by applying in analogous manner the procedures described in example D.1 (method 1, steps 1-2). Obtained after chromatographic purification of the crude product ($SiO_2$, 0-75% AcOEt/heptane) as a light brown solid (0.49 g, 33%). MS (ISP) 186.1 [(M−H)−]; mp 114-116° C.

Example D.4

2-(4-Ethynyl-phenyl)-propan-2-ol

Step 1) 5-Trimethylsilanylethynyl-pyrimidin-2-ylamine
To a solution of ethyl 4-(trimethylsilyl-ethynyl)-benzoate (1.23 g, 5.0 mal) in diethyl ether (25 mL) was added at 20° C. a 3 M methylmagnesium bromide/$Et_2O$ solution (3.7 mL, 11 mmol) and the mixture was stirred at 20° C. for 3 h. The mixture was partitioned between 5% aqueous $H_2SO_4$ (40 mL) and AcOEt (80 mL). The organic phase was washed with $H_2O$ and 5% NaCl solution, dried ($Na_2SO_4$), and evaporated. The residual oil (1.28) g was subjected in analogous manner to the procedure described in example D.1 (method 1, step 1) to give the title compound. Light-brown oil (0.47 g, 58%). NMR (DMSO-$d_6$) □1.49 (s, 6H), 4.16 (s, 1H), 5.15 (s, 1H), 7.47 (d, J=6.5 Hz, 2H), 7.55 (d, J=6.5 Hz, 2H) ppm.

Compounds of Formula I According to the Invention

Example 1

3-[7-Trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 3-bromobenzene-1-sulfonamide [CAS 89599-01-9; commercially available] (236 mg, 1.0 mmol) according to General Procedure II as Follows:
To a stirred solution of a 3-ethynyl-5-aryl-pyrazolo[1,5-a]pyrimidine (1.0 mmol) and an aryl- or heteroaryl-bromide, -iodide, -chloride or -trifluoromethansulfonate (0.9 to 1.2 mmol) in a solvent (THF or DMF, 2.0 mL) was added at room temperature triethylamine (2.0 to 3.0 mmol) and the mixture was purged with argon gas for about 10-20 min. Then $PdCl_2$ $(PPh_3)_2$ (0.5 to 5.0 mol %), triphenylphosphine (0.25 to 10 mol %) and a copper(I)-iodide (0.1 to 3.0 mol %) were added and the mixture was stirred at 70 to 90° C. until thin layer chromatography or HPLC analysis revealed complete conversion of the minor component. The reaction mixture was cooled to room temperature, then either diluted with ethyl acetate, washed with aqueous solutions (depending on the moieties of the material varying from 1 N HCl, 5% citric acid, water to sat. $NaHCO_3$-sol.) and sat. NaCl-sol., dried over $Na_2SO_4$. Filtration and removal of the solvent in vacuum left the crude product, which was purified by flash chromatography on silica gel (with heptane/ethyl acetate or dichloromethane/methanol) to yield the product (compound of formula (I)), which can be further purified (e.g. by crystallization from ethanol/ether/heptane). Alternative workup: the reaction mixture was diluted with THF, silica gel was added and the mixture was evaporated to dryness to yield the crude product directly coated on silica gel. This material was subjected to flash chromatography on silica gel (with heptane/ethyl acetate or dichloromethane/methanol) to yield the product (compound of formula (I)), which can be further purified (e.g. by crystallization from ethanol/ether/heptane). Obtained as a yellow solid (143 mg, 28%). MS (ISP) 511 [(M+H)+]; mp 243° C.

Example 2

3-(2-Methyl-pyridin-4-ylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (710 mg, 2.0 mmol) and 2-chloro-4-iodopyridine [CAS 153034-86-7; commercially available] (479 mg, 2.0 mmol) according to general procedure II to produce the intermediate 3-(2-chloro-pyridin-4-ylethynyl)-7-trifluoromethyl-5-(4-trifluoromethyl-phenyl)-pyrazolo[1,5-a]pyrimidine (569 mg, 61%) as a yellow solid. MS (ISP) 467 [(M+H)+] and 469 [(M+2+H)+]; mp 200° C. This material was transformed to the title compound as follows: In a dried flask under argon, dimethylzinc-solution (2M in toluene, 0.16 mL, 0.33 mmol) was added to a solution of the above prepared 3-(2-chloro-pyridin-4-ylethynyl)-7-trifluoromethyl-5-(4-trifluoromethyl-phenyl)-pyrazolo[1,5-a]pyrimidine (233 mg, 0.50 mmol) and Pd(PPh$_3$)$_4$ (17 mg, 3 mol %) in THF (1.7 mL) at 23° C. The reaction mixture was warmed up slowly and refluxed for 2 h. The reaction mixture was poured in sat. $NaHCO_3$-sol., shaken with EtOAc and filtered through Celite. The organic layer was extracted twice with 1N HCl, the combined aqueous layer were made alkaline with 32% NaOH-sol., extracted with EtOAc, the organic washed with sat. NaCl-sol., dried over $Na_2SO_4$ and evaporated. The obtained crude product was purified by MPLC with heptane/EtOAc, followed by trituration with ether to give the title 3-(2-methyl-pyridin-4-ylethynyl)-7-trifluoromethyl-5-(4-trifluoromethyl-phenyl)-pyrazolo[1,5-a]pyrimidine (59 mg, 26%) as a yellow solid. MS (ISP) 447 [(M+H)+]; mp 206° C.

Example 3

3-Pyridin-3-ylethynyl-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 3-bromopyridine [CAS 626-55-1; commercially available] (158 mg, 1.0 mmol) according to general procedure II. Obtained as an orange solid (94 mg, 22%). MS (ISP) 433.3 [(M+H)$^+$]; mp 187-188° C.

Example 4

N-(2-Hydroxy-1,1-dimethyl-ethyl)-3-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (370 mg, 1.04 mmol) and 3-bromo-N-(2-hydroxy-1,1-dimethyl-ethyl)-benzenesulfonamide (example B.6) (321 mg, 1.04 mmol) according to general procedure II. Obtained as an orange solid (164 mg, 27%). MS (ISN) 581 [(M−H)$^−$]; mp 201-204° C.

Example 5

5-[7-Trifluoromethyl-5-(4-trifluoromethyl-phenyl)-pyrazolo[1,5-a]pyrimidin-3-ylethynyl]-pyridine-3-sulfonic acid amide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 5-bromo-pyridine-3-sulfonic acid amide (example B.1) (356 mg, 1.5 mmol) according to general procedure II. Obtained as a yellow solid (90 mg, 18%). MS (ISP) 512.3 [(M+H)$^+$]; mp 239-240° C.

Example 6

3-Pyridin-2-ylethynyl-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 2-bromopyridine [CAS 109-04-6; commercially available] (237 mg, 1.5 mmol) according to general procedure II. Obtained as a yellow solid (345 mg, 80%). MS (ISP) 433.2 [(M+H)$^+$]; mp 158-159° C.

Example 7

3-Pyridin-4-ylethynyl-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 4-iodopyridine [CAS 15854-87-2; commercially available] (225 mg, 1.1 mmol) according to general procedure II. Obtained as a yellow solid (92 mg, 21%). MS (ISP) 433.2 [(M+H)$^+$]; mp 252-256° C.

Example 8

3-(2-Cyclopropyl-pyridin-3-ylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and trifluoromethanesulfonic acid 2-cyclopropyl-pyridin-3-yl ester (Example B.10) (294 mg, 1.3 mmol) according to general procedure II. Obtained as a yellow solid (220 mg, 46%). MS (ISP) 473.3 [(M+H)$^+$]; mp 202° C.

Example 9

3-(6-Methyl-pyridin-3-ylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 5-bromo-2-methyl-pyridine [CAS 3430-13-5; commercially available] (237 mg, 1.1 mmol) according to general procedure II. Obtained as a light brown solid (230 mg, 52%). MS (ISP) 447.2 [(M+H)$^+$]; mp 195° C.

Example 10

3-(2-Cyclopropyl-pyridin-5-ylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 5-bromo-2-cyclopropyl-pyridine (Example B.11) (257 mg, 1.3 mmol) according to general procedure II. Obtained as an orange solid (110 mg, 23%). MS (ISP) 473.0 [(M+H)$^+$]; mp 138-140° C.

Example 11

5-[7-Trifluoromethyl-5-(4-trifluoromethyl-phenyl)-pyrazolo[1,5-a]pyrimidin-3-ylethynyl]-pyridine-3-sulfonic acid (2-hydroxy-1,1-dimethyl-ethyl)-amide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 5-bromo-pyridine-3-sulfonic acid (2-hydroxy-1,1-dimethyl-ethyl)-amide (example B.2) (402 mg, 1.3 mmol) according to general procedure II. Obtained as a yellow solid (310 mg, 53%). MS (ISN) 582.0 [(M−H)$^−$]; mp 226-227° C.

Example 12

3-(2-Methyl-pyridin-3-ylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 3-bromo-2-methyl-pyridine [CAS 38749-79-0; commercially available] (252 mg, 1.3 mmol) according to general proce-

Example 13

5-[7-Trifluoromethyl-5-(4-trifluoromethyl-phenyl)-pyrazolo[1,5-a]pyrimidin-3-ylethynyl]-pyridine-3-sulfonic acid bis-(2-hydroxy-ethyl)-amide The title compound was prepared from 3-ethynyl-7-trifluoromethyl-5-(4-trifluoromethyl-phenyl)-pyrazolo[1,5-a]pyrimidine (example C.1) (388 mg, 1.1 mmol) and 5-bromo-pyridine-3-sulfonic acid bis-(2-hydroxy-ethyl)-amide (example B.5) (325 mg, 1.0 mmol) according to general procedure II. Obtained as a yellow solid (160 mg, 29%). MS (ISP) 600.2 [(M+H)$^+$]; mp 173-178° C.

Example 14

5-[7-Trifluoromethyl-5-(4-trifluoromethyl-phenyl)-pyrazolo[1,5-a]pyrimidin-3-ylethynyl]-pyridine-3-sulfonic acid (2-hydroxy-1-hydroxymethyl-1-methyl-ethyl)-amide The title compound was prepared from 3-ethynyl-7-trifluoromethyl-5-(4-trifluoromethyl-phenyl)-pyrazolo[1,5-a]pyrimidine (example C.1) (200 mg, 0.56 mmol) and 5-bromo-pyridine-3-sulfonic acid (2-hydroxy-1-hydroxymethyl-1-methyl-ethyl)-amide (example B.4) (165 mg, 0.5 mmol) according to general procedure II. Obtained as a yellow solid (120 mg, 35%). MS (ISP) 600.2 [(M+H)$^+$]; mp 228-231° C.

Example 15

5-[7-Trifluoromethyl-5-(4-trifluoromethyl-phenyl)-pyrazolo[1,5-a]pyrimidin-3-ylethynyl]-nicotinamide The title compound was prepared from 3-ethynyl-7-trifluoromethyl-5-(4-trifluoromethyl-phenyl)-pyrazolo[1,5-a]pyrimidine (example C.1) (400 mg, 1.13 mmol) and 5-bromonicotinamide [CAS 28733-43-9; commercially available] (204 mg, 1.0 mmol) according to general procedure II. Obtained as a yellow solid (140 mg, 26%). MS (ISP) 476.2 [(M+H)$^+$]; mp 285-287° C.

Example 16

N-(2-Hydroxy-1,1-dimethyl-ethyl)-2-methoxy-5-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 5-bromo-N-(2-hydroxy-1,1-dimethyl-ethyl)-2-methoxy-benzenesulfonamide (example B.7) (439 mg, 1.3 mmol) according to general procedure II. Obtained as an orange solid (300 mg, 49%). MS (ISP) 541.3 [(M+H)$^+$]; mp 209-213° C.

Example 17

5-[7-Trifluoromethyl-5-(4-trifluoromethyl-phenyl)-pyrazolo[1,5-a]pyrimidin-3-ylethynyl]-pyridine-3-sulfonic acid tert-butylamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 5-bromo-pyridine-3-sulfonic acid tert-butylamide (example B.3) (439 mg, 1.3 mmol) according to general procedure II. Obtained as an orange solid (390 mg, 70%). MS (ISP) 568.2 [(M+H)$^+$]; mp 224° C.

Example 18

6-Methoxy-5-[7-trifluoromethyl-5-(4-trifluoromethyl-phenyl)-pyrazolo[1,5-a]pyrimidin-3-ylethynyl]-pyridine-3-sulfonic acid (2-hydroxy-1,1-dimethyl-ethyl)-amide The title compound was prepared from 3-ethynyl-7-trifluoromethyl-5-(4-trifluoromethyl-phenyl)-pyrazolo[1,5-a]pyrimidine (example C.1) (355 mg, 1 mmol) and 5-Bromo-6-methoxy-pyridine-2-sulfonic acid (2-hydroxy-1,1-dimethyl-ethyl)-amide (example B.12) (305 mg, 0.9 mmol) according to general procedure II. Obtained as an orange solid (230 mg, 37%). MS (ISP) 614.3 [(M+H)$^+$]; mp 209-210° C.

Example 19

2,4-Difluoro-5-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 5-bromo-2,4-difluorobenzenesulphonamide (245 mg, 0.9 mmol) according to general procedure II. Obtained as a yellow solid (230 mg, 42%). MS (ISP) 614.3 [(M+H)$^+$]; mp 281-284° C.

Example 20

2-[7-Trifluoromethyl-5-(4-trifluoromethyl-phenyl)-pyrazolo[1,5-a]pyrimidin-3-ylethynyl]-thiazole-5-sulfonic acid The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 2-bromo-thiazole-5-sulfonic acid (220 mg, 0.9 mmol, prepared according to: *Helv. Chim. Acta*, 1945, 28, 985) according to general procedure II. Obtained as an orange solid (75 mg, 14%). MS (ISN) 516.8 [(M−H)$^−$]; mp >295° C.

Example 21

5-(4-Chloro-phenyl)-3-pyridin-3-ylethynyl-7-trifluoromethyl-pyrazolo[1,5-a]pyrimidine The title compound was prepared from 5-(4-chloro-phenyl)-3-iodo-7-trifluoromethyl-pyrazolo[1,5-a]pyrimidine (example C.4) (420 mg, 1.0 mmol) and commercially available 3-Ethynylpyridine (102 mg, 0.9 mmol) according to

Example 22

5-[7-Trifluoromethyl-5-(4-trifluoromethyl-phenyl)-pyrazolo[1,5-a]pyrimidin-3-ylethynyl]-pyridine-3-sulfonic acid (2-hydroxy-1,1-bis-hydroxymethyl-ethyl)-amide To a solution of 5-bromo-pyridine-3-sulfonyl chloride (Example B.2, step 2)(500 mg, 2 mmol) in DMF (5 mL) at 5° C. was added Tris (260 mg, 2 mmol) in DMF (5 mL) and the mixture was vigorously stirred at room temp. for 16 h, then addition of 3-ethynyl-7-trifluoromethyl-5-(4-trifluoromethyl-phenyl)-pyrazolo[1,5-a]pyrimidine (example C.1) (692 mg, 2 mmol), triethylamine (0.82 mL, 6 mmol), $PdCl_2$ $(PPH_3)_2$ (41 mg, 3 mol %), $PPh_3$ (31 mg, 6 mol %) were stirred for 10 minutes at 23° C. while being purged with Argon, then CuI (3 mg, 1 mol %) was added. Stirring was continued for 16 h at 90° C. Purification by $SiO_2$ column chromatography (heptane/EtOAc 3:1), trituration with ether, filtration and dried to give the product as an orange solid (120 mg, 10%). MS (ISN) 613.8 [(M–H)⁻]; mp 230-232° C.

Example 23

2-[7-Trifluoromethyl-5-(4-trifluoromethyl-phenyl)-pyrazolo[1,5-a]pyrimidin-3-ylethynyl]-thiazole-5-sulfonic acid (2-hydroxy-1,1-dimethyl-ethyl)-amide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 2-Chloro-thiazole-5-sulfonic acid (2-hydroxy-1,1-dimethyl-ethyl)-amide (example B.14) (244 mg, 0.9 mmol) according to general procedure II. Obtained as an orange solid (110 mg, 18%). MS (ISP) 590.3 [(M+H)⁺]; mp 252-253° C.

Example 24

N-tert-Butyl-3-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1)(355 mg, 1.0 mmol) and 3-Bromo-N-tert-butyl-benzenesulfonamide (example B.9) (321 mg, 1.1 mmol) according to general procedure II. Obtained as a light-brown solid (110 mg, 20%). MS (ISP) 567.2 [(M+H)⁺]; mp 192-200° C.

Example 25

6-Methoxy-5-[7-trifluoromethyl-5-(4-trifluoromethyl-phenyl)-pyrazolo[1,5-a]pyrimidin-3-ylethynyl]-pyridine-3-sulfonic acid (2-hydroxy-1-hydroxymethyl-1-methyl-ethyl)-amide The title compound was prepared from 3-ethynyl-7-trifluoromethyl-5-(4-trifluoromethyl-phenyl)-pyrazolo[1,5-a]pyrimidine (example C.1)(300 mg, 1.0 mmol) and 5-Bromo-pyridine-3-sulfonic acid (2-hydroxy-1-hydroxymethyl-1-methyl-ethyl)-amide (example B.4)(270 mg, 1.0 mmol) according to general procedure II. Obtained as an orange solid (300 mg, 56%). MS (ISP) 630.3 [(M+H)⁺]; mp 233-235° C.

Example 26

5-[7-Difluoromethyl-5-(4-trifluoromethyl-phenyl)-pyrazolo[1,5-a]pyrimidin-3-ylethynyl]-pyridine-3-sulfonic acid (2-hydroxy-1-hydroxymethyl-1-methyl-ethyl)-amide The title compound was prepared from 7-Difluoromethyl-3-ethynyl-5-(4-trifluoromethyl-phenyl)-pyrazolo[1,5-a]pyrimidine (example C.2)(340 mg, 1.0 mmol) and 5-Bromo-pyridine-3-sulfonic acid (2-hydroxy-1-hydroxymethyl-1-methyl-ethyl)-amide (example B.4)(295 mg, 1.0 mmol) according to general procedure II. Obtained as a light-brown solid (240 mg, 40%). MS (ISP) 582.2 [(M+H)⁺]; mp 204-206° C.

Example 27

5-[7-Difluoromethyl-5-(4-trifluoromethyl-phenyl)-pyrazolo[1,5-a]pyrimidin-3-ylethynyl]-pyridine-3-sulfonic acid (2-hydroxy-1,1-dimethyl-ethyl)-amide The title compound was prepared from 7-Difluoromethyl-3-ethynyl-5-(4-trifluoromethyl-phenyl)-pyrazolo[1,5-a]pyrimidine (example C.2)(340 mg, 1.0 mmol) and 5-Bromo-pyridine-3-sulfonic acid (2-hydroxy-1,1-dimethyl-ethyl)-amide (example B.2)(281 mg, 1.0 mmol) according to general procedure II. Obtained as a light-brown solid (200 mg, 35%). MS (ISP) 566.2 [(M+H)⁺]; mp 200-201° C.

Example 28

5-[7-Trifluoromethyl-5-(4-trifluoromethyl-phenyl)-pyrazolo[1,5-a]pyrimidin-3-ylethynyl]-pyridine-3-sulfonic acid (2-hydroxy-1-methyl-ethyl)-amide The title compound was prepared from 3-ethynyl-7-trifluoromethyl-5-(4-trifluoromethyl-phenyl)-pyrazolo[1,5-a]pyrimidine (example C.1) (300 mg, 1.0 mmol) and 5-Bromo-pyridine-3-sulfonic acid (2-hydroxy-1-methyl-ethyl)-amide (example B.16) (265 mg, 1.0 mmol) according to general procedure II. Obtained as a yellow solid (390 mg, 65%). MS (ISP) 570.2 [(M+H)⁺]; mp 225-226° C.

Example 29

2-[7-Trifluoromethyl-5-(4-trifluoromethyl-phenyl)-pyrazolo[1,5-a]pyrimidin-3-ylethynyl]-thiazole-5-sulfonic acid amide The title compound was prepared from 3-ethynyl-7-trifluoromethyl-5-(4-trifluoromethyl-phenyl)-pyrazolo[1,5-a]pyrimidine (example C.1) (300 mg, 1.0 mmol) and 2-Chloro-thiazole-5-sulfonic acid amide (example B.13) (179 mg, 1.0 mmol) according to general procedure II. Obtained as a yellow solid (120 mg, 23%). MS (ISP) 518.1 [(M+H)⁺]; mp 235° C.

Example 30

5-[7-Difluoromethyl-5-(4-trifluoromethyl-phenyl)-pyrazolo[1,5-a]pyrimidin-3-ylethynyl]-pyridine-3-sulfonic acid amide The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and 5-Bromo- (continued on page 95, paragraph: "general procedure II. Obtained as an orange solid (230 mg, 58%). MS (ISP) 398.9 [(M+H)⁺]; mp 214-215° C.")

pyridine-3-sulfonic acid amide (example B.1) (215 mg, 1.0 mmol) according to general procedure II. Obtained as a yellow solid (330 mg, 66%). MS (ISP) 494.3 [(M+H)⁺]; mp 238° C.

Example 31

5-[7-Difluoromethyl-5-(4-trifluoromethyl-phenyl)-pyrazolo[1,5-a]pyrimidin-3-ylethynyl]-2,4-difluoro-benzenesulfonamide The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and commercially available 5-bromo-2,4-difluorobenzenesulfonamide [CAS 287172-65-0] (247 mg, 1.0 mmol) according to general procedure II. Obtained as a yellow solid (310 mg, 58%). MS (ISP) 529.2 [(M+H)⁺]; mp 256-258° C.

Example 32

3-[7-Difluoromethyl-5-(4-trifluoromethyl-phenyl)-pyrazolo[1,5-a]pyrimidin-3-ylethynyl]-N-(2-hydroxy-1,1-dimethyl-ethyl)-benzenesulfonamide The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and 3-Bromo-N-(2-hydroxy-1,1-dimethyl-ethyl)-benzenesulfonamide (example B.6) (281 mg, 1.0 mmol) according to general procedure II. Obtained as a yellow solid (310 mg, 54%). MS (ISP) 565.4 [(M+H)⁺]; mp 161-162° C.

Example 33

3-[7-Difluoromethyl-5-(4-trifluoromethyl-phenyl)-pyrazolo[1,5-a]pyrimidin-3-ylethynyl]-N-(2-hydroxy-1-hydroxymethyl-1-methyl-ethyl)-benzenesulfonamide The title compound was prepared from 7-Difluoromethyl-3-ethynyl-5-(4-trifluoromethyl-phenyl)-pyrazolo[1,5-a]pyrimidine (example C.2)(340 mg, 1.0 mmol) and 3-Bromo-N-(2-hydroxy-1-hydroxymethyl-1-methyl-ethyl)-benzenesulfonamide (example B.9) (294 mg, 1.0 mmol) according to general procedure II. Obtained as a yellow solid (240 mg, 41%). MS (ISP) 581.2[(M+H)⁺]; mp 172-174° C.

Example 34

N-(2-Hydroxy-ethyl)-2-methyl-5-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (150 mg, 0.9 mmol) and 5-Bromo-N-(2-hydroxy-ethyl)-2-methyl-benzenesulfonamide (example B.17) (129 mg, 1.0 mmol) according to general procedure II. Obtained as an orange solid (59 mg, 25%). MS (ISP) 569.2 [(M+H)⁺]; mp 174-175° C.

Example 35

2-Methyl-5-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (156 mg, 0.4 mmol) and 5-Bromo-2-methyl-benzenesulfonamide (example B.18)(124 mg, 0.5 mmol) according to general procedure II. Obtained as an orange solid (22 mg, 10%). MS (ISP) 525.3[(M+H)⁺]; mp 255-267° C.

Example 36

4-[7-Trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 4-bromobenzenesulfonamide [CAS 701-34-8] (307 mg, 1.3 mmol) according to general procedure II. Obtained as a yellow solid (325 mg, 64%). MS (ISP) 511.3 [(M+H)⁺]; mp 266-267° C.

Example 37

5-[7-Trifluoromethyl-5-(4-trifluoromethyl-phenyl)-pyrazolo[1,5-a]pyrimidin-3-ylethynyl]-pyridine-3-sulfonic acid The title compound was prepared from 3-ethynyl-7-trifluoromethyl-5-(4-trifluoromethyl-phenyl)-pyrazolo[1,5-a]pyrimidine (example C.1) (300 mg, 1.0 mmol) and 5-Bromo-pyridine-3-sulfonic acid (example B.2, step 1) (214 mg, 1.0 mmol) according to general procedure II. Obtained as an orange solid (280 mg, 54%). MS (ISN) 510.9 [(M−H)⁻]; mp >288° C.

Example 38

3-(5-Methanesulfonyl-pyridin-3-ylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (300 mg, 1.0 mmol) and 3-Bromo-5-methanesulfonyl-pyridine (example B.19) (212 mg, 1.0 mmol) according to general procedure II. Obtained as a yellow solid (350 mg, 68%). MS (ISP) 511.1 [(M+H)⁺]; mp 241-242° C.

Example 39

3-[5-(3-Ethoxy-4-trifluoromethyl-phenyl)-7-trifluoromethyl-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1)(399 mg, 1.0 mmol) and commercially available 3-bromobenzene-1-sulfonamide [CAS 89599-01-9] (307 mg, 1.0 mmol) according to general procedure II. Obtained as a yellow solid (170 mg, 31%). MS (ISP) 279.1[(M+H)⁺]; mp 231-233° C.

Example 40

3-(3-Methanesulfonyl-phenylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (300 mg, 1.0 mmol) and commercially available 3-bromomethylsulfone [CAS 34896-80-5] (211 mg, 1.0 mmol) according to general procedure II. Obtained as an orange solid (300 mg, 59%). MS (ISP) 510.4 [(M+H)⁺]; mp 214° C.

Example 41

3-[5-(3-Ethoxy-4-trifluoromethyl-phenyl)-7-trifluoromethyl-pyrazolo[1,5-a]pyrimidin-3-ylethynyl]-N-(2-hydroxy-1,1-dimethyl-ethyl)-benzenesulfonamide The title compound was prepared from 3-ethynyl-7-trifluoromethyl-5-(4-trifluoromethyl-phenyl)-pyrazolo[1,5-a]pyrimidine (example C.1) (399 mg, 1.0 mmol) and 3-Bromo-N-(2-hydroxy-1,1-dimethyl-ethyl)-benzenesulfonamide (example B.6) (401 mg, 1.3 mmol) according to general procedure II. Obtained as a yellow solid (175 mg, 28%). MS (ISP) 627.1[(M+H)⁺]; mp 209-211° C.

Example 42

3-[7-Difluoromethyl-5-(4-trifluoromethyl-phenyl)-pyrazolo[1,5-a]pyrimidin-3-ylethynyl]-benzenesulfonamide The title compound was prepared 7-Difluoromethyl-3-ethynyl-5-(4-trifluoromethyl-phenyl)-pyrazolo[1,5-a]pyrimidine (example C.2) (337 mg, 1.0 mmol) and commercially available 3-bromobenzene-1-sulfonamide [CAS 89599-01-9] (307 mg, 1.3 mmol) according to general procedure II. Obtained as a yellow solid (150 mg, 31%). MS (ISP) 493.0 [(M+H)⁺]; mp 246-247° C.

Example 43

5-[7-Difluoromethyl-5-(4-trifluoromethyl-phenyl)-pyrazolo[1,5-a]pyrimidin-3-ylethynyl]-N-(2-hydroxy-1,1-dimethyl-ethyl)-2-methoxy-benzenesulfonamide The title compound was prepared from 7-Difluoromethyl-3-ethynyl-5-(4-trifluoromethyl-phenyl)-pyrazolo[1,5-a]pyrimidine (example C.2)(337 mg, 1.0 mmol) and 5-Bromo-N-(2-hydroxy-1,1-dimethyl-ethyl)-2-methoxy-benzenesulfonamide (example B.7) (440 mg, 1.3 mmol) according to general procedure II. Obtained as a yellow solid (135 mg, 23%). MS (ISP) 595.3[(M+H)⁺]; mp 178-180° C.

Example 44

3-Pyrimidin-5-ylethynyl-7-trifluoromethyl-5-(4-trifluoromethyl-phenyl)-pyrazolo[1,5-a]pyrimidine To a flask was added 3-ethynyl-7-trifluoromethyl-5-(4-trifluoromethyl-phenyl)-pyrazolo[1,5-a]pyrimidine (example C.1) (159 mg, 0.45 mmol), 4-Bromopyrimidine (87 mg, 0.55 mmol, commercially available [CAS 4595-59-9]), PdCl₂(NCPh)₂ (13 mg, 7 mol %), and CuI (10 mg, 12 mol %). The flask was charged with Ar, then 3 mL of dioxane (degassed with Ar), tri-(tert-butyl)phosphine (0.12 mL of a 0.25M soln in dioxane, 33 mol %), and diisopropylamine (0.15mL) were added. The rxn mixture was stirred at 23° C. under Ar overnight, then filtered through a pad of Si-gel, concentrated, purified by Si-gel chromatography (EtOAc/heptane 5-40:95-60) to give an orange solid. Recrytallization from EtOAc/heptane (1:2) yielded the product as an orange solid (131 mg, 68%). MS (ISP) 434.1[(M+H)⁺]; mp 175° C.

Example 45

3-Fluoro-4-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 4-bromo-2-fluorobenzenesulfonamide (330 mg, 1.3 mmol) according to general procedure II. Obtained as a light-brown solid (190 mg, 36%). MS (ISP) 529.1[(M+H)⁺]; mp 230-232° C.

Example 46

N-(2-Morpholin-4-yl-ethyl)-3-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 3-Bromo-N-(2-morpholin-4-yl-ethyl)-benzenesulfonamide (example B.20)(454 mg, 1.3 mmol) according to general procedure II. Obtained as a yellow amorphous solid (60 mg, 10%). MS (ISP) 624.2 [(M+H)⁺].

Example 47

N-(2-Cyano-ethyl)-3-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 3-Bromo-N-(2-cyano-ethyl)-benzenesulfonamide (example B.21) (376 mg, 1.3 mmol) according to general procedure II. Obtained as a yellow solid (254 mg, 45%). MS (ISP) 564.3 [(M+H)⁺]; mp 174-182° C.

Example 48

4-[7-Difluoromethyl-5-(4-trifluoromethyl-phenyl)-pyrazolo[1,5-a]pyrimidin-3-ylethynyl]-3-fluoro-benzenesulfonamide The title compound was prepared from 7-Difluoromethyl-3-ethynyl-5-(4-trifluoromethyl-phenyl)-pyrazolo[1,5-a]pyrimidine (example C.2) (337 mg, 1.0 mmol) and commercially available 4-bromo-2-fluorobenzenesulfonamide (330 mg, 1.3 mmol) according to general procedure II. Obtained as a yellow solid (137 mg, 27%). MS (ISP) 511.3[(M+H)⁺]; mp 230-232° C.

Example 49

4-[7-Difluoromethyl-5-(4-trifluoromethyl-phenyl)-pyrazolo[1,5-a]pyrimidin-3-ylethynyl]-benzenesulfonamide The title compound was prepared from 7-Difluoromethyl-3-ethynyl-5-(4-trifluoromethyl-phenyl)-pyrazolo[1,5-a]pyrimidine (example C.2)(337 mg, 1.0 mmol) and 4-bromobenzenesulfonamide [CAS 701-34-8] (307 mg, 1.3 mmol) according to general procedure II. Obtained as a yellow solid (150 mg, 30%). MS (ISP) 493.2[(M+H)$^+$]; mp 254° C.

Example 50

2-Fluoro-5-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 4-Bromo-2-fluorosulfonamide (330 mg, 1.3 mmol) according to general procedure II. Obtained as a yellow solid (197 mg, 37%). MS (ISP) 529.1[(M+H)$^+$]; mp 254-255° C.

Example 51

2-[5-(3-Ethoxy-4-trifluoromethyl-phenyl)-7-trifluoromethyl-pyrazolo[1,5-a]pyrimidin-3-ylethynyl]-thiazole-5-sulfonic acid (2-hydroxy-1,1-dimethyl-ethyl)-amide The title compound was prepared from 5-(3-Ethoxy-4-trifluoromethyl-phenyl)-3-ethynyl-7-trifluoromethyl-pyrazolo[1,5-a]pyrimidine (example C.3) (400 mg, 1.0 mmol) and 2-chloro-thiazole-5-sulfonic acid(2-hydroxy-1,1-dimethyl-ethyl)-amide (example B.14) (244 mg, 1.0 mmol) according to general procedure II. Obtained as an orange solid (80 mg, 12%). MS (ISP) 634.1 [(M+H)$^+$]; mp 209-211° C.

Example 52

1-{4-[7-Trifluoromethyl-5-(4-trifluoromethyl-phenyl)-pyrazolo[1,5-a]pyrimidin-3-ylethynyl]-phenyl}-ethanol The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 4-bromo-methylbenzylalcohol (181 mg, 1.0 mmol, [CAS 5391-88-8]) according to general procedure II. Obtained as an orange solid (115 mg, 24%). MS (ISP) 476.2 [(M+H)$^+$]; mp 175-178° C.

Example 53

4-Methyl-2-[7-trifluoromethyl-5-(4-trifluoromethyl-phenyl)-pyrazolo[1,5-a]pyrimidin-3-ylethynyl]-thiazole-5-sulfonic acid (2-hydroxy-1,1-dimethyl-ethyl)-amide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 2-Chloro-4-methyl-thiazole-5-sulfonic acid (2-hydroxy-1,1-dimethyl-ethyl)-amide (example B.22)(256 mg, 1.0 mmol) according to general procedure II. Obtained as a yellow solid (190 mg, 32%). MS (ISP) 604.0[(M+H)$^+$]; mp 216-218° C.

Example 54

4-Methyl-2-[7-trifluoromethyl-5-(4-trifluoromethyl-phenyl)-pyrazolo[1,5-a]pyrimidin-3-ylethynyl]-thiazole-5-sulfonic acid amide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 2-Chloro-4-methyl-thiazole-5-sulfonic acid amide (example B.23)(191 mg, 1.0 mmol) according to general procedure II. Obtained as a yellow solid (160 mg, 30%). MS (ISP) 532.1[(M+H)$^+$]; mp 245-246° C.

Example 55

5-[7-Trifluoromethyl-5-(4-trifluoromethyl-phenyl)-pyrazolo[1,5-a]pyrimidin-3-ylethynyl]-pyridin-2-ylamine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 2-amino-5-bromopyridine (156 mg, 1.0 mmol) according to general procedure II. Obtained as a dark-red solid (80 mg, 17%). MS (ISP) 448.2[(M+H)$^+$]; mp 227-229° C.

Example 56

3-(6-Methoxy-pyridin-3-ylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 5-bromo-2-methoxypyridine (169 mg, 1.0 mmol) according to general procedure II. Obtained as a red solid (85 mg, 18%). MS (ISP) 463.2[(M+H)$^+$]; mp 166-168° C.

Example 57

3-(5-Methoxy-pyridin-3-ylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1)(355 mg, 1.0 mmol) and commercially available 5-bromo-3-methoxypyridine (169 mg, 1.0 mmol) according to general procedure II. Obtained as a yellow solid (210 mg, 45%). MS (ISP) 463.2[(M+H)$^+$]; mp 232-234° C.

Example 58

5-[7-Trifluoromethyl-5-(4-trifluoromethyl-phenyl)-pyrazolo[1,5-a]pyrimidin-3-ylethynyl]-pyridin-3-ol The title compound was prepared from 3-ethynyl-7-trifluoromethyl-5-(4-trifluoromethyl-phenyl)-pyrazolo[1,5-a]

pyrimidine (example C.1) (355 mg, 1.0 mmol) and commercially available 5-bromo-3-pyridinol (156 mg, 1.0 mmol) according to general procedure II. Obtained as a yellow solid (280 mg, 62%). MS (ISP) 449.2[(M+H)$^+$]; mp 258-260° C.

Example 59

5-[7-Difluoromethyl-5-(4-trifluoromethyl-phenyl)-pyrazolo[1,5-a]pyrimidin-3-ylethynyl]-2-fluoro-benzenesulfonamide The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and 5-bromo-2-fluorobenzenesulfonamide (231 mg, 1.0 mmol) according to general procedure II. Obtained as a yellow solid (180 mg, 35%). MS (ISP) 587.2[(M+H)$^+$]; mp 247-249° C.

Example 60

5-[7-Difluoromethyl-5-(4-trifluoromethyl-phenyl)-pyrazolo[1,5-a]pyrimidin-3-ylethynyl]-2-methyl-benzenesulfonamide The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and 5-bromo-2-fluorobenzenesulfonamide (example B.18) (227 mg, 1.0 mmol) according to general procedure II. Obtained as a yellow solid (220 mg, 43%). MS (ISP) 507.3[(M+H)$^+$]; mp 265-267° C.

Example 61

5-[7-Difluoromethyl-5-(4-trifluoromethyl-phenyl)-pyrazolo[1,5-a]pyrimidin-3-ylethynyl]-N-(2-hydroxy-ethyl)-2-methyl-benzenesulfonamide The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and 5-bromo-N-(2-hydroxy-ethyl)-2-methyl-benzenesulfonamide (example B.17) (267 mg, 1.0 mmol) according to general procedure II. Obtained as a yellow solid (230 mg, 41%). MS (ISP) 551.3 [(M+H)$^+$]; mp 184-186° C.

Example 62

3-Phenylethynyl-7-trifluoromethyl-5-(4-trifluoromethyl-phenyl)-pyrazolo[1,5-a]pyrimidine The title compound was prepared from 3-Iodo-7-trifluoromethyl-5-(4-trifluoromethyl-phenyl)-pyrazolo[1,5-a]pyrimidine (example C.1, method 2, step 2) (340 mg, 1.0 mmol) and phenylacetylene (267 mg, 1.0 mmol) according to general procedure II. Obtained as an orange solid (250 mg, 58%). MS (ISP) 432.3[(M+H)$^+$]; mp 144-145° C.

Example 63

4-[5-(4-Chloro-phenyl)-7-cyclopropyl-pyrazolo[1,5-a]pyrimidin-3-ylethynyl]-benzenesulfonamide The title compound was prepared from 5-(4-chloro-phenyl)-7-cyclopropyl-3-ethynyl-pyrazolo[1,5-a]pyrimidine (example C.5) (73 mg, 0.25 mmol) and 4-bromo-benzenesulfonamide (59 mg, 0.25 mmol) according to general procedure II. Obtained as a yellow solid (79 mg, 71%). MS (ISP) 449.3 [(M+H)$^+$]; mp 225-228° C.

Example 64

2-[5-(4-Chloro-phenyl)-7-cyclopropyl-pyrazolo[1,5-a]pyrimidin-3-ylethynyl]-thiazole-5-sulfonic acid (2-hydroxy-1,1-dimethyl-ethyl)-amide The title compound was prepared from 5-(4-chloro-phenyl)-7-cyclopropyl-3-ethynyl-pyrazolo[1,5-a]pyrimidine (example C.5) (73 mg, 0.25 mmol) and 2-chloro-thiazole-5-sulfonic acid (2-hydroxy-1,1-dimethyl-ethyl)-amide (68 mg, 0.25 mmol) (example B.14) according to general procedure II. Obtained as a yellow solid (60 mg, 45%). MS (ISP) 528.0 [(M+H)$^+$]; mp 204-207° C.

Example 65

3-[5-(4-Chloro-phenyl)-7-cyclopropyl-pyrazolo[1,5-a]pyrimidin-3-ylethynyl]-N-(2-hydroxy-1,1-dimethyl-ethyl)-benzenesulfonamide The title compound was prepared from 5-(4-chloro-phenyl)-7-cyclopropyl-3-ethynyl-pyrazolo[1,5-a]pyrimidine (example C.5) (118 mg, 0.4 mmol) and 3-bromo-N-(2-hydroxy-1,1-dimethyl-ethyl)-benzenesulfonamide (148 mg, 0.48 mmol) (example B.6) according to general procedure II. Obtained as a yellow solid (46 mg, 22%). MS (ISP) 521.5 [(M+H)$^+$]; mp 202-204° C.

Example 66

5-[5-(4-Chloro-phenyl)-7-cyclopropyl-pyrazolo[1,5-a]pyrimidin-3-ylethynyl]-pyridine-3-sulfonic acid amide The title compound was prepared from 5-(4-chloro-phenyl)-7-cyclopropyl-3-ethynyl-pyrazolo[1,5-a]pyrimidine (example C.5) (147 mg, 0.5 mmol) and 5-bromo-pyridine-3-sulfonic acid amide (119 mg, 0.5 mmol) according to general procedure II. Obtained as a yellow solid (177 mg, 79%). MS (ISP) 449.9 [(M+H)$^+$]; mp 252-254° C.

Example 67

5-[5-(4-Chloro-phenyl)-7-cyclopropyl-pyrazolo[1,5-a]pyrimidin-3-ylethynyl]-pyridine-3-sulfonic acid (2-hydroxy-1,1-dimethyl-ethyl)-amide The title compound was prepared from 5-(4-chloro-phenyl)-7-cyclopropyl-3-ethynyl-pyrazolo[1,5-a]pyrimidine (example C.5) (147 mg, 0.5 mmol) and 5-bromo-pyridine-3-sulfonic acid (2-hydroxy-1,1-dimethyl-ethyl)-amide (155 mg, 0.5 mmol) (example B.2) according to general procedure II. Obtained as a yellow solid (137 mg, 52%). MS (ISP) 522.2 [(M+H)$^+$]; mp 230-231° C.

Example 68

5-[5-(4-Chloro-phenyl)-7-cyclopropyl-pyrazolo[1,5-a]pyrimidin-3-ylethynyl]-pyridine-3-sulfonic acid (2-hydroxy-1-hydroxymethyl-1-methyl-ethyl)-amide The title compound was prepared from 5-(4-chloro-phenyl)-7-cyclopropyl-3-ethynyl-pyrazolo[1,5-a]pyrimidine (example C.5) (73 mg, 0.25 mmol) and 5-bromo-pyridine-3-

Example 69

5-[5-(4-Chloro-phenyl)-7-cyclopropyl-pyrazolo[1,5-a]pyrimidin-3-ylethynyl]-N-(2-hydroxy-1,1-dimethyl-ethyl)-2-methoxy-benzenesulfonamide The title compound was prepared from 5-(4-chloro-phenyl)-7-cyclopropyl-3-ethynyl-pyrazolo[1,5-a]pyrimidine (example C.5) (73 mg, 0.25 mmol) and 5-bromo-N-(2-hydroxy-1,1-dimethyl-ethyl)-2-methoxy-benzenesulfonamide (85 mg, 0.25 mmol) (Example B.7) according to general procedure II. Obtained as a yellow solid (38 mg, 28%). MS (ISP) 551.3[(M+H)$^+$]; mp 253-256° C.

Example 70

5-[5-(4-Chloro-phenyl)-7-cyclopropyl-pyrazolo[1,5-a]pyrimidin-3-ylethynyl]-2,4-difluoro-benzenesulfonamide The title compound was prepared from 5-(4-chloro-phenyl)-7-cyclopropyl-3-ethynyl-pyrazolo[1,5-a]pyrimidine (example C.5) (73 mg, 0.25 mmol) and 5-bromo-2,4-difluoro-benzenesulfonamide (68 mg, 0.25 mmol) according to general procedure II. Obtained as a yellow solid (91 mg, 75%). MS (ISP) 485.1 [(M+H)$^+$]; mp 272-275° C.

Example 71

5-[5-(4-Chloro-phenyl)-7-cyclopropyl-pyrazolo[1,5-a]pyrimidin-3-ylethynyl]-thiophene-2-sulfonic acid amide The title compound was prepared from 5-(4-chloro-phenyl)-7-cyclopropyl-3-ethynyl-pyrazolo[1,5-a]pyrimidine (example C.5) (73 mg, 0.25 mmol) and 5-bromo-thiophene-2-sulfonic acid amide (61 mg, 0.25 mmol) according to general procedure II. Obtained as a yellow solid (52 mg, 45%). MS (ISP) 445.4 [(M+H)$^+$]; mp 218-220° C.

Example 72

3-[5-(4-Chloro-phenyl)-7-cyclopropyl-pyrazolo[1,5-a]pyrimidin-3-ylethynyl]-benzenesulfonamide The title compound was prepared from 5-(4-chloro-phenyl)-7-cyclopropyl-3-ethynyl-pyrazolo[1,5-a]pyrimidine (example C.5) (73 mg, 0.25 mmol) and 3-bromo-benzenesulfonamide (59 mg, 0.25 mmol) according to general procedure II. Obtained as a yellow solid (44 mg, 39%). MS (ISP) 449.3 [(M+H)$^+$]; mp 236-237° C.

Example 73

5-[5-(4-Chloro-phenyl)-pyrazolo[1,5-a]pyrimidin-3-ylethynyl]-pyridine-3-sulfonic acid amide The title compound was prepared from 5-(4-chloro-phenyl)-3-ethynyl-pyrazolo[1,5-a]pyrimidine (example C.6) (63 mg, 0.25 mmol) and 5-bromo-pyridine-3-sulfonic acid amide (59 mg, 0.25 mmol) according to general procedure II. Obtained as a yellow solid (59 mg, 58%). MS (ISP) 410.3 [(M+H)$^+$]; mp 248-249° C.

Example 74

5-[5-(4-Chloro-phenyl)-pyrazolo[1,5-a]pyrimidin-3-ylethynyl]-pyridine-3-sulfonic acid (2-hydroxy-1,1-dimethyl-ethyl)-amide The title compound was prepared from 5-(4-chloro-phenyl)-3-ethynyl-pyrazolo[1,5-a]pyrimidine (example C.6) (63 mg, 0.25 mmol) and 5-bromo-pyridine-3-sulfonic acid (2-hydroxy-1,1-dimethyl-ethyl)-amide (77 mg, 0.25 mmol) according to general procedure II. Obtained as a yellow solid (74 mg, 62%). MS (ISP) 482.0 [(M+H)$^+$]; mp 185-186° C.

Example 75

5-[5-(4-Chloro-phenyl)-pyrazolo[1,5-a]pyrimidin-3-ylethynyl]-N-(2-hydroxy-1,1-dimethyl-ethyl)-2-methoxy-benzenesulfonamide The title compound was prepared from 5-(4-chloro-phenyl)-3-ethynyl-pyrazolo[1,5-a]pyrimidine (example C.6) (63 mg, 0.25 mmol) and 5-bromo-N-(2-hydroxy-1,1-dimethyl-ethyl)-2-methoxy-benzenesulfonamide (85 mg, 0.25 mmol) according to general procedure II. Obtained as a yellow solid (52 mg, 41%). MS (ISP) 511.1 [(M+H)$^+$]; mp 264-266° C.

Example 76

4-[7-Cyclopropyl-5-(4-trifluoromethyl-phenyl)-pyrazolo[1,5-a]pyrimidin-3-ylethynyl]-benzenesulfonamide The title compound was prepared from 7-cyclopropyl-3-ethynyl-5-(4-trifluoromethyl-phenyl)-pyrazolo[1,5-a]pyrimidine (example C.7) (82 mg, 0.25 mmol) and 4-bromo-benzenesulfonamide (59 mg, 0.25 mmol) according to general procedure II. Obtained as a yellow solid (60 mg, 50%). MS (ISN) 480.9 [(M−H)$^-$]; mp 228-230° C.

Example 77

5-[7-Cyclopropyl-5-(4-trifluoromethyl-phenyl)-pyrazolo[1,5-a]pyrimidin-3-ylethynyl]-2,4-difluoro-benzenesulfonamide The title compound was prepared from 7-cyclopropyl-3-ethynyl-5-(4-trifluoromethyl-phenyl)-pyrazolo[1,5-a]pyrimidine (example C.7) (82 mg, 0.25 mmol) and 5-bromo-2,4-difluoro-benzenesulfonamide (68 mg, 0.25 mmol) according to general procedure II. Obtained as a yellow solid (85 mg, 65%). MS (ISN) 517.0 [(M−H)$^-$]; mp 255-257° C.

Example 78

5-[7-Cyclopropyl-5-(4-trifluoromethyl-phenyl)-pyrazolo[1,5-a]pyrimidin-3-ylethynyl]-pyridine-3-sulfonic acid (2-hydroxy-1,1-dimethyl-ethyl)-amide The title compound was prepared from 7-cyclopropyl-3-ethynyl-5-(4-trifluoromethyl-phenyl)-pyrazolo[1,5-a]pyrimidine (example C.7) (82 mg, 0.25 mmol) and 5-bromo-pyridine-3-sulfonic acid (2-hydroxy-1,1-dimethyl-ethyl)-amide (77 mg, 0.25 mmol) (Example B.2) according to general procedure II. Obtained as a yellow solid (93 mg, 67%). MS (ISP) 556.3 [(M+H)$^+$]; mp 190-191° C.

Example 79

5-[7-Cyclopropyl-5-(4-trifluoromethyl-phenyl)-pyrazolo[1,5-a]pyrimidin-3-ylethynyl]-pyridine-3-sulfonic acid amide The title compound was prepared from 7-cyclopropyl-3-ethynyl-5-(4-trifluoromethyl-phenyl)-pyrazolo[1,5-a]pyrimidine (example C.7) (82 mg, 0.25 mmol) and 5-bromo-pyridine-3-sulfonic acid amide (59 mg, 0.25 mmol) (Example B.1) according to general procedure II. Obtained as a yellow solid (57 mg, 47%). MS (ISP) 484.0 [(M+H)$^+$]; mp 276-277° C.

Example 80

5-[7-Cyclopropyl-5-(4-trifluoromethyl-phenyl)-pyrazolo[1,5-a]pyrimidin-3-ylethynyl]-pyridine-3-sulfonic acid (2-hydroxy-1-hydroxymethyl-1-methyl-ethyl)-amide The title compound was prepared from 7-cyclopropyl-3-ethynyl-5-(4-trifluoromethyl-phenyl)-pyrazolo[1,5-a]pyrimidine (example C.7) (82 mg, 0.25 mmol) and 5-bromo-pyridine-3-sulfonic acid (2-hydroxy-1-hydroxymethyl-1-methyl-ethyl)-amide (81 mg, 0.25 mmol) (Example B.4) according to general procedure II. Obtained as a yellow solid (81 mg, 57%). MS (ISP) 572.3 [(M+H)$^+$]; mp 190-191° C.

Example 81

5-[7-Cyclopropyl-5-(4-trifluoromethyl-phenyl)-pyrazolo[1,5-a]pyrimidin-3-ylethynyl]-N-(2-hydroxy-1,1-dimethyl-ethyl)-2-methoxy-benzenesulfonamide The title compound was prepared from 7-cyclopropyl-3-ethynyl-5-(4-trifluoromethyl-phenyl)-pyrazolo[1,5-a]pyrimidine (example C.7) (82 mg, 0.25 mmol) and 5-bromo-N-(2-hydroxy-1,1-dimethyl-ethyl)-2-methoxy-benzenesulfonamide (85 mg, 0.25 mmol) (Example B.7) according to general procedure II. Obtained as a yellow solid (61 mg, 42%). MS (ISP) 585.3 [(M+H)$^+$]; mp 192-195° C.

Example 82

2-[7-Cyclopropyl-5-(4-trifluoromethyl-phenyl)-pyrazolo[1,5-a]pyrimidin-3-ylethynyl]-thiazole-5-sulfonic acid (2-hydroxy-1,1-dimethyl-ethyl)-amide The title compound was prepared from 7-cyclopropyl-3-ethynyl-5-(4-trifluoromethyl-phenyl)-pyrazolo[1,5-a]pyrimidine (example C.7) (82 mg, 0.25 mmol) and 2-chloro-thiazole-5-sulfonic acid (2-hydroxy-1,1-dimethyl-ethyl)-amide (68 mg, 0.25 mmol) (Example B.14) according to general procedure II. Obtained as a yellow solid (24 mg, 17%). MS (ISP) 562.0 [(M+H)$^+$]; mp 243-245° C.

Example 83

5-[7-Cyclopropyl-5-(4-trifluoromethyl-phenyl)-pyrazolo[1,5-a]pyrimidin-3-ylethynyl]-thiophene-2-sulfonic acid amide The title compound was prepared from 7-cyclopropyl-3-ethynyl-5-(4-trifluoromethyl-phenyl)-pyrazolo[1,5-a]pyrimidine (example C.7) (82 mg, 0.25 mmol) and commercially available 5-bromo-thiophene-2-sulfonic acid amide (61 mg, 0.25 mmol) according to general procedure II. Obtained as a yellow solid (77 mg, 63%). MS (ISP) 489.3 [(M+H)$^+$]; mp 231-233° C.

Example 84

3-[7-Cyclopropyl-5-(4-trifluoromethyl-phenyl)-pyrazolo[1,5-a]pyrimidin-3-ylethynyl]-benzenesulfonamide The title compound was prepared from 7-cyclopropyl-3-ethynyl-5-(4-trifluoromethyl-phenyl)-pyrazolo[1,5-a]pyrimidine (example C.7) (82 mg, 0.25 mmol) and commercially available 3-bromo-benzenesulfonamide (59 mg, 0.25 mmol) according to general procedure II. Obtained as a yellow solid (36 mg, 28%). MS (ISP) 483.5 [(M+H)$^+$]; mp 262-264° C.

Example 85

5-[7-Cyclopropyl-5-(3,4-dichloro-phenyl)-pyrazolo[1,5-a]pyrimidin-3-ylethynyl]-2,4-difluoro-benzenesulfonamide The title compound was prepared from 7-cyclopropyl-5-(3,4-dichloro-phenyl)-3-ethynyl-pyrazolo[1,5-a]pyrimidine (example C.8) (82 mg, 0.25 mmol) and commercially available 5-bromo-2,4-difluoro-benzenesulfonamide (68 mg, 0.25 mmol) according to general procedure II. Obtained as a yellow solid (39 mg, 30%). MS (ISP) 519.0 [(M+H)$^+$]; mp 280-281° C.

Example 86

5-[7-Cyclopropyl-5-(3,4-dichloro-phenyl)-pyrazolo[1,5-a]pyrimidin-3-ylethynyl]-thiophene-2-sulfonic acid amide The title compound was prepared from 7-cyclopropyl-5-(3,4-dichloro-phenyl)-3-ethynyl-pyrazolo[1,5-a]pyrimidine (Example C.8) (82 mg, 0.25 mmol) and 5-bromo-thiophene-2-sulfonic acid amide (61 mg, 0.25 mmol) according to general procedure II. Obtained as a yellow solid (35 mg, 28%). MS (ISP) 489.3 [(M+H)$^+$]; mp 213-214° C.

Example 87

3-(7-Cyclopropyl-5-(3,4-dichloro-phenyl)-pyrazolo[1,5-a]pyrimidin-3-ylethynyl]-benzenesulfonamide The title compound was prepared from 7-cyclopropyl-5-(3,4-dichloro-phenyl)-3-ethynyl-pyrazolo[1,5-a]pyrimidine (example C.8) (82 mg, 0.25 mmol) and 4-bromo-benzenesulfonamide (59 mg, 0.25 mmol) according to general procedure II. Obtained as a yellow solid (37 mg, 30%). MS (ISP) 483.5 [(M+H)$^+$]; mp 200-202° C.

Example 88

4-[7-Cyclopropyl-5-(3,4-dichloro-phenyl)-pyrazolo[1,5-a]pyrimidin-3-ylethynyl]-benzenesulfonamide The title compound was prepared from 7-cyclopropyl-5-(3,4-dichloro-phenyl)-3-ethynyl-pyrazolo[1,5-a]pyrimidine (example C.8) (167 mg, 0.51 mmol) and 4-bromo-benzenesulfonamide (121 mg, 0.51 mmol) according to general procedure II. Obtained as a yellow solid (140 mg, 57%). MS (ISP) 483.4 [(M+H)$^+$]; mp 259-261° C.

Example 89

5-[5-(3,4-Dichloro-phenyl)-7-trifluoromethyl-pyrazolo[1,5-a]pyrimidin-3-ylethynyl]-thiophene-2-sulfonic acid amide The title compound was prepared from 5-(3,4-dichloro-phenyl)-3-ethynyl-7-trifluoromethyl-pyrazolo[1,5-a]pyrimidine (example C.9) (89 mg, 0.25 mmol) and 5-bromo-thiophene-2-sulfonic acid amide (61 mg, 0.25 mmol) according to general procedure II. Obtained as a yellow solid (42 mg, 32%). MS (ISP) 517.0 [(M+H)+]; mp 231-232° C.

Example 90

2-[5-(3,4-Dichloro-phenyl)-7-trifluoromethyl-pyrazolo[1,5-a]pyrimidin-3-ylethynyl]-thiazole-5-sulfonic acid (2-hydroxy-1,1-dimethyl-ethyl)-amide The title compound was prepared from 5-(3,4-dichloro-phenyl)-3-ethynyl-7-trifluoromethyl-pyrazolo[1,5-a]pyrimidine (example C.9) (89 mg, 0.25 mmol) and 2-chloro-thiazole-5-sulfonic acid (2-hydroxy-1,1-dimethyl-ethyl)-amide (68 mg, 0.25 mmol) (example B.14) according to general procedure II. Obtained as a yellow solid (44 mg, 30%). MS (ISP) 590.0 [(M+H)+]; mp 220-223° C.

Example 91

5-[5-(3,4-Dichloro-phenyl)-7-trifluoromethyl-pyrazolo[1,5-a]pyrimidin-3-ylethynyl]-pyridine-3-sulfonic acid (2-hydroxy-1-hydroxymethyl-1-methyl-ethyl)-amide The title compound was prepared from 5-(3,4-dichloro-phenyl)-3-ethynyl-7-trifluoromethyl-pyrazolo[1,5-a]pyrimidine (example C.9) (89 mg, 0.25 mmol) and 5-bromo-pyridine-3-sulfonic acid (2-hydroxy-1-hydroxymethyl-1-methyl-ethyl)-amide (Example B.4) (81 mg, 0.25 mmol) according to general procedure II. Obtained as a yellow solid (24 mg, 16%). MS (ISN) 598.2 [(M−H)−].

Example 92

5-[5-(3,4-Dichloro-phenyl)-7-trifluoromethyl-pyrazolo[1,5-a]pyrimidin-3-ylethynyl]-2,4-difluoro-benzenesulfonamide The title compound was prepared from 5-(3,4-dichloro-phenyl)-3-ethynyl-7-trifluoromethyl-pyrazolo[1,5-a]pyrimidine (example C.9) (89 mg, 0.25 mmol) and 5-bromo-2,4-difluoro-benzenesulfonamide (68 mg, 0.25 mmol) according to general procedure II. Obtained as a yellow solid (10 mg, 7%). MS (ISP) 547.0 [(M+H)+]; mp 308-310° C.

Example 93

3-[5-(3,4-Dichloro-phenyl)-7-trifluoromethyl-pyrazolo[1,5-a]pyrimidin-3-ylethynyl]-benzenesulfonamide The title compound was prepared from 5-(3,4-dichloro-phenyl)-3-ethynyl-7-trifluoromethyl-pyrazolo[1,5-a]pyrimidine (example C.9) (89 mg, 0.25 mmol) and 3-bromo-benzenesulfonamide (59 mg, 0.25 mmol) according to general procedure II. Obtained as a yellow solid (13 mg, 10%). MS (ISP) 511.5 [(M+H)+]; mp 230-231° C.

Example 94

4-[5-(3,4-Dichloro-phenyl)-7-trifluoromethyl-pyrazolo[1,5-a]pyrimidin-3-ylethynyl]-benzenesulfonamide The title compound was prepared from 5-(3,4-dichloro-phenyl)-3-ethynyl-7-trifluoromethyl-pyrazolo[1,5-a]pyrimidine (example C.9) (89 mg, 0.25 mmol) and 4-bromo-benzenesulfonamide (59 mg, 0.25 mmol) according to general procedure II. Obtained as a yellow solid (43 mg, 33%). MS (ISN) 509.0 [(M−H)−]; mp 273-274° C.

Example 95

3-[5-(4-Chloro-phenyl)-7-trifluoromethyl-pyrazolo[1,5-a]pyrimidin-3-ylethynyl]-N-(2-hydroxy-1,1-dimethyl-ethyl)-benzenesulfonamide The title compound was prepared from 5-(4-chloro-phenyl)-3-ethynyl-7-trifluoromethyl pyrazolo[1,5-a]pyrimidine (example C.4) (322 mg, 1.0 mmol) and 3-bromo-N-(2-hydroxy-1,1-dimethyl-ethyl)-benzenesulfonamide (370 mg, 1.2 mmol) according to general procedure II. Obtained as a yellow solid (244 mg, 44%). MS (ISP) 549.3 [(M+H)+]; mp 226-229° C.

Example 96

5-[5-(4-Chloro-phenyl)-7-trifluoromethyl-pyrazolo[1,5-a]pyrimidin-3-ylethynyl]-2,4-difluoro-benzenesulfonamide The title compound was prepared from 5-(4-chloro-phenyl)-3-ethynyl-7-trifluoromethyl pyrazolo[1,5-a]pyrimidine (example C.4) (161 mg, 0.5 mmol) and 5-bromo-2,4-difluoro-benzenesulfonamide (136 mg, 0.5 mmol) according to general procedure II. Obtained as a yellow solid (146 mg, 57%). MS (ISP) 513.3 [(M+H)+]; mp 292-293° C.

Example 97

5-[5-(4-Chloro-phenyl)-7-trifluoromethyl-pyrazolo[1,5-a]pyrimidin-3-ylethynyl]-thiophene-2-sulfonic acid amide The title compound was prepared from 5-(4-chloro-phenyl)-3-ethynyl-7-trifluoromethyl pyrazolo[1,5-a]pyrimidine (example C.4) (322 mg, 1.0 mmol) and 5-bromo-thiophene-2-sulfonic acid amide (242 mg, 1.0 mmol) according to general procedure II. Obtained as a yellow solid (247 mg, 51%). MS (ISP) 483.5 [(M+H)+]; mp 239-240° C.

Example 98

3-[5-(4-Chloro-phenyl)-7-trifluoromethyl-pyrazolo[1,5-a]pyrimidin-3-ylethynyl]-benzenesulfonamide The title compound was prepared from 5-(4-chloro-phenyl)-3-ethynyl-7-trifluoromethyl pyrazolo[1,5-a]pyrimidine (example C.4) (161 mg, 0.5 mmol) and 3-bromo-benzenesulfonamide (118 mg, 0.5 mmol) according to general procedure II. Obtained as a yellow solid (133 mg, 56%). MS (ISP) 477.1 [(M+H)+]; mp 218-220° C.

Example 99

3-[5-(4-Chloro-phenyl)-7-trifluoromethyl-pyrazolo
[1,5-a]pyrimidin-3-ylethynyl]-benzenesulfonamide The title compound was prepared from 5-(4-Chloro-phenyl)-3-ethynyl-7-trifluoromethyl pyrazolo[1,5-a]pyrimidine (example C.4) (322 mg, 1.0 mmol) and 4-bromo-benzenesulfonamide (236 mg, 1.0 mmol) according to general procedure II. Obtained as a yellow solid (320 mg, 67%). MS (ISP) 477.0 [(M+H)$^+$]; mp 290-293° C.

Example 100

5-[7-Trifluoromethyl-5-(4-trifluoromethyl-phenyl)-pyrazolo[1,5-a]pyrimidin-3-ylethynyl]-thiophene-2-sulfonic acid amide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 5-bromo-thiophene-2-sulfonamide (242 mg, 1.0 mmol) according to general procedure II. Obtained as an orange solid (377 mg, 73%). MS (ISN) 510.0 [(M-H)-]; mp 240° C.

Example 101

5-(4-Chloro-3-methyl-phenyl)-3-pyridin-3-ylethynyl-7-trifluoromethyl-pyrazolo[1,5-a]pyrimidine The title compound was prepared from 5-(4-chloro-3-methyl-phenyl)-3-ethynyl-7-trifluoromethyl-pyrazolo[1,5-a]pyrimidine (example C.11) (336 mg, 1.0 mmol) and commercially available 3-bromopyridine (158 mg, 1.0 mmol) according to general procedure II. Obtained as a yellow solid (90 mg, 22%). MS (ISP) 413.0 [(M+H)$^+$]; mp 196° C.

Example 102

3-[5-(4-Chloro-3-methyl-phenyl)-7-trifluoromethyl-pyrazolo[1,5-a]pyrimidin-3-ylethynyl]-N-(2-hydroxy-1,1-dimethyl-ethyl)-benzenesulfonamide The title compound was prepared from 5-(4-chloro-3-methyl-phenyl)-3-ethynyl-7-trifluoromethyl-pyrazolo[1,5-a]pyrimidine (example C.11) (336 mg, 1.0 mmol) and 3-bromo-N-(2-hydroxy-1,1-dimethyl-ethyl)-benzenesulfonamide (example B.6) (308 mg, 1.0 mmol) according to general procedure II. Obtained as a yellow solid (269 mg, 48%). MS (ISN) 561.3 [(M-H)$^-$]; mp 204° C.

Example 103

3-Pyridin-3-ylethynyl-7-trifluoromethyl-5-(3-trifluoromethyl-phenyl)-pyrazolo[1,5-a]pyrimidine The title compound was prepared from 3-ethynyl-7-trifluoromethyl-5-(3-trifluoromethyl-phenyl)-pyrazolo[1,5-a]pyrimidine (example C.10) (355 mg, 1.0 mmol) and commercially available 3-bromo-pyridine (158 mg, 1.0 mmol) according to general procedure II. Obtained as a yellow solid (211 mg, 49%). MS (EI) 432.2 [(M)$^+$]; mp 173° C.

Example 104

2-[5-(4-Chloro-3-methyl-phenyl)-7-trifluoromethyl-pyrazolo[1,5-a]pyrimidin-3-ylethynyl]-thiazole-5-sulfonic acid amide The title compound was prepared from 5-(4-chloro-3-methyl-phenyl)-3-ethynyl-7-trifluoromethyl-pyrazolo[1,5-a]pyrimidine (example C.1) (336 mg, 1.0 mmol) and 2-chloro-thiazole-5-sulfonamide (199 mg, 1.0 mmol) according to general procedure II. Obtained as a yellow solid (209 mg, 42%). MS (ISN) 496.0 [(M−H)$^-$]; mp 123° C.

Example 105

2-[7-Trifluoromethyl-5-(3-trifluoromethyl-phenyl)-pyrazolo[1,5-a]pyrimidin-3-ylethynyl]-thiazole-5-sulfonic acid amide The title compound was prepared from 3-ethynyl-7-trifluoromethyl-5-(3-trifluoromethyl-phenyl)-pyrazolo[1,5-a]pyrimidine (example C.10) (355 mg, 1.0 mmol) and 2-chloro-thiazole-5-sulfonamide (199 mg, 1.0 mmol) according to general procedure II. Obtained as a yellow solid (270 mg, 52%). MS (ISN) 516.1 [(M−H)$^-$]; mp 251° C.

Example 106

2-[5-(4-Chloro-3-methyl-phenyl)-7-trifluoromethyl-pyrazolo[1,5-a]pyrimidin-3-ylethynyl]-thiazole-5-sulfonic acid (2-hydroxy-1,1-dimethyl-ethyl)-amide The title compound was prepared from 5-(4-chloro-3-methyl-phenyl)-3-ethynyl-7-trifluoromethyl-pyrazolo[1,5-a]pyrimidine (example C.11) (168 mg, 0.5 mmol) and 2-chloro-thiazole-5-sulfonic acid (2-hydroxy-1,1-dimethyl-ethyl)-amide (example B.14) (135 mg, 0.5 mmol) according to general procedure II. Obtained as a yellow solid (162 mg, 57%). MS (ISN) 568.1 [(M−H)$^-$]; mp 217° C.

Example 107

N-(2-Hydroxy-1,1-dimethyl-ethyl)-3-[7-trifluoromethyl-5-(3-trifluoromethyl-phenyl)-pyrazolo[1,5-a]pyrimidin-3-ylethynyl]-benzenesulfonamide The title compound was prepared from 3-ethynyl-7-trifluoromethyl-5-(3-trifluoromethyl-phenyl)-pyrazolo[1,5-a]pyrimidine (example C.10) (355 mg, 1.0 mmol) and 3-bromo-N-(2-hydroxy-1,1-dimethyl-ethyl)-benzenesulfonamide (example B.6) (308 mg, 1.0 mmol) according to general procedure II. Obtained as a yellow solid (560 mg, 96%). MS (ISN) 581.1 [(M−H)$^-$]; mp 132° C.

Example 108

2-[7-Trifluoromethyl-5-(3-trifluoromethyl-phenyl)-pyrazolo[1,5-a]pyrimidin-3-ylethynyl]-thiazole-5-sulfonic acid (2-hydroxy-1,1-dimethyl-ethyl)-amide The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and 2-chloro-thiazole-5-sulfonic acid (2-hydroxy-1,1-dimethyl-ethyl)-amide (example B.14) (135 mg, 0.5 mmol) according to general procedure II. Obtained as a yellow solid (163 mg, 55%). MS (ISN) 588.2 [(M+H)$^+$]; mp 200° C.

Example 109

5-[7-Trifluoromethyl-5-(4-trifluoromethyl-phenyl)-pyrazolo[1,5-a]pyrimidin-3-ylethynyl]-thiophene-2-sulfonic acid tert-butylamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 5-bromo-thiophene-2-N-tert-butylsulfonamide (298 mg, 1.0 mmol) according to general procedure II. Obtained as an orange solid (272 mg, 48%). MS (ISN) 571.1 [(M−H)⁻]; mp 226° C.

Example 110

4-[5-(4-Chloro-3-methyl-phenyl)-7-trifluoromethyl-pyrazolo[1,5-a]pyrimidin-3-ylethynyl]-benzenesulfonamide The title compound was prepared from 5-(4-chloro-3-methyl-phenyl)-3-ethynyl-7-trifluoromethyl-pyrazolo[1,5-a]pyrimidine (example C.11) (168 mg, 0.5 mmol) and commercially available 4-bromo-benzenesulfonamide (118 mg, 0.5 mmol) according to general procedure II. Obtained as a yellow solid (136 mg, 55%). MS (ISN) 489.0 [(M−H)⁻]; mp 275° C.

Example 111

5-[5-(4-Chloro-3-methyl-phenyl)-7-trifluoromethyl-pyrazolo[1,5-a]pyrimidin-3-ylethynyl]-2,4-difluoro-benzenesulfonamide The title compound was prepared from 5-(4-chloro-3-methyl-phenyl)-3-ethynyl-7-trifluoromethyl-pyrazolo[1,5-a]pyrimidine (example C.11) (178 mg, 0.5 mmol) and commercially available 5-bromo-2,4-difluoro-benzenesulfonamide (136 mg, 0.5 mmol) according to general procedure II. Obtained as a yellow solid (125 mg, 47%). MS (ISN) 525.2 [(M−H)⁻]; mp 294° C.

Example 112

3-[5-(4-Chloro-3-methyl-phenyl)-7-trifluoromethyl-pyrazolo[1,5-a]pyrimidin-3-ylethynyl]-benzenesulfonamide The title compound was prepared from 5-(4-chloro-3-methyl-phenyl)-3-ethynyl-7-trifluoromethyl-pyrazolo[1,5-a]pyrimidine (example C.11) (168 mg, 0.5 mmol) and commercially available 3-bromo-benzenesulfonamide (118 mg, 0.5 mmol) according to general procedure II. Obtained as a yellow solid (114 mg, 46%). MS (ISN) 489.2 [(M−H)⁻]; mp 234° C.

Example 113

4-[7-Trifluoromethyl-5-(3-trifluoromethyl-phenyl)-pyrazolo[1,5-a]pyrimidin-3-ylethynyl]-benzenesulfonamide The title compound was prepared from 3-ethynyl-7-trifluoromethyl-5-(3-trifluoromethyl-phenyl)-pyrazolo[1,5-a]pyrimidine (example C.1) (178 mg, 0.5 mmol) and commercially available 4-bromo-benzenesulfonamide (118 mg, 0.5 mmol) according to general procedure II. Obtained as a yellow solid (106 mg, 42%). MS (ISN) 509.2 [(M−H)⁻]; mp 264° C.

Example 114

5-[5-(4-Chloro-3-methyl-phenyl)-7-trifluoromethyl-pyrazolo[1,5-a]pyrimidin-3-ylethynyl]-thiophene-2-sulfonic acid amide The title compound was prepared from 5-(4-chloro-3-methyl-phenyl)-3-ethynyl-7-trifluoromethyl-pyrazolo[1,5-a]pyrimidine (example C.11) (168 mg, 0.5 mmol) and commercially available 5-bromo-thiophene-2-sulfonamide (121 mg, 0.5 mmol) according to general procedure II. Obtained as a yellow solid (119 mg, 48%). MS (ISN) 495.2 [(M−H)⁻]; mp 216° C.

Example 115

5-[5-(4-Chloro-3-methyl-phenyl)-7-trifluoromethyl-pyrazolo[1,5-a]pyrimidin-3-ylethynyl]-thiophene-2-sulfonic acid tert-butylamide The title compound was prepared from 5-(4-chloro-3-methyl-phenyl)-3-ethynyl-7-trifluoromethyl-pyrazolo[1,5-a]pyrimidine (example C.11) (168 mg, 0.5 mmol) and commercially available 5-bromo-thiophene-2-N-tert-butylsulfonamide (149 mg, 0.5 mmol) according to general procedure II. Obtained as a yellow solid (170 mg, 61%). MS (ISP) 551.0 [(M−H)⁻]; mp 244° C.

Example 116

2,4-Difluoro-5-[7-trifluoromethyl-5-(3-trifluoromethyl-phenyl)-pyrazolo[1,5-a]pyrimidin-3-ylethynyl]-benzenesulfonamide The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and commercially available 5-bromo-2,4-difluoro-benzenesulfonamide (136 mg, 0.5 mmol) according to general procedure II. Obtained as a yellow solid (138 mg, 51%). MS (ISN) 545.1 [(M−H)⁻]; mp 264° C.

Example 117

5-[7-Trifluoromethyl-5-(3-trifluoromethyl-phenyl)-pyrazolo[1,5-a]pyrimidin-3-ylethynyl]-thiophene-2-sulfonic acid tert-butylamide The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and commercially available 5-bromo-thiophene-2-N-tert.-butylsulfonamide (149 mg, 0.5 mmol) according to general procedure II. Obtained as a yellow solid (102 mg, 36%). MS (ISN) 571.1 [(M−H)⁻]; mp 168° C.

Example 118

3-[7-Trifluoromethyl-5-(3-trifluoromethyl-phenyl)-pyrazolo[1,5-a]pyrimidin-3-ylethynyl]-benzenesulfonamide The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and commercially available 3-bromo-benzenesulfonylchloride (118 mg, 0.5 mmol) according to general procedure II. Obtained as a yellow solid (103 mg, 40%). MS (ISN) 509.3 [(M−H)$^−$]; mp 193° C.

Example 119

5-[7-Trifluoromethyl-5-(3-trifluoromethyl-phenyl)-pyrazolo[1,5-a]pyrimidin-3-ylethynyl]-thiophene-2-sulfonic acid amide The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and commercially available 5-bromo-thiophene-2-sulfonamide (121 mg, 0.5 mmol) according to general procedure II. Obtained as a yellow solid (102 mg, 40%). MS (ISN) 515.0 [(M−H)$^−$]; mp 250° C.

Example 120

5-[7-Trifluoromethyl-5-(4-trifluoromethyl-phenyl)-pyrazolo[1,5-a]pyrimidin-3-ylethynyl]-thiophene-2-sulfonic acid (2-hydroxy-1,1-dimethyl-ethyl)-amide The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and 5-chloro-thiophene-2-sulfonic acid (2-hydroxy-1,1-dimethyl-ethyl)-amide (example B.24) (135 mg, 1.0 mmol) according to general procedure II. Obtained as an orange solid (43 mg, 15%). MS (ISN) 587.3 [(M−H)$^−$]; mp 272° C.

Example 121

N,N-Dimethyl-4-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 4-bromo-N-(2-dimethylamino-ethyl)-benzenesulfonamide (example B.25) (276 mg, 1.0 mmol) according to general procedure II. Obtained as an orange solid (390 mg, 72%). MS (ISP) 539.2 [(M+H)$^+$]; mp 226-227° C.

Example 122

3-[4-(Morpholine-4-sulfonyl)-phenylethynyl]-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 4-(4-bromo-benzenesulfonyl)-morpholine (example B.26) (276 mg, 1.0 mmol) according to general procedure II. Obtained as an orange solid (450 mg, 77%). MS (ISP) 581.2 [(M+H)$^+$]; mp 229-231° C.

Example 123

N-Methyl-4-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 4-bromo-N-methyl-benzenesulfonamide (example B.27) (276 mg, 1.0 mmol) according to general procedure II. Obtained as a yellow solid (390 mg, 74%). MS (ISP) 525.2 [(M+H)$^+$]; mp 231-233° C.

Example 124

N-(2-Methoxy-ethyl)-4-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 4-bromo-N-(2-methoxy-ethyl)-benzenesulfonamide (example B.28) (276 mg, 1.0 mmol) according to general procedure II. Obtained as a yellow solid (400 mg, 70%). MS (ISP) 569.1 [(M+H)$^+$]; mp 185-187° C.

Example 125

N-(2-Hydroxy-ethyl)-4-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 4-bromo-N-(2-hydroxy-ethyl)-benzenesulfonamide (example B.29) (276 mg, 1.0 mmol) according to general procedure II. Obtained as a yellow solid (370 mg, 66%). MS (ISP) 555.2 [(M+H)$^+$]; mp 206-208° C.

Example 126

N-(2-Dimethylamino-ethyl)-4-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 4-bromo-N-(2-dimethylamino-ethyl)-benzenesulfonamide (example B.30) (276 mg, 1.0 mmol) according to general procedure II. Obtained as a yellow solid (340 mg, 58%). MS (ISP) 582.2 [(M+H)$^+$]; mp 193-194° C.

Example 127

3-Methyl-5-[7-trifluoromethyl-5-(4-trifluoromethyl-phenyl)-pyrazolo[1,5-a]pyrimidin-3-ylethynyl]-pyridin-2-ylamine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 2-amino-5-bromo-3-methylpyridine (168 mg, 1.0 mmol) according to general procedure II. Obtained as a dark-red solid (140 mg, 30%). MS (ISP) 462.2 [(M+H)$^+$]; mp 233-234° C.

Example 128

6-Methyl-5-[7-trifluoromethyl-5-(4-trifluoromethyl-phenyl)-pyrazolo[1,5-a]pyrimidin-3-ylethynyl]-pyridin-2-ylamine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 6-amino-3-bromo-2-methylpyridine (168 mg, 1.0 mmol) according to general procedure II. Obtained as a dark-red solid (90 mg, 19%). MS (ISP) 462.2 [(M+H)$^+$]; mp 251-254° C.

Example 129

3-[3-(morpholine-4-sulfonyl)-phenylethynyl]-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 4-(3-bromo-benzenesulfonyl)-morpholine (example B.31) (275 mg, 1.0 mmol) according to general procedure II. Obtained as a yellow solid (490 mg, 84%). MS (ISP) 581.2 [(M+H)$^+$]; mp 203-204° C.

Example 130

N-Methyl-3-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 3-bromo-N-methyl-benzenesulfonamide (example B.32) (225 mg, 1.0 mmol) according to general procedure II. Obtained as a yellow solid (360 mg, 68%). MS (ISP) 525.2 [(M+H)$^+$]; mp 213-214° C.

Example 131

N-(2-Methoxy-ethyl)-3-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 3-bromo-N-(2-methoxy-ethyl)-benzenesulfonamide (example B.33) (265 mg, 1.0 mmol) according to general procedure II. Obtained as a yellow solid (320 mg, 56%). MS (ISP) 569.1 [(M+H)$^+$]; mp 186-188° C.

Example 132

N-(2-Hydroxy-ethyl)-3-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 3-bromo-N-(2-hydroxy-ethyl)-benzenesulfonamide (example B.34) (252 mg, 1.0 mmol) according to general procedure II. Obtained as a yellow solid (340 mg, 61%). MS (ISP) 555.1 [(M+H)$^+$]; mp 213° C.

Example 133

N-(2-Dimethylamino-ethyl)-3-[7-trifluoromethyl-5-(4-trifluoromethyl-phenyl)-pyrazolo[1,5-a]pyrimidin-3-ylethynyl]-benzenesulfonamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and 3-bromo-N-(2-dimethylamino-ethyl)-benzenesulfonamide (example B.35) (276 mg, 1.0 mmol) according to general procedure II. Obtained as a yellow solid (200 mg, 34%). MS (ISP) 582.2 [(M+H)$^+$]; mp 146-147° C.

Example 134

5-[7-Difluoromethyl-5-(4-trifluoromethyl-phenyl)-pyrazolo[1,5-a]pyrimidin-3-ylethynyl]-N-(2-dimethylamino-ethyl)-2,4-difluoro-benzenesulfonamide The title compound was prepared from 7-Difluoromethyl-3-ethynyl-5-(4-trifluoromethyl-phenyl)-pyrazolo[1,5-a]pyrimidine (example C.2) (337 mg, 1.0 mmol) and 5-bromo-N-(2-dimethylamino-ethyl)-2,4-difluoro-benzenesulfonamide (example B.36) (446 mg, 1.0 mmol) according to general procedure II. Obtained as a yellow solid (300 mg, 50%). MS (ISP) 600.2 [(M+H)$^+$]; mp 165-166° C.

Example 135

5-[7-Difluoromethyl-5-(4-trifluoromethyl-phenyl)-pyrazolo[1,5-a]pyrimidin-3-ylethynyl]-2,4-difluoro-N-(2-hydroxy-ethyl)-benzenesulfonamide The title compound was prepared from 7-Difluoromethyl-3-ethynyl-5-(4-trifluoromethyl-phenyl)-pyrazolo[1,5-a]pyrimidine (example C.2) (337 mg, 1.0 mmol) and 5-bromo-2,4-difluoro-N-(2-hydroxy-ethyl)-benzenesulfonamide (example B.37) (411 mg, 1.0 mmol) according to general procedure II. Obtained as a yellow solid (100 mg, 17%). MS (ISP) 573.1 [(M+H)$^+$]; mp 149-150° C.

Example 136

4-[7-Difluoromethyl-5-(4-trifluoromethyl-phenyl)-pyrazolo[1,5-a]pyrimidin-3-ylethynyl]-N,N-dimethyl-benzenesulfonamide The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and 4-bromo-N,N-dimethyl-benzenesulfonamide (example B.25) (276 mg, 1.0 mmol) according to general procedure II. Obtained as a yellow solid (390 mg, 74%). MS (ISP) 521.3 [(M+H)$^+$]; mp 211-212° C.

Example 137

7-Difluoromethyl-3-[4-(morpholine-4-sulfonyl)-phenylethynyl]-5-(4-trifluoromethyl-phenyl)-pyrazolo[1,5-a]pyrimidine The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and 4-(4-bromo-benzenesulfonyl)-morpholine (example B.26) (276 mg, 1.0 mmol) according to general procedure II. Obtained as a yellow solid (420 mg, 74%). MS (ISP) 563.4 [(M+H)$^+$]; mp 227-228° C.

Example 138

4-[7-difluoromethyl-5-(4-trifluoromethyl-phenyl)-pyrazolo[1,5-a]pyrimidin-3-ylethynyl]-N-methyl-benzenesulfonamide The title compound was prepared from 7-difluoromethyl-3-ethynyl-5-(4-trifluoromethyl-phenyl)-pyrazolo[1,5-a]pyrimidine (example C.2) (340 mg, 1.0 mmol) and 4-bromo-N-methyl-benzenesulfonamide (example B.27) (276 mg, 1.0 mmol) according to general procedure II. Obtained as a yellow solid (300 mg, 58%). MS (ISP) 508.3 [(M+H)$^+$]; mp 202-203° C.

Example 139

4-[7-Difluoromethyl-5-(4-trifluoromethyl-phenyl)-pyrazolo[1,5-a]pyrimidin-3-ylethynyl]-N-(2-methoxy-ethyl)-benzenesulfonamide The title compound was prepared from 7-difluoromethyl-3-ethynyl-5-(4-trifluoromethyl-phenyl)-pyrazolo[1,5-a]pyrimidine (example C.2) (340 mg, 1.0 mmol) and 4-bromo-N-(2-methoxy-ethyl)-benzenesulfonamide (example B.28) (276 mg, 1.0 mmol) according to general procedure II. Obtained as a yellow solid (400 mg, 72%). MS (ISP) 551.3 [(M+H)$^+$]; mp 184-186° C.

Example 140

4-[7-Difluoromethyl-5-(4-trifluoromethyl-phenyl)-pyrazolo[1,5-a]pyrimidin-3-ylethynyl]-N-(2-hydroxy-ethyl)-benzenesulfonamide The title compound was prepared from 7-difluoromethyl-3-ethynyl-5-(4-trifluoromethyl-phenyl)-pyrazolo[1,5-a]pyrimidine (example C.2) (340 mg, 1.0 mmol) and 4-bromo-N-(2-hydroxy-ethyl)-benzenesulfonamide (example B.29) (276 mg, 1.0 mmol) according to general procedure II. Obtained as a yellow solid (360 mg, 66%). MS (ISP) 537.3 [(M+H)$^+$]; mp 191-194° C.

Example 141

4-[7-Difluoromethyl-5-(4-trifluoromethyl-phenyl)-pyrazolo[1,5-a]pyrimidin-3-ylethynyl]-N-(2-dimethylamino-ethyl)-benzenesulfonamide The title compound was prepared from 7-difluoromethyl-3-ethynyl-5-(4-trifluoromethyl-phenyl)-pyrazolo[1,5-a]pyrimidine (example C.2) (340 mg, 1.0 mmol) and 4-bromo-N-(2-dimethylamino-ethyl)-benzenesulfonamide (example B.30) (276 mg, 1.0 mmol) according to general procedure II. Obtained as a yellow solid (260 mg, 45%). MS (ISP) 564.3 [(M+H)$^+$]; mp 157-159° C.

Example 142

5-[7-Difluoromethyl-5-(4-trifluoromethyl-phenyl)-pyrazolo[1,5-a]pyrimidin-3-ylethynyl]-3-methyl-pyridin-2-ylamine The title compound was prepared from 7-difluoromethyl-3-ethynyl-5-(4-trifluoromethyl-phenyl)-pyrazolo[1,5-a]pyrimidine (example C.2) (340 mg, 1.0 mmol) and 2-amino-5-bromo-3-methylpyridine (168 mg, 1.0 mmol) according to general procedure II. Obtained as a red solid (210 mg, 46%). MS (ISP) 444.3 [(M+H)$^+$]; mp 194-195° C.

Example 143

5-[7-Difluoromethyl-5-(4-trifluoromethyl-phenyl)-pyrazolo[1,5-a]pyrimidin-3-ylethynyl]-6-methyl-pyridin-2-ylamine The title compound was prepared from 7-difluoromethyl-3-ethynyl-5-(4-trifluoromethyl-phenyl)-pyrazolo[1,5-a]pyrimidine (example C.2) (340 mg, 1.0 mmol) and 6-amino-3-bromo-2-methylpyridine (168 mg, 1.0 mmol) according to general procedure II. Obtained as a red solid (65 mg, 15%). MS (ISP) 444.3 [(M+H)$^+$]; mp 243-246° C.

Example 144

7-Difluoromethyl-3-[3-(morpholine-4-sulfonyl)-phenylethynyl]-5-(4-trifluoromethyl-phenyl)-pyrazolo[1,5-a]pyrimidine The title compound was prepared from 7-difluoromethyl-3-ethynyl-5-(4-trifluoromethyl-phenyl)-pyrazolo[1,5-a]pyrimidine (example C.2) (340 mg, 1.0 mmol) and 4-(3-bromo-benzenesulfonyl)-morpholine (example B.31) (275 mg, 1.0 mmol) according to general procedure II. Obtained as a yellow solid (390 mg, 68%). MS (ISP) 563.4 [(M+H)$^+$]; mp 175-176° C.

Example 145

3-[7-Difluoromethyl-5-(4-trifluoromethyl-phenyl)-pyrazolo[1,5-a]pyrimidin-3-ylethynyl]-N-methyl-benzenesulfonamide The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and X (example B.32) (225 mg, 1.0 mmol) according to general procedure II. Obtained as a yellow solid (340 mg, 66%). MS (ISP) 507.2 [(M+H)⁺]; mp 192-194° C.

Example 146

3-[7-Difluoromethyl-5-(4-trifluoromethyl-phenyl)-pyrazolo[1,5-a]pyrimidin-3-ylethynyl]-N-(2-methoxy-ethyl)-benzenesulfonamide The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and 3-bromo-N-(2-methoxy-ethyl)-benzenesulfonamide (example B.33) (265 mg, 1.0 mmol) according to general procedure II. Obtained as a yellow solid (320 mg, 57%). MS (ISP) 551.3 [(M+H)⁺]; mp 147-148° C.

Example 147

3-[7-Difluoromethyl-5-(4-trifluoromethyl-phenyl)-pyrazolo[1,5-a]pyrimidin-3-ylethynyl]-N-(2-hydroxy-ethyl)-benzenesulfonamide The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and 3-bromo-N-(2-hydroxy-ethyl)-benzenesulfonamide (example B.34) (252 mg, 1.0 mmol) according to general procedure II. Obtained as a yellow solid (300 mg, 55%). MS (ISP) 537.3 [(M+H)⁺]; mp 113-115° C.

Example 148

3-[7-Difluoromethyl-5-(4-trifluoromethyl-phenyl)-pyrazolo[1,5-a]pyrimidin-3-ylethynyl]-N-(2-dimethylamino-ethyl)-benzenesulfonamide The title compound was prepared from 7-Difluoromethyl-3-ethynyl-5-(4-trifluoromethyl-phenyl)-pyrazolo[1,5-a]pyrimidine (example C.2) (340 mg, 1.0 mmol) and 3-bromo-N-(2-dimethylamino-ethyl)-benzenesulfonamide (example B.35) (276 mg, 1.0 mmol) according to general procedure II. Obtained as a yellow solid (340 mg, 59%). MS (ISP) 564.3 [(M+H)⁺]; mp 160-162° C.

Example 149

3-(6-Fluoro-pyridin-3-ylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 5-bromo-2-fluoropyridine (237 mg, 1.0 mmol) according to general procedure II. Obtained as an orange solid (470 mg, 69%). MS (ISP) 451.1 [(M+H)⁺]; mp 213-216° C.

Example 150

4-[7-Methyl-5-(4-trifluoromethyl-phenyl)-pyrazolo[1,5-a]pyrimidin-3-ylethynyl]-benzenesulfonamide The title compound was prepared from 3-ethynyl-7-methyl-5-(4-trifluoromethyl-phenyl)-pyrazolo[1,5-a]pyrimidine (example C.12) (75 mg, 0.25 mmol) and 4-bromo-benzenesulfonamide (59 mg, 0.25 mmol) according to general procedure II. Obtained as a yellow solid (62 mg, 54%). MS (ISN) 454.9 [(M−H)⁻]; mp 282-284° C.

Example 151

3-[7-Methyl-5-(4-trifluoromethyl-phenyl)-pyrazolo[1,5-a]pyrimidin-3-ylethynyl]-benzenesulfonamide The title compound was prepared from 3-ethynyl-7-methyl-5-(4-trifluoromethyl-phenyl)-pyrazolo[1,5-a]pyrimidine (example C.12) (75 mg, 0.25 mmol) and 3-bromo-benzenesulfonamide (59 mg, 0.25 mmol) according to general procedure II. Obtained as a yellow solid (48 mg, 42%). MS (ISN) 454.9 [(M−H)⁻]; mp 214-216° C.

Example 152

5-[7-Methyl-5-(4-trifluoromethyl-phenyl)-pyrazolo[1,5-a]pyrimidin-3-ylethynyl]-thiophene-2-sulfonic acid amide The title compound was prepared from 3-ethynyl-7-methyl-5-(4-trifluoromethyl-phenyl)-pyrazolo[1,5-a]pyrimidine (example C.12) (75 mg, 0.25 mmol) and 5-bromothiophene-2-sulfonic acid amide (61 mg, 0.25 mmol) according to general procedure II. Obtained as a yellow solid (33 mg, 28%). MS (ISN) 461.0 [(M−H)⁻]; mp 214-215° C.

Example 153

4-[5-(4-Chloro-phenyl)-7-(1-hydroxy-1-methyl-ethyl)-pyrazolo[1,5-a]pyrimidin-3-ylethynyl]-benzenesulfonamide The title compound was prepared from 3-ethynyl-7-methyl-5-(4-chloro-phenyl)-pyrazolo[1,5-a]pyrimidine (example C.13) (78 mg, 0.25 mmol) and 4-bromo-benzenesulfonamide (59 mg, 0.25 mmol) according to general procedure II. Obtained as a yellow solid (59 mg, 50%). MS (ISP) 467.0 [(M+H)⁺]; mp 267-269° C.

Example 154

5-[5-(4-Chloro-phenyl)-7-(1-hydroxy-1-methyl-ethyl)-pyrazolo[1,5-a]pyrimidin-3-ylethynyl]-thiophene-2-sulfonic acid amide The title compound was prepared from 2-[5-(4-chloro-phenyl)-3-ethynyl-pyrazolo[1,5-a]pyrimidin-7-yl]-propan-2-ol (example C.13) (78 mg, 0.25 mmol) and 5-bromothiophene-2-sulfonic acid amide (61 mg, 0.25 mmol) according to general procedure II. Obtained as a yellow solid (76 mg, 64%). MS (ISP) 473.0 [(M+H)⁺]; mp 206-208° C.

Example 155

4-[5-(4-Chloro-phenyl)-7-hydroxymethyl-pyrazolo[1,5-a]pyrimidin-3-ylethynyl]-benzenesulfonamide The title compound was prepared from 2-[5-(4-chloro-phenyl)-3-ethynyl-pyrazolo[1,5-a]pyrimidin-7-yl]-propan-2-ol (example C.13) (28 mg, 0.10 mmol) and 4-bromo-benzenesulfonamide (24 mg, 0.10 mmol) according to general procedure II. Obtained as a yellow solid (12 mg, 27%). MS (ISP) 439.0 [(M+H)⁺]; mp 238-240° C.

Example 156

5-[5-(4-Chloro-phenyl)-7-hydroxymethyl-pyrazolo[1,5-a]pyrimidin-3-ylethynyl]-thiophene-2-sulfonic acid amide

The title compound was prepared 2-[5-(4-chloro-phenyl)-3-ethynyl-pyrazolo[1,5-a]pyrimidin-7-yl]-propan-2-ol (example C.14) (28 mg, 0.1 mmol) and 5-bromo-thiophene-2-sulfonic acid amide (24 mg, 0.10 mmol) according to general procedure II. Obtained as a yellow solid (9 mg, 20%). MS (ISP) 445.0 [(M+H)$^+$]; mp 194-196° C.

Example 157

3-[5-(4-Methyl-piperazine-1-sulfonyl)-thiophen-2-ylethynyl]-7-trifluoromethyl-5-(4-trifluoromethyl-phenyl)-pyrazolo[1,5-a]pyrimidine

The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and 1-(5-chloro-thiophene-2-sulfonyl)-4-methyl-piperazine hydrochloride (example B.41) (159 mg, 0.5 mmol) according to general procedure II. Obtained as an orange solid (48 mg, 16%). MS (ISP) 600.2 [(M+H)$^+$]; mp 250° C.

Example 158

5-[7-Trifluoromethyl-5-(4-trifluoromethyl-phenyl)-pyrazolo[1,5-a]pyrimidin-3-ylethynyl]-thiophene-2-sulfonic acid (2-morpholin-4-yl-ethyl)-amide

The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and 5-chloro-thiophene-2-sulfonic acid (2-morpholin-4-yl-ethyl)-amide (example B.38) (155 mg, 0.5 mmol) according to general procedure II. Obtained as an orange solid (51 mg, 16%). MS (ISP) 630.1 [(M+H)$^+$]; mp 219° C.

Example 159

5-[7-Trifluoromethyl-5-(4-trifluoromethyl-phenyl)-pyrazolo[1,5-a]pyrimidin-3-ylethynyl]-thiophene-2-sulfonic acid (2-dimethylamino-ethyl)-amide

The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and 5-chloro-thiophene-2-sulfonic acid (2-dimethylamino-ethyl)-amide (example B.39) (134 mg, 0.5 mmol) according to general procedure II. Obtained as an orange solid (32 mg, 11%). MS (ISN) 586.1 [(M−H)$^-$]; mp 178° C.

Example 160

5-[7-Difluoromethyl-5-(3-trifluoromethyl-phenyl)-pyrazolo[1,5-a]pyrimidin-3-ylethynyl]-thiophene-2-sulfonic acid amide

The title compound was prepared from 3-ethynyl-7-difluoromethyl-5-(3-trifluoromethyl-phenyl)-pyrazolo[1,5-a]pyrimidine (example C.15) (169 mg, 0.5 mmol) and commercially available 5-bromo-thiophene-2-sulfonamide (121 mg, 0.5 mmol) according to general procedure II. Obtained as a yellow solid (180 mg, 72%). MS (ISN) 497.0 [(M−H)$^-$]; mp 225° C.

Example 161

5-[7-Difluoromethyl-5-(3-trifluoromethyl-phenyl)-pyrazolo[1,5-a]pyrimidin-3-ylethynyl]-thiophene-2-sulfonic acid tert-butylamide

The title compound was prepared from 3-ethynyl-7-difluoromethyl-5-(3-trifluoromethyl-phenyl)-pyrazolo[1,5-a]pyrimidine (example C.15) (169 mg, 0.5 mmol) and commercially available 5-bromo-thiophene-2-N-tert.-butylsulfonamide (149 mg, 0.5 mmol) according to general procedure II. Obtained as a yellow solid (220 mg, 79%). MS (ISN) 553.3 [(M−H)$^-$]; mp 201° C.

Example 162

5-[7-Trifluoromethyl-5-(4-trifluoromethyl-phenyl)-pyrazolo[1,5-a]pyrimidin-3-ylethynyl]-thiophene-2-sulfonic acid bis-(2-hydroxy-ethyl)-amide

The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and 5-chloro-thiophene-2-sulfonic acid bis-(2-hydroxy-ethyl)-amide (example B.40) (143 mg, 0.5 mmol) according to general procedure II. Obtained as a yellow solid (60 mg, 20%). MS (ISP) 622.0 [(M+NH$_4$)$^+$]; mp 137° C.

Example 163

5-[7-Trifluoromethyl-5-(4-trifluoromethyl-phenyl)-pyrazolo[1,5-a]pyrimidin-3-ylethynyl]-thiophene-2-sulfonic acid (2-hydroxy-1-hydroxymethyl-ethyl)-amide

The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and 5-chloro-thiophene-2-sulfonic acid (2-hydroxy-1-hydroxymethyl-ethyl)-amide (example B.42) (138 mg, 0.5 mmol) according to general procedure II. Obtained as an orange solid (52 mg, 18%). MS (ISN) 589.1 [(M−H)$^-$]; mp 247° C.

Example 164

5-[7-Difluoromethyl-5-(4-trifluoromethyl-phenyl)-pyrazolo[1,5-a]pyrimidin-3-ylethynyl]-thiophene-2-sulfonic acid amide

The title compound was prepared from 7-difluoromethyl-3-ethynyl-5-(4-trifluoromethyl-phenyl)-pyrazolo[1,5-a]pyrimidine (example C.2) (169 mg, 0.5 mmol) and commercially available 5-bromo-thiophene-2-sulfonamide (121 mg, 0.5 mmol) according to general procedure II. Obtained as a yellow solid (192 mg, 77%). MS (ISN) 497.0 [(M−H)$^-$]; mp 210° C.

Example 165

5-[7-Difluoromethyl-5-(4-trifluoromethyl-phenyl)-pyrazolo[1,5-a]pyrimidin-3-ylethynyl]-thiophene-2-sulfonic acid tert-butylamide

The title compound was prepared from 7-difluoromethyl-3-ethynyl-5-(4-trifluoromethyl-phenyl)-pyrazolo[1,5-a]pyrimidine (example C.2) (169 mg, 0.5 mmol) and commercially available 5-bromo-thiophene-2-N-tert.- butylsulfonamide (149 mg, 0.5 mmol) according to general procedure II. Obtained as an orange solid (234 mg, 84%). MS (ISN) 552.9 [(M−H)⁻]; mp 187° C.

Example 166

5-[7-Difluoromethyl-5-(3-trifluoromethyl-phenyl)-pyrazolo[1,5-a]pyrimidin-3-ylethynyl]-2,4-difluoro-benzenesulfonamide The title compound was prepared from 7-difluoromethyl-3-ethynyl-5-(3-trifluoromethyl-phenyl)-pyrazolo[1,5-a]pyrimidine (example C.2) (169 mg, 0.5 mmol) and commercially available 5-bromo-2,4-difluoro-benzenesulfonamide (136 mg, 0.5 mmol) according to general procedure II. Obtained as a yellow solid (76 mg, 29%). MS (ISN) 527.0 [(M−H)⁻]; mp 277° C.

Example 167

3-[7-Difluoromethyl-5-(3-trifluoromethyl-phenyl)-pyrazolo[1,5-a]pyrimidin-3-ylethynyl]-benzene-sulfonamide The title compound was prepared from 7-difluoromethyl-3-ethynyl-5-(3-trifluoromethyl-phenyl)-pyrazolo[1,5-a]pyrimidine (example C.15) (169 mg, 0.5 mmol) and commercially available 3-bromo-benzenesulfonylchloride (118 mg, 0.5 mmol) according to general procedure II. Obtained as an orange solid (160 mg, 65%). MS (ISN) 491.1 [(M−H)⁻]; mp 199° C.

Example 168

3-[5-(4-Chloro-3-methyl-phenyl)-7-difluoromethyl-pyrazolo[1,5-a]pyrimidin-3-ylethynyl]-benzene-sulfonamide The title compound was prepared from 5-(4-chloro-3-methyl-phenyl)-7-difluoromethyl-3-ethynyl-pyrazolo[1,5-a]pyrimidine (example C.16) (159 mg, 0.5 mmol) and commercially available 3-bromo-benzenesulfonamide (118 mg, 0.5 mmol) according to general procedure II. Obtained as a yellow solid (140 mg, 59%). MS (ISP) 473.2 [(M+H)⁺]; mp 215° C.

Example 169

5-[7-Difluoromethyl-5-(4-trifluoromethyl-phenyl)-pyrazolo[1,5-a]pyrimidin-3-ylethynyl]-thiophene-2-sulfonic acid (2-hydroxy-1,1-dimethyl-ethyl)-amide The title compound was prepared from 7-difluoromethyl-3-ethynyl-5-(4-trifluoromethyl-phenyl)-pyrazolo[1,5-a]pyrimidine (example C.2) (169 mg, 0.5 mmol) and 5-chloro-thiophene-2-sulfonic acid (2-hydroxy-1,1-dimethyl-ethyl)-amide (example B.22) (135 mg, 1.0 mmol) according to general procedure II. Obtained as a light brown orange solid (66 mg, 23%). MS (ISP) 571.3 [(M+H)⁺]; mp 157° C.

Example 170

5-[7-Difluoromethyl-5-(3-trifluoromethyl-phenyl)-pyrazolo[1,5-a]pyrimidin-3-ylethynyl]-thiophene-2-sulfonic acid (2-hydroxy-1,1-dimethyl-ethyl)-amide The title compound was prepared from 7-difluoromethyl-3-ethynyl-5-(3-trifluoromethyl-phenyl)-pyrazolo[1,5-a]pyrimidine (example C.15) (169 mg, 0.5 mmol) and 5-chloro-thiophene-2-sulfonic acid (2-hydroxy-1,1-dimethyl-ethyl)-amide (example B.22) (135 mg, 1.0 mmol) according to general procedure II. Obtained as an orange solid (20 mg, 7%). MS (ISN) 569.2 [(M−H)⁻]; mp 168° C.

Example 171

5-[5-(4-Chloro-3-methyl-phenyl)-7-difluoromethyl-pyrazolo[1,5-a]pyrimidin-3-ylethynyl]-thiophene-2-sulfonic acid tert-butylamide The title compound was prepared from 5-(4-chloro-3-methyl-phenyl)-7-difluoromethyl-3-ethynyl-pyrazolo[1,5-a]pyrimidine (example C.16) (159 mg, 0.5 mmol) and commercially available 5-bromo-thiophene-2-N-tert.-butylsulfonamide (149 mg, 0.5 mmol) according to general procedure II. Obtained as a yellow solid (215 mg, 80%). MS (ISP) 533.1 [(M−H)⁻]; mp 220° C.

Example 172

5-[5-(4-Chloro-3-methyl-phenyl)-7-difluoromethyl-pyrazolo[1,5-a]pyrimidin-3-ylethynyl]-thiophene-2-sulfonic acid amide The title compound was prepared from 5-(4-chloro-3-methyl-phenyl)-7-difluoromethyl-3-ethynyl-pyrazolo[1,5-a]pyrimidine (example C.16) (159 mg, 0.5 mmol) and commercially available 5-bromo-thiophene-2-sulfonamide (121 mg, 0.5 mmol) according to general procedure II. Obtained as a yellow solid (190 mg, 79%). MS (ISN) 477.0 [(M−H)⁻]; mp 216° C.

Example 173

4-[5-(4-Chloro-3-methyl-phenyl)-7-difluoromethyl-pyrazolo[1,5-a]pyrimidin-3-ylethynyl]-benzene-sulfonamide The title compound was prepared from 5-(4-chloro-3-methyl-phenyl)-7-difluoromethyl-3-ethynyl-pyrazolo[1,5-a]pyrimidine (example C.16) (168 mg, 0.5 mmol) and commercially available 4-bromo-benzenesulfonamide (118 mg, 0.5 mmol) according to general procedure II. Obtained as a yellow solid (110 mg, 46%). MS (ISN) 471.0 [(M−H)⁻]; mp 237° C.

Example 174

5-[5-(4-Chloro-3-methyl-phenyl)-7-difluoromethyl-pyrazolo[1,5-a]pyrimidin-3-ylethynyl]-2,4-difluoro-benzenesulfonamide The title compound was prepared from 5-(4-chloro-3-methyl-phenyl)-7-difluoromethyl-3-ethynyl-pyrazolo[1,5-a]pyrimidine (example C.16) (159 mg, 0.5 mmol) and commercially available 5-bromo-2,4-difluoro-benzenesulfonamide (136 mg, 0.5 mmol) according to general procedure II. Obtained as an orange solid (67 mg, 26%). MS (ISN) 507.2 [(M−H)⁻]; mp 270° C.

Example 175

5-[5-(4-Chloro-3-methyl-phenyl)-7-difluoromethyl-pyrazolo[1,5-a]pyrimidin-3-ylethynyl]-thiophene-2-sulfonic acid (2-hydroxy-1,1-dimethyl-ethyl)-amide The title compound was prepared from 5-(4-chloro-3-methyl-phenyl)-7-difluoromethyl-3-ethynyl-pyrazolo[1,5-a]pyrimidine (example C.16) (159 mg, 0.5 mmol) and 2-chloro-thiazole-5-sulfonic acid (2-hydroxy-1,1-dimethyl-ethyl)-amide (example B.22) (135 mg, 0.5 mmol) according to general procedure II. Obtained as a yellow solid (12 mg, 4%). MS (ISN) 549.1 [(M−H)⁻]; mp 145° C.

Example 176

4-[7-Difluoromethyl-5-(3-trifluoromethyl-phenyl)-pyrazolo[1,5-a]pyrimidin-3-ylethynyl]-benzene-sulfonamide The title compound was prepared from 7-difluoromethyl-3-ethynyl-5-(3-trifluoromethyl-phenyl)-pyrazolo[1,5-a]pyrimidine (example C.15) (169 mg, 0.5 mmol) and commercially available 4-bromo-benzenesulfonylchloride (118 mg, 0.5 mmol) according to general procedure II. Obtained as a yellow solid (70 mg, 28%). MS (ISN) 491.0 [(M−H)⁻]; mp 245° C.

Example 177

2,4-Difluoro-5-[4-trifluoromethyl-2-(4-trifluoromethyl-phenyl)-imidazo[1,5-a]pyrimidin-8-ylethynyl]-benzenesulfonamide The title compound was prepared from 8-ethynyl-4-trifluoromethyl-2-(4-trifluoromethyl-phenyl)-imidazo[1,5-a]pyrimidine (example C.17) (178 mg, 0.5 mmol) and commercially available 5-bromo-2,4-difluoro-benzenesulfonamide (136 mg, 0.5 mmol) according to general procedure II. Obtained as a brown solid (112 mg, 41%). MS (ISN) 545.0 [(M−H)⁻]; mp 247° C.

Example 178

4-[4-Trifluoromethyl-2-(4-trifluoromethyl-phenyl)-imidazo[1,5-a]pyrimidin-8-ylethynyl]-benzene-sulfonamide The title compound was prepared from 8-ethynyl-4-trifluoromethyl-2-(4-trifluoromethyl-phenyl)-imidazo[1,5-a]pyrimidine (example C.17) (178 mg, 0.5 mmol) and commercially available 4-bromo-benzenesulfonamide (118 mg, 0.5 mmol) according to general procedure II. Obtained as a brown solid (176 mg, 69%). MS (ISN) 511.2 [(M+H)⁺]; mp 290° C.

Example 179

5-[4-Trifluoromethyl-2-(4-trifluoromethyl-phenyl)-imidazo[1,5-a]pyrimidin-8-ylethynyl]-thiophene-2-sulfonic acid amide The title compound was prepared from 8-ethynyl-4-trifluoromethyl-2-(4-trifluoromethyl-phenyl)-imidazo[1,5-a]pyrimidine (example C.17) (178 mg, 0.5 mmol) and commercially available 5-bromo-thiophene-2-sulfonamide (121 mg, 0.5 mmol) according to general procedure II. Obtained as a red solid (159 mg, 62%). MS (ISN) 517.1 [(M+H)⁺]; mp 255° C.

Example 180

2,4-Difluoro-5-[8-trifluoromethyl-6-(4-trifluoromethyl-phenyl)-imidazo[1,2-a]pyridin-3-ylethynyl]-benzenesulfonamide The title compound was prepared from 3-ethynyl-8-trifluoromethyl-6-(4-trifluoromethyl-phenyl)-imidazo[1,2-a]pyridine (example C.18) (310 mg, 0.88 mmol) and 5-Bromo-2,4,-difluorobenzenesulfonamide (226 mg, 0.83 mmol) according to general procedure II. Obtained as an off-white solid (56 mg, 12%). MS (ISP) 546.2 [(M+H)⁺]; mp 306-307° C.

Example 181

4-[8-Trifluoromethyl-6-(4-trifluoromethyl-phenyl)-imidazo[1,2-a]pyridin-3-ylethynyl]-benzenesulfonamide The title compound was prepared from 3-ethynyl-8-trifluoromethyl-6-(4-trifluoromethyl-phenyl)-imidazo[1,2-a]pyridine (example C.18) (354 mg, 1.0 mmol) and 4-bromobenzenesulfonamide (230 mg, 1.0 mmol) according to general procedure II. Obtained as an off-white (120 mg, 23%). MS (ISP) 511.3 [(M+H)⁺]; mp 278-280° C.

Example 182

3-(2-Chloro-pyrimidin-5-ylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 5-bromo-2-chloropyrimidine (251 mg, 1.3 mmol) according to general procedure II. Obtained as an orange solid (30 mg, 6.8%). MS (ISN) 467.2 [(M)⁻]; mp 157-159° C.

Example 183

3-(2-Chloro-pyrimidin-4-ylethynyl)-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and commercially available 2,4-dichloropyrimidine (194 mg, 1.3 mmol)

according to general procedure II. Obtained as an orange solid (220 mg, 47%). MS (ISP) 468.1 [(M+H)⁺]; mp 192-195° C.

Example 184

{4-[7-Trifluoromethyl-5-(4-trifluoromethyl-phenyl)-pyrazolo[1,5-a]pyrimidin-3-ylethynyl]-phenyl}-methanol The title compound was prepared from 3-ethynyl-7-trifluoromethyl-5-(4-trifluoromethyl-phenyl)-pyrazolo[1,5-a]pyrimidine (example C.1) (2.0 g, 6 mmol) and commercially available 4-bromobenzyl alcohol (1.37 g, 7 mmol) according to general procedure II. Obtained as a light brown solid (575 mg, 22%). MS (ISP) 462.1 [(M+H)⁺]; mp 200-202° C.

Example 185

(2-{5-[7-Difluoromethyl-5-(4-trifluoromethyl-phenyl)-pyrazolo[1,5-a]pyrimidin-3-ylethynyl]-2,4-difluoro-benzenesulfonylamino}-ethyl)-carbamic acid tert-butyl ester The title compound was prepared from 7-difluoromethyl-3-ethynyl-5-(4-trifluoromethyl-phenyl)-pyrazolo[1,5-a]pyrimidine (example C.2) (675 mg, 2 mmol) and [2-(5-bromo-2,4-difluoro-benzenesulfonylamino)-ethyl]-carbamic acid tert-butyl ester (1080 mg, 2.6 mmol) according to general procedure II. Obtained as a yellow solid (670 mg, 50%). MS (ISP) 572.0 [(M+H)⁺]; mp 203-204° C. (dec.).

Example 186

1-{4-[7-Trifluoromethyl-5-(4-trifluoromethyl-phenyl)-pyrazolo[1,5-a]pyrimidin-3-ylethynyl]-phenyl}-ethylamine The title compound was prepared from 3-ethynyl-7-trifluoromethyl-5-(4-trifluoromethyl-phenyl)-pyrazolo[1,5-a]pyrimidine (example C.1) (355 g, 1.0 mmol) and commercially available (rac)-4-bromo-alpha-methylbenzyl amine (0.14 mL, 1.0 mmol) according to general procedure II. Obtained as an orange solid (200 mg, 42%). MS (ISN) 533.1 [(M−H+OAc)⁻]; mp 156-157° C.

Example 187

4-[7-Difluoromethyl-5-(3-ethoxy-phenyl)-pyrazolo[1,5-a]pyrimidin-3-ylethynyl]-benzenesulfonamide The title compound was prepared from 7-difluoromethyl-5-(3-ethoxy-phenyl)-3-ethynyl-pyrazolo[1,5-a]pyrimidine (example C.19) (313 g, 1.0 mmol) and commercially available 4-bromobenzenesulfonamide (230 mg, 1.0 mmol) according to general procedure II. Obtained as a yellow solid (190 mg, 41%). MS (ISN) 467.1 [(M−H)⁻]; mp 245° C.

Example 188

5-[7-Difluoromethyl-5-(4-trifluoromethyl-phenyl)-pyrazolo[1,5-a]pyrimidin-3-ylethynyl]-pyridin-2-ylamine The title compound was prepared from 7-difluoromethyl-3-ethynyl-5-(4-trifluoromethyl-phenyl)-pyrazolo[1,5-a]pyrimidine (example C.2) (340 mg, 1 mmol) and commercially available 2-amino-5-bromopyridine (157 mg, 1 mmol) according to general procedure II. Obtained as a dark red solid (13 mg, 3%). MS (ISP) 430.3 [(M+H)⁺]; mp 216° C.

Example 189

5-[5-(3-Ethoxy-4-trifluoromethyl-phenyl)-7-trifluoromethyl-pyrazolo[1,5-a]pyrimidin-3-ylethynyl]-pyridin-2-ylamine The title compound was prepared from 5-(3-ethoxy-4-trifluoromethyl-phenyl)-3-ethynyl-7-trifluoromethyl-pyrazolo[1,5-a]pyrimidine (example C.3) (400 mg, 1 mmol) and commercially available 2-amino-5-bromopyridine (156 mg, 1 mmol) according to general procedure II. Obtained as a red solid (62 mg, 12%). MS (ISP) 492.2 [(M+H)⁺]; mp 218° C.

Example 190

3-Pyridin-3-ylethynyl-8-trifluoromethyl-6-(4-trifluoromethyl-phenyl)-imidazo[1,2-a]pyridine The title compound was prepared from 3-iodo-8-trifluoromethyl-6-(4-trifluoromethyl-phenyl)-imidazo[1,2-a]pyridine (example C.18 step 6) (460 mg, 1 mmol) and commercially available 3-ethynylpyridine (105 mg, 1 mmol) according to general procedure II. Obtained as a white solid (330 mg, 75%). MS (ISP) 432.1 [(M+H)⁺]; mp 169-170° C.

Example 191

5-[8-Trifluoromethyl-6-(4-trifluoromethyl-phenyl)-imidazo[1,2-a]pyridin-3-ylethynyl]-pyridin-2-ylamine The title compound was prepared from 3-iodo-8-trifluoromethyl-6-(4-trifluoromethyl-phenyl)-imidazo[1,2-a]pyridine (example C.18 step 6) (460 mg, 1 mmol) and 5-ethynyl-pyridin-2-ylamine (example D.1) (119 mg, 1 mmol) according to general procedure II. Obtained as a light yellow solid (300 mg, 66%). MS (ISP) 446.9 [(M+H)⁺]; mp 260-262° C.

Example 192

5-[7-Difluoromethyl-5-(3-ethoxy-phenyl)-pyrazolo[1,5-a]pyrimidin-3-ylethynyl]-thiophene-2-sulfonic acid amide The title compound was prepared from 7-difluoromethyl-5-(3-ethoxy-phenyl)-3-ethynyl-pyrazolo[1,5-a]pyrimidine (example C.19) (313 g, 1.0 mmol) and commercially available 5-bromothiophene-2-sulfonamide (315 mg, 1.3 mmol) according to general procedure II. Obtained as a yellow solid (160 mg, 34%). MS (ISP) 489.2 [(M+NH₄)⁺]; mp 214° C.

Example 193

5-[8-Trifluoromethyl-6-(4-trifluoromethyl-phenyl)-imidazo[1,2-a]pyridin-3-ylethynyl]-thiophene-2-sulfonic acid amide The title compound was prepared from 3-ethynyl-8-trifluoromethyl-6-(4-trifluoromethyl-phenyl)-imidazo[1,2-a]pyridine (example C.18) (360 mg, 1 mmol) and commercially available 5-bromothiophene-2-sulfonamide (221 mg, 1 mmol) according to general procedure II. Obtained as an off-white solid (300 mg, 57%). MS (ISP) 516.2 [(M+H)⁺]; mp 248-250° C.

Example 194

3-[8-Trifluoromethyl-6-(4-trifluoromethyl-phenyl)-imidazo[1,2-a]pyridin-3-ylethynyl]-benzenesulfonamide The title compound was prepared from 3-ethynyl-8-trifluoromethyl-6-(4-trifluoromethyl-phenyl)-imidazo[1,2-a]pyridine (example C.18) (360 mg, 1 mmol) and commercially available 3-bromobenzene-1-sulfonamide (216 mg, 1 mmol) according to general procedure II. Obtained as an off-white solid (70 mg, 13%). MS (ISP) 510.4 [(M+H)⁺]; mp 240° C.

Example 195

1-{4-[8-Trifluoromethyl-6-(4-trifluoromethyl-phenyl)-imidazo[1,2-a]pyridin-3-ylethynyl]-phenyl}-ethanol The title compound was prepared from 3-ethynyl-8-trifluoromethyl-6-(4-trifluoromethyl-phenyl)-imidazo[1,2-a]pyridine (example C.18) (360 mg, 1 mmol) and commercially available 4-bromo-methylbenzyl alcohol (184 mg, 1 mmol) according to general procedure II. Obtained as an off-white solid (65 mg, 13%). MS (ISP) 475.2 [(M+H)⁺]; mp 157-158° C.

Example 196

2-[8-Trifluoromethyl-6-(4-trifluoromethyl-phenyl)-imidazo[1,2-a]pyridin-3-ylethynyl]-thiazole-5-sulfonic acid (2-hydroxy-1,1-dimethyl-ethyl)-amide The title compound was prepared from 3-ethynyl-8-trifluoromethyl-6-(4-trifluoromethyl-phenyl)-imidazo[1,2-a]pyridine (example C.18) (354 mg, 1 mmol) and 2-chloro-thiazole-5-sulfonic acid (2-hydroxy-1,1-dimethyl-ethyl)-amide (example B.19) (244 mg, 0.9 mmol) according to general procedure II. Obtained as a yellow solid (77 mg, 13%). MS (ISP) 589.3 [(M+H)⁺]; mp 202-203° C.

Example 197

4-[7-Trifluoromethyl-5-(4-trifluoromethyl-phenyl)-pyrazolo[1,5-a]pyrimidin-3-ylethynyl]-benzamide The title compound was prepared from 3-ethynyl-7-trifluoromethyl-5-(4-trifluoromethyl-phenyl)-pyrazolo[1,5-a]pyrimidine (example C.1) (355 g, 1.0 mmol) and commercially available 4-bromobenzamide (180 mg, 0.9 mmol) according to general procedure II. Obtained as a yellow solid (290 mg, 61%). MS (ISP) 475.1 [(M+H)⁺]; mp 260° C.

Example 198

5-[7-Trifluoromethyl-5-(4-trifluoromethyl-phenyl)-pyrazolo[1,5-a]pyrimidin-3-ylethynyl]-pyridin-3-ylamine The title compound was prepared from 3-ethynyl-7-trifluoromethyl-5-(4-trifluoromethyl-phenyl)-pyrazolo[1,5-a]pyrimidine (example C.1) (355 g, 1.0 mmol) and 5-bromo-pyridin-3-ylamine (example B.44) (156 mg, 0.9 mmol) according to general procedure II. Obtained as a light brown solid (40 mg, 9%). MS (ISN) 506.1 [(M+OAc)⁻]; mp 216-217° C.

Example 199

Methyl-{5-[7-trifluoromethyl-5-(4-trifluoromethyl-phenyl)-pyrazolo[1,5-a]pyrimidin-3-ylethynyl]-pyridin-2-yl}-amine The title compound was prepared from 3-ethynyl-7-trifluoromethyl-5-(4-trifluoromethyl-phenyl)-pyrazolo[1,5-a]pyrimidine (example C.1) (355 g, 1.0 mmol) and (5-bromo-pyridin-2-yl)-methyl-amine (example B.45) (168 mg, 0.9 mmol) according to general procedure II. Obtained as a red solid (25 mg, 5%). MS (ISP) 462.0 [(M+H)⁺]; mp 187° C.

Example 200

2-{5-[7-Trifluoromethyl-5-(4-trifluoromethyl-phenyl)-pyrazolo[1,5-a]pyrimidin-3-ylethynyl]-pyridin-2-ylamino}-ethanol The title compound was prepared from 3-ethynyl-7-trifluoromethyl-5-(4-trifluoromethyl-phenyl)-pyrazolo[1,5-a]pyrimidine (example C.1) (355 g, 1.0 mmol) and 2-(5-bromo-pyridin-2-ylamino)-ethanol (example B.46) (195 mg, 0.9 mmol) according to general procedure II. Obtained as a red solid (50 mg, 10%). MS (ISP) 492.0 [(M+H)⁺]; mp 202-203° C.

Example 201

3-[7-Difluoromethyl-5-(3-ethoxy-phenyl)-pyrazolo[1,5-a]pyrimidin-3-ylethynyl]-benzenesulfonamide The title compound was prepared from 7-difluoromethyl-5-(3-ethoxy-phenyl)-3-ethynyl-pyrazolo[1,5-a]pyrimidine (example C.19) (313 g, 1.0 mmol) and commercially available 3-bromobenzene-sulfonamide (307 mg, 1.3 mmol) according to general procedure II. Obtained as a yellow foam (50 mg, 11%). MS (ISP) 469.3 [(M+H)⁺]; mp 167-168° C.

Example 202

2-{4-[7-Trifluoromethyl-5-(4-trifluoromethyl-phenyl)-pyrazolo[1,5-a]pyrimidin-3-ylethynyl]-phenyl}-propan-2-ol The title compound was prepared from 3-iodo-7-trifluoromethyl-5-(4-trifluoromethyl-phenyl)-pyrazolo[1,5-a]pyrimidine (example C.1 method 2 step 2) (460 g, 1.0 mmol) and 2-(4-ethynyl-phenyl)-propan-2-ol (example D.4) (161 mg, 1.0 mmol) according to general procedure II. Obtained as an orange solid (300 mg, 60%). MS (ISP) 490.2 [(M+H)⁺]; mp 170-171° C.

Example 203

4-[8-Trifluoromethyl-6-(4-trifluoromethyl-phenyl)-imidazo[1,2-a]pyridin-3-ylethynyl]-benzamide The title compound was prepared from 3-ethynyl-8-trifluoromethyl-6-(4-trifluoromethyl-phenyl)-imidazo[1,2-a]pyridine (example C.18) (360 mg, 1 mmol) and commercially available 4-bromobenzamide (203 mg, 1 mmol) according to general procedure II. Obtained as a white solid (80 mg, 16%). MS (ISP) 474.2 [(M+H)$^+$]; mp 286° C.

Example 204

{3-[7-Trifluoromethyl-5-(4-trifluoromethyl-phenyl)-pyrazolo[1,5-a]pyrimidin-3-ylethynyl]-phenyl}-methanol The title compound was prepared from 3-ethynyl-7-trifluoromethyl-5-(4-trifluoromethyl-phenyl)-pyrazolo[1,5-a]pyrimidine (example C.1) (355 g, 1.0 mmol) and commercially available 3-bromobenzyl alcohol (243 mg, 1.3 mmol) according to general procedure II. Obtained as a brown solid (60 mg, 13%). MS (ISP) 462.2 [(M+H)$^+$]; mp 177° C.

Example 205

5-[7-Trifluoromethyl-5-(4-trifluoromethyl-phenyl)-pyrazolo[1,5-a]pyrimidin-3-ylethynyl]-pyrimidin-2-ylamine The title compound was prepared from 3-ethynyl-7-trifluoromethyl-5-(4-trifluoromethyl-phenyl)-pyrazolo[1,5-a]pyrimidine (example C.1) (355 g, 1.0 mmol) and commercially available 2-amino-5-bromopyrimidine (226 mg, 1.3 mmol) according to general procedure II. Obtained as a brown solid (60 mg, 14%). MS (ISP) 449.2 [(M+H)$^+$]; mp 255-256° C.

Example 206

5-[7-Difluoromethyl-5-(4-trifluoromethyl-phenyl)-pyrazolo[1,5-a]pyrimidin-3-ylethynyl]-pyridine-2-carboxylic acid amide The title compound was prepared from 3-ethynyl-7-difluoromethyl-5-(4-trifluoromethyl-phenyl)-pyrazolo[1,5-a]pyrimidine (example C.2) (340 g, 1.0 mmol) and 5-bromo-pyridine-2-carboxylic acid amide (example B.47) (181 mg, 0.9 mmol) according to general procedure II. Obtained as a yellow solid (300 mg, 65%). MS (ISP) 458.1 [(M+H)$^+$]; mp 276-277° C.

Example 207

N-{4-[7-Trifluoromethyl-5-(4-trifluoromethyl-phenyl)-pyrazolo[1,5-a]pyrimidin-3-ylethynyl]-phenyl}-acetamide The title compound was prepared from 3-ethynyl-7-trifluoromethyl-5-(4-trifluoromethyl-phenyl)-pyrazolo[1,5-a]pyrimidine (example C.1) (355 g, 1.0 mmol) and commercially available 4-bromoacetanilide (278 mg, 1.3 mmol) according to general procedure II. Obtained as a yellow solid (26 mg, 5.3%). MS (ISP) 489.3 [(M+H)$^+$]; mp 238° C.

Example 208

5-[7-Difluoromethyl-5-(3-ethoxy-phenyl)-pyrazolo[1,5-a]pyrimidin-3-ylethynyl]-pyridin-2-ylamine The title compound was prepared from 7-difluoromethyl-5-(3-ethoxy-phenyl)-3-ethynyl-pyrazolo[1,5-a]pyrimidine (example C.19) (627 g, 2.0 mmol) and commercially available 2-amino-5-bromopyridine (450 mg, 2.6 mmol) according to general procedure II. Obtained as a yellow solid (93 mg, 12%). MS (ISP) 406.2 [(M+H)$^+$]; mp 162° C.

Example 209

5-[8-Methyl-6-(4-trifluoromethyl-phenyl)-imidazo[1,2-a]pyridin-3-ylethynyl]-pyridin-2-ylamine The title compound was prepared from 3-iodo-8-methyl-6-(4-trifluoromethyl-phenyl)-imidazo[1,2-a]pyridine (example C.20 step 3) (804 mg, 2 mmol) and 5-ethynyl-pyridin-2-ylamine (example D.1) (307 mg, 2.6 mmol) according to general procedure II. Obtained as an off-white solid (160 mg, 20%). MS (ISP) 393.1 [(M+H)$^+$]; mp 239-240° C.

Example 210

5-[6-(4-Chloro-phenyl)-8-methyl-imidazo[1,2-a]pyridin-3-ylethynyl]-pyridin-2-ylamine The title compound was prepared from 6-(4-chloro-phenyl)-3-iodo-8-methyl-imidazo[1,2-a]pyridine (example C.21 step 2) (737 mg, 2 mmol) and 5-ethynyl-pyridin-2-ylamine (example D.1) (307 mg, 2.6 mmol) according to general procedure II. Obtained as an off-white solid (240 mg, 33%). MS (ISP) 359.0 [(M+H)$^+$], 361.0 [(M+2+H)$^+$]; mp 231-234° C.

Example 211

5-[6-(4-Chloro-phenyl)-8-methyl-imidazo[1,2-a]pyridin-3-ylethynyl]-thiophene-2-sulfonic acid amide The title compound was prepared from 6-(4-chloro-phenyl)-3-ethynyl-8-methyl-imidazo[1,2-a]pyridine (example C.21) (267 mg, 1 mmol) and commercially available 5-bromothiophene-2-sulfonamide (230 mg, 1 mmol) according to general procedure II. Obtained as a light brown solid (158 mg, 44%). MS (ISP) 427.9 [(M+H)$^+$], 429.9 [(M+2+H)$^+$]; mp 265-266° C.

Example 212

5-[8-Methyl-6-(4-trifluoromethyl-phenyl)-imidazo[1,2-a]pyridin-3-ylethynyl]-thiophene-2-sulfonic acid amide The title compound was prepared from 3-ethynyl-8-methyl-6-(4-trifluoromethyl-phenyl)-imidazo[1,2-a]pyridine (example C.20) (300 mg, 1 mmol) and commercially available 5-bromothiophene-2-sulfonamide (230 mg, 1 mmol) according to general procedure II. Obtained as a light brown solid (200 mg, 50%). MS (ISP) 462 [(M+H)$^+$]; mp 270° C.

Example 213

5-[7-Difluoromethyl-5-(4-trifluoromethyl-phenyl)-pyrazolo[1,5-a]pyrimidin-3-ylethynyl]-pyrimidin-2-ylamine The title compound was prepared from 7-difluoromethyl-3-ethynyl-5-(4-trifluoromethyl-phenyl)-pyrazolo[1,5-a]pyrimidine (example C.2) (337 g, 1.0 mmol) and commercially available 2-amino-5-iodopyrimidine (287 mg, 1.3 mmol) according to general procedure II. Obtained as an orange solid (52 mg, 12%). MS (ISP) 431.3 [(M+H)$^+$]; mp 242-243° C.

Example 214

5-[8-Cyano-6-(4-trifluoromethyl-phenyl)-imidazo[1,2-a]pyridin-3-ylethynyl]-thiophene-2-sulfonic acid amide The title compound was prepared from 3-ethynyl-6-(4-trifluoromethyl-phenyl)-imidazo[1,2-a]pyridine-8-carbonitrile (example C.23) (150 mg, 0.5 mmol) and commercially available 5-bromothiophene-2-sulfonamide (117 mg, 0.5 mmol) according to general procedure II. Obtained as an off-white solid (80 mg, 35%). MS (ISP) 473.1 [(M+H)$^+$]; mp 267-269° C.

Example 215

N-(Methylsulfonyl)-N-{5-[7-trifluoromethyl-5-(4-trifluoromethyl-phenyl)-pyrazolo[1,5-a]pyrimidin-3-ylethynyl]-pyridin-2-yl}-methanesulfonamide To a solution of 5-[7-trifluoromethyl-5-(4-trifluoromethyl-phenyl)-pyrazolo[1,5-a]pyrimidin-3-ylethynyl]-pyridin-2-ylamine (example 55) (183 mg, 0.41 mmol) in 10 mL of THF was added methanesulfonic anhydride (0.16 g, 0.92 mmol) and triethylamine (0.20 mL, 1 mmol) and the mixture was stirred at 23° C. for 4 h, then poured into aq. NaHCO$_3$-solution, extracted with EtOAc, dried over Na$_2$SO$_4$, filtered and concentrated in vacuum to give a crude yellow solid mixture, which was purified by silica gel column chromatography with heptane/EtOAc to give the title compound as an orange solid (120 mg, 48%). MS [ISN] 662.0 [(M−H+OAc)$^-$], 524.2[(M−SO$_2$Me−H)$^-$]; mp 250-251° C.

Example 216

N-{5-[7-Trifluoromethyl-5-(4-trifluoromethyl-phenyl)-pyrazolo[1,5-a]pyrimidin-3-ylethynyl]-pyridin-2-yl}-methanesulfonamide To a solution of 5-[7-trifluoromethyl-5-(4-trifluoromethyl-phenyl)-pyrazolo[1,5-a]pyrimidin-3-ylethynyl]-pyridin-2-ylamine (example 55) (182 mg, 0.41 mmol) in 2 mL of pyridine was added methanesulfonic anhydride (128 mg, 0.73 mmol) and the mixture was stirred at 50° C. for 1 h, then added dioxane (4 mL) and stirred at 76° C. for 3 h. Added more methanesulfonic anhydride (50 mg) and continued at 80° C. for 3 h. Cooled to 23° C., poured into 1N HCl solution, extracted with EtOAc, dried over Na$_2$SO$_4$, filtered and concentrated in vacuum to give a crude yellow solid mixture, which was purified by silica gel column chromatography with heptane/EtOAc to give the title compound as an orange solid (112 mg, 52%). MS [ISN] 524.2[(M−H)$^-$]; mp 261-263° C.

Example 217

5-[6-(4-Trifluoromethyl-phenyl)-imidazo[1,2-a]pyridin-3-ylethynyl]-thiophene-2-sulfonic acid amide The title compound was prepared from 3-ethynyl-6-(4-trifluoromethyl-phenyl)-imidazo[1,2-a]pyridine (example C.24) (400 mg, 1.3 mmol) and commercially available 5-bromothiophene-2-sulfonamide (338 mg, 1.3 mmol) according to general procedure II. Obtained as a white solid (90 mg, 14%). MS (ISP) 448.1 [(M+H)$^+$]; mp 206-210° C.

Example 218

2-Amino-5-[7-difluoromethyl-5-(4-trifluoromethyl-phenyl)-pyrazolo[1,5-a]pyrimidin-3-ylethynyl]-nicotinonitrile The title compound was prepared from 7-difluoromethyl-3-ethynyl-5-(4-trifluoromethyl-phenyl)-pyrazolo[1,5-a]pyrimidine (example C.2) (340 g, 1.0 mmol) and 2-amino-5-bromo-nicotinonitrile (example C.23 step 1) (200 mg, 1.0 mmol) according to general procedure II. Obtained as a yellow solid (240 mg, 52%). MS (ISP) 455.3 [(M+H)$^+$]; mp 255° C.

Example 219

2-Amino-5-[7-trifluoromethyl-5-(4-trifluoromethyl-phenyl)-pyrazolo[1,5-a]pyrimidin-3-ylethynyl]-nicotinonitrile The title compound was prepared from 3-ethynyl-7-trifluoromethyl-5-(4-trifluoromethyl-phenyl)-pyrazolo[1,5-a]pyrimidine (example C.1) (355 g, 1.0 mmol) and 2-amino-5-bromo-nicotinonitrile (example C.23 step 1) (200 mg, 1.0 mmol) according to general procedure II. Obtained as a red solid (280 mg, 59%). MS (ISP) 473.2 [(M+H)$^+$]; mp 264° C.

Example 220

5-[8-Methyl-6-(4-trifluoromethyl-phenyl)-imidazo[1,2-a]pyridin-3-ylethynyl]-pyrimidin-2-ylamine The title compound was prepared from 3-ethynyl-8-methyl-6-(4-trifluoromethyl-phenyl)-imidazo[1,2-a]pyridine (example C.20) (300 mg, 1 mmol) and commercially available 2-amino-5-iodopyrimidine (221 mg, 1 mmol) according to general procedure II. Obtained as an off-white solid (110 mg, 28%). MS (ISP) 394.1 [(M+H)$^+$]; mp 236° C.

Example 221

5-[6-(4-Chloro-phenyl)-8-methyl-imidazo[1,2-a]pyridin-3-ylethynyl]-pyrimidin-2-ylamine The title compound was prepared from 6-(4-chloro-phenyl)-3-ethynyl-8-methyl-imidazo[1,2-a]pyridine (example C.21) (267 mg, 1 mmol) and commercially available 2-amino-5-iodopyrimidine (221 mg, 1 mmol) according to general procedure II. Obtained as an off-white solid (60 mg, 17%). MS (ISP) 360.1 [(M+H)$^+$], 362 [(M+2+H)$^+$]; mp 263° C.

Example 222

3-Trifluoromethyl-5-[7-trifluoromethyl-5-(4-trifluoromethyl-phenyl)-pyrazolo[1,5-a]pyrimidin-3-ylethynyl]-pyridin-2-ylamine The title compound was prepared from 3-ethynyl-7-trifluoromethyl-5-(4-trifluoromethyl-phenyl)-pyrazolo[1,5-a]pyrimidine (example C.1) (355 g, 1.0 mmol) and 5-iodo-3-trifluoromethyl-pyridin-2-ylamine (example B.48) (288 mg, 1.0 mmol) according to general procedure II. Obtained as an off-white solid (370 mg, 72%). MS (ISP) 516.2 [(M+H)$^+$]; mp 230° C.

Example 223

5-[5-(4-Chloro-phenyl)-7-trifluoromethyl-pyrazolo[1,5-a]pyrimidin-3-ylethynyl]-3-trifluoromethyl-pyridin-2-ylamine The title compound was prepared from 5-(4-chloro-phenyl)-3-ethynyl-7-trifluoromethyl-pyrazolo[1,5-a]pyrimidine (example C.4) (322 g, 1.0 mmol) and 5-iodo-3-trifluoromethyl-pyridin-2-ylamine (example B.48) (288 mg, 1.0 mmol) according to general procedure II. Obtained as an orange solid (290 mg, 60%). MS (ISP) 482.3 [(M+H)$^+$], 484 [(M+2+H)$^+$]; mp 209° C.

Example 224

5-[8-Cyclopropyl-6-(4-trifluoromethyl-phenyl)-imidazo[1,2-a]pyridin-3-ylethynyl]-thiophene-2-sulfonic acid amide The title compound was prepared from 8-cyclopropyl-3-ethynyl-6-(4-trifluoromethyl-phenyl)-imidazo[1,2-a]pyridine (example C.25) (450 mg, 1.3 mmol) and commercially available 5-bromothiophene-2-sulfonamide (334 mg, 1.3 mmol) according to general procedure II. Obtained as a light yellow solid (200 mg, 29%). MS (ISP) 488.2 [(M+H)$^+$]; mp 261° C.

Example 225

N-{5-[7-Trifluoromethyl-5-(4-trifluoromethyl-phenyl)-pyrazolo[1,5-a]pyrimidin-3-ylethynyl]-pyridin-2-yl}-acetamide A mixture of 5-[7-trifluoromethyl-5-(4-trifluoromethyl-phenyl)-pyrazolo[1,5-a]pyrimidin-3-ylethynyl]-pyridin-2-ylamine (example 55) (2.00 g, 4.47 mmol) in acetic anhydride (15 mL) was stirred at 120° C. for 1 h. Cooled to 60° C., concentrated in vaccum to dryness (water bath temperature 60° C.) and dried in HV to give an orange solid (2.465 g, 113%, mixture of mono- and diacetylated compound). Suspended in THF (30 mL) at 23° C., added NH$_4$OH (25%, 13.3M, 1.0 mL, 13.4 mmol) and stirred at 23° C. for 1.5 h resulting in a clear red solution, adjusted pH with 1N HCl until pH 1, added H$_2$O (total volume 200 mL), filtered the precipitate off, washed with H$_2$O and dried in HV, followed by trituration with ether and drying in HV to give the title compound as an orange solid (2.130 g, 97%). MS [ISN] 488.1[(M−H)$^−$]; mp 266° C.

Example 226

3-(6-Amino-pyridin-3-ylethynyl)-6-(4-trifluoromethyl-phenyl)-imidazo[1,2-a]pyridine-8-carbonitrile The title compound was prepared from 3-ethynyl-6-(4-trifluoromethyl-phenyl)-imidazo[1,2-a]pyridine-8-carbonitrile (example C.23) (150 mg, 0.5 mmol) and commercially available 2-amino-5-iodopyridine (106 mg, 0.5 mmol) according to general procedure II. Obtained as a light brown solid (15 mg, 7%). MS (ISP) 404.3 [(M+H)$^+$].

Example 227

3-(2-Amino-pyrimidin-5-ylethynyl)-6-(4-trifluoromethyl-phenyl)-imidazo[1,2-a]pyridine-8-carbonitrile The title compound was prepared from 3-ethynyl-6-(4-trifluoromethyl-phenyl)-imidazo[1,2-a]pyridine-8-carbonitrile (example C.23) (150 mg, 0.5 mmol) and commercially available 2-amino-5-iodopyrimidine (107 mg, 0.5 mmol) according to general procedure II. Obtained as a dark brown solid (5 mg, 2%). MS (ISP) 405.3 [(M+H)$^+$]; mp 290° C.

Example 228

5-[8-Methyl-6-(4-trifluoromethyl-phenyl)-imidazo[1,2-a]pyridin-3-ylethynyl]-pyridine-3-sulfonic acid (2-hydroxy-1,1-dimethyl-ethyl)-amide The title compound was prepared from 3-ethynyl-8-methyl-6-(4-trifluoromethyl-phenyl)-imidazo[1,2-a]pyridine (example C.20) (300 mg, 1 mmol) and 5-bromo-pyridine-3-sulfonic acid (2-hydroxy-1,1-dimethyl-ethyl)-amide (example B.2) (278 mg, 0.9 mmol) according to general procedure II. Obtained as a white solid (60 mg, 11%). MS (ISP) 529.1 [(M+H)$^+$]; mp 189° C.

Example 229

5-[8-Methyl-6-(4-trifluoromethyl-phenyl)-imidazo[1,2-a]pyridin-3-ylethynyl]-pyridine-3-sulfonic acid amide The title compound was prepared from 3-ethynyl-8-methyl-6-(4-trifluoromethyl-phenyl)-imidazo[1,2-a]pyridine (example C.20) (300 mg, 1 mmol) and 5-bromo-pyridine-3-sulfonic acid amide (example B.1) (278 mg, 0.9 mmol) according to general procedure II. Obtained as an off-white solid (290 mg, 63%). MS (ISP) 457.1 [(M+H)$^+$]; mp 294° C.

Example 230

5-[6-(4-Chloro-phenyl)-8-methyl-imidazo[1,2-a]pyridin-3-ylethynyl]-pyridine-3-sulfonic acid (2-hydroxy-1,1-dimethyl-ethyl)-amide The title compound was prepared from 6-(4-chloro-phenyl)-3-ethynyl-8-methyl-imidazo[1,2-a]pyridine (example C.21) (270 mg, 1 mmol) and 5-bromo-pyridine-3-sulfonic acid (2-hydroxy-1,1-dimethyl-ethyl)-amide (example B.2) (282 mg, 0.9 mmol) according to general procedure II. Obtained as a light yellow solid (180 mg, 35%). MS (ISP) 495.0 [(M+H)$^+$], 497 [(M+2+H)$^+$]; mp 215-217° C.

Example 231

5-[6-(4-Chloro-phenyl)-8-methyl-imidazo[1,2-a]pyridin-3-ylethynyl]-pyridine-3-sulfonic acid amide The title compound was prepared from 6-(4-chloro-phenyl)-3-ethynyl-8-methyl-imidazo[1,2-a]pyridine (example C.21) (270 mg, 1 mmol) and 5-bromo-pyridine-3-sulfonic acid amide (example B.1) (216 mg, 0.9 mmol) according to general procedure II. Obtained as a yellow solid (20 mg, 5%). MS (ISP) 495.0 [(M+H)$^+$], 497 [(M+2+H)$^+$]; mp 282° C.

Example 232

5-[8-Trifluoromethyl-6-(4-trifluoromethyl-phenyl)-imidazo[1,2-b]pyridazin-3-ylethynyl]-pyridin-2-ylamine The title compound was prepared from 3-iodo-8-trifluoromethyl-6-(4-trifluoromethyl-phenyl)-imidazo[1,2-b]pyridazine (example C.26 step 11) (229 mg, 0.5 mmol) and 5-ethynyl-pyridin-2-ylamine (example D.1) (101 mg, 0.85 mmol) according to general procedure II. Obtained as a bright orange solid (180 mg, 80%). MS (ISP) 448.2 [(M+H)$^+$]; mp 267° C.

Example 233

5-[6-(4-Chloro-phenyl)-8-cyclopropyl-imidazo[1,2-a]pyridin-3-ylethynyl]-pyridin-2-ylamine The title compound was prepared from 6-(4-chloro-phenyl)-8-cyclopropyl-3-iodo-imidazo[1,2-a]pyridine (example C.27 step 5) (592 mg, 2 mmol) and 5-ethynyl-pyridin-2-ylamine (example D.1) (230 mg, 2 mmol) according to general procedure II. Obtained as a yellow solid (128 mg, 22%). MS (ISP) 385.2 [(M+H)$^+$], 387 [(M+2+H)$^+$]; mp 246° C.

Example 234

5-[7-Cyclopropyl-5-(4-trifluoromethyl-phenyl)-pyrazolo[1,5-a]pyridin-3-ylethynyl]-pyridin-2-ylamine The title compound was prepared from 7-cyclopropyl-3-iodo-5-(4-trifluoromethyl-phenyl)-pyrazolo[1,5-a]pyridine (example C.28 step 7) (204 mg, 0.48 mmol) and 5-ethynyl-pyridin-2-ylamine (example D.1) (101 mg, 0.85 mmol) according to general procedure II. Obtained as a yellow solid (40 mg, 20%). MS (ISP) 419.1 [(M+H)$^+$].

Example 235

5-[7-Trifluoromethyl-5-(4-trifluoromethyl-phenyl)-pyrazolo[1,5-a]pyridin-3-ylethynyl]-pyridin-2-ylamine The title compound was prepared from 3-iodo-7-trifluoromethyl-5-(4-trifluoromethyl-phenyl)-pyrazolo[1,5-a]pyridine (example C.22 step 9) (300 mg, 0.7 mmol) and 5-ethynyl-pyridin-2-ylamine (example D.1) (93 mg, 0.8 mmol) according to general procedure II. Obtained as a yellow solid (230 mg, 78%). MS (ISP) 447.2 [(M+H)$^+$]; mp 243-245° C.

Example 236

5-[8-Trifluoromethyl-6-(4-trifluoromethyl-phenyl)-imidazo[1,2-b]pyridazin-3-ylethynyl]-thiophene-2-sulfonic acid amide The title compound was prepared from 3-iodo-8-trifluoromethyl-6-(4-trifluoromethyl-phenyl)-imidazo[1,2-b]pyridazine (example C.26 step 11) (457 mg, 1 mmol) and 5-ethynyl-thiophene-2-sulfonic acid amide (example D.3) (243 mg, 1.3 mmol) according to general procedure II. Obtained as a light yellow solid (210 mg, 41%). MS (ISP) 517.1 [(M+H)$^+$]; mp 261-263° C.

Example 237

5-[6-(4-Trifluoromethyl-phenyl)-imidazo[1,2-a]pyridin-3-ylethynyl]-pyridin-2-ylamine The title compound was prepared from 3-ethynyl-6-(4-trifluoromethyl-phenyl)-imidazo[1,2-a]pyridine (example C.24) (300 mg, 1.0 mmol) and commercially available 2-amino-5-iodopyridine (230 mg, 1.0 mmol) according to general procedure II. Obtained as a white solid (210 mg, 53%). MS (ISP) 379.2 [(M+H)$^+$]; mp 241-244° C.

Example 238

5-[6-(4-Trifluoromethyl-phenyl)-imidazo[1,2-a]pyridin-3-ylethynyl]-pyrimidin-2-ylamine The title compound was prepared from 3-ethynyl-6-(4-trifluoromethyl-phenyl)-imidazo[1,2-a]pyridine (example C.24) (300 mg, 1.0 mmol) and commercially available 2-amino-5-iodopyrimidine (230 mg, 1.0 mmol) according to general procedure II. Obtained as a yellow solid (270 mg, 67%). MS (ISP) 380.3 [(M+H)$^+$]; mp 244-246° C.

Example 239

5-[8-Fluoro-6-(4-trifluoromethyl-phenyl)-imidazo[1,2-a]pyridin-3-ylethynyl]-pyridin-2-ylamine The title compound was prepared from 8-fluoro-3-iodo-6-(4-trifluoromethyl-phenyl)-imidazo[1,2-a]pyridine (example C.29 step 6) (350 mg, 0.85 mmol) and 5-ethynyl-pyridin-2-ylamine (example D.1) (122 mg, 0.85 mmol) according to general procedure II. Obtained as an off-white solid (130 mg, 38%). MS (ISP) 397.2 [(M+H)$^+$]; mp 281-282° C.

Example 240

5-[8-Fluoro-6-(4-trifluoromethyl-phenyl)-imidazo[1,2-a]pyridin-3-ylethynyl]-pyrimidin-2-ylamine The title compound was prepared from 8-fluoro-3-iodo-6-(4-trifluoromethyl-phenyl)-imidazo[1,2-a]pyridine (example C.29 step 6) (350 mg, 0.85 mmol) and 5-ethynyl-pyrimidin-2-ylamine (example D.2) (122 mg, 0.85 mmol) according to general procedure II. Obtained as an off-white solid (116 mg, 29%). MS (ISP) 398.2 [(M+H)$^+$]; mp 286° C.

Example 241

5-[6-(4-Chloro-phenyl)-8-fluoro-imidazo[1,2-a]pyridin-3-ylethynyl]-pyridin-2-ylamine The title compound was prepared from 6-(4-chloro-phenyl)-8-fluoro-3-iodo-imidazo[1,2-a]pyridine (example C.30 step 2) (300 mg, 0.8 mmol) and 5-ethynyl-pyridin-2-ylamine (example D.1) (114 mg, 0.8 mmol) according to general procedure II. Obtained as a light brown solid (170 mg, 58%). MS (ISP) 363.2 [(M+H)$^+$], 365 [(M+2+H)$^+$]; mp 259° C.

Example 242

5-[6-(4-Chloro-phenyl)-8-fluoro-imidazo[1,2-a]pyridin-3-ylethynyl]-pyrimidin-2-ylamine The title compound was prepared from 6-(4-chloro-phenyl)-8-fluoro-3-iodo-imidazo[1,2-a]pyridine (example C.30 step 2) (300 mg, 0.8 mmol) and 5-ethynyl-pyrimidin-2- ylamine (example D.2) (115 mg, 0.8 mmol) according to general procedure II. Obtained as an off-white solid (101 mg, 34%). MS (ISP) 364.1 [(M+H)$^+$], 366 [(M+2+H)$^+$]; mp 279-280° C.

Example 243

5-[8-Trifluoromethyl-6-(4-trifluoromethyl-phenyl)-imidazo[1,2-b]pyridazin-3-ylethynyl]-pyrimidin-2-ylamine The title compound was prepared from 3-iodo-8-trifluoromethyl-6-(4-trifluoromethyl-phenyl)-imidazo[1,2-b]pyridazine (example C.26 step 11) (457 mg, 1 mmol) and 5-ethynyl-pyrimidin-2-ylamine (example D.2) (155 mg, 1.3 mmol) according to general procedure II. Obtained as a light yellow solid (50 mg, 11%). MS (ISP) 449.2 [(M+H)$^+$]; mp 220-221° C.

Example 244

N-Acetyl-N-{5-[7-trifluoromethyl-5-(4-trifluoromethyl-phenyl)-pyrazolo[1,5-a]pyrimidin-3-ylethynyl]-pyrimidin-2-yl}-acetamide 5-[7-Trifluoromethyl-5-(4-trifluoromethyl-phenyl)-pyrazolo[1,5-a]pyrimidin-3-ylethynyl]-pyrimidin-2-ylamine (example 205) (250 mg, 0.5 mmol) in acetic anhydride (5 mL) was refluxed for 2 h. The reaction mixture was poured onto water (200 mL) and stirred for 30 min at 23° C. The precipitate was coated on silica gel, then purified by flash chromatography with n-heptane and ethyl acetate to give the title compound as a yellow solid (145 mg, 49%). MS (ISP) 533.2 [(M+H)$^+$]; mp 253-254° C.

Example 245

N-{5-[7-Trifluoromethyl-5-(4-trifluoromethyl-phenyl)-pyrazolo[1,5-a]pyrimidin-3-ylethynyl]-pyrimidin-2-yl}-acetamide N-Acetyl-N-{5-[7-trifluoromethyl-5-(4-trifluoromethyl-phenyl)-pyrazolo[1,5-a]pyrimidin-3-ylethynyl]-pyrimidin-2-yl}-acetamide (example 244) (56 mg, 0.1 mmol) was dissolved in ammonia (200 uL) and THF (5 mL), stirred for 15 minutes at 23° C., then 1N HCl and water added until pH=1. The product was filtered off, washed with water and dried in vacuum to give the title compound as a yellow solid (49 mg, 95%). MS (ISP) 491.2 [(M+H)$^+$]; mp 293° C.

Example 246

6-[7-Trifluoromethyl-5-(4-trifluoromethyl-phenyl)-pyrazolo[1,5-a]pyrimidin-3-ylethynyl]-pyridazin-3-ylamine The title compound was prepared from 3-ethynyl-7-trifluoromethyl-5-(4-trifluoromethyl-phenyl)-pyrazolo[1,5-a]pyrimidine (example C.1) (355 g, 1.0 mmol) and commercially available 6-bromo-3-pyridazinamine (226 mg, 1.3 mmol) according to general procedure II. Obtained as a light brown solid (270 mg, 60%). MS (ISP) 449.2 [(M+H)$^+$]; mp 214-216° C.

Example 247

6-[5-(4-Chloro-phenyl)-7-trifluoromethyl-pyrazolo[1,5-a]pyrimidin-3-ylethynyl]-pyridazin-3-ylamine The title compound was prepared from 5-(4-chloro-phenyl)-3-iodo-7-trifluoromethyl-pyrazolo[1,5-a]pyrimidine (example C.4) (322 mg, 1 mmol) and commercially available 6-bromo-3-pyridazinamine (226 mg, 1.3 mmol) according to general procedure II. Obtained as an orange solid (210 mg, 51%). MS (ISP) 415.1 [(M+H)$^+$], 417 [(M+2+H)$^+$]; mp 247-248° C.

Example 248

7-Difluoromethyl-3-[5-(4-methyl-piperazine-1-sulfonyl)-thiophen-2-ylethynyl]-5-(3-trifluoromethyl-phenyl)-pyrazolo[1,5-a]pyrimidine The title compound was prepared from 3-ethynyl-7-difluoromethyl-5-(3-trifluoromethyl-phenyl)-pyrazolo[1,5-a]pyrimidine (example C.15) (169 mg, 0.5 mmol) and 1-(5-bromo-thiophene-2-sulfonyl)-4-methyl-piperazine (example B.50) (163 mg, 0.5 mmol) according to general procedure II. Obtained as a yellow solid (220 mg, 76%). MS (EI) 581.1 [(M)$^+$]; mp 214° C.

Example 249

3-[5-(4-Methyl-piperazine-1-sulfonyl)-thiophen-2-ylethynyl]-7-trifluoromethyl-5-(3-trifluoromethyl-phenyl)-pyrazolo[1,5-a]pyrimidine The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and 1-(5-bromo-thiophene-2-sulfonyl)-4-methyl-piperazine (example B.50) (163 mg, 0.5 mmol) according to general procedure II. Obtained as an orange solid (210 mg, 70%). MS (EI) 599.1 [(M)$^+$]; mp 191° C.

Example 250

5-[7-Difluoromethyl-5-(3-trifluoromethyl-phenyl)-pyrazolo[1,5-a]pyrimidin-3-ylethynyl]-thiophene-2-sulfonic acid (2-dimethylamino-ethyl)-amide The title compound was prepared from 3-ethynyl-7-difluoromethyl-5-(3-trifluoromethyl-phenyl)-pyrazolo[1,5-a]pyrimidine (example C.15) (169 mg, 0.5 mmol) and 5-bomo-thiophene-2-sulfonic acid (2-dimethylamino-ethyl)-amide (example B.49) (157 mg, 0.5 mmol) according to general procedure II. Obtained as a yellow solid (180 mg, 63%). MS (ISN) 568.2 [(M−H)$^−$]; mp 170° C.

Example 251

5-[7-Trifluoromethyl-5-(3-trifluoromethyl-phenyl)-pyrazolo[1,5-a]pyrimidin-3-ylethynyl]-thiophene-2-sulfonic acid (2-dimethylamino-ethyl)-amide The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and 5-bomo-thiophene-2-sulfonic acid (2-dimethylamino-ethyl)-amide (example B.49) (157 mg, 0.5 mmol) according to general procedure II. Obtained as a yellow solid (210 mg, 71%). MS
To a solution of the compound of formula (XIX) in a solvent (e.g. acetonitrile, EtOH) is added a brominating agent (ISN) 586.1 [(M−H)$^−$]; mp 197° C.

Example 252

7-Difluoromethyl-3-[5-(4-methyl-piperazine-1-sulfonyl)-thiophen-2-ylethynyl]-5-(4-trifluoromethyl-phenyl)-pyrazolo[1,5-a]pyrimidine The title compound was prepared from 7-difluoromethyl-3-ethynyl-5-(4-trifluoromethyl-phenyl)-pyrazolo[1,5-a]pyrimidine (example C.2) (169 mg, 0.5 mmol) and 1-(5-bromo-thiophene-2-sulfonyl)-4-methyl-piperazine (example B.50) (163 mg, 0.5 mmol) according to general procedure II. Obtained as a yellow solid (200 mg, 69%). MS (EI) 581.1 [(M)$^+$]; mp 226° C.

Example 253

5-[7-Difluoromethyl-5-(4-trifluoromethyl-phenyl)-pyrazolo[1,5-a]pyrimidin-3-ylethynyl]-thiophene-2-sulfonic acid (2-dimethylamino-ethyl)-amide The title compound was prepared from 7-difluoromethyl-3-ethynyl-5-(4-trifluoromethyl-phenyl)-pyrazolo[1,5-a]pyrimidine (example C.2) (169 mg, 0.5 mmol) and 5-bomo-thiophene-2-sulfonic acid (2-dimethylamino-ethyl)-amide (example B.49) (157 mg, 0.5 mmol) according to general procedure II. Obtained as a yellow solid (170 mg, 60%). MS (ISP) 570.2 [(M+H)$^+$]; mp 132° C.

Example 254

5-[7-Difluoromethyl-5-(3-trifluoromethyl-phenyl)-pyrazolo[1,5-a]pyrimidin-3-ylethynyl]-pyridin-2-ylamine The title compound was prepared from 3-ethynyl-7-difluoromethyl-5-(3-trifluoromethyl-phenyl)-pyrazolo[1,5-a]pyrimidine (example C.15) (169 mg, 0.5 mmol) and commercially available 6-amino-3-bromo-pyridine (87 mg, 0.5 mmol) according to general procedure II. Obtained as a red solid (48 mg, 22%). MS (EI) 429.1 [(M)$^+$]; mp 164° C.

Example 255

5-(4-Chloro-3-methyl-phenyl)-7-difluoromethyl-3-[5-(4-methyl-piperazine-1-sulfonyl)-thiophen-2-ylethynyl]-pyrazolo[1,5-a]pyrimidine The title compound was prepared from 5-(4-chloro-3-methyl-phenyl)-7-difluoromethyl-3-ethynyl-pyrazolo[1,5-a]pyrimidine (example C.16) (159 mg, 0.5 mmol) and 1-(5-bromo-thiophene-2-sulfonyl)-4-methyl-piperazine (example B.50) (163 mg, 0.5 mmol) according to general procedure II. Obtained as a yellow solid (200 mg, 71%). MS (ISP) 562.3 [(M+H)$^+$]; mp 191° C.

Example 256

5-[5-(4-Chloro-3-methyl-phenyl)-7-difluoromethyl-pyrazolo[1,5-a]pyrimidin-3-ylethynyl]-thiophene-2-sulfonic acid (2-dimethylamino-ethyl)-amide The title compound was prepared from 5-(4-chloro-3-methyl-phenyl)-7-difluoromethyl-3-ethynyl-pyrazolo[1,5-a]pyrimidine (example C.16) (159 mg, 0.5 mmol) and 5-bomo-thiophene-2-sulfonic acid (2-dimethylamino-ethyl)-amide (example B.49) (157 mg, 0.5 mmol) according to general procedure II. Obtained as a yellow solid (200 mg, 73%). MS (ISN) 548.1 [(M−H)$^-$]; mp 149° C.

Example 257

5-[5-(4-Chloro-3-methyl-phenyl)-7-trifluoromethyl-pyrazolo[1,5-a]pyrimidin-3-ylethynyl]-thiophene-2-sulfonic acid (2-dimethylamino-ethyl)-amide The title compound was prepared from 5-(4-chloro-3-methyl-phenyl)-3-ethynyl-7-trifluoromethyl-pyrazolo[1,5-a]pyrimidine (example C.11) (168 mg, 0.5 mmol) and 5-bomo-thiophene-2-sulfonic acid (2-dimethylamino-ethyl)-amide (example B.49) (157 mg, 0.5 mmol) according to general procedure II. Obtained as a yellow solid (200 mg, 70%). MS (ISN) 566.2 [(M−H)$^-$]; mp 179° C.

Example 258

5-(4-Chloro-3-methyl-phenyl)-3-[5-(4-methyl-piperazine-1-sulfonyl)-thiophen-2-ylethynyl]-7-trifluoromethyl-pyrazolo[1,5-a]pyrimidine The title compound was prepared from 5-(4-chloro-3-methyl-phenyl)-3-ethynyl-7-trifluoromethyl-pyrazolo[1,5-a]pyrimidine (example C.11) (168 mg, 0.5 mmol) and 1-(5-bromo-thiophene-2-sulfonyl)-4-methyl-piperazine (example B.50) (163 mg, 0.5 mmol) according to general procedure II. Obtained as a yellow solid (220 mg, 76%). MS (ISP) 580.0 [(M+H)$^+$]; mp 229° C.

Example 259

5-[7-Trifluoromethyl-5-(3-trifluoromethyl-phenyl)-pyrazolo[1,5-a]pyrimidin-3-ylethynyl]-pyridin-2-ylamine The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and commercially available 6-amino-3-bromo-pyridine (87 mg, 0.5 mmol) according to general procedure II. Obtained as an orange solid (19 mg, 9%). MS (ISP) 447.9 [(M+H)$^+$]; mp 177° C.

Example 260

3-[5-(Piperazine-1-sulfonyl)-thiophen-2-ylethynyl]-7-trifluoromethyl-5-(4-trifluoromethyl-phenyl)-pyrazolo[1,5-a]pyrimidine The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and 4-(5-bromo-thiophene-2-sulfonyl)-piperazine-1-carboxylic acid tert-butyl ester (example B.52) (206 mg, 0.5 mmol) according to general procedure II and subsequent cleavage of the protecting group with TFA in dichloromethane at 0° C. Obtained as an orange solid (145 mg, 50%). MS (ISP) 586.1 [(M+H)$^+$]; mp 223° C.

Example 261

3-[5-(Piperazine-1-sulfonyl)-thiophen-2-ylethynyl]-7-trifluoromethyl-5-(3-trifluoromethyl-phenyl)-pyrazolo[1,5-a]pyrimidine The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and 4-(5-bromo-thiophene-2-sulfonyl)-piperazine-1-carboxylic acid tert-butyl ester (example B.52) (206 mg, 0.5 mmol) according to general procedure II and subsequent cleavage of the protecting group with TFA in dichloromethane at 0° C. Obtained as an orange solid (96 mg, 33%). MS (ISP) 586.1 [(M+H)$^+$]; mp 160° C.

Example 262

5-[7-Trifluoromethyl-5-(3-trifluoromethyl-phenyl)-pyrazolo[1,5-a]pyrimidin-3-ylethynyl]-thiophene-2-sulfonic acid (2-amino-ethyl)-amide The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and [2-(5-bromo-thiophene-2-sulfonylamino)-ethyl]-carbamic acid tert-butyl ester (example B.51) (193 mg, 0.5 mmol) according to general procedure II and subsequent cleavage of the protecting group with TFA in dichloromethane at 0° C. Obtained as a yellow solid (89 mg, 32%). MS (ISN) 558.0 [(M−H)$^-$]; mp 196° C.

Example 263

5-[7-Trifluoromethyl-5-(4-trifluoromethyl-phenyl)-pyrazolo[1,5-a]pyrimidin-3-ylethynyl]-thiophene-2-sulfonic acid (2-amino-ethyl)-amide The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and [2-(5-bromo-thiophene-2-sulfonylamino)-ethyl]-carbamic acid tert-butyl ester (example B.51) (193 mg, 0.5 mmol) according to general procedure II and subsequent cleavage of the protecting group with TFA in dichloromethane at 0° C. Obtained as an orange solid (158 mg, 56%). MS (ISN) 558.0 [(M−H)$^-$]; mp 161° C.

Example 264

5-[7-Difluoromethyl-5-(3-trifluoromethyl-phenyl)-pyrazolo[1,5-a]pyrimidin-3-ylethynyl]-thiophene-2-sulfonic acid bis-(2-hydroxy-ethyl)-amide The title compound was prepared from 3-ethynyl-7-difluoromethyl-5-(3-trifluoromethyl-phenyl)-pyrazolo[1,5-a]pyrimidine (example C.15) (169 mg, 0.5 mmol) and 5-bromo-thiophene-2-sulfonic acid bis-(2-hydroxy-ethyl)-amide (example B.53) (165 mg, 0.5 mmol) according to general procedure II. Obtained as a yellow solid (210 mg, 72%). MS (ISP) 587.1 [(M+H)$^+$]; mp 174° C.

Example 265

5-[7-Difluoromethyl-5-(3-trifluoromethyl-phenyl)-pyrazolo[1,5-a]pyrimidin-3-ylethynyl]-thiophene-2-sulfonic acid (2-hydroxy-1-hydroxymethyl-ethyl)-amide The title compound was prepared from 3-ethynyl-7-difluoromethyl-5-(3-trifluoromethyl-phenyl)-pyrazolo[1,5-a]pyrimidine (example C.15) (169 mg, 0.5 mmol) and 5-bromo-thiophene-2-sulfonic acid (2-hydroxy-1-hydroxymethyl-ethyl)-amide (example B.54) (158 mg, 0.5 mmol) according to general procedure II. Obtained as a yellow solid (230 mg, 80%). MS (ISN) 571.0 [(M−H)$^-$]; mp 153° C.

Example 266

5-[7-Trifluoromethyl-5-(3-trifluoromethyl-phenyl)-pyrazolo[1,5-a]pyrimidin-3-ylethynyl]-thiophene-2-sulfonic acid bis-(2-hydroxy-ethyl)-amide The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and 5-bromo-thiophene-2-sulfonic acid bis-(2-hydroxy-ethyl)-amide (example B.53) (165 mg, 0.5 mmol) according to general procedure II. Obtained as an orange solid (61 mg, 20%). MS (EI) 604.1 [(M)$^+$]; mp 129° C.

Example 267

5-[4-Trifluoromethyl-2-(4-trifluoromethyl-phenyl)-imidazo[1,5-a]pyrimidin-8-ylethynyl]-thiophene-2-sulfonic acid (2-dimethylamino-ethyl)-amide The title compound was prepared from 8-ethynyl-4-trifluoromethyl-2-(4-trifluoromethyl-phenyl)-imidazo[1,5-a]pyrimidine (example C.18) (130 mg, 0.37 mmol) and 5-bomo-thiophene-2-sulfonic acid (2-dimethylamino-ethyl)-amide (example B.49) (115 mg, 0.37 mmol) according to general procedure II. Obtained as a red solid (150 mg, 70%). MS (ISN) 586.0 [(M−H)$^-$]; mp 178° C.

Example 268

8-Pyridin-3-ylethynyl-4-trifluoromethyl-2-(4-trifluoromethyl-phenyl)-imidazo[1,5-a]pyrimidine The title compound was prepared from 8-ethynyl-4-trifluoromethyl-2-(4-trifluoromethyl-phenyl)-imidazo[1,5-a]pyrimidine (example C.18) (130 mg, 0.37 mmol) and commercially available 3-bromo-pyridine (58 mg, 0.37 mmol) according to general procedure II. Obtained as a dark red solid (54 mg, 34%). MS (ISP) 433.0 [(M+H)$^+$]; mp 199° C.

Example 269

5-[7-Difluoromethyl-5-(4-trifluoromethyl-phenyl)-pyrazolo[1,5-a]pyrimidin-3-ylethynyl]-thiophene-2-sulfonic acid bis-(2-hydroxy-ethyl)-amide The title compound was prepared from 7-difluoromethyl-3-ethynyl-5-(4-trifluoromethyl-phenyl)-pyrazolo[1,5-a]pyrimidine (example C.2) (169 mg, 0.5 mmol) and 5-bromo-thiophene-2-sulfonic acid bis-(2-hydroxy-ethyl)-amide (example B.53) (165 mg, 0.5 mmol) according to general procedure II. Obtained as a light brown solid (78 mg, 27%). MS (ISP) 587.1 [(M+H)+]; mp 122° C.

Example 270

5-[7-Difluoromethyl-5-(4-trifluoromethyl-phenyl)-pyrazolo[1,5-a]pyrimidin-3-ylethynyl]-thiophene-2-sulfonic acid (2-hydroxy-1-hydroxymethyl-ethyl)-amide The title compound was prepared from 7-difluoromethyl-3-ethynyl-5-(4-trifluoromethyl-phenyl)-pyrazolo[1,5-a]pyrimidine (example C.2) (169 mg, 0.5 mmol) and 5-bromo-thiophene-2-sulfonic acid (2-hydroxy-1-hydroxymethyl-ethyl)-amide (example B.54) (158 mg, 0.5 mmol) according to general procedure II. Obtained as a light brown solid (53 mg, 18%). MS (ISN) 571.0 [(M−H)−]; mp 152° C.

Example 271

5-[7-Trifluoromethyl-5-(3-trifluoromethyl-phenyl)-pyrazolo[1,5-a]pyrimidin-3-ylethynyl]-thiophene-2-sulfonic acid (2-hydroxy-1-hydroxymethyl-ethyl)-amide The title compound was prepared from 3-ethynyl-7-trifluoromethyl-5-(3-trifluoromethyl-phenyl)-pyrazolo[1,5-a]pyrimidine (example C.10) (178 mg, 0.5 mmol) and 5-bromo-thiophene-2-sulfonic acid (2-hydroxy-1-hydroxymethyl-ethyl)-amide (example B.54) (158 mg, 0.5 mmol) according to general procedure II. Obtained as an orange solid (117 mg, 40%). MS (ISN) 589.3 [(M−H)−]; mp 210° C.

Example 272

5-[7-Trifluoromethyl-5-(4-trifluoromethyl-phenyl)-pyrazolo[1,5-a]pyrimidin-3-ylethynyl]-thiophene-2-sulfonic acid (pyridin-4-ylmethyl)-amide The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and 5-bromo-thiophene-2-sulfonic acid (pyridin-4-ylmethyl)-amide (example B.55) (167 mg, 0.5 mmol) according to general procedure II. Obtained as a yellow solid (115 mg, 38%). MS (ISN) 606.2 [(M−H)−]; mp 170° C.

Example 273

5-[7-Trifluoromethyl-5-(4-trifluoromethyl-phenyl)-pyrazolo[1,5-a]pyrimidin-3-ylethynyl]-thiophene-2-sulfonic acid (pyridin-3-ylmethyl)-amide The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and 5-bromo-thiophene-2-sulfonic acid (pyridin-3-ylmethyl)-amide (example B.x) (example B.56) (167 mg, 0.5 mmol) according to general procedure II and subsequent cleavage of the protecting group with TFA in dichloromethane at 0° C. Obtained as an orange solid (132 mg, 43%). MS (ISN) 606.2 [(M−H)−]; mp 177° C.

Example 274

5-[4-Difluoromethyl-2-(4-trifluoromethyl-phenyl)-imidazo[1,5-a]pyrimidin-8-ylethynyl]-2,4-difluoro-benzenesulfonamide The title compound was prepared from 4-difluoromethyl-8-ethynyl-2-(4-trifluoromethyl-phenyl)-imidazo[1,5-a]pyrimidine (example C.31) (190 mg, 0.56 mmol) and commercially available 5-bromo-2,4-difluoro-benzenesulfonamide (153 mg, 0.56 mmol) according to general procedure II. Obtained as a brown solid (192 mg, 64%). MS (ISN) 527.1 [(M−H)−]; mp 149° C.

Example 275

5-[4-Difluoromethyl-2-(4-trifluoromethyl-phenyl)-imidazo[1,5-a]pyrimidin-8-ylethynyl]-thiophene-2-sulfonic acid amide The title compound was prepared from 4-difluoromethyl-8-ethynyl-2-(4-trifluoromethyl-phenyl)-imidazo[1,5-a]pyrimidine (example C.31) (190 mg, 0.56 mmol) and commercially available 5-bromo-thiophene-2-sulfonamide (136 mg, 0.56 mmol) according to general procedure II. Obtained as an orange solid (236 mg, 84%). MS (ISN) 497.1 [(M−H)−]; mp 223° C.

Example 276

4-[4-Difluoromethyl-2-(4-trifluoromethyl-phenyl)-imidazo[1,5-a]pyrimidin-8-ylethynyl]-benzenesulfonamide The title compound was prepared from 4-difluoromethyl-8-ethynyl-2-(4-trifluoromethyl-phenyl)-imidazo[1,5-a]pyrimidine (example C.31) (190 mg, 0.56 mmol) and commercially available 4-bromo-benzenesulfonamide (133 mg, 0.56 mmol) according to general procedure II. Obtained as a brown solid (184 mg, 66%). MS (ISN) 491.2 [(M−H)−]; mp 282° C.

Example 277

5-[7-Difluoromethyl-5-(4-trifluoromethyl-phenyl)-pyrazolo[1,5-a]pyrimidin-3-ylethynyl]-thiophene-2-sulfonic acid (pyridin-4-ylmethyl)-amide The title compound was prepared from 7-difluoromethyl-3-ethynyl-5-(4-trifluoromethyl-phenyl)-pyrazolo[1,5-a]pyrimidine (example C.2) (169 mg, 0.5 mmol) and 5-bromo-thiophene-2-sulfonic acid (pyridin-4-ylmethyl)-amide (example B.55) (167 mg, 0.5 mmol) according to general procedure II. Obtained as a yellow solid (96 mg, 33%). MS (ISN) 588.2 [(M−H)−]; mp 141° C.

Example 278

5-[7-Difluoromethyl-5-(4-trifluoromethyl-phenyl)-pyrazolo[1,5-a]pyrimidin-3-ylethynyl]-thiophene-2-sulfonic acid (pyridin-3-ylmethyl)-amide The title compound was prepared from 7-difluoromethyl-3-ethynyl-5-(4-trifluoromethyl-phenyl)-pyrazolo[1,5-a]pyrimidine (example C.2) (169 mg, 0.5 mmol) and 5-bromo-thiophene-2-sulfonic acid (pyridin-3-ylmethyl)-amide (example B.56) (167 mg, 0.5 mmol) according to general

Example 279

5-[7-Trifluoromethyl-5-(4-trifluoromethyl-phenyl)-pyrazolo[1,5-a]pyrimidin-3-ylethynyl]-thiophene-2-sulfonic acid pyridin-3-ylamide The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and commercially available 5-bromo-thiophene-2-sulfonic acid pyridin-3-ylamide [CAS-No. 439934-18-6] (160 mg, 0.5 mmol) according to general procedure II and subsequent cleavage of the protecting group with TFA in dichloromethane at 0° C. Obtained as a yellow solid (200 mg, 67%). MS (ISN) 592.1 [(M–H)$^-$]; mp 248° C.

Example 280

5-[7-Trifluoromethyl-5-(4-trifluoromethyl-phenyl)-pyrazolo[1,5-a]pyrimidin-3-ylethynyl]-thiophene-2-sulfonic acid pyridin-4-ylamide The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and 5-bromo-thiophene-2-sulfonic acid pyridin-4-ylamide (example B.57) (160 mg, 0.5 mmol) according to general procedure II and subsequent cleavage of the protecting group with TFA in dichloromethane at 0° C. Obtained as an orange solid (160 mg, 54%). MS (ISN) 592.1 [(M–H)$^-$]; mp 209° C.

Example 281

5-[7-Difluoromethyl-5-(4-trifluoromethyl-phenyl)-pyrazolo[1,5-a]pyrimidin-3-ylethynyl]-thiophene-2-sulfonic acid pyridin-3-ylamide The title compound was prepared from 7-difluoromethyl-3-ethynyl-5-(4-trifluoromethyl-phenyl)-pyrazolo[1,5-a]pyrimidine (example C.2) (169 mg, 0.5 mmol) and commercially available 5-bromo-thiophene-2-sulfonic acid pyridin-3-ylamide [CAS-No. 439934-18-6] (160 mg, 0.5 mmol) according to general procedure II. Obtained as a yellow solid (220 mg, 76%). MS (ISN) 574.1 [(M–H)$^-$]; mp 226° C.

Example 282

5-[7-Difluoromethyl-5-(4-trifluoromethyl-phenyl)-pyrazolo[1,5-a]pyrimidin-3-ylethynyl]-thiophene-2-sulfonic acid pyridin-4-ylamide The title compound was prepared from 7-difluoromethyl-3-ethynyl-5-(4-trifluoromethyl-phenyl)-pyrazolo[1,5-a]pyrimidine (example C.2) (169 mg, 0.5 mmol) and 5-bromo-thiophene-2-sulfonic acid pyridin-4-ylamide (example B.57) (160 mg, 0.5 mmol) according to general procedure II. Obtained as an orange solid (140 mg, 49%). MS (ISN) 574.1 [(M–H)$^-$]; mp 215° C.

Example 283

5-[7-Trifluoromethyl-5-(4-trifluoromethyl-phenyl)-pyrazolo[1,5-a]pyrimidin-3-ylethynyl]-thiophene-2-sulfonic acid (2,6-dimethyl-pyridin-4-ylmethyl)-amide The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and 5-bromo-thiophene-2-sulfonic acid (2,6-dimethyl-pyridin-4-ylmethyl)-amide (example B.58) (181 mg, 0.5 mmol) according to general procedure II. Obtained as an orange solid (120 mg, 38%). MS (ISN) 634.0 [(M–H)$^-$]; mp 200° C.

Example 284

5-[4-Trifluoromethyl-2-(4-trifluoromethyl-phenyl)-imidazo[1,5-a]pyrimidin-8-ylethynyl]-pyridin-2-ylamine The title compound was prepared from 8-ethynyl-4-trifluoromethyl-2-(4-trifluoromethyl-phenyl)-imidazo[1,5-a]pyrimidine (example C.x) (178 mg, 0.5 mmol) and commercially available 6-amino-3-bromo-pyridine (86 mg, 0.5 mmol) according to general procedure II. Obtained as a dark red solid (70 mg, 31%). MS (EI) 448.1 [(M+)$^+$]; mp 225° C.

Example 285

5-[4-Trifluoromethyl-2-(4-trifluoromethyl-phenyl)-imidazo[1,5-a]pyrimidin-8-ylethynyl]-pyrimidin-2-ylamine The title compound was prepared from 8-ethynyl-4-trifluoromethyl-2-(4-trifluoromethyl-phenyl)-imidazo[1,5-a]pyrimidine (example C.18) (178 mg, 0.5 mmol) and commercially available 2-amino-5-bromo-pyrimidine (87 mg, 0.5 mmol) according to general procedure II. Obtained as a dark red solid (92 mg, 41%). MS (EI) 447.1 [(M$^+$)]; mp 294° C.

Example 286

5-[7-Trifluoromethyl-5-(4-trifluoromethyl-phenyl)-pyrazolo[1,5-a]pyrimidin-3-ylethynyl]-pyrazin-2-ylamine The title compound was prepared from 3-ethynyl-7-trifluoromethyl-5-(4-trifluoromethyl-phenyl)-pyrazolo[1,5-a]pyrimidine (example C.1) (178 mg, 0.5 mmol) and commercially available 2-amino-5-bromo-pyrazine (87 mg, 0.5 mmol) according to general procedure II. Obtained as an orange solid (63 mg, 28%). MS (EI) 448.0 [(M)$^+$]; mp 200° C.

Example 287

5-[7-Difluoromethyl-5-(4-trifluoromethyl-phenyl)-pyrazolo[1,5-a]pyrimidin-3-ylethynyl]-pyrazin-2-ylamine The title compound was prepared from 7-difluoromethyl-3-ethynyl-5-(4-trifluoromethyl-phenyl)-pyrazolo[1,5-a]pyrimidine (example C.2) (169 mg, 0.5 mmol) and commercially available 2-amino-5-bromo-pyrazine (87 mg, 0.5 mmol) according to general procedure II. Obtained as an orange solid (53 mg, 25%). MS (ISP) 431.2 [(M+H)$^+$]; mp 233° C.

(Preceding text: procedure II. Obtained as a yellow solid (139 mg, 47%). MS (ISN) 588.0 [(M–H)$^-$]; mp 152° C.)

Example 288

5-[7-Trifluoromethyl-5-(4-trifluoromethyl-phenyl)-pyrazolo[1,5-a]pyrimidin-3-ylethynyl]-pyridine-2-carbonitrile The title compound was prepared from 3-ethynyl-7-trifluoromethyl-5-(4-trifluoromethyl-phenyl)-pyrazolo[1,5-a]pyrimidine (example C.1) (710 mg, 2.0 mmol) and commercially available 5-bromo-2-cyano-pyridine (366 mg, 2.0 mmol) according to general procedure II. Obtained as an orange solid (730 mg, 80%). MS (EI) 457.1 [(M)$^+$]; mp 212° C.

Example 289

5-[5-(3-Methyl-4-trifluoromethyl-phenyl)-7-trifluoromethyl-pyrazolo[1,5-a]pyrimidin-3-ylethynyl]-pyridin-2-ylamine The title compound was prepared from 3-iodo-5-(3-methyl-4-trifluoromethyl-phenyl)-7-trifluoromethyl-pyrazolo[-a]pyrimidine (example C.32) (236 mg, 0.5 mmol) and 5-ethynyl-pyridin-2-ylamine (example D.1) (59 mg, 0.5 mmol) according to general procedure II. Obtained as a red solid (165 mg, 71%). MS (EI) 461.1 [(M)$^+$]; mp 201° C.

Example 290

5-[5-(3-Methyl-4-trifluoromethyl-phenyl)-7-trifluoromethyl-pyrazolo[1,5-a]pyrimidin-3-ylethynyl]-pyrimidin-2-ylamine The title compound was prepared from 3-iodo-5-(3-methyl-4-trifluoromethyl-phenyl)-7-trifluoromethyl-pyrazolo[-a]pyrimidine (example C.32) (236 mg, 0.5 mmol) and 5-ethynyl-pyrimidin-2-ylamine (example D.2) (60 mg, 0.5 mmol) according to general procedure II. Obtained as an orange solid (139 mg, 60%). MS (EI) 462.1 [(M)$^+$]; mp 240° C.

Example 291

N-{5-[7-Trifluoromethyl-5-(4-trifluoromethyl-phenyl)-pyrazolo[1,5-a]pyrimidin-3-ylethynyl]-thiazol-2-yl}-acetamide The title compound was prepared from 3-ethynyl-7-trifluoromethyl-5-(4-trifluoromethyl-phenyl)-pyrazolo[1,5-a]pyrimidine (example C.1) (355 mg, 1.0 mmol) and N-(5-iodo-thiazol-2-yl)-acetamide [CAS-No. 252662-43-4] (268 mg, 1.0 mmol) according to general procedure II. Obtained as an orange solid (240 mg, 48%). MS (EI) 495.1 [(M)$^+$]; mp 302° C.

Example 292

4-[5-(4-Chloro-phenyl)-7-methyl-pyrazolo[1,5-a]pyrimidin-3-ylethynyl]-benzenesulfonamide The title compound was prepared from 5-(4-chloro-phenyl)-3-iodo-7-methyl-pyrazolo[1,5-a]pyrimidine (92 mg, 0.25 mmol) and 4-ethynyl-benzenesulfonamide (45 mg, 0.25 mmol) according to general procedure II. Obtained as an orange solid (52 mg, 49%). MS (ISP) 423.3 [(M+H)$^+$]; mp 230-233° C.

Preparation of 5-(4-chloro-phenyl)-3-iodo-7-methyl-pyrazolo[1,5-a]pyrimidine

Obtained by applying in analogous manner the procedures described in example C.12 step 1-2, but in step 1, ethyl 7-chloro-5-(4-trifluoromethyl-phenyl)-pyrazolo[1,5-a]pyrimidine was replaced by 7-chloro-5-(4-chloro-phenyl)-pyrazolo[1,5-a]pyrimidine (example C.5 step 2). Yellow solid. MS (ISP) 370.0 [(M+H)$^+$]; mp 147-148° C.

Example 293

5-[7-Cyclopropyl-5-(4-trifluoromethyl-phenyl)-pyrazolo[1,5-a]pyrimidin-3-ylethynyl]-pyridin-2-ylamine The title compound was prepared from 7-cyclopropyl-3-ethynyl-5-(4-trifluoromethyl-phenyl)-pyrazolo[1,5-a]pyrimidine (example C.7) (82 mg, 0.25 mmol) and 2-amino-5-bromopyridine (43 mg, 0.25 mmol) according to general procedure II. Obtained as an orange solid (9 mg, 9%). MS (ISP) 420.2 [(M+H)$^+$]; mp 228-231° C.

Example 294

5-[5-(4-Chloro-phenyl)-7-cyclopropyl-pyrazolo[1,5-a]pyrimidin-3-ylethynyl]-pyridin-2-ylamine The title compound was prepared from 5-(4-chloro-phenyl)-7-cyclopropyl-3-ethynyl-pyrazolo[1,5-a]pyrimidine (example C.5) (73 mg, 0.25 mmol) and 2-amino-5-bromopyridine (43 mg, 0.25 mmol) according to general procedure II. Obtained as an orange solid (14 mg, 15%). MS (ISP) 386.3 [(M+H)$^+$]; mp 233-235° C.

Example 295

5-[5-(4-Chloro-phenyl)-7-methyl-pyrazolo[1,5-a]pyrimidin-3-ylethynyl]-pyridin-2-ylamine The title compound was prepared from 5-(4-chloro-phenyl)-3-iodo-7-methyl-pyrazolo[1,5-a]pyrimidine (example 292) (185 mg, 0.5 mmol) and 5-ethynyl-pyridin-2-ylamine (example D.1) (59 mg, 0.5 mmol) according to general procedure II. Obtained as a yellow solid (113 mg, 63%). MS (ISP) 360.0 [(M+H)$^+$]; mp 244-246° C.

Example 296

2-[5-(4-Chloro-phenyl)-3-(4-hydroxymethyl-phenylethynyl)-pyrazolo[1,5-a]pyrimidin-7-yl]-propan-2-ol The title compound was prepared from 2-[5-(4-chlorophenyl)-3-ethynyl-pyrazolo[1,5-a]pyrimidin-7-yl]-propan-2-ol (example C.13) (78 mg, 0.25 mmol) and 4-bromobenzyl alcohol (47 mg, 0.25 mmol) according to general procedure II. Obtained as a yellow solid (16 mg, 15%). MS (ISP) 418.1 [(M+H)$^+$].

Example 297

5-[5-(4-Chloro-phenyl)-7-methyl-pyrazolo[1,5-a]pyrimidin-3-ylethynyl]-thiophene-2-sulfonic acid amide The title compound was prepared from 5-(4-chloro-phenyl)-3-iodo-7-methyl-pyrazolo[1,5-a]pyrimidine (example 292) (185 mg, 0.5 mmol) and 5-ethynyl-thiophene-2-sulfonic acid amide (example D.3) (94 mg, 0.5 mmol) according to general procedure II. Obtained as a yellow solid (94 mg, 44%). MS (ISP) 429.5 [(M+H)$^+$].

Example 298

[3-(6-Amino-pyridin-3-ylethynyl)-5-(4-chloro-phenyl)-pyrazolo[1,5-a]pyrimidin-7-yl]-methanol The title compound was prepared from [5-(4-chloro-phenyl)-3-iodo-pyrazolo[1,5-a]pyrimidin-7-yl]-methanol (example C.14 step 2) (193 mg, 0.5 mmol) and 5-ethynyl-pyridin-2-ylamine (example D.1) (59 mg, 0.5 mmol) according to general procedure II. Obtained as an orange solid (111 mg, 59%). MS (ISP) 376.4 [(M+H)$^+$]; mp 215-217° C.

Example 299

2-{4-[5-(4-Chloro-phenyl)-7-hydroxymethyl-pyrazolo[1,5-a]pyrimidin-3-ylethynyl]-phenyl}-propan-2-ol The title compound was prepared from [5-(4-chloro-phenyl)-3-iodo-pyrazolo[1,5-a]pyrimidin-7-yl]-methanol (example C.14 step 2) (193 mg, 0.5 mmol) and 2-(4-ethynyl-phenyl)-propan-2-ol (example D.4) (80 mg, 0.5 mmol) according to general procedure II. Obtained as a yellow solid (97 mg, 46%). MS (ISP) 418.1 [(M+H)$^+$]; mp 118-120° C.

Example 300

2-{4-[5-(4-Chloro-phenyl)-7-cyclopropyl-pyrazolo[1,5-a]pyrimidin-3-ylethynyl]-phenyl}-propan-2-ol The title compound was prepared from 5-(4-chloro-phenyl)-7-cyclopropyl-3-iodo-pyrazolo[1,5-a]pyrimidine (example C.5 step 4) (198 mg, 0.5 mmol) and 2-(4-ethynyl-phenyl)-propan-2-ol (example D.4) (80 mg, 0.5 mmol) according to general procedure II. Obtained as a yellow solid (143 mg, 67%). MS (ISP) 428.3 [(M+H)$^+$]; mp 148-150° C.

Example 301

2-{4-[5-(4-Chloro-phenyl)-7-methyl-pyrazolo[1,5-a]pyrimidin-3-ylethynyl]-phenyl}-propan-2-ol The title compound was prepared from 5-(4-chloro-phenyl)-3-iodo-7-methyl-pyrazolo[1,5-a]pyrimidine (example 292) (185 mg, 0.5 mmol) and 2-(4-ethynyl-phenyl)-propan-2-ol (example D.4) (80 mg, 0.5 mmol) according to general procedure II. Obtained as a yellow solid (94 mg, 47%). MS (ISP) 402.3 [(M+H)$^+$]; mp 112-115° C.

Example 302

5-[7-Methyl-5-(4-trifluoromethyl-phenyl)-pyrazolo[1,5-a]pyrimidin-3-ylethynyl]-pyridin-2-ylamine The title compound was prepared from 3-ethynyl-7-methyl-5-(4-trifluoromethyl-phenyl)-pyrazolo[1,5-a]pyrimidine (example C.12) (151 mg, 0.5 mmol) and 2-amino-5-bromopyridine (87 mg, 0.5 mmol) according to general procedure II. Obtained as an orange solid (37 mg, 19%). MS (ISP) 394.0 [(M+H)$^+$].

Example 303

5-[5-(4-Chloro-phenyl)-pyrazolo[1,5-a]pyrimidin-3-ylethynyl]-thiophene-2-sulfonic acid amide The title compound was prepared from 5-(4-chloro-phenyl)-3-ethynyl-pyrazolo[1,5-a]pyrimidine (example C.6) (37 mg, 0.17 mmol) and 5-bromo-thiophene-2-sulfonamide (35 mg, 0.17 mmol) according to general procedure II. Obtained as a yellow solid (45 mg, 74%). MS (ISP) 415.0 [(M+H)$^+$].

Example 304

5-[5-(4-Chloro-phenyl)-7-ethyl-pyrazolo[1,5-a]pyrimidin-3-ylethynyl]-pyridin-2-ylamine The title compound was prepared 5-(4-chloro-phenyl)-7-ethyl-3-iodo-pyrazolo[1,5-a]pyrimidine (96 mg, 0.25 mmol) and 5-ethynyl-pyridin-2-ylamine (example D.1) (30 mg, 0.25 mmol) according to general procedure II. Obtained as a yellow solid (41 mg, 44%). MS (ISP) 374.3 [(M+H)$^+$]; mp 205-206° C.

Preparation of 5-(4-chloro-phenyl)-7-ethyl-3-iodo-pyrazolo[1,5-a]pyrimidine

Obtained by applying in analogous manner the procedures described in example C.5, steps 3-4, but in step 3, cyclopropylmagnesium bromide was replaced by ethylmagnesium chloride. Yellow solid. MS (ISP) 383.9 [(M+H)$^+$]; mp 150-152° C.

Example 305

5-[5-(4-Chloro-phenyl)-7-propyl-pyrazolo[1,5-a]pyrimidin-3-ylethynyl]-pyridin-2-ylamine The title compound was prepared from 5-(4-chloro-phenyl)-3-iodo-7-propyl-pyrazolo[1,5-a]pyrimidine (99 mg, 0.25 mmol) and 5-ethynyl-pyridin-2-ylamine (example D.1) (30 mg, 0.25 mmol) according to general procedure II. Obtained as a yellow solid (48 mg, 50%). MS (ISP) 388.4 [(M+H)$^+$]; mp 215-217° C.

Preparation of 5-(4-chloro-phenyl)-3-iodo-7-propyl-pyrazolo[1,5-a]pyrimidine

Obtained by applying in analogous manner the procedures described in example C.5, steps 3-4, but in step 3, cyclopropylmagnesium bromide was replaced by propylmagnesium chloride. Yellow solid. MS (ISP) 398.0 [(M+H)$^+$]; mp 108-110° C.

Example 306

4-[5-(4-Chloro-phenyl)-7-cyclopropyl-pyrazolo[1,5-a]pyrimidin-3-ylethynyl]-N-methyl-benzamide The title compound was prepared by reacting 5-(4-chloro-phenyl)-7-cyclopropyl-3-iodo-pyrazolo[1,5-a]pyrimidine (example C.5 step 4) (792 mg, 2.0 mmol) and ethyl 4-ethynyl-benzoate (350 mg, 2.0 mmol) according to general procedure II, and subsequently, heating the suspension of the obtained product in 1 M NH$_3$/THF-MeOH (1:1) to 60° C. for 75 h. Obtained as a yellow solid (6 mg, 14%). MS (ISP) 427.3 [(M+H)$^+$]; mp 214-216° C.

Example 307

5-[7-tert.-Butyl-5-(4-chloro-phenyl)-pyrazolo[1,5-a]pyrimidin-3-ylethynyl]-thiophene-2-sulfonic acid amide The title compound was prepared from 7-tert.-butyl-5-(4-chloro-phenyl)-3-iodo-pyrazolo[1,5-a]pyrimidine (70 mg, 0.17 mmol) and 5-ethynyl-thiophene-2-sulfonamide (example D.3) (32 mg, 0.17 mmol) according to general procedure II. Obtained as a yellow solid (28 mg, 28%). MS (ISP) 471.1 [(M+H)$^+$]; mp 253-255° C.

Preparation of 7-tert.-butyl-5-(4-chloro-phenyl)-3-iodo-pyrazolo[1,5-a]pyrimidine (S668)

Obtained by applying in analogous manner the procedures described in example C.5 steps 3-4, but in step 3, cyclopropylmagnesium bromide/THF was replaced by tert.-butylmagnesium chloride/Et$_2$O. Yellow solid. MS (ISP) 412.1 [(M+H)$^+$].

Example 308

5-[7-Methyl-5-(4-trifluoromethyl-phenyl)-pyrazolo[1,5-a]pyrimidin-3-ylethynyl]-thiophene-2-sulfonic acid (2-hydroxy-1-hydroxymethyl-ethyl)-amide The title compound was prepared from 3-ethynyl-7-methyl-5-(4-trifluoromethyl-phenyl)-pyrazolo[1,5-a]pyrimidine (example C.12) (75 mg, 0.25 mmol) and 5-bromo-thiophene-2-sulfonic acid (2-hydroxy-1-hydroxymethyl-ethyl)-amide (example B.53) (79 mg, 0.25 mmol) according to general procedure II. Obtained as a yellow solid (99 mg, 74%). MS (ISP) 537.3 [(M+H)$^+$]; mp 148-152° C.

Example 309

5-[7-Methyl-5-(4-trifluoromethyl-phenyl)-pyrazolo[1,5-a]pyrimidin-3-ylethynyl]-thiophene-2-sulfonic acid (2-hydroxy-ethyl)-amide The title compound was prepared from 3-ethynyl-7-methyl-5-(4-trifluoromethyl-phenyl)-pyrazolo[1,5-a]pyrimidine (example C.12) (75 mg, 0.25 mmol) and 5-bromo-thiophene-2-sulfonic acid (2-hydroxy-ethyl)-amide (example B.59) according to general procedure II. Obtained as a yellow solid (87 mg, 68%). MS (ISP) 503.3 [(M+H)$^+$]; mp 162-164° C.

Example 310

5-[5-(4-Trifluoromethyl-phenyl)-pyrazolo[1,5-a]pyrimidin-3-ylethynyl]-pyridin-2-ylamine The title compound was prepared from 3-iodo-5-(4-trifluoromethyl-phenyl)-pyrazolo[1,5-a]pyrimidine (example C.33 step 1) (195 mg, 0.5 mmol) and 5-ethynyl-pyridin-2-ylamine (example D.1) (59 mg, 0.5 mmol) according to general procedure II. Obtained as an orange solid (101 mg, 53%). MS (ISP) 380.0 [(M+H)$^+$]; mp 213-214° C.

Example 311

5-[5-(4-Trifluoromethyl-phenyl)-pyrazolo[1,5-a]pyrimidin-3-ylethynyl]-thiophene-2-sulfonic acid amide The title compound was prepared from 3-ethynyl-5-(4-trifluoromethyl-phenyl)-pyrazolo[1,5-a]pyrimidine (example C.33) (144 mg, 0.5 mmol) and 5-bromo-thiophene-2-sulfonic acid amide (121 mg, 0.5 mmol) according to general procedure II. Obtained as a yellow solid (153 mg, 68%). MS (ISP) 449.3 [(M+H)$^+$]; mp 224-226° C.

Example 312

5-[5-(4-Chloro-phenyl)-7-trifluoromethyl-pyrazolo[1,5-a]pyrimidin-3-ylethynyl]-pyridin-2-ylamine The title compound was prepared from 5-(4-chloro-phenyl)-3-ethynyl-7-trifluoromethyl-pyrazolo[1,5-a]pyrimidine (example C.4) (322 mg, 1.0 mmol) and 2-amino-5-bromopyridine (173 mg, 1.0 mmol) according to general procedure II. Obtained as an orange solid (71 mg, 17%). MS (ISP) 414.3 [(M+H)$^+$].

Example 313

5-[5-(4-Chloro-phenyl)-7-cyclopropyl-pyrazolo[1,5-a]pyrimidin-3-ylethynyl]-pyrimidin-2-ylamine The title compound was prepared from 5-(4-chloro-phenyl)-7-cyclopropyl-3-iodo-pyrazolo[1,5-a]pyrimidine (example C.5 step 4) (198 mg, 0.5 mmol) and 5-ethynyl-pyrimidin-2-ylamine (example D.2 step 2) (60 mg, 0.5 mmol) according to general procedure II. Obtained as a yellow solid (88 mg, 46%). MS (ISP) 387.1 [(M+H)$^+$]; mp 243-246° C.

Example 314

5-[7-Cyclopropyl-5-(4-trifluoromethyl-phenyl)-pyrazolo[1,5-a]pyrimidin-3-ylethynyl]-pyrimidin-2-ylamine The title compound was prepared from 7-cyclopropyl-3-iodo-5-(4-trifluoromethyl-phenyl)-pyrazolo[1,5-a]pyrimidine (example C.7 step 4) (215 mg, 0.5 mmol) and 5-ethynyl-pyrimidin-2-ylamine (example D.2 step 2) (60 mg, 0.5 mmol) according to general procedure II. Obtained as a yellow solid (59 mg, 28%). MS (ISP) 421.1 [(M+H)$^+$].

Example 315

5-[7-Methyl-5-(4-trifluoromethyl-phenyl)-pyrazolo[1,5-a]pyrimidin-3-ylethynyl]-pyrimidin-2-ylamine The title compound was prepared from 3-iodo-7-methyl-5-(4-trifluoromethyl-phenyl)-pyrazolo[1,5-a]pyrimidine (example C.12 step 2) (202 g, 0.5 mmol) and 5-ethynyl-pyrimidin-2-ylamine (example D.2, step 2) (60 mg, 0.5 mmol) according to general procedure II. Obtained as a yellow solid (90 mg, 46%). MS (ISP) 395.0 [(M+H)$^+$]; mp 246-248° C.

Example 316

5-[5-(4-Chloro-phenyl)-7-methyl-pyrazolo[1,5-a]pyrimidin-3-ylethynyl]-pyrimidin-2-ylamine The title compound was prepared from 5-(4-chloro-phenyl)-3-iodo-7-methyl-pyrazolo[1,5-a]pyrimidine (example 292) (185 mg, 0.5 mmol) and 5-ethynyl-pyrimidin-2-ylamine (example D.2 step 2) (60 mg, 0.5 mmol) according to general procedure II. Obtained as yellow solid (80 mg, 44%). MS (ISP) 361.4 [(M+H)$^+$]; mp 280-282° C.

Example 317

5-[5-(4-Chloro-phenyl)-7-trifluoromethyl-pyrazolo[1,5-a]pyrimidin-3-ylethynyl]-pyrimidin-2-ylamine The title compound was prepared from 5-(4-chloro-phenyl)-3-ethynyl-7-trifluoromethyl-pyrazolo[1,5-a]pyrimidine (example C.4) (161 mg, 0.5 mmol) and 2-amino-5-iodopyridine (111 mg, 0.5 mmol) according to general procedure II. Obtained as an orange solid (77 mg, 37%). MS (ISP) 415.1 [(M+H)$^+$]; mp 303-305° C.

Example 318

5-[5-(4-Chloro-phenyl)-7-cyclopropyl-pyrazolo[1,5-a]pyrimidin-3-ylethynyl]-thiophene-2-sulfonic acid (2-pyridin-4-yl-ethyl)-amide The title compound was prepared from 5-(4-chloro-phenyl)-7-cyclopropyl-3-ethynyl-pyrazolo[1,5-a]pyrimidine (example C.5) (147 mg, 0.5 mmol) and 5-bromo-thiophene-2-sulfonic acid (2-pyridin-4-yl-ethyl)-amide (example B.60) (174 mg, 0.5 mmol) according to general procedure II. Obtained as a yellow solid (112 mg, 40%). MS (ISP) 560.2 [(M+H)$^+$]; mp 172-174° C.

Preparation of Pharmaceutical Compositions Comprising Compounds of the Invention:

Example I

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

|  | mg/Tablet |
| --- | --- |
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

|  | mg/Capsule |
| --- | --- |
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound of formula (Ib):

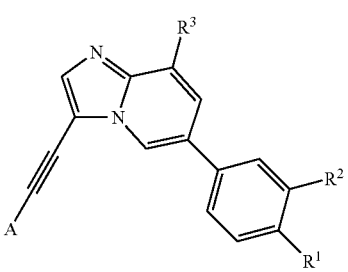

(Ib)

wherein
R$^1$ is H, halo, CF$_3$, CHF$_2$, or C$_{1-6}$-alkyl;
R$^2$ is H, halo, C$_{1-6}$-alkyl, C$_{1-6}$-alkoxy, CF$_3$ or CHF$_2$;
R$^3$ is H, —C(CH$_3$)$_2$OH, or linear C$_{1-4}$-alkyl or C$_{3-4}$-cycloalkyl each of which is optionally substituted by one or more substituents selected from the group consisting of 1 to 6 F and 1 to 2 OH;
A is selected from the group consisting of aryl or 5 or 6-membered heteroaryl each of which is optionally substituted by one to four R$^a$;
R$^a$ is halo,
hydroxy,
cyano,
CF$_3$, NR$^e$R$^f$,
C$_{1-6}$-alkyl optionally substituted by amino or by hydroxy,
C$_{1-6}$-alkoxy,
C$_{3-4}$-cycloalkyl,
CO—NR$^b$R$^c$,
SO$_2$—NR$^b$R$^c$, or
SO$_2$—R$^d$;
R$^b$ and R$^c$ are the same or different and are selected from the group consisting of:
H;
straight or branched C$_{1-6}$-alkyl optionally substituted by one or more substituents selected from the group consisting of:
F, cyano, hydroxy, C$_{1-6}$-alkoxy, —NH—C(O)—O—C$_{1-6}$-alkyl, amino, (C$_{1-6}$-alkyl)amino, di(C$_{1-6}$-alkyl)amino, C$_{3-6}$-cycloalkyl, heterocycloalkyl having 5 or 6 ring atoms, aryl and 5 or 6-membered heteroaryl;
C$_{3-6}$-cycloalkyl;
aryl; and
heteroaryl;
or R$^b$ and R$^c$, together with the nitrogen atom to which they are attached, form a heterocyclic ring of 4 to 6 ring members which are optionally substituted by hydroxy or by C$_{1-6}$-alkyl;
R$^d$ is OH or C$_{1-6}$-alkyl; and
R$^e$ and R$^f$ are each independently H, C$_{1-6}$-alkyl optionally substituted by hydroxy, —C(O)—C$_{1-6}$-alkyl, or S(O)$_2$—C$_{1-6}$-alkyl,
or a pharmaceutically acceptable salt thereof.

2. The compound of claim 1, wherein:
R$^a$ is F,
hydroxy,
NR$^e$R$^f$,
C$_{1-6}$-alkyl optionally substituted by hydroxy,
C$_{1-6}$-alkoxy,
C$_{3-4}$-cycloalkyl,
CO—NR$^b$R$^c$,
SO$_2$—R$^d$, or
SO$_2$—NR$^b$R$^c$;
or a pharmaceutically acceptable salt thereof.

3. The compound according to claim 1, wherein A is phenyl.

4. The compound of claim 1, selected from the group consisting of:
4-[8-Trifluoromethyl-6-(4-trifluoromethyl-phenyl)-imidazo[1,2-a]pyridin-3-ylethynyl]-benzenesulfonamide;
2,4-Difluoro-5-[8-trifluoromethyl-6-(4-trifluoromethyl-phenyl)-imidazo[1,2-a]pyridin-3-ylethynyl]-benzenesulfonamide;
3-[8-Trifluoromethyl-6-(4-trifluoromethyl-phenyl)-imidazo[1,2-a]pyridin-3-ylethynyl]-benzenesulfonamide;
1-{4-[8-Trifluoromethyl-6-(4-trifluoromethyl-phenyl)-imidazo[1,2-a]pyridin-3-ylethynyl]-phenyl}-ethanol; and
4-[8-Trifluoromethyl-6-(4-trifluoromethyl-phenyl)-imidazo[1,2-a]pyridin-3-ylethynyl]-benzamide.

5. The compound of claim 1, wherein A is pyridine-3-yl.

6. The compound of claim 1, selected from the group consisting of:
3-Pyridin-3-ylethynyl-8-trifluoromethyl-6-(4-trifluoromethyl-phenyl)-imidazo[1,2-a]pyridine;
5-[8-Trifluoromethyl-6-(4-trifluoromethyl-phenyl)-imidazo[1,2-a]pyridin-3-ylethynyl]-pyridin-2-ylamine;
5-[8-Methyl-6-(4-trifluoromethyl-phenyl)-imidazo[1,2-a]pyridin-3-ylethynyl]-pyridin-2-ylamine;
5-[6-(4-Chloro-phenyl)-8-methyl-imidazo[1,2-a]pyridin-3-ylethynyl]-pyridin-2-ylamine;
3-(6-Amino-pyridin-3-ylethynyl)-6-(4-trifluoromethyl-phenyl)-imidazo[1,2-a]pyridine-8-carbonitrile;
5-[8-Methyl-6-(4-trifluoromethyl-phenyl)-imidazo[1,2-a]pyridin-3-ylethynyl]-pyridine-3-sulfonic acid (2-hydroxy-1,1-dimethyl-ethyl)-amide;
5-[8-Methyl-6-(4-trifluoromethyl-phenyl)-imidazo[1,2-a]pyridin-3-ylethynyl]-pyridine-3-sulfonic acid amide;
5-[6-(4-Chloro-phenyl)-8-methyl-imidazo[1,2-a]pyridin-3-ylethynyl]-pyridine-3-sulfonic acid (2-hydroxy-1,1-dimethyl-ethyl)-amide;
5-[6-(4-Chloro-phenyl)-8-methyl-imidazo[1,2-a]pyridin-3-ylethynyl]-pyridine-3-sulfonic acid amide;
5-[6-(4-Chloro-phenyl)-8-cyclopropyl-imidazo[1,2-a]pyridin-3-ylethynyl]-pyridin-2-ylamine;
5-[6-(4-Trifluoromethyl-phenyl)-imidazo[1,2-a]pyridin-3-ylethynyl]-pyridin-2-ylamine;
5-[8-Fluoro-6-(4-trifluoromethyl-phenyl)-imidazo[1,2-a]pyridin-3-ylethynyl]-pyridin-2-ylamine; and
5-[6-(4-Chloro-phenyl)-8-fluoro-imidazo[1,2-a]pyridin-3-ylethynyl]-pyridin-2-ylamine.

7. The compound of claim 1, wherein A is thiophen-2-yl.

8. The compound of claim 1, selected from the group consisting of:
5-[8-Trifluoromethyl-6-(4-trifluoromethyl-phenyl)-imidazo[1,2-a]pyridin-3-ylethynyl]-thiophene-2-sulfonic acid amide;
5-[6-(4-Chloro-phenyl)-8-methyl-imidazo[1,2-a]pyridin-3-ylethynyl]-thiophene-2-sulfonic Acid amide;
5-[8-Methyl-6-(4-trifluoromethyl-phenyl)-imidazo[1,2-a]pyridin-3-ylethynyl]-thiophene-2-sulfonic acid amide;
5-[8-Cyano-6-(4-trifluoromethyl-phenyl)-imidazo[1,2-a]pyridin-3-ylethynyl]-thiophene-2-sulfonic acid amide;
5-[6-(4-Trifluoromethyl-phenyl)-imidazo[1,2-a]pyridin-3-ylethynyl]-thiophene-2-sulfonic acid amide; and
5-[8-Cyclopropyl-6-(4-trifluoromethyl-phenyl)-imidazo[1,2-a]pyridin-3-ylethynyl]-thiophene-2-sulfonic acid amide.

9. The compound of claim 1, wherein A is thiazol-2-yl.

10. The compound according to claim 1, which is 2-[8-Trifluoromethyl-6-(4-trifluoromethyl-phenyl)-imidazo[1,2-a]pyridin-3-ylethynyl]-thiazole-5-sulfonic acid (2-hydroxy-1,1-dimethyl-ethyl)-amide.

11. The compound of claim 1, wherein A is pyrimidin-5-yl.

12. The compound of claim 1, selected from the group consisting of
5-[8-Methyl-6-(4-trifluoromethyl-phenyl)-imidazo[1,2-a]pyridin-3-ylethynyl]-pyrimidin-2-ylamine;
5-[6-(4-Chloro-phenyl)-8-methyl-imidazo[1,2-a]pyridin-3-ylethynyl]-pyrimidin-2-ylamine;
3-(2-Amino-pyrimidin-5-ylethynyl)-6-(4-trifluoromethyl-phenyl)-imidazo[1,2-a]pyridine-8-carbonitrile;
5-[6-(4-Trifluoromethyl-phenyl)-imidazo[1,2-a]pyridin-3-ylethynyl]-pyrimidin-2-ylamine;
5-[8-Fluoro-6-(4-trifluoromethyl-phenyl)-imidazo[1,2-a]pyridin-3-ylethynyl]-pyrimidin-2-ylamine; and
5-[6-(4-Chloro-phenyl)-8-fluoro-imidazo[1,2-a]pyridin-3-ylethynyl]-pyrimidin-2-ylamine.

13. A pharmaceutical composition comprising a compound of formula (Ib):

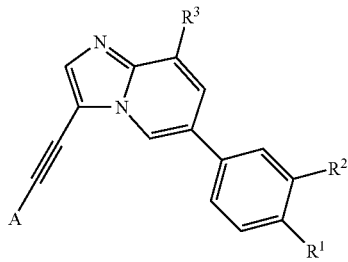

(Ib)

wherein
- $R^1$ is H, halo, $CF_3$, $CHF_2$, or $C_{1-6}$-alkyl;
- $R^2$ is H, halo, $C_{1-6}$-alkyl, $C_{1-6}$-alkoxy, $CF_3$ or $CHF_2$;
- $R^3$ is H, —C(CH$_3$)$_2$OH, or linear $C_{1-4}$-alkyl or $C_{3-4}$-cycloalkyl each of which is optionally substituted by one or more substituents selected from the group consisting of 1 to 6 F and 1 to 2 OH;
- A is selected from the group consisting of aryl or 5 or 6-membered heteroaryl each of which is optionally substituted by one to four $R^a$;
- $R^a$ is halo,
  - hydroxy,
  - cyano,
  - $CF_3$,
  - $NR^e R^f$,
  - $C_{1-6}$-alkyl optionally substituted by amino or by hydroxy,
  - $C_{1-6}$-alkoxy,
  - $C_{3-4}$-cycloalkyl,
  - CO—$NR^b R^c$,
  - $SO_2$—$NR^b R^c$, or
  - $SO_2$—$R^d$;
- $R^b$ and $R^c$ are the same or different and are selected from the group consisting of:
  - H;
  - straight or branched $C_{1-6}$-alkyl optionally substituted by one or more substituents selected from the group consisting of:
    - F, cyano, hydroxy, $C_{1-6}$-alkoxy, —NH—C(O)—O—$C_{1-6}$-alkyl, amino, ($C_{1-6}$-alkyl)amino, di($C_{1-6}$-alkyl)amino, $C_{3-6}$-cycloalkyl, heterocycloalkyl having 5 or 6 ring atoms, aryl and 5 or 6-membered heteroaryl;
  - $C_{3-6}$-cycloalkyl;
  - aryl; and
  - heteroaryl;
- or $R^b$ and $R^c$, together with the nitrogen atom to which they are attached, form a heterocyclic ring of 4 to 6 ring members which are optionally substituted by hydroxy or by $C_{1-6}$-alkyl;
- $R^d$ is OH or $C_{1-6}$-alkyl; and
- $R^e$ and $R^f$ are each independently H, $C_{1-6}$-alkyl optionally substituted by hydroxy, —C(O)—$C_{1-6}$-alkyl, or $S(O)_2$—$C_{1-6}$-alkyl,
- or a pharmaceutically acceptable salt thereof and a pharmaceutically acceptable carrier.

* * * * *